(12) United States Patent
Bamdad et al.

(10) Patent No.: US 11,591,565 B2
(45) Date of Patent: Feb. 28, 2023

(54) MEDIA FOR STEM CELL PROLIFERATION AND INDUCTION

(71) Applicant: Minerva Biotechnologies Corporation, Waltham, MA (US)

(72) Inventors: Cynthia Bamdad, Waltham, MA (US); Benoit Smagghe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 747 days.

(21) Appl. No.: 14/254,749

(22) Filed: Apr. 16, 2014

(65) Prior Publication Data

US 2015/0017726 A1 Jan. 15, 2015

Related U.S. Application Data

(63) Continuation-in-part of application No. PCT/US2012/060684, filed on Oct. 17, 2012.

(60) Provisional application No. 61/693,712, filed on Aug. 27, 2012, provisional application No. 61/684,654, filed on Aug. 17, 2012, provisional application No.
(Continued)

(51) Int. Cl.
*C12N 5/074* (2010.01)
*C12N 5/0735* (2010.01)
*C12N 5/00* (2006.01)

(52) U.S. Cl.
CPC ......... *C12N 5/0607* (2013.01); *C12N 5/0037* (2013.01); *C12N 5/0056* (2013.01); *C12N 5/0606* (2013.01); *C12N 2500/90* (2013.01); *C12N 2501/00* (2013.01); *C12N 2501/10* (2013.01); *C12N 2501/115* (2013.01); *C12N 2501/15* (2013.01); *C12N 2501/727* (2013.01); *C12N 2501/90* (2013.01)

(58) Field of Classification Search
CPC .............. C12N 5/0607; C12N 2501/00; C12N 2500/90; C12N 2501/115; C12N 2501/15; C12N 2501/727; C12N 2501/90; C12N 5/0037; C12N 5/0056; C12N 5/0606
See application file for complete search history.

(56) References Cited

U.S. PATENT DOCUMENTS 8,535,944 B2 * 9/2013 Bamdad ............... C12N 5/0606
435/384
8,859,495 B2 * 10/2014 Bamdad ............... A61K 38/193
514/7.5
(Continued)

FOREIGN PATENT DOCUMENTS

WO 2008/035110 A1 3/2008
WO WO 2008/070171 A2 6/2008
(Continued)

OTHER PUBLICATIONS

Sanjeev Mahanta, Shawn P. Fessler, Jaehong Park, Cynthia Bamdad, A Minimal Fragment of MUC1 Mediates Growth of Cancer Cells, 2008, PLoS ONE, vol. 3, Issue 4, e2054, pp. 1-12.*
(Continued)

*Primary Examiner* — David W Berke-Schlessel
*Assistant Examiner* — Trent R Clarke
(74) *Attorney, Agent, or Firm* — Wilson Sonsini Goodrich & Rosati

(57) ABSTRACT

The present application discloses a cell culture media for growth, maintenance and induction of reversion to a less mature state of a cell comprising a MUC1* activating ligand.

19 Claims, 64 Drawing Sheets

Specification includes a Sequence Listing.

Recombinant NME7 novel variant containing NDPK domains A and B, "NME7-AB", expresses well with high yield in E. *coli* and as the soluble protein A) FPLC purification of NME7-AB B) SDS-PAGE of NME7-AB C) NME7-AB is purified

Related U.S. Application Data

61/683,155, filed on Aug. 14, 2012, provisional application No. 61/679,021, filed on Aug. 2, 2012, provisional application No. 61/677,442, filed on Jul. 30, 2012, provisional application No. 61/675,264, filed on Jul. 24, 2012, provisional application No. 61/675,292, filed on Jul. 24, 2012, provisional application No. 61/673,617, filed on Jul. 19, 2012, provisional application No. 61/671,558, filed on Jul. 13, 2012, provisional application No. 61/671,588, filed on Jul. 13, 2012, provisional application No. 61/622,422, filed on Apr. 10, 2012, provisional application No. 61/618,578, filed on Mar. 30, 2012, provisional application No. 61/548,199, filed on Oct. 17, 2011.

(56) References Cited

U.S. PATENT DOCUMENTS

| | | | |
|---|---|---|---|
| 2007/0243171 A1* | 10/2007 | Bunce | C12N 5/0647 424/93.7 |
| 2009/0148535 A1* | 6/2009 | Bamdad | A61K 9/5115 424/499 |
| 2010/0093092 A1* | 4/2010 | Bamdad | C12N 5/0606 435/377 |
| 2010/0278788 A1 | 11/2010 | Badoer et al. | |
| 2010/0316688 A1 | 12/2010 | Bamdad | |
| 2011/0014164 A1 | 1/2011 | Huangfu et al. | |
| 2012/0156246 A1* | 6/2012 | Bamdad | C12N 5/0603 424/277.1 |

FOREIGN PATENT DOCUMENTS

| | | |
|---|---|---|
| WO | WO-2009123349 A1 | 10/2009 |
| WO | WO 2010/042891 A1 | 4/2010 |
| WO | WO-2013059373 A2 | 4/2013 |

OTHER PUBLICATIONS

NPL document "BD ITS+", a screenprint of Becton Dickinson's webpage detailing the composition of ITS+ accessed at https://www.americanpharmaceuticalreview.com/25243-Cell-Culture-Growth-Factors/5821288-ITS-Universal-Cell-Culture-Supplement-Premix/ on May 5, 2018, available online since Apr. 1, 2002 (Year: 2002).*
Thomas Desvignes, Pierre Pontarotti, Christian Fauvel and Julien Bobe, Nme protein family evolutionary history, a vertebrate perspective, 2009, BMC Evolutionary Biology, 9:256, pp. 1-25 (Year: 2009).*
Kalamegam Gauthaman, Chui-Yee Fong and Ariff Bongso, Effect of ROCK Inhibitor Y-27632 on Normal and Variant Human Embryonic Stem Cells (hESCs) In Vitro: Its Benefits in hESC Expansion, 2010, Stem Cell Rev and Rep, vol. 6, pp. 86-95 (Year: 2010).*
Liguo Chen, Jaspal S. Khillan, A Novel Signaling by Vitamin A/Retinol Promotes Self Renewal of Mouse Embryonic Stem Cells by Activating PI3K/Akt Signaling Pathway via Insulin-Like Growth Factor-1 Receptor, 2010, STEM CELLS, vol. 28, pp. 57-63 (Year: 2010).*
Hikita, Sherry et al., "MUC1* Mediates the Growth of Human Pluripotent Stem Cells," PLOS ONE, Public Library of Sceince, 3(10), p. E3312, DOI: 10.1371/JOURNAL.PONE.0003312, Oct. 3, 2008.
Amendola et al., "DR-nm23 gene expression in neuroblastoma cells: relationship to integrin expression, adhesion characteristics, and differentiation," Journal of the National Cancer Institute vol. 89, No. 17, pp. 1300-1310, Sep. 1997.
Dearolf et al., Developmental Consequences of awdb3, a Cell-Autonomous Lethal Mutation of Drosophila Induced by Hybrid Dysgenesis Developmental Biology vol. 129, pp. 159-168, Accepted May 1988.

Gervasi et al., Nm23 influences proliferation and differentiation of PC12 cells in response to nerve growth factor, Cell Growth and Differentiation vol. 7, No. 12, pp. 1689-1695, Dec. 1996.
Lasko, et al., "Embryonic Expression of NM23 during Mouse Organogenesis," Cell Growth and Differentiation vol. 3, p. 873-879, Dec. 1992.
Lombardi et al., "The association of the Nm23-M1 protein and beta-tubulin correlates with cell differentiation," Experiemental Cell Research vol. 217, No. 2, pp. 267-271, Apr. 1995.
Munoz-Dorado et al., "Nucleoside diphosphate kinase from Myxococcus xanthus. II. Biochemical characterization," Journal of Biological Chemistry vol. 265, pp. 2707-2712, Feb. 1990.
Okabe-Kado et al., "A New Function of Nm23/NDP Kinase as a Differentiation Inhibitory Factor, Which Does Not Require it's Kinase Activity," FEBS Letters vol. 363, pp. 311-315, 1995.
Okabe-Kado et al., "Identity of a Differentiation Inhibiting Factor for Mouse Myeloid Leukemia Cells with NM23/Nucleoside Diphosphate Kinase," Biochemical and Biophysical Research Communications vol. 182, No. 3, pp. 987-994, 1992.
Okabe-Kado et al., "Inhibitory Action of nm23 Proteins on Induction of Erythroid Differentiation of Human Leukemia Cells," Biochimica et Biophysica Acta. vol. 1267 pp. 101-106, 1995.
Rosengard et al., "Reduced Nm23/Awd protein in tumour metastasis and aberrant Drosophila development," Nature vol. 342, No. 6246, pp. 177-180, Nov. 1989.
Timmons et al., "The expression of the Drosophila awd gene during normal development and in neoplastic brain tumors caused by lgl mutations," Developmental Biology vol. 158, No. 2, pp. 364-379, Aug. 1993.
Venturelli et al., "Overexpression of DR-nm23, a Protein Encoded by a Member of the nm23 Gene Family, Inhibits Granulocyte Differentiation and Induces Apoptosis in 32Dc13 Myeloid Cells," Proceeding of the National Academy of Sciences USA vol. 92, pp. 7435-7439, Aug. 1995.
Willems et al., "Decrease in Nucleoside Diphosphate Kinase [NDPK/nm23] Expression During Hematopoietic Maturation*," The Journal of Biological Chemistry vol. 273, No. 22, pp. 13663-13668, 1998.
Willems et al., Extracellular Nucleoside Diphosphate Kinase NM23/NDPK Modulates Normal Hematopoietic Differentiation, Experimental Hematology vol. 30, pp. 640-648, 2002.
Yamashiro et al., "Alteration of nm23 gene expression during the induced differentiation of human leukemia cell lines," Oncogene vol. 9, No. 9, pp. 2461-2468, Sep. 1994.
Guokai Chen et al., "Chemically Defined Conditions For Human iPSC Derivation and Culture", ARTICLES, 424, vol. 8 No. 5, May 2011, Nature Methods, 9 pages.
Translation of Japanese Office Action cited in JP2016-231442, dated Oct. 29, 2019, 2 pages.
Lilly, Andrew J. et al., "Nm23-H1 Indirectly Promotes the Survival of Acute Myeloid Leukemia Blast Cells by Binding to More Mature Components of the Leukemic Clone", Cancer Research, Tumor and Stem Cell Biology, 71(3) Feb. 1, 2011, pp. 1177-1186; Published Online First Dec. 17, 2010.
Aoi et al. Generation of pluripotent stem cells from adult mouse liver and stomach cells. Science 321:699-702 (2008).
Boissan et al. The mammalian Nm23/NDPK family: from metastasis control to cilia movement. Mol Cell Biochem. 329(1-2):51-62 (2009).
Boyer et al. Core transcriptional regulatory circuitry in human embryonic stem cells. Cell 122:947-56 (2005).
Breitenlechner et al. Protein kinase A in complex with Rho-kinase inhibitors Y-27632, Fasudil, and H-1152P: structural basis of selectivity. Structure 11(12):1595-607 (2003).
Database UniProt[online], Accession No. P15531,Nov. 30, 2010 uploaded, [retrieved on Aug. 19, 2021],https://www.uniprot.org/uniprot/P15531.txt?version=131 ,Definition:RecName: Full= Nucleoside diphosphate kinase A.
Dexheimer et al. NM23-H2 may play an indirect role in transcriptional activation of c-myc gene expression but does not cleave the nuclease hypersensitive element III(1). Mol Cancer They 5(5):1363-1377 (2009).

(56) References Cited

OTHER PUBLICATIONS

Fessler et al. MUC1* is a determinant of trastuzumab (Herceptin) resistance in breast cancer cells. Breast Cancer Res Treat 118:113-134 (2009).
Fletcher et al.: Variations in humanized and defined culture conditions supporting derivation of new human embryonic stem cell lines. Cloning Stem Cells 8(4):319-334 (2006).
Foster et al. Induction of KLF4 in basal keratinocytes blocks the proliferation-differentiation switch and initiates squamous epithelial dysplasia. Oncogene 211(9):1491-1590 (2005).
Greber et al. FGF signalling inhibits neural induction in human embryonic stem cells. The EMBO Journal 30:4874-4884 (2011).
Hanna et al. Human embryonic stem cells with biological and epigenetic characteristics similar to those of mouse ESCs. PNAS USA 107(20):9222-9227 (2010).
Huang et al. MUC1 oncoprotein blocks glycogen synthase kinase 3beta-mediated phosphorylation and degradation of beta-catenin. Cancer Res 65(22):10413-22 (2005).
Huangfu et al. Induction of pluripotent stem cells by defined factors is greatly improved by small-molecule compounds. Nat Biotechnol 26(7):795-797 (2006).
Huangfu et al. Induction of pluripotent stem cells from primary human fibroblasts with only Oct4 and Sox2. Nat Biotechnol. 26(11):1269-75 (2008).
Jaenisch et al. Stem cells, the molecular circuitry of pluripotency and nuclear reprogramming. Cell 132:567-582 (2008).
Kaji et al. Virus-free induction of pluripotency and subsequent excision of reprogramming factors. Nature 458:771-775 (2009).
Kawamura et al. Linking the p53 tumour suppressor pathway to somatic cell reprogramming. Nature 436:1140-4 (2009).
Kim et al. Point Mutations Affecting the Oligomeric Structure of Nrri23-H1 Abrogates its Inhibitory Activity on Colonization and Invasion of Prostate Cancer Cells. Biochemical and Biophysical Research Communications 307:281-289 (2003).
Komander et al. Mechanism of multi-site phosphorylation from a ROCK-LRhoE complex structure. EMBO J 27:3175-3185 (2008).
Komarov et al. A chemical inhibitor of p53 that protects mice from the side effects of cancer therapy. Science 235:1733-7 (1999).
Lin et al. A chemical platform for improved induction of human iPSCs. Nature Methods 6(11):805-808 (2009).
Lin et al. p53 induces differentiation of mouse embryonic stem cells by suppressing Nanog expression. Nat Cell Biol 7(2):165-171 (2005).
Lombardi et al. nm23: Unraveling its Biological Function in Cell Differentiation. J Cell Physiol 182:144-149 (2000).
Lowry et al. Generation of human induced pluripotent stem cells from dermal fibroblasts. PNAS USA 105(8):2883-8 (2008).
Lyssiotis et al. Reprogramming of murine fibroblasts to induced pluripotent stem cells with chemical complementation of KIf4. PNAS USA 106:8912-8917 (2009).
Maherali et al. Directly reprogrammed fibroblasts show global epigenetic remodeling and widespread tissue contribution. Cell Stem Cell 1:55-70 (2007).
Maimets et al. Activation of p53 by nutlin leads to rapid differentiation of human embryonic stem cells. Oncogene 27:5277-5237 (2008).
Mehus et al.: NDK7_HUMAN UniProt Submission Accession No. Q9Y5B8 https://www.uniprot.org/uniprot/Q9Y5B8.txt?version=97 [1-4](May 31, 2011).
Mehus et al. NME6: a new member of the nm23/nucleoside diphosphate kinase gene family located on human chromosome 3p21.3. Hum Genet. 104(6):454-459 (1999).
Miyamoto et al. Role of nm23 in the regulation of cell shape and migration via Rho family GTPase signals. Mol Cell Biochem. 329:175-9 (2009).
Murakami et al. Nm23-H1 modulates the activity of the guanine exchange factor Dbl-1. Int J Cancer. 123:500-10 (2008).
Nakagawa et al., Generation of induced pluripotent stem cells without Myc from mouse and human fibroblasts. Nature Biotechnology 26:101-106 (2008).
Nichols et al. Naive and primed pluripotent states. Cell Stem Cell 4(6):487 (2009).
Ohata et al. Induction of the Stem-like Cell Regulator CD44 by Rho Kinase Inhibition Contributes to the Maintenance of Colon Cancer-Initiating Cells. Cancer Res. 72(19):5101-10 (2012).
Ohgushi et al. Molecular pathway and cell state responsible for dissociation-induced apoptosis in human pluripotent stem cells. Cell Stem Cell.7(2):225-39 (2010).
Okabe-Kado et al., Characterization of a Differentiation-Inhibitory Activity from Nondifferentiating Mouse Myeloid Leukemia cells. Cancer Research. 45:4848-4852 (1985).
Okita et al., Generation of germline-competent induced pluripotent stem cells. Nature 448:313-317 (2007).
Okita et al. Generation of mouse induced pluripotent stem cells without viral vectors. Science 322(5903):949-953 (2008).
OLSON. Applications for ROCK kinase inhibition. Curr Opin Cell Biol. 20(2):242-8 (2008).
Park et al. Reprogramming of human somatic cells to pluripotency with defined factors. Nature. 451(7175):141-6 (2008).
PCT/US2012/060684 International Search Report and Written Opinion dated Apr. 5, 2013.
Pease et al. Isolation of embryonic stem (ES) cells in media supplemented with recombinant leukemia inhibitory factor (LIF). Dev Biol 141:344-352 (1990).
Perina et al. Characterization of Nme6-like gene/protein from marine sponge Suberites domuncula. Naunyn-Schmiedeberg's Arch Pharmacol, 384:451-460 (2011).
Raina et al. Direct targeting of the mucin 1 oncoprotein blocks survival and tumorigenicity of human breast carcinoma cells. Cancer Res 69(12):5133-5141 (2009).
Rath et al., Rho-associated kinases in tumorigenesis: re-considering ROCK inhibition for cancer therapy. EMBO Rep. 13(10):900-908 (2012).
Riento et al. RhoE binds to ROCKI and inhibits downstream signaling. Mol Cell Biol 23:4219-4229 (2003).
Soldner et al. Parkinson's Disease Patient-Derived Induced Pluripotent Stem Cells Free of Viral Reprogramming Factors. Cell 136(5):964-977 (2009).
Sommer et al.: Induced pluripotent stem cell generation using a single lentiviral stem cell cassette. Stem Cells 27(3):543-549 (2009).
Stadtfeld et al. Induced pluripotent stem cells generated without viral integration. Science 322(5903):945-9 (2008).
Strom et al. Small-molecule inhibitor of p53 binding to mitochondria protects mice from gamma radiation. Nat Chem Biol. 2(9)474-9 (2006).
Sumer et al. The use of signalling pathway inhibitors and chromatin modifiers for enhancing pluripotency. Theriogenology 74(4):525-533 (2010).
Takahashi et al. Induction of pluripotent stem cells from adult human fibroblasts by defined factors. Cell 131(5):861-72 (2007).
Takahashi et al. Induction of pluripotent stem cells from mouse embryonic and adult fibroblast cultures by defined factors. Cell 126(4):663-676 (2006).
Thathiah et al., Tumor Necrosis Factor-alpha Converting Enzyme/Adam 17 Mediates Muc1 Shedding. J Biol Chem 278(5):3386-3394 (2003).
Thomson et al. Embryonic stem cell lines derived from human blastocysts. Science 282(5391):1145-1147 (1998).
Vassilev et al. In vivo activation of the p53 pathway by small-molecule antagonists of MDM2. Science 303:844-848 (2004).
Ward et al. The GTP binding proteins Gem and Rad are negative regulators of the Rho—Rho kinase pathway. J Cell Biol 157:291-302 (2002).
Watanabe et al., "A ROCK inhibitor permits survival of dissociated human embryonic stem cells," Nature Biotechnology 25(6): 681-686 (2007).
Wei et al. Human mucin 1 oncoprotein represses transcription of the p53 tumor suppressor gene. Cancer Res 67(4):1853-1858 (2007).
Wernig et al. c-Myc is dispensable for direct reprogramming of mouse fibroblasts. Cell Stem Cell 2:10-12 (2008).
Wernig et al. In vitro reprogramming of fibroblasts into a pluripotent ES-cell-like state. Nature. 448:318-324 (2007).

(56) References Cited

OTHER PUBLICATIONS

Yamanaka. Strategies and new developments in the generation of patient-specific pluripotent stem cells. Cell Stem Cell 1:39-49 (2007).
Yu et al. Human Induced Pluripotent Stem Cells Free of Vector and Transgene Sequences. Science. 324(5928):797-801 (2009).
Yu et al. Induced pluripotent stem cell lines derived from human somatic cells. Science 318:1917-1920 (2007).
Zhou et al. Generation of induced pluripotent stem cells using recombinant proteins. Cell Stem Cell 4(5):381-384 (2009).
Zou et al. p53 deficiency increases transformation by v-Abl and rescues the ability of a C-terminally truncated v-Abl mutant to induce pre-B lymphoma in vivo. Mol Cell Biol 20(2):628-633 (2000).

\* cited by examiner

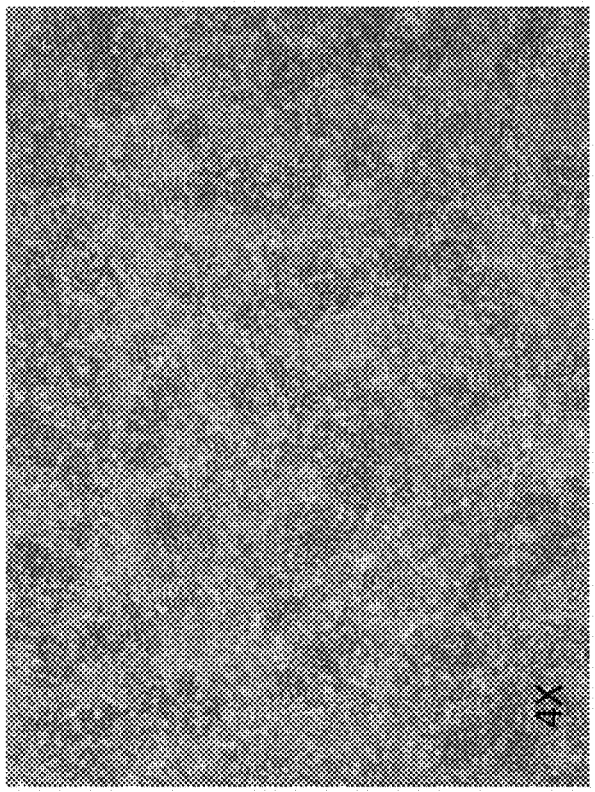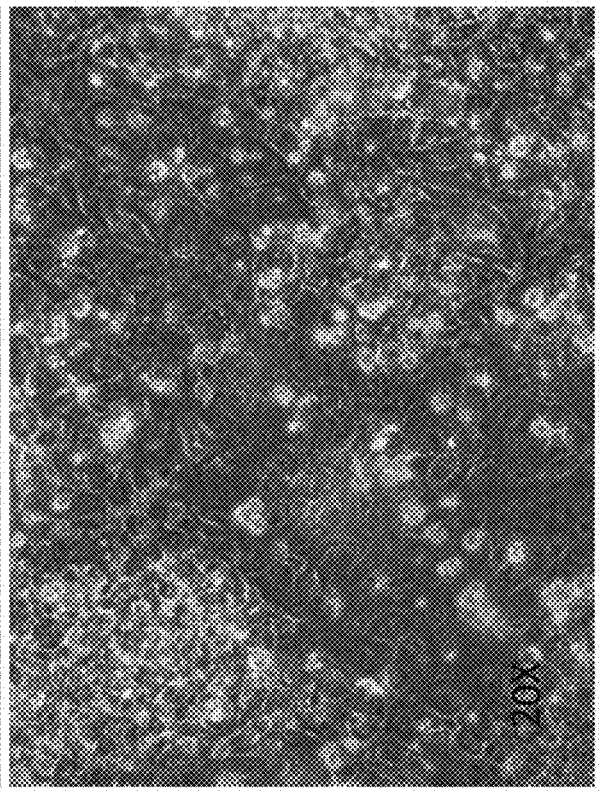
Upper left: MM +NM23 +ROCi 4x day 4
Upper right: MM +NM23 +ROCi 10x day 4
Lower left: MM +NM23 +ROCi 20x day 4
100% confluent, undifferentiated
Figure 1

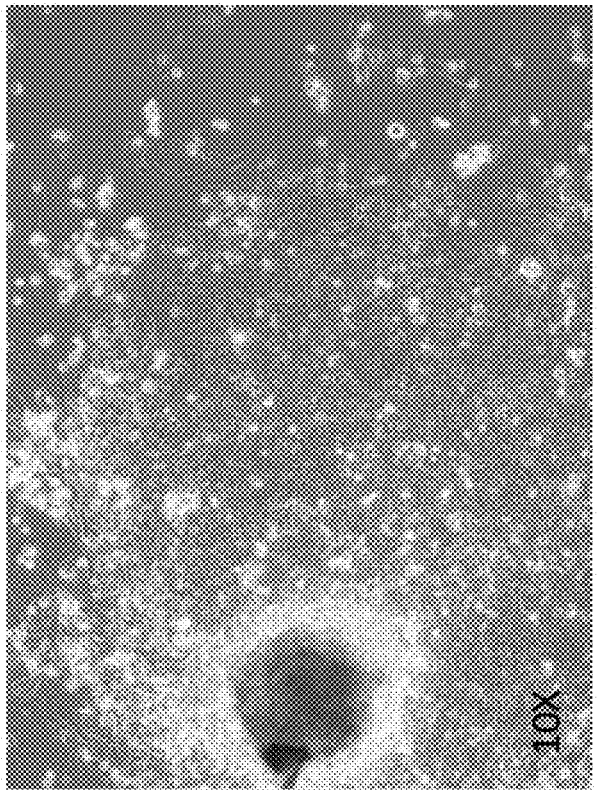
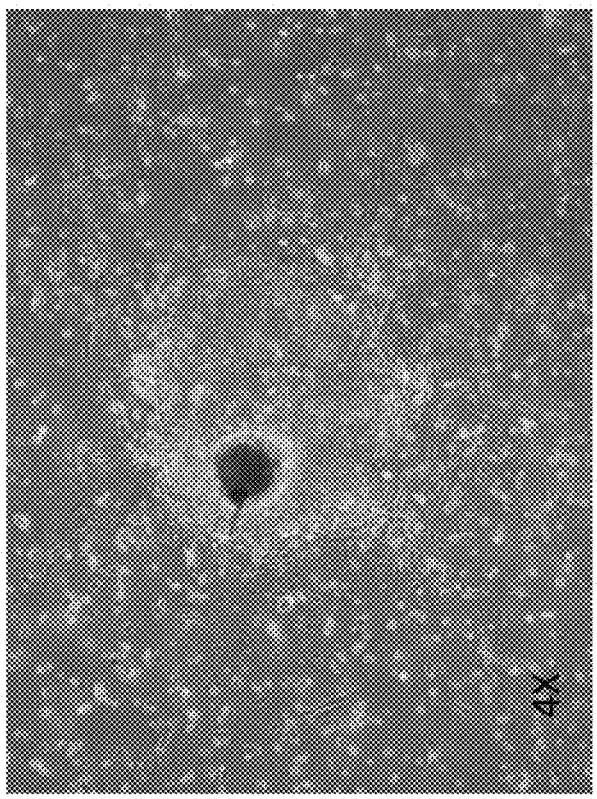
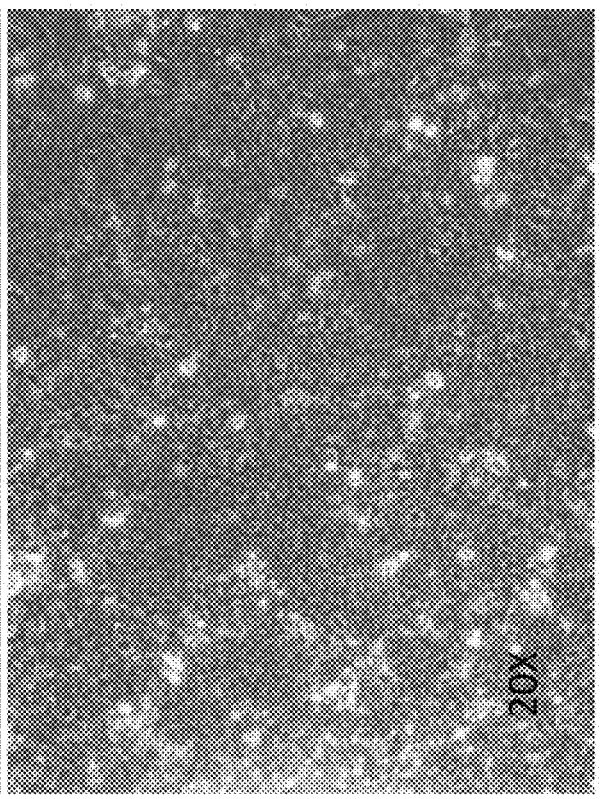
Upper left: MM +NM23 no ROCi 4x day 4
Upper right: MM +NM23 no ROCi 10x day 4
Lower left: MM +NM23 no ROCi 20x day 4
30% confluent, undifferentiated colony
Figure 2

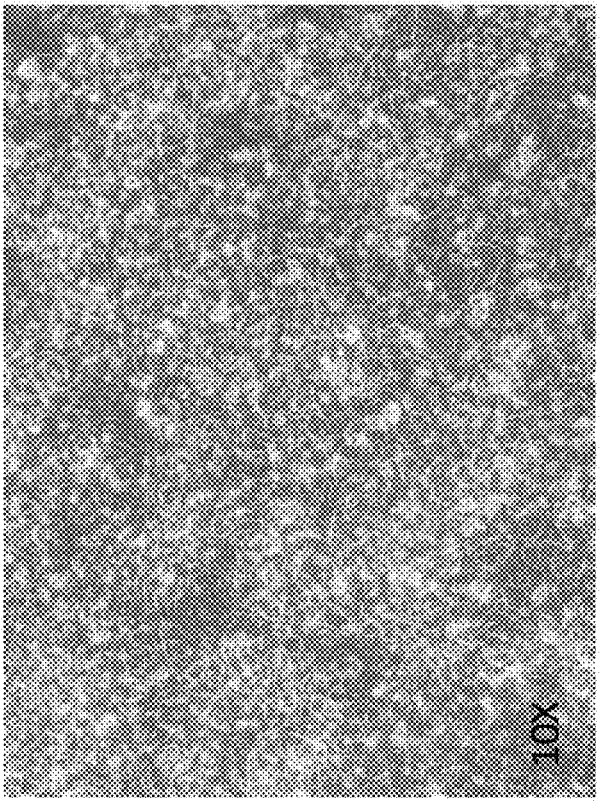
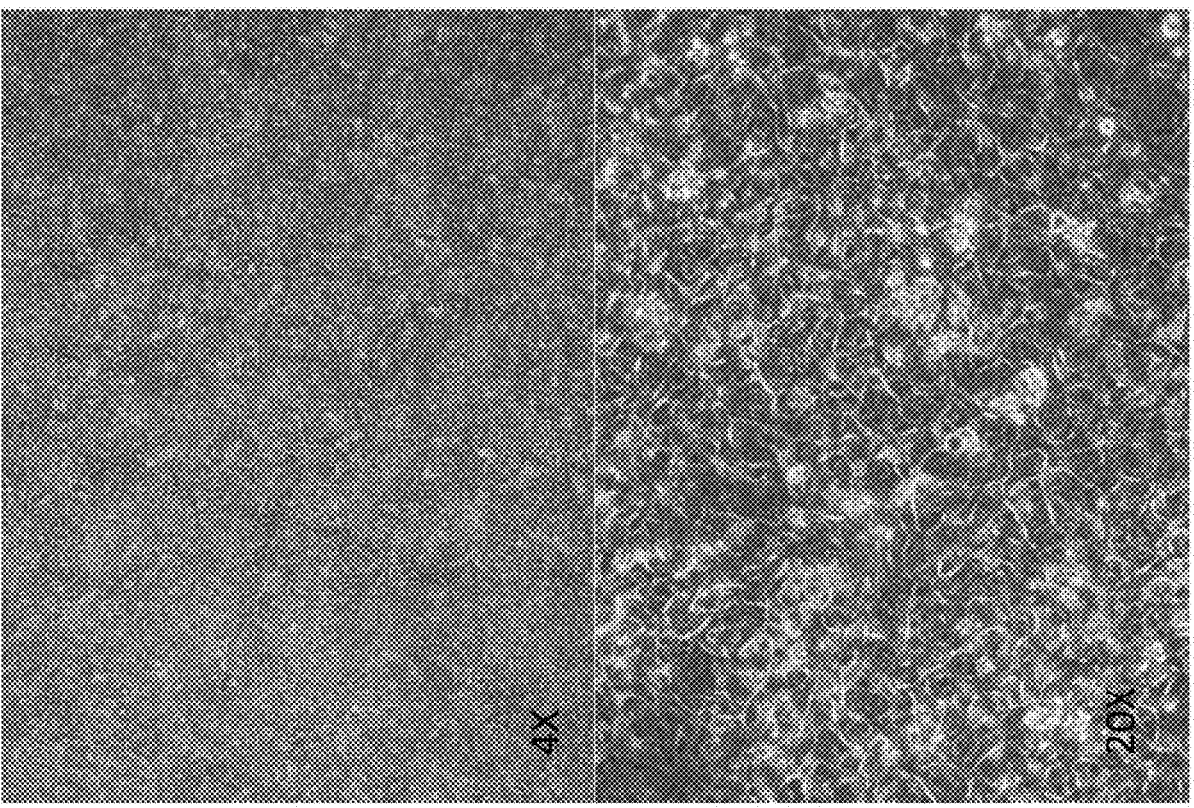
Upper left: 50% Hs27 cond med (CM) +FGF +ROCi 4x day 4
Upper right: 50% Hs27CM +FGF +ROCi 10x day 4
Lower left: 50% Hs27CM +FGF +ROCi 20x day 4
100% confluent, undifferentiated
Figure 3

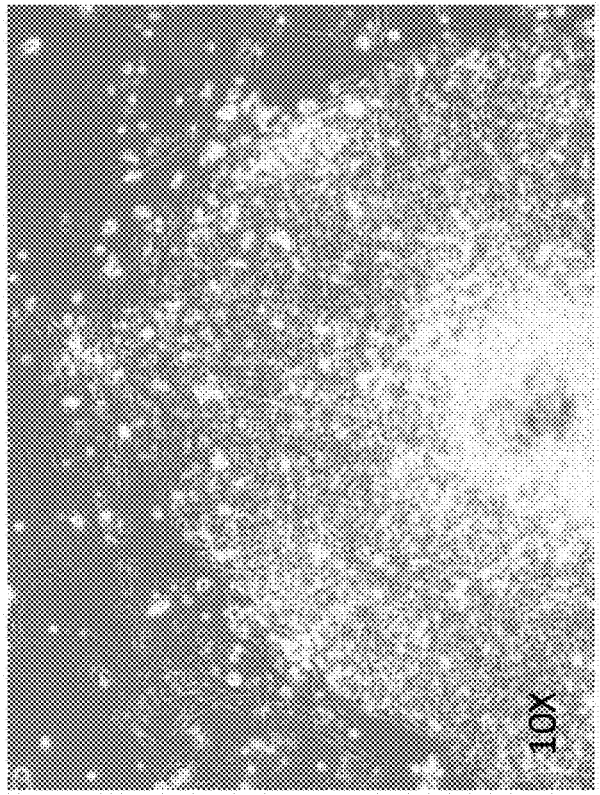
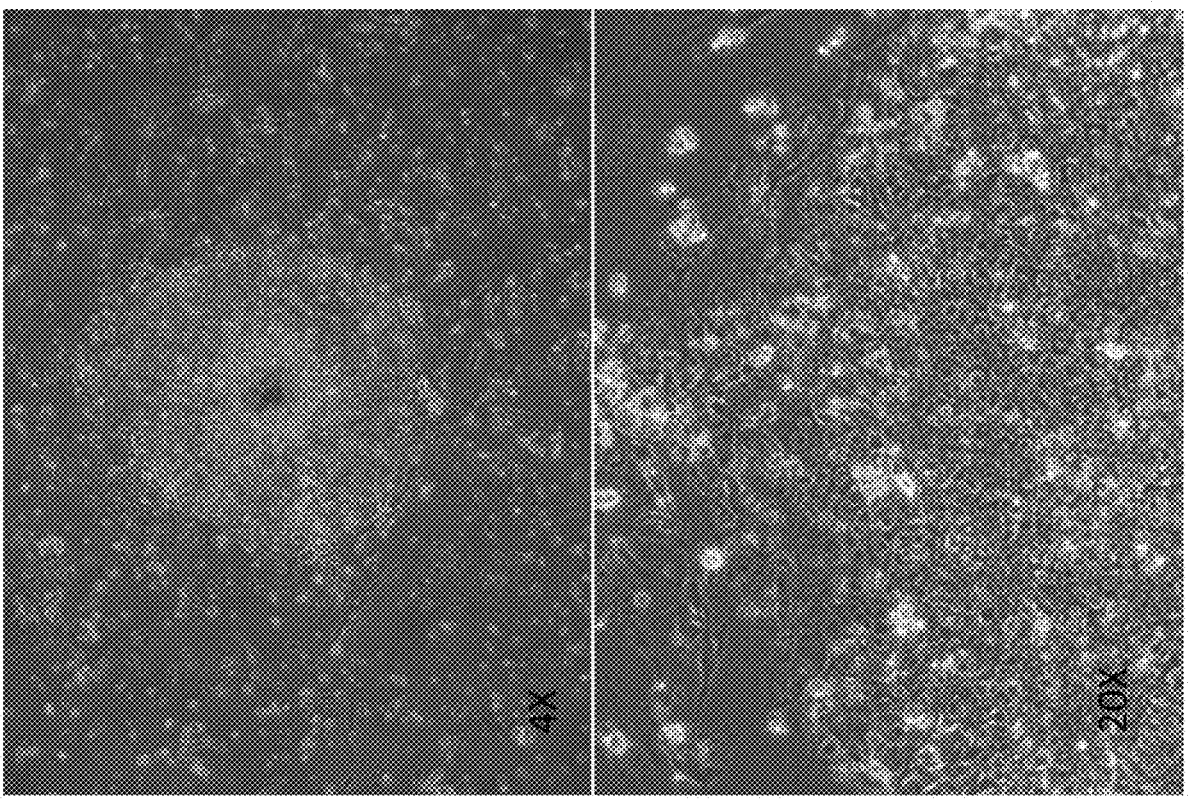
Upper left: 50% Hs27CM +FGF no ROCi 4x day 4
Upper right: 50% Hs27CM +FGF no ROCi 10x day 4
Lower left: 50% Hs27CM +FGF no ROCi 20x day 4
5% confluent
Figure 4

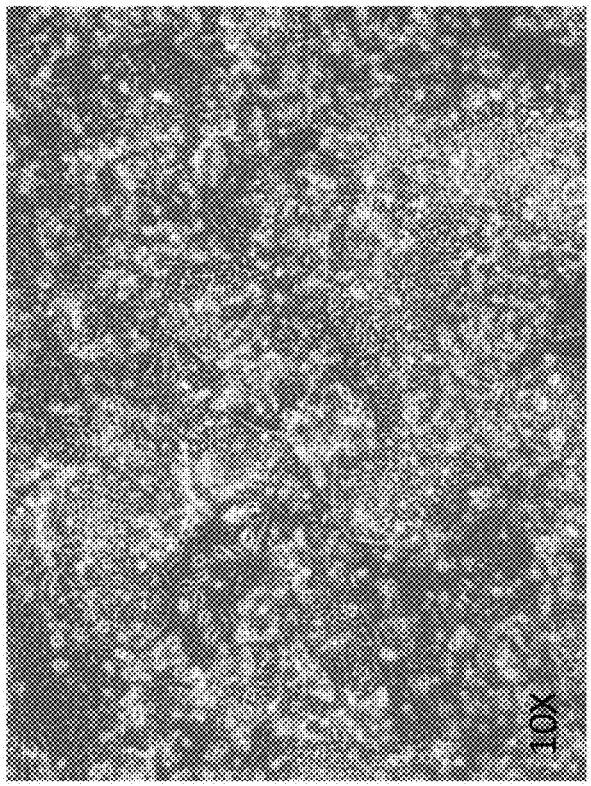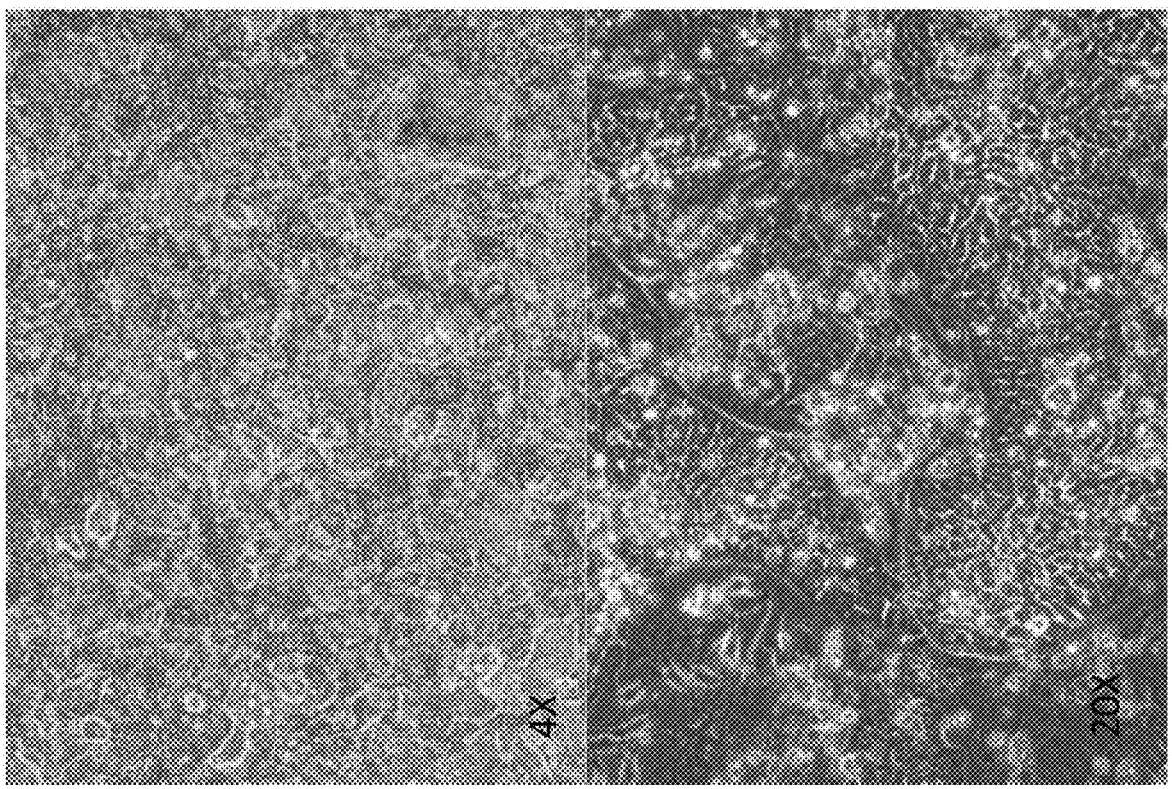
Upper left: MN6 +NM23 +ROCi 4x day 4
Upper right: MN6 +NM23 +ROCi 10x day 4
Lower left: MN6 +NM23 +ROCi 20x day 4
100% confluent, essentially all undifferentiated
Figure 5

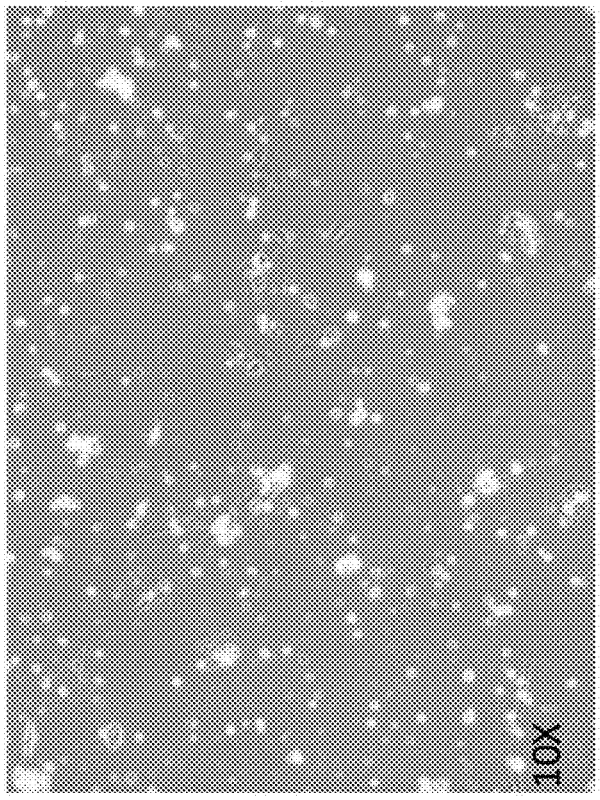
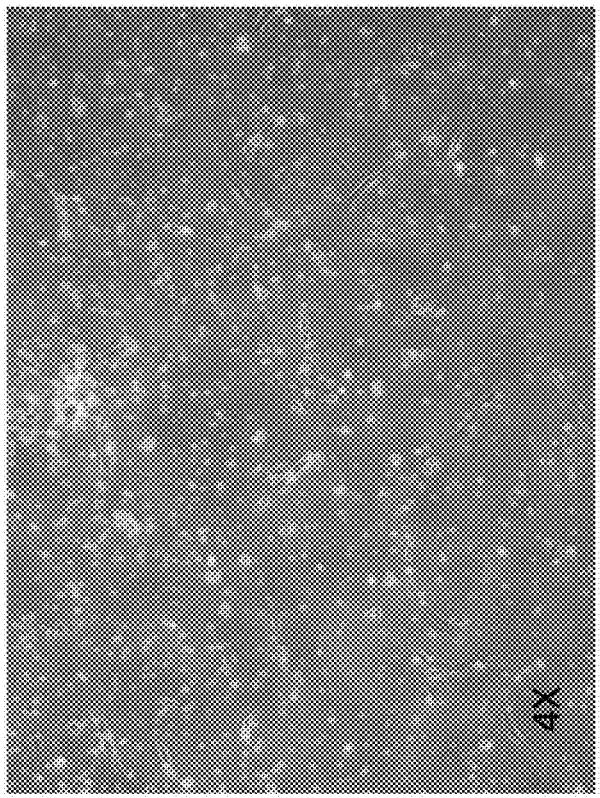
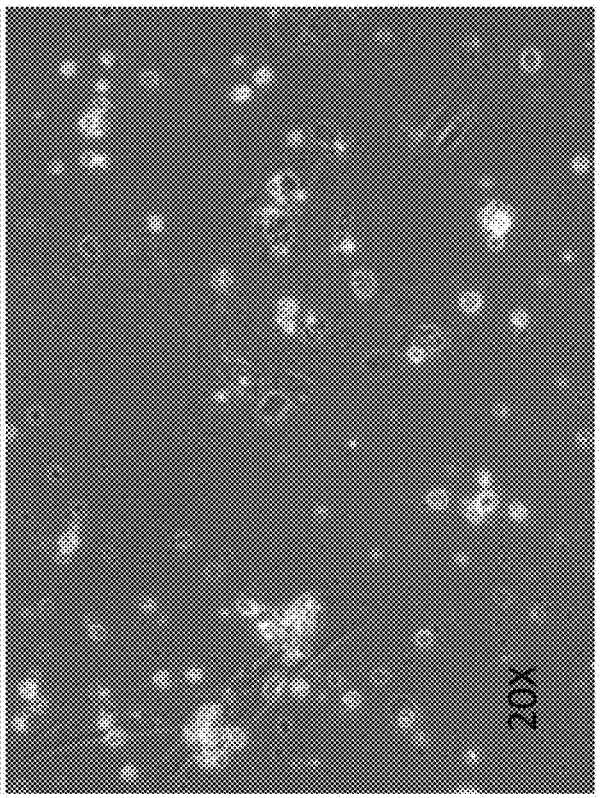
Upper left: MN6 +NM23 no ROCi 4x day 4
Upper right: MN6 +NM23 no ROCi 10x day 4
Lower left: MN6 +NM23 no ROCi 20x day 4
5% confluent
Figure 6

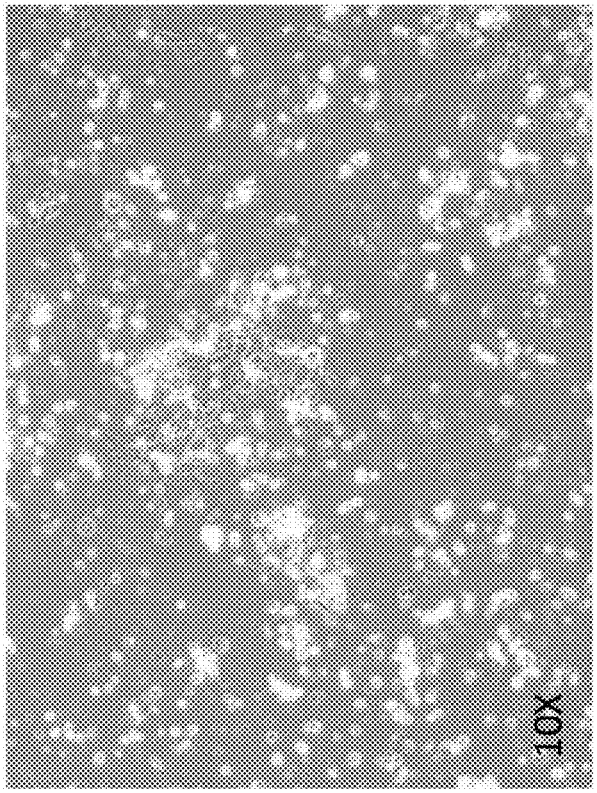
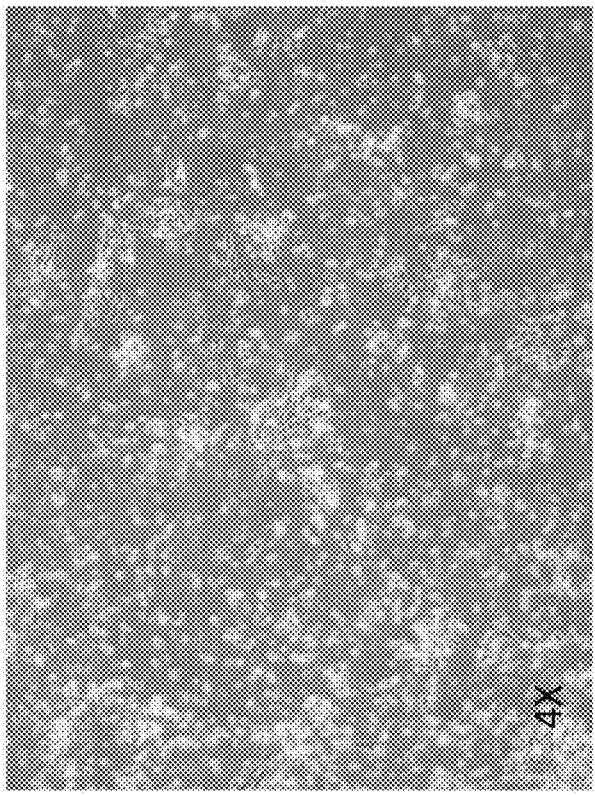
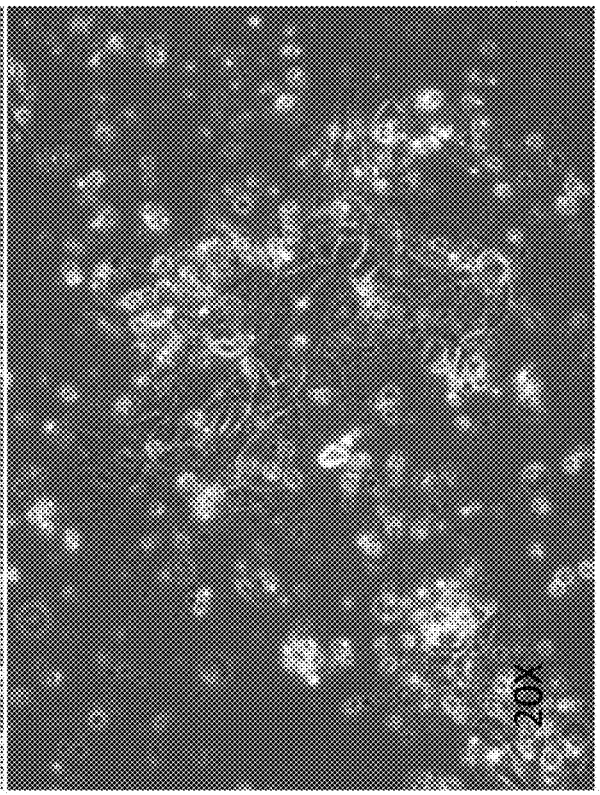
Upper left: MN2 +NM23 +ROCi 4x day 4
Upper right: MN2 +NM23 +ROCi 10x day 4
Lower left: MN2 +NM23 +ROCi 20x day 4
30% confluent
Figure 7

Upper left: H9P90 NM23P14 Hs27 with MN2 +NM23
no ROCi 4x day 4

5% confluent

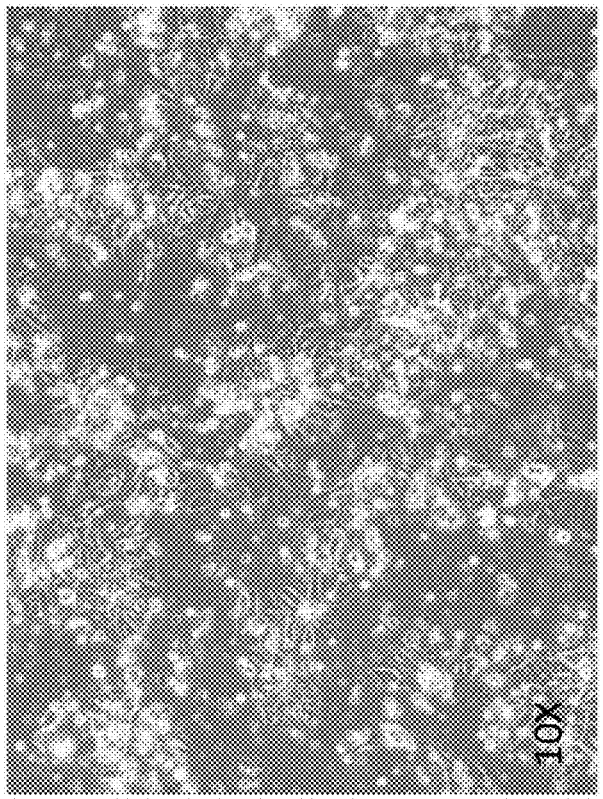
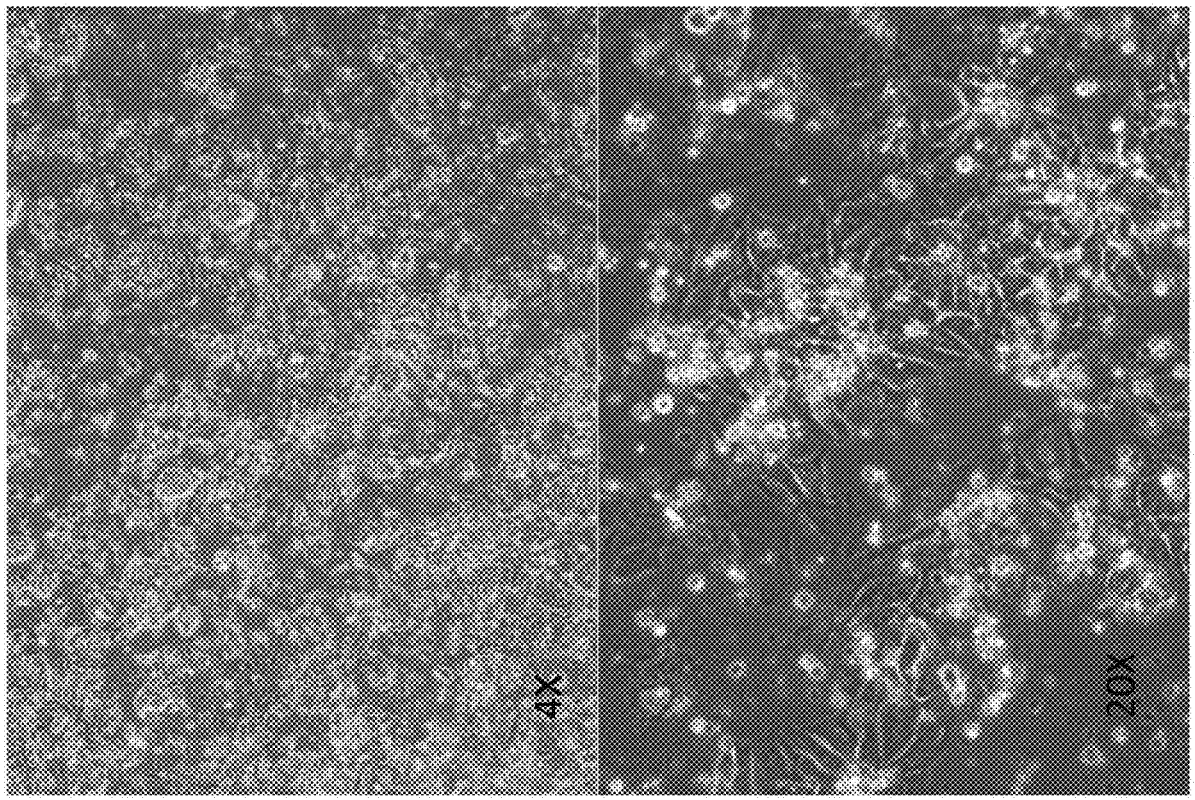
Upper left: MN6 +100ng/ml FGF + TGF-betaROCi 4x day 4
Upper right: MN6 +100ng/ml FGF + TGF-beta ROCi 4x day 4
Lower left: MN6 +100ng/ml FGF + TGF-beta ROCi4x day 4
75% confluent, mostly undifferentiated
Figure 9

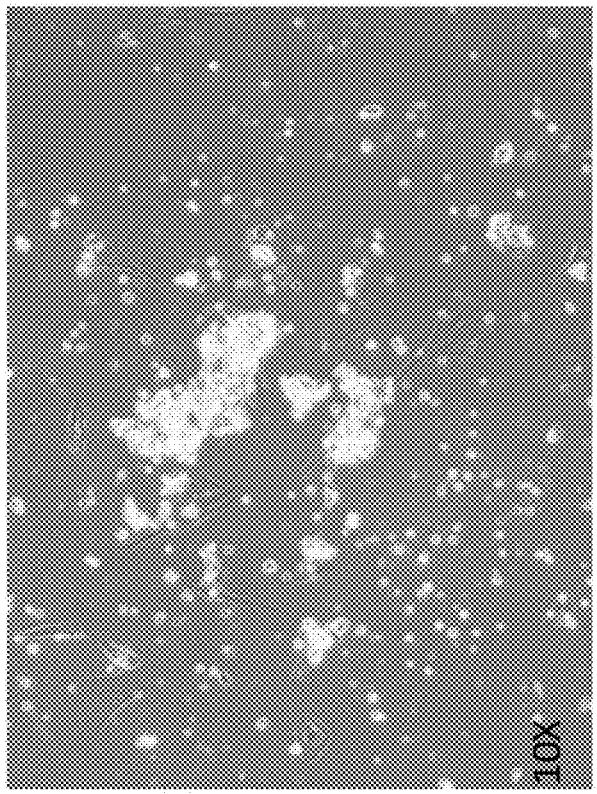
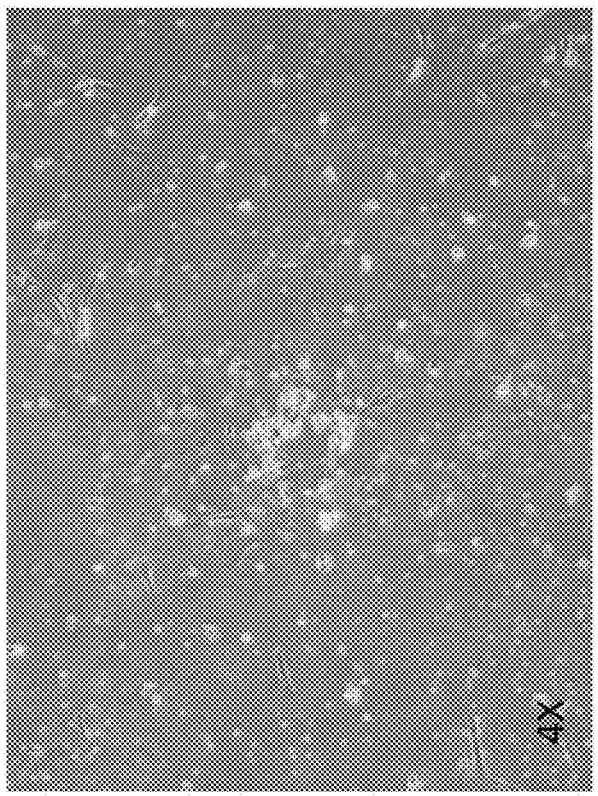
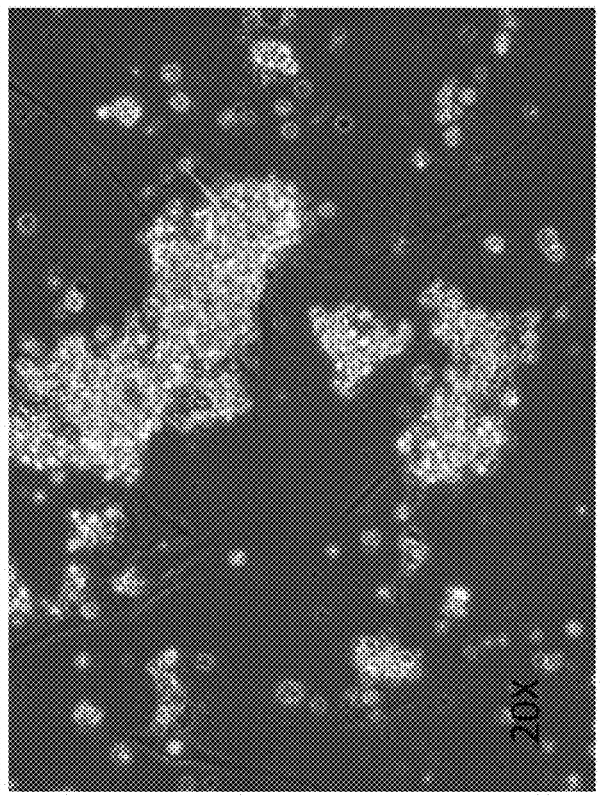
Upper left: MN6 +100ng/ml FGF + TGF-beta without ROCi 4X day 4
Upper right: MN6 +100ng/ml FGF + TGF-beta without ROCi 4X day 4
Lower left: MN6 +100ng/ml FGF + TGF-beta without ROCi 4X day 4
5% confluent, look like fibroblasts
Figure 10

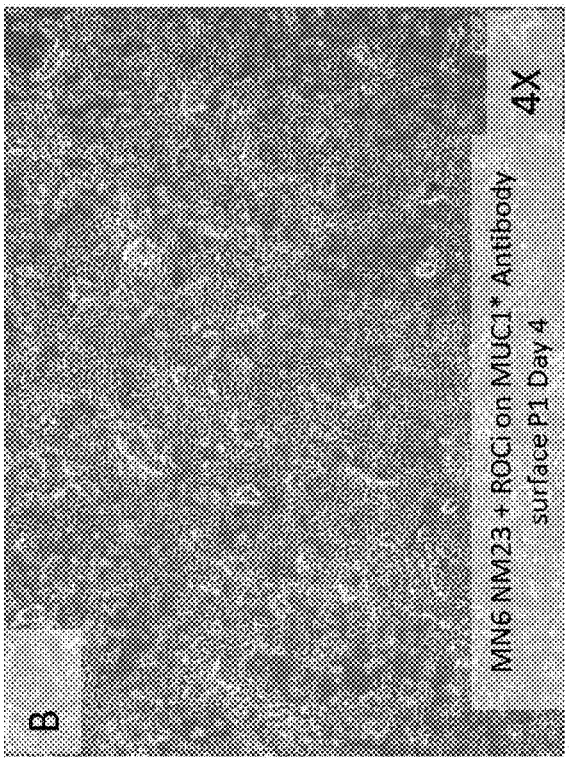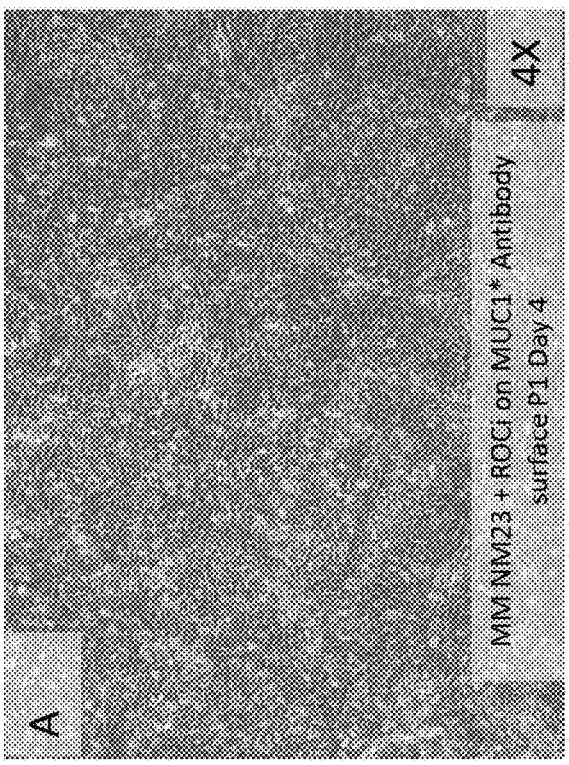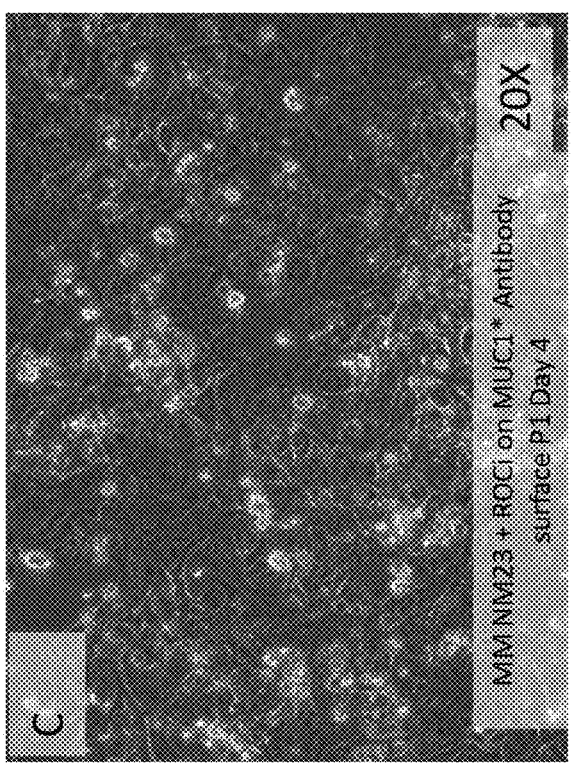
Fig. 11

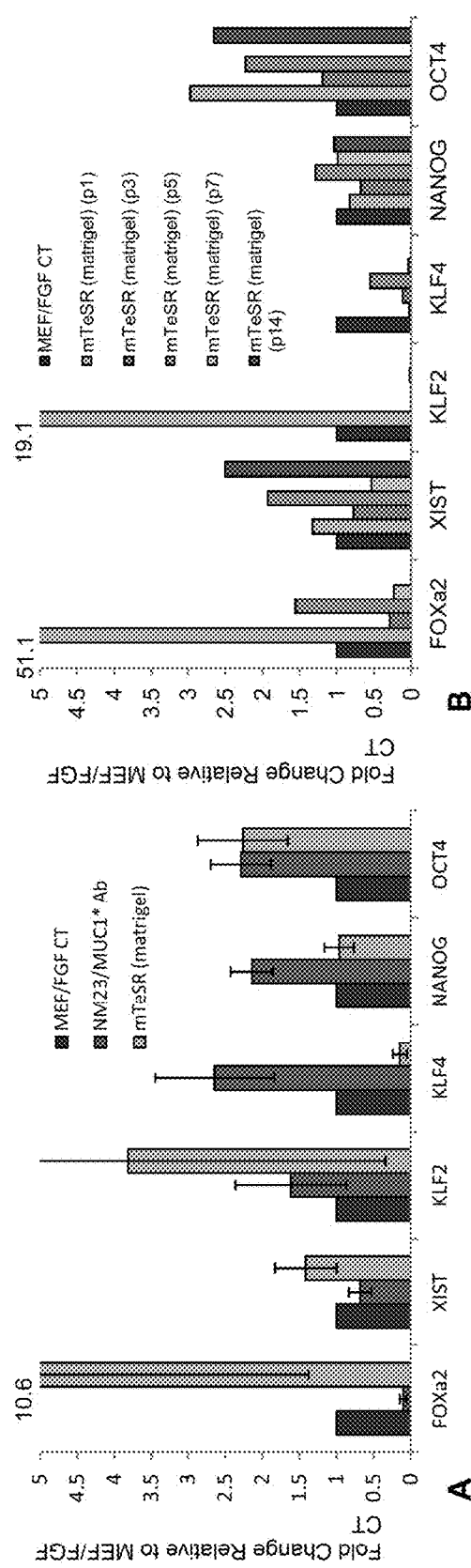
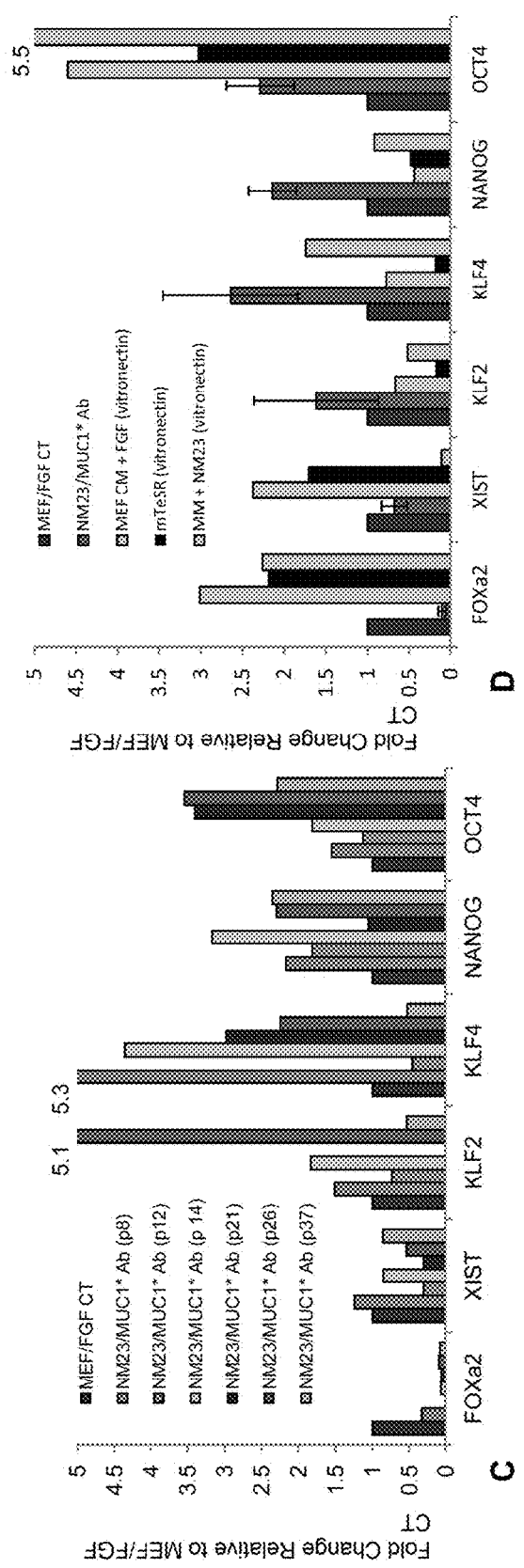
Fig. 13

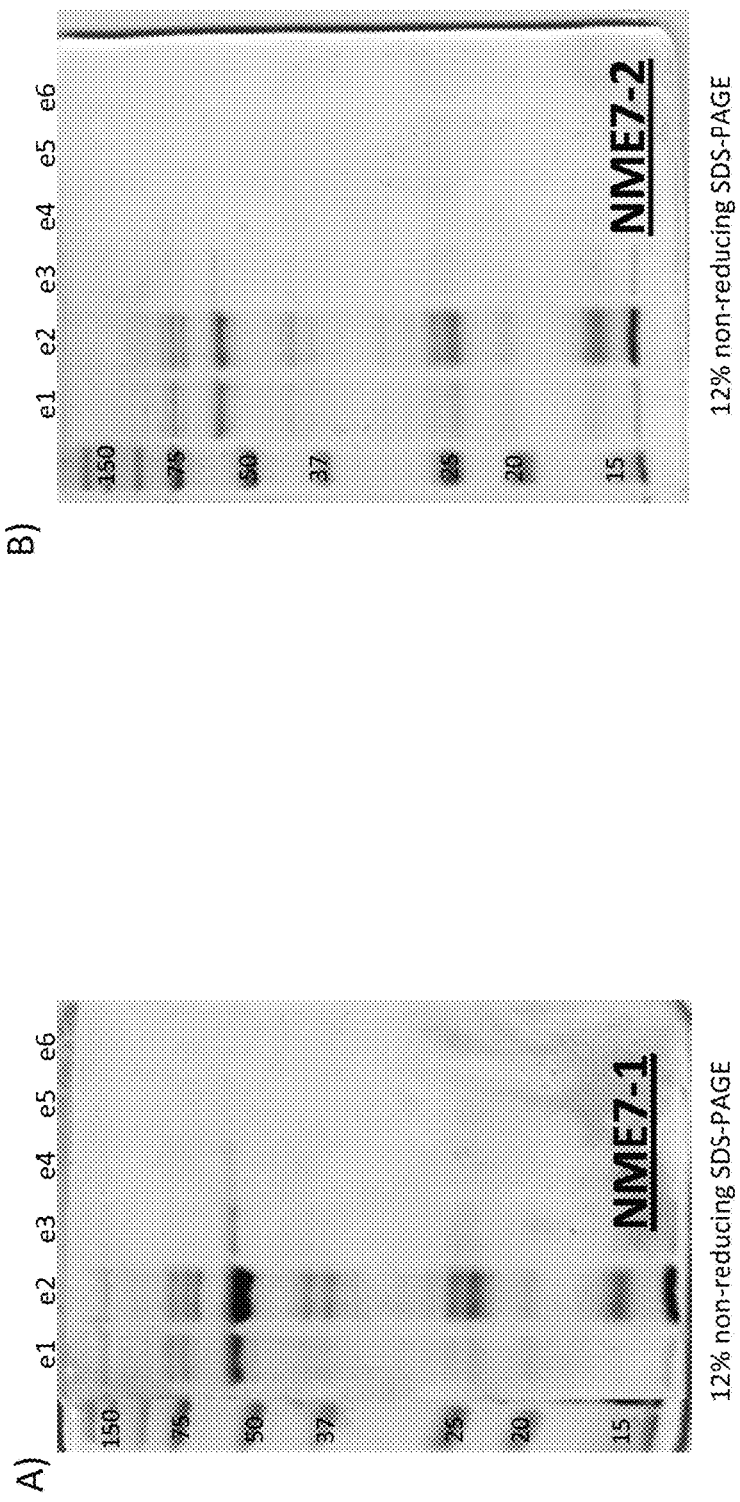
Figure 25.1

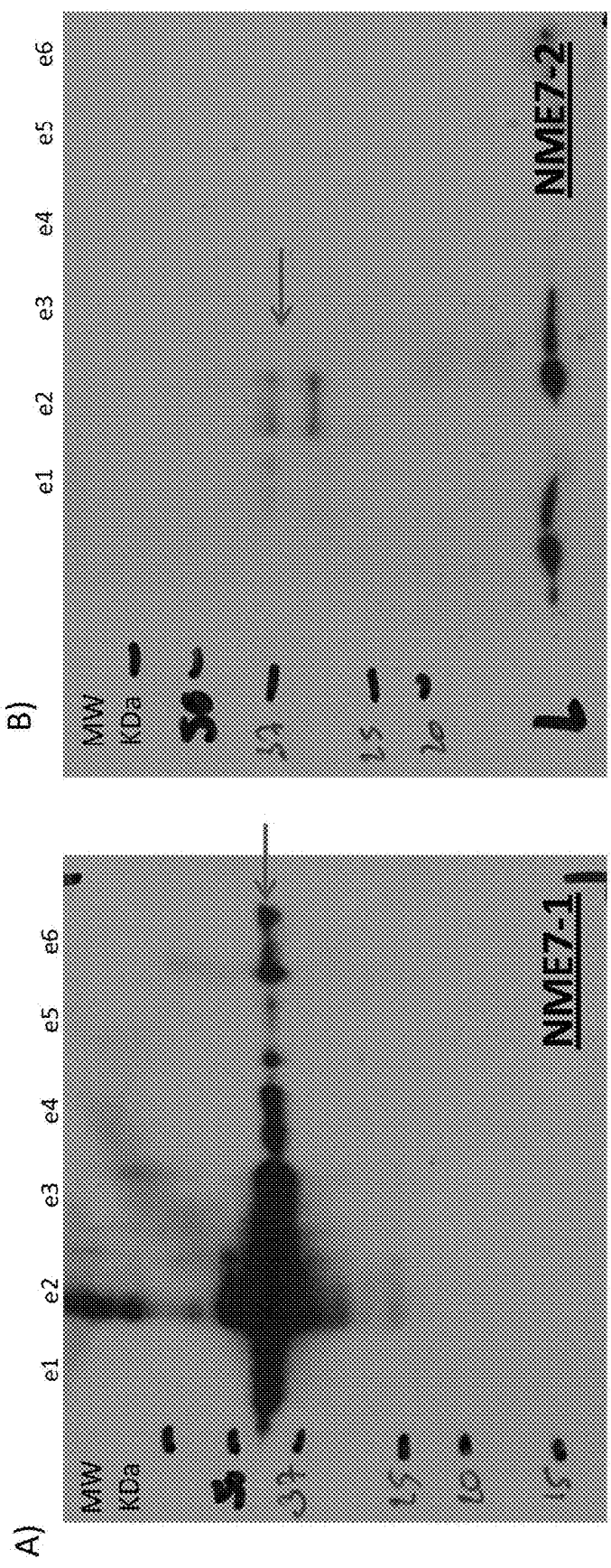
Figure 25.2

Recombinant NME7 novel variant containing NDPK domains A and B, "NME7-AB", expresses well with high yield in E. coli and as the soluble protein
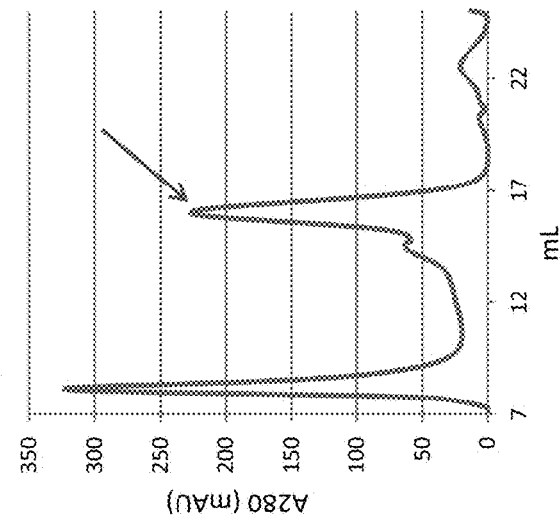
A) FPLC purification of NME7-AB
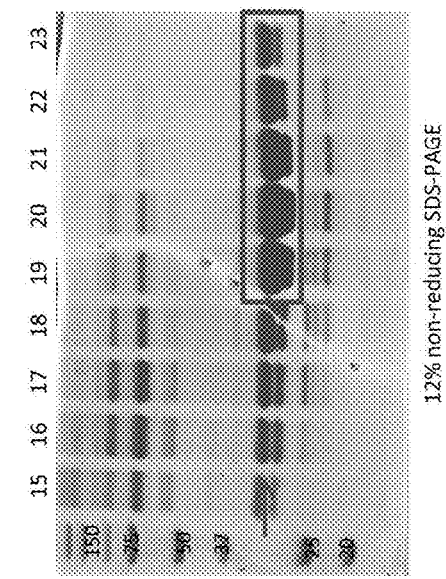
B) SDS-PAGE of NME7-AB
12% non-reducing SDS-PAGE
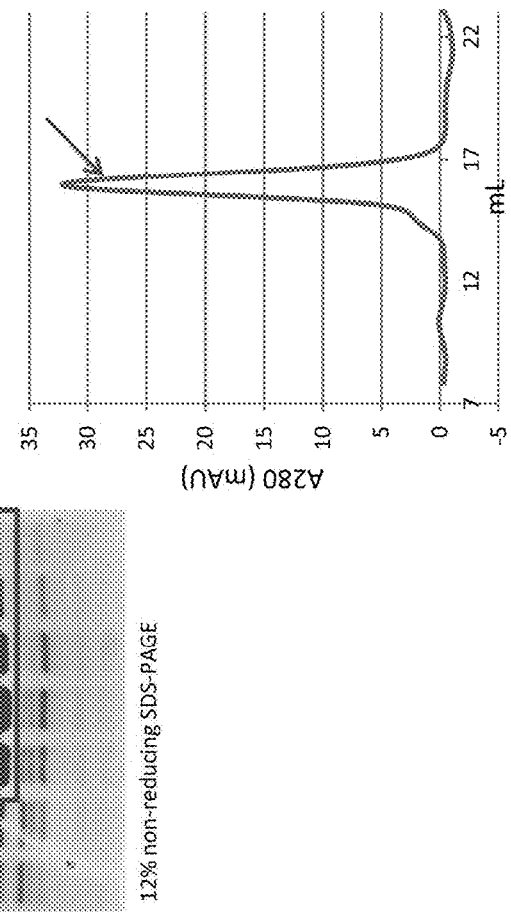
C) NME7-AB is purified
Figure 27

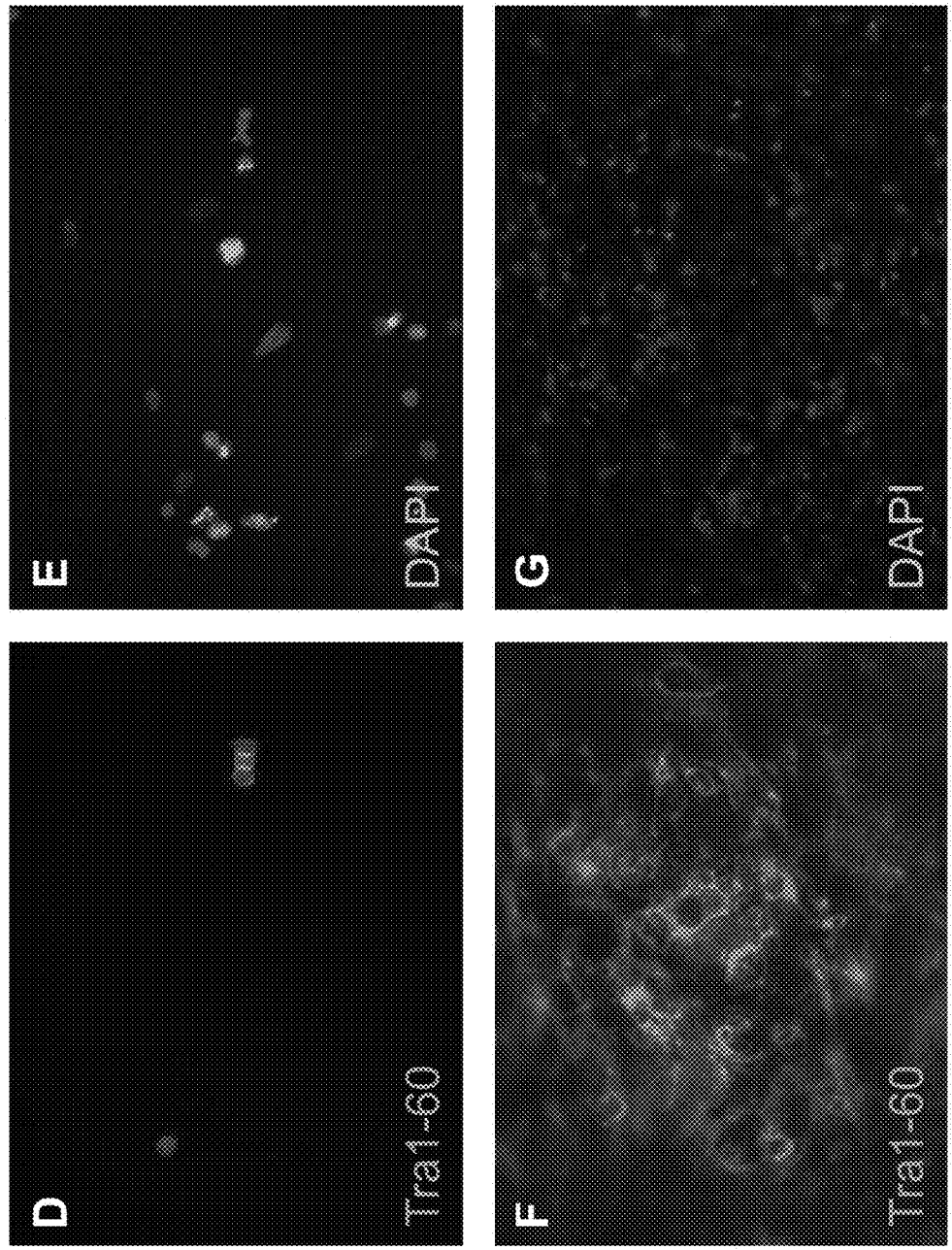

Fig 31

D,E: Standard Media (MM+bFGF) used with all 4 Pluripotency Genes Oct4, Sox2, Klf4 & c-Myc (OSKM) Stained with Tra 1-60 (green) that Indicates a Pluripotent Stem Cell; Blue is a Nuclear Stain, showing other cells that were not Induced.
F,G: NME-based media (MM + NME1 dimers) used with all only 3 Pluripotency Genes Oct4, Sox2, Klf4(OSK) Stained with Tra 1-60 (green) that Indicates a Pluripotent Stem Cell; Blue is a Nuclear Stain, showing other cells that all cells were induced to be pluripotent. Images taken Day 20 for each condition.

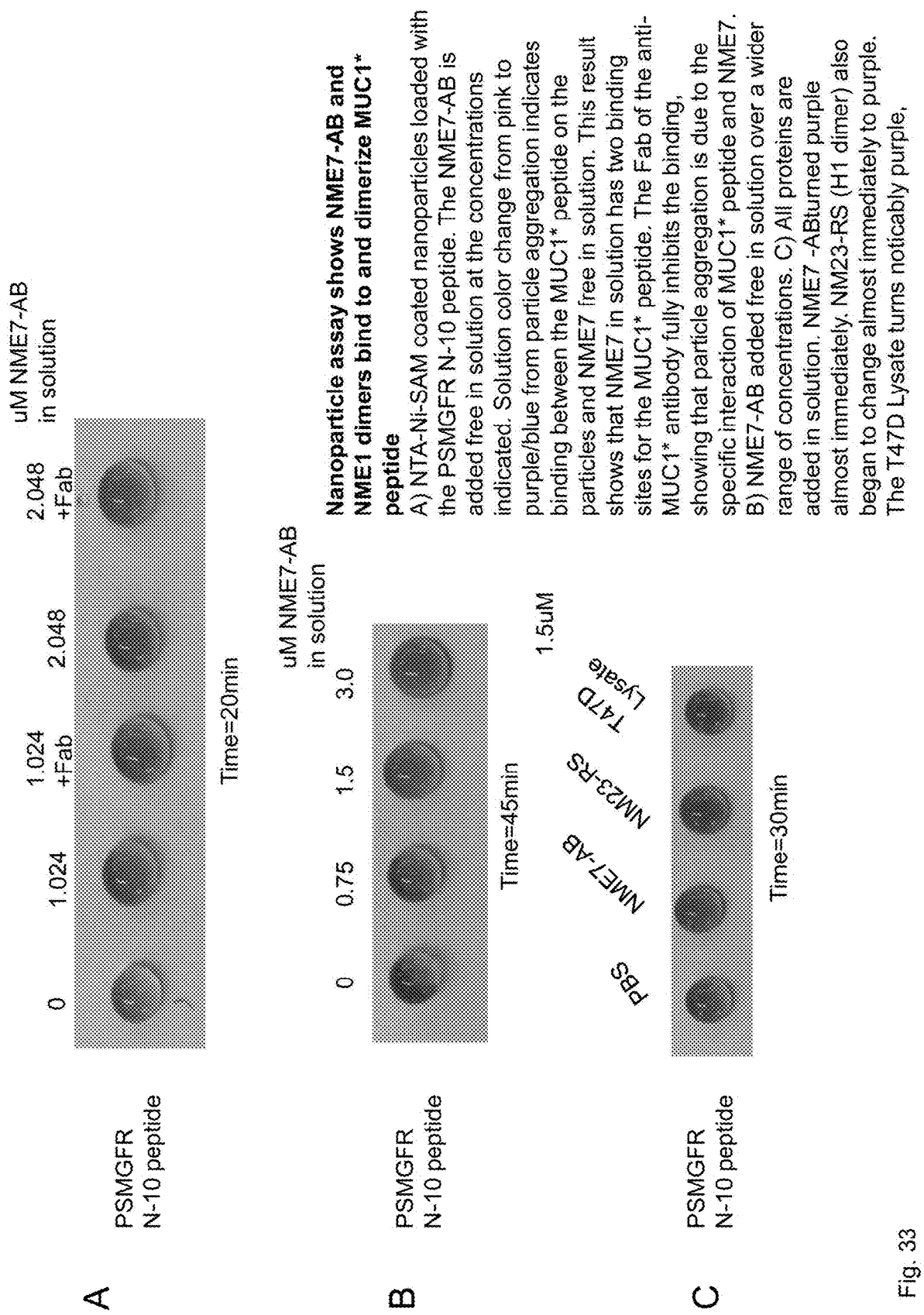

Fig. 33

**Nanoparticle assay shows NME7-AB and NME1 dimers bind to and dimerize MUC1* peptide**

A) NTA-Ni-SAM coated nanoparticles loaded with the PSMGFR N-10 peptide. The NME7-AB is added free in solution at the concentrations indicated. Solution color change from pink to purple/blue from particle aggregation indicates binding between the MUC1* peptide on the particles and NME7 free in solution. This result shows that NME7 in solution has two binding sites for the MUC1* peptide. The Fab of the anti-MUC1* antibody fully inhibits the binding, showing that particle aggregation is due to the specific interaction of MUC1* peptide and NME7. B) NME7-AB added free in solution over a wider range of concentrations. C) All proteins are added in solution. NME7-AB turned purple almost immediately. NM23-RS (H1 dimer) also began to change almost immediately to purple. The T47D Lysate turns noticably purple.

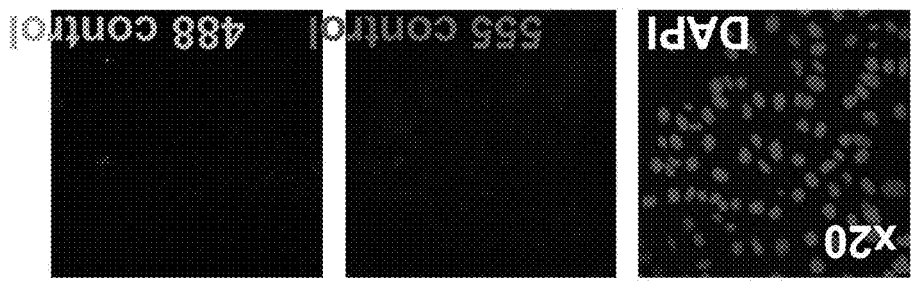
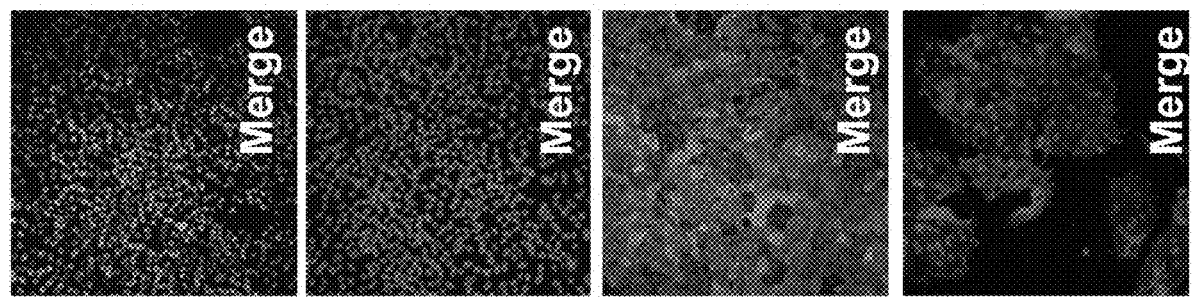
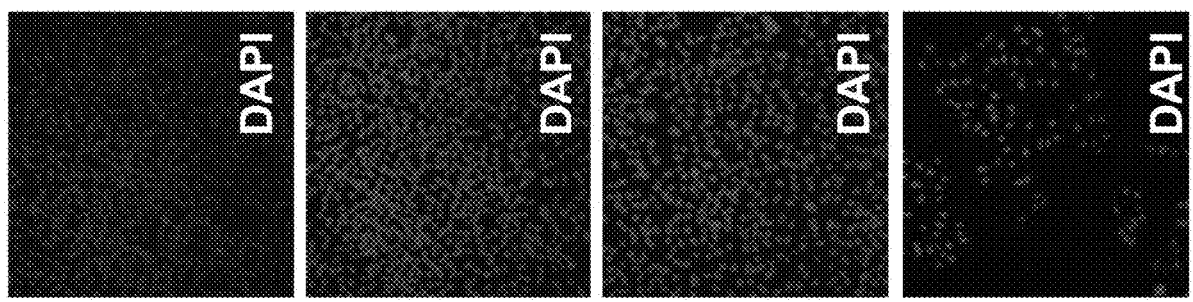
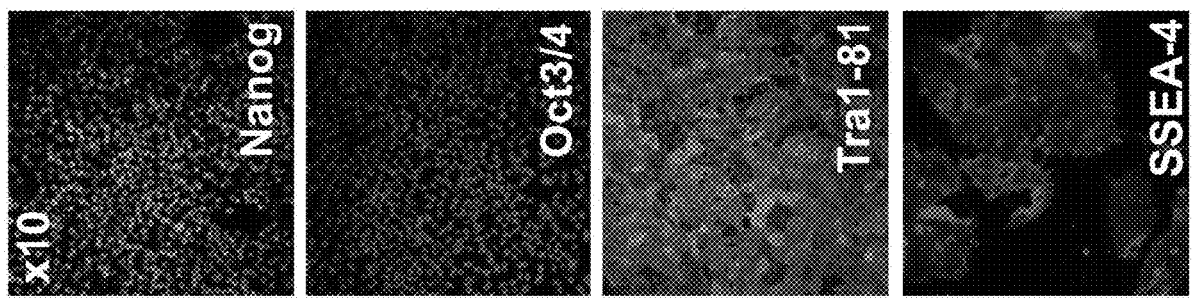
Fig. 35

Histone-3 staining as discrete dot in nucleus indicates cells are NOT in naïve state and have undergone X-inactivation. White arrows indicate cells that are naïve and have no condensed Histone-3. Cells are 100% positive for NANOG, indicating that they are all pluripotent stem cells.

Histone-3 staining as discrete dot in nucleus indicates cells are NOT in naïve state and have undergone X-inactivation. White arrows indicate cells that are naïve and have no condensed Histone-3. Cells are 100% positive for NANOG, indicating that they are all pluripotent stem cells.

Histone-3 staining as discrete dot in nucleus indicates cells are NOT in naïve state and have undergone X-inactivation. White arrows indicate cells that are naïve and have no condensed Histone-3. Cells are 100% positive for NANOG, indicating that they are all pluripotent stem cells.

Histone-3 staining as discrete dot in nucleus indicates cells are NOT in naïve state and have undergone X-inactivation. White arrows indicate cells that are naïve and have no condensed Histone-3. Cells are 100% positive for NANOG, indicating that they are all pluripotent stem cells.   Fig. 39

| Cells Plated per well | HES-3.MEF.FGF Alkphos+ colonies | HES-3.MEF.FGF cloning efficiency | HES-3.VITA.C3.NM23 Alkphos+ colonies | HES-3.VITA.C3.NM23 Cloning efficiency |
|---|---|---|---|---|
| 1,000 | 11, 13 | 1.2% | 184, 176 (D4) | 18.0% |
| 3,000 | 37, 48 | 1.4% | 596, 675 (D4) | 21.2% |
| 5,000 | 68, 74 | 1.4% | TNTC* (D4) | |

* Too numerous to count.

Fig. 41 C

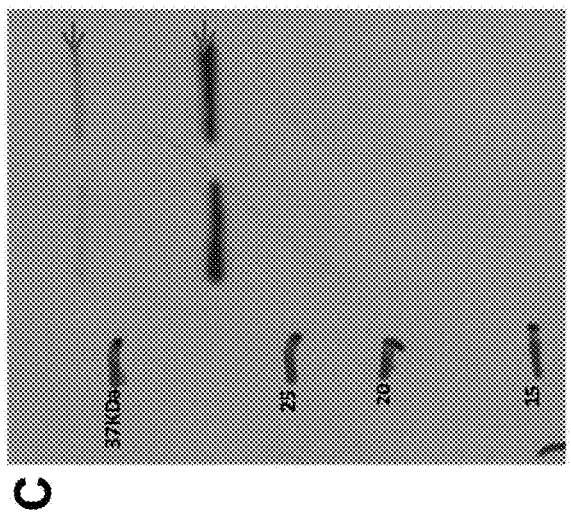
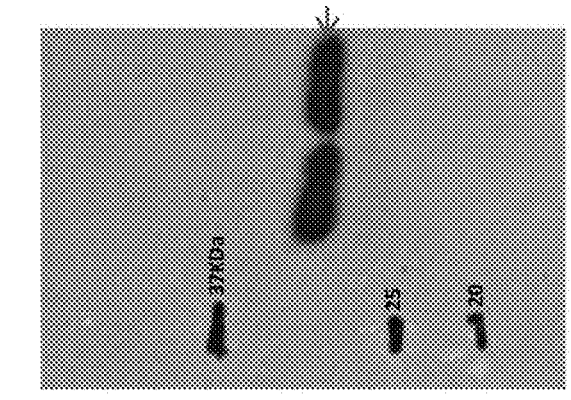
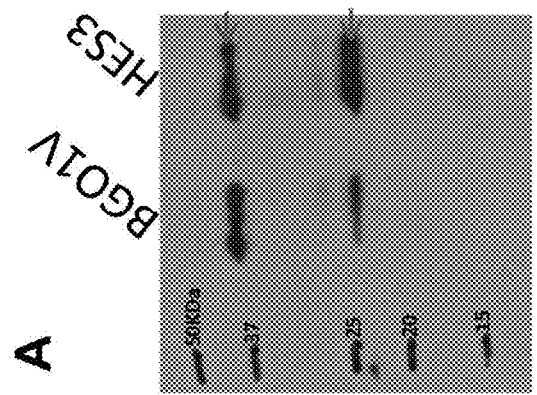
Fig. 55

1- lyse cells with RIPA buffer
2- add 10ug of recombinant NME7 AB
3- incubate 2h at 4°C
4- add Dynabeads protein G (Life Technologies) coupled to anti NM23-H7 (B9, Santa Cruz Biotechnology)
5- incubate o/n at 4°C
6- wash beads 2x with PBS
7- add reducing buffer
8- run reducing SDS-PAGE
9- detect proteins using Silver Stain (Pierce)

MNHSERFVFIAEWYDPNASLLRRYELLFYPGDGSVEMHDVKNHR
TFLKRTKYDNLHLEDLFIGNKVNVFSRQLVLIDYGDQYTARQLGSR
KE*KTLALIKPDAISKAGEIIEIINK*AGFTITKLKMMMLSRKEALDFHV
DHQSRPFFNELIQFITTGPIIAMEILRDDAICEWKR*LLGPANSGVAR*
TDASESIR*ALFGTDGIRNAAHGPDSFASAARE*MELFFPSSGGCGP
ANTAKFTNCTCCIVKPHAVSEGLLGKILMAIRDAGFEISAMQMFN
MDRVNVEEFYEVYKGVVTEYHDMVTEMYSGPCVAMEIQQNNA
TKTFREFCGPADPEIARHLRPGTLRAIFGKTKIQNAVHCTDLPEDG
LLEVQJYFFKILDN

———— NDPKA (italic/underline=peptides from mass spec)
······ NDPKB

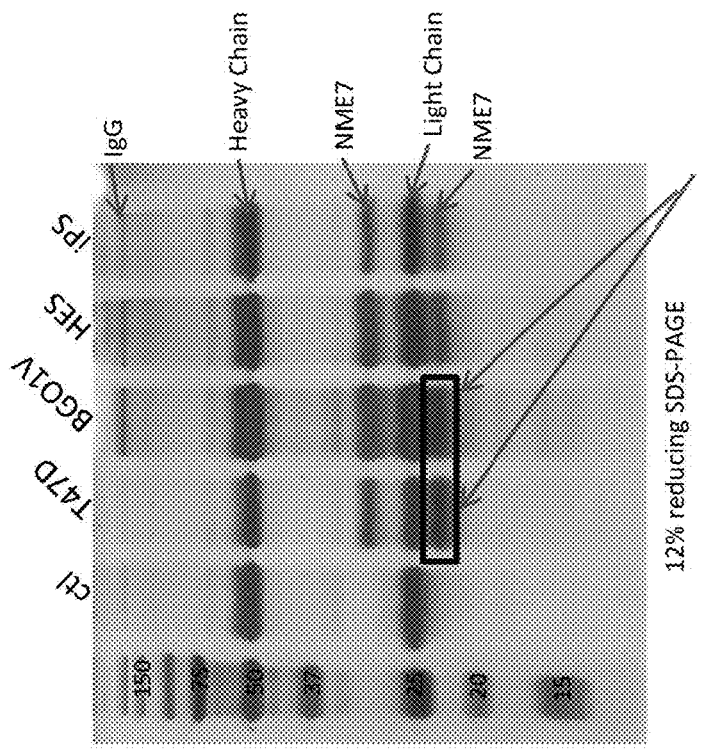

12% reducing SDS-PAGE

Fig. 57

SEQUENCE LISTING

<160> NUMBER OF SEQ ID NOS: 124

<210> SEQ ID NO 1
<211> LENGTH: 1255
<212> TYPE: PRT
<213> ORGANISM: Artificial Sequence
<220> FEATURE:
<223> OTHER INFORMATION: full-length MUC1 Receptor

<400> SEQUENCE: 1

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
```

```
                 355                 360                 365
Gly Ser Thr Ala Pro Pro Ala His Gly Val Thr Ser Ala Pro Asp Thr
            370                 375                 380
Arg Pro Ala Pro Gly Ser Thr Ala Pro Pro Ala His Gly Val Thr Ser
385                 390                 395                 400
Ala Pro Asp Thr Arg Pro Ala Pro Gly Ser Thr Ala Pro Pro Ala His
                405                 410                 415
Gly Val Thr Ser Ala Pro Asp Thr Arg Pro Ala Pro Gly Ser Thr Ala
            420                 425                 430
Pro Pro Ala His Gly Val Thr Ser Ala Pro Asp Thr Arg Pro Ala Pro
            435                 440                 445
Gly Ser Thr Ala Pro Pro Ala His Gly Val Thr Ser Ala Pro Asp Thr
            450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
            515                 520                 525
Gly Ser Thr Ala Pro Pro Ala His Gly Val Thr Ser Ala Pro Asp Thr
            530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
Gly Val Thr Ser Ala Pro Asp Thr Arg Pro Ala Pro Gly Ser Thr Ala
            580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
            610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
            675                 680                 685
Gly Ser Thr Ala Pro Pro Ala His Gly Val Thr Ser Ala Pro Asp Thr
            690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
            770                 775                 780
```

```
Arg Pro Ala Pro Gly Ser Thr Ala Pro Ala His Gly Val Thr Ser
785                 790                 795                 800

Ala Pro Asp Thr Arg Pro Ala Pro Gly Ser Thr Ala Pro Ala His
            805                 810                 815

Gly Val Thr Ser Ala Pro Asp Thr Arg Pro Ala Pro Gly Ser Thr Ala
        820                 825                 830

Pro Pro Ala His Gly Val Thr Ser Ala Pro Asp Thr Arg Pro Ala Pro
        835                 840                 845

Gly Ser Thr Ala Pro Ala His Gly Val Thr Ser Ala Pro Asp Thr
    850                 855                 860

Arg Pro Ala Pro Gly Ser Thr Ala Pro Ala His Gly Val Thr Ser
865                 870                 875                 880

Ala Pro Asp Thr Arg Pro Ala Pro Gly Ser Thr Ala Pro Ala His
            885                 890                 895

Gly Val Thr Ser Ala Pro Asp Thr Arg Pro Ala Pro Gly Ser Thr Ala
        900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
            965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
        995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185
```

```
Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Ala Ser Ala Asn Leu
    1250            1255

<210> SEQ ID NO 2
<211> LENGTH: 19
<212> TYPE: PRT
<213> ORGANISM: Artificial Sequence
<220> FEATURE:
<223> OTHER INFORMATION: N-terminal MUC-1 signaling sequence

<400> SEQUENCE: 2

Met Thr Pro Gly Thr Gln Ser Pro Phe Phe Leu Leu Leu Leu Thr
1               5                   10                  15

Val Leu Thr

<210> SEQ ID NO 3
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 3

Met Thr Pro Gly Thr Gln Ser Pro Phe Phe Leu Leu Leu Leu Thr
1               5                   10                  15

Val Leu Thr Val Val Thr Ala
            20

<210> SEQ ID NO 4
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 4

Met Thr Pro Gly Thr Gln Ser Pro Phe Phe Leu Leu Leu Leu Thr
1               5                   10                  15

Val Leu Thr Val Val Thr Gly
            20

<210> SEQ ID NO 5
<211> LENGTH: 146
<212> TYPE: PRT
<213> ORGANISM: Artificial Sequence
<220> FEATURE:
<223> OTHER INFORMATION: truncated MUC1 receptor isoform having
      nat-PSMGFR at its N-terminus

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30
```

```
Ser Asp Val Pro Phe Pro Phe Ser Ala Gln Ser Gly Ala Gly Val Pro
        35                  40                  45

Gly Trp Gly Ile Ala Leu Leu Val Leu Val Cys Val Leu Val Ala Leu
 50                  55                  60

Ala Ile Val Tyr Leu Ile Ala Leu Ala Val Cys Gln Cys Arg Arg Lys
 65                  70                  75                  80

Asn Tyr Gly Gln Leu Asp Ile Phe Pro Ala Arg Asp Thr Tyr His Pro
                 85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
    130                 135                 140

Asn Leu
145

<210> SEQ ID NO 6
<211> LENGTH: 45
<212> TYPE: PRT
<213> ORGANISM: Artificial Sequence
<220> FEATURE:
<223> OTHER INFORMATION: Native Primary Sequence of the MUC1 Growth
      Factor Receptor

<400> SEQUENCE: 6

Gly Thr Ile Asn Val His Asp Val Glu Thr Gln Phe Asn Gln Tyr Lys
 1               5                  10                  15

Thr Glu Ala Ala Ser Arg Tyr Asn Leu Thr Ile Ser Asp Val Ser Val
                20                  25                  30

Ser Asp Val Pro Phe Pro Phe Ser Ala Gln Ser Gly Ala
        35                  40                  45

<210> SEQ ID NO 7
<211> LENGTH: 44
<212> TYPE: PRT
<213> ORGANISM: Artificial Sequence
<220> FEATURE:
<223> OTHER INFORMATION: Native Primary Sequence of the MUC1 Growth
      Factor Receptor

<400> SEQUENCE: 7

Thr Ile Asn Val His Asp Val Glu Thr Gln Phe Asn Gln Tyr Lys Thr
 1               5                  10                  15

Glu Ala Ala Ser Arg Tyr Asn Leu Thr Ile Ser Asp Val Ser Val Ser
                20                  25                  30

Asp Val Pro Phe Pro Phe Ser Ala Gln Ser Gly Ala
        35                  40

<210> SEQ ID NO 8
<211> LENGTH: 45
<212> TYPE: PRT
<213> ORGANISM: Artificial Sequence
<220> FEATURE:
<223> OTHER INFORMATION: "SPY" functional variant of the native Primary
      Sequence of the MUC1 Growth Factor Receptor

<400> SEQUENCE: 8

Gly Thr Ile Asn Val His Asp Val Glu Thr Gln Phe Asn Gln Tyr Lys
 1               5                  10                  15

Thr Glu Ala Ala Ser Pro Tyr Asn Leu Thr Ile Ser Asp Val Ser Val
```

```
            20                  25                  30

Ser Asp Val Pro Phe Pro Phe Ser Ala Gln Ser Gly Ala
        35                  40                  45

<210> SEQ ID NO 9
<211> LENGTH: 44
<212> TYPE: PRT
<213> ORGANISM: Artificial Sequence
<220> FEATURE:
<223> OTHER INFORMATION: SPY" functional variant of the native Primary
      Sequence of the MUC1 Growth Factor Receptor

<400> SEQUENCE: 9

Thr Ile Asn Val His Asp Val Glu Thr Gln Phe Asn Gln Tyr Lys Thr
1               5                  10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 10
<211> LENGTH: 216
<212> TYPE: DNA
<213> ORGANISM: Artificial Sequence
<220> FEATURE:
<223> OTHER INFORMATION: MUC1 cytoplasmic domain nucleotide sequence

<400> SEQUENCE: 10
tgtcagtgcc gccgaaagaa ctacgggcag ctggacatct ttccagcccg ggatacctac     60
catcctatga gcgagtaccc cacctaccac acccatgggc gctatgtgcc ccctagcagt    120
accgatcgta gcccctatga gaaggtttct gcaggtaacg gtggcagcag cctctcttac    180
acaaacccag cagtggcagc cgcttctgcc aacttg                              216

<210> SEQ ID NO 11
<211> LENGTH: 72
<212> TYPE: PRT
<213> ORGANISM: Artificial Sequence
<220> FEATURE:
<223> OTHER INFORMATION: MUC1 cytoplasmic domain amino acid sequence

<400> SEQUENCE: 11

Cys Gln Cys Arg Arg Lys Asn Tyr Gly Gln Leu Asp Ile Phe Pro Ala
1               5                  10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Ala Ser Ala Asn Leu
65                  70

<210> SEQ ID NO 12
<211> LENGTH: 854
<212> TYPE: DNA
<213> ORGANISM: Artificial Sequence
<220> FEATURE:
<223> OTHER INFORMATION: NME7 nucleotide sequence

<400> SEQUENCE: 12
gagatcctga gacaatgaat catagtgaaa gattcgtttt cattgcagag tggtatgatc     60
```

```
caaatgcttc acttcttcga cgttatgagc tttattttta cccaggggat ggatctgttg    120
aaatgcatga tgtaaagaat catcgcacct ttttaaagcg gaccaaatat gataacctgc    180
acttggaaga tttatttata ggcaacaaag tgaatgtctt ttctcgacaa ctggtattaa    240
ttgactatgg ggatcaatat acagctcgcc agctgggcag taggaaagaa aaaacgctag    300
ccctaattaa accagatgca atatcaaagg ctggagaaat aattgaaata ataaacaaag    360
ctggatttac tataaccaaa ctcaaaatga tgatgctttc aaggaaagaa gcattggatt    420
ttcatgtaga tcaccagtca agacccttt tcaatgagct gatccagttt attacaactg     480
gtcctattat tgccatggag attttaagag atgatgctat atgtgaatgg aaaagactgc    540
tgggacctgc aaactctgga gtggcacgca cagatgcttc tgaaagcatt agagccctct    600
ttggaacaga tggcataaga aatgcagcgc atggccctga ttcttttgct tctgcggcca    660
gagaaatgga gttgtttttt ccttcaagtg gaggttgtgg gccggcaaac actgctaaat    720
ttactaattg tacctgttgc attgttaaac cccatgctgt cagtgaaggt atgttgaata    780
cactatattc agtacatttt gttaatagga gagcaatgtt tattttcttg atgtacttta    840
tgtatagaaa ataa                                                     854
```

<210> SEQ ID NO 13
<211> LENGTH: 283
<212> TYPE: PRT
<213> ORGANISM: Artificial Sequence
<220> FEATURE:
<223> OTHER INFORMATION: NME7 amino acid sequence

<400> SEQUENCE: 13

```
Asp Pro Glu Thr Met Asn His Ser Glu Arg Phe Val Phe Ile Ala Glu
1               5                   10                  15

Trp Tyr Asp Pro Asn Ala Ser Leu Leu Arg Arg Tyr Glu Leu Leu Phe
            20                  25                  30

Tyr Pro Gly Asp Gly Ser Val Glu Met His Asp Val Lys Asn His Arg
        35                  40                  45

Thr Phe Leu Lys Arg Thr Lys Tyr Asp Asn Leu His Leu Glu Asp Leu
    50                  55                  60

Phe Ile Gly Asn Lys Val Asn Val Phe Ser Arg Gln Leu Val Leu Ile
65                  70                  75                  80

Asp Tyr Gly Asp Gln Tyr Thr Ala Arg Gln Leu Gly Ser Arg Lys Glu
                85                  90                  95

Lys Thr Leu Ala Leu Ile Lys Pro Asp Ala Ile Ser Lys Ala Gly Glu
            100                 105                 110

Ile Ile Glu Ile Ile Asn Lys Ala Gly Phe Thr Ile Thr Lys Leu Lys
        115                 120                 125

Met Met Met Leu Ser Arg Lys Glu Ala Leu Asp Phe His Val Asp His
    130                 135                 140

Gln Ser Arg Pro Phe Phe Asn Glu Leu Ile Gln Phe Ile Thr Thr Gly
145                 150                 155                 160

Pro Ile Ile Ala Met Glu Ile Leu Arg Asp Asp Ala Ile Cys Glu Trp
                165                 170                 175

Lys Arg Leu Leu Gly Pro Ala Asn Ser Gly Val Ala Arg Thr Asp Ala
            180                 185                 190

Ser Glu Ser Ile Arg Ala Leu Phe Gly Thr Asp Gly Ile Arg Asn Ala
        195                 200                 205

Ala His Gly Pro Asp Ser Phe Ala Ser Ala Ala Arg Glu Met Glu Leu
```

Phe Phe Pro Ser Ser Gly Gly Cys Gly Pro Ala Asn Thr Ala Lys Phe
225                 230                 235                 240

Thr Asn Cys Thr Cys Cys Ile Val Lys Pro His Ala Val Ser Glu Gly
            245                 250                 255

Met Leu Asn Thr Leu Tyr Ser Val His Phe Val Asn Arg Arg Ala Met
            260                 265                 270

Phe Ile Phe Leu Met Tyr Phe Met Tyr Arg Lys
        275                 280

<210> SEQ ID NO 14
<211> LENGTH: 534
<212> TYPE: DNA
<213> ORGANISM: Artificial Sequence
<220> FEATURE:
<223> OTHER INFORMATION: NM23-H1 nucleotide sequence

<400> SEQUENCE: 14
atggtgctac tgtctacttt agggatcgtc tttcaaggcg aggggcctcc tatctcaagc      60
tgtgatacag gaaccatggc caactgtgag cgtaccttca ttgcgatcaa accagatggg     120
gtccagcggg gtcttgtggg agagattatc aagcgttttg agcagaaagg attccgcctt     180
gttggtctga aattcatgca agcttccgaa gatcttctca aggaacacta cgttgacctg     240
aaggaccgtc cattctttgc cggcctggtg aaatacatgc actcagggcc ggtagttgcc     300
atggtctggg aggggctgaa tgtggtgaag acgggccgag tcatgctcgg ggagaccaac     360
cctgcagact ccaagcctgg gaccatccgt ggagacttct gcatacaagt ggcaggaac     420 attatacatg gcagtgattc tgtggagagt gcagagaagg agatcggctt gtggtttcac     480
cctgaggaac tggtagatta cacgagctgt gctcagaact ggatctatga atga            534

<210> SEQ ID NO 15
<211> LENGTH: 177
<212> TYPE: PRT
<213> ORGANISM: Artificial Sequence
<220> FEATURE:
<223> OTHER INFORMATION: NM23-H1 amino acid sequence

<400> SEQUENCE: 15

Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

```
Ser Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
            165                 170                 175

Glu

<210> SEQ ID NO 16
<211> LENGTH: 534
<212> TYPE: DNA
<213> ORGANISM: Artificial Sequence
<220> FEATURE:
<223> OTHER INFORMATION: NM23-H1 S120G mutant nucleotide sequence

<400> SEQUENCE: 16
atggtgctac tgtctacttt agggatcgtc tttcaaggcg aggggcctcc tatctcaagc      60
tgtgatacag gaaccatggc caactgtgag cgtaccttca ttgcgatcaa accagatggg     120
gtccagcggg gtcttgtggg agagattatc aagcgttttg agcagaaagg attccgcctt     180
gttggtctga aattcatgca agcttccgaa gatcttctca ggaacactac gttgacctg     240 aaggaccgtc cattctttgc cggcctggtg aaatacatgc actcagggcc ggtagttgcc     300
atggtctggg aggggctgaa tgtggtgaag acgggccgag tcatgctcgg ggagaccaac     360
cctgcagact ccaagcctgg gaccatccgt ggagacttct gcatacaagt tggcaggaac     420
attatacatg gcggtgattc tgtggagagt gcagagaagg agatcggctt gtggtttcac     480
cctgaggaac tggtagatta cacgagctgt gctcagaact ggatctatga atga          534

<210> SEQ ID NO 17
<211> LENGTH: 177
<212> TYPE: PRT
<213> ORGANISM: Artificial Sequence
<220> FEATURE:
<223> OTHER INFORMATION: NM23-H1 S120G mutant amino acid sequence

<400> SEQUENCE: 17

Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

Gly Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175
```

Glu

<210> SEQ ID NO 18
<211> LENGTH: 459
<212> TYPE: DNA
<213> ORGANISM: Artificial Sequence
<220> FEATURE:
<223> OTHER INFORMATION: NM23-H2 nucleotide sequence

<400> SEQUENCE: 18

```
atggccaacc tggagcgcac cttcatcgcc atcaagccgg acggcgtgca gcgcggcctg        60
gtgggcgaga tcatcaagcg cttcgagcag aagggattcc gcctcgtggc catgaagttc       120
ctccgggcct ctgaagaaca cctgaagcag cactacattg acctgaaaga ccgaccattc       180
ttccctgggc tggtgaagta catgaactca gggccggttg tggccatggt ctgggagggg       240
ctgaacgtgg tgaagacagg ccgagtgatg cttggggaga ccaatccagc agattcaaag       300
ccaggcacca ttcgtgggga cttctgcatt caggttggca ggaacatcat tcatggcagt       360
gattcagtaa aaagtgctga aaaagaaatc agcctatggt ttaagcctga agaactggtt       420
gactacaagt cttgtgctca tgactgggtc tatgaataa                              459
```

<210> SEQ ID NO 19
<211> LENGTH: 152
<212> TYPE: PRT
<213> ORGANISM: Artificial Sequence
<220> FEATURE:
<223> OTHER INFORMATION: NM23-H2 amino acid sequence

<400> SEQUENCE: 19

```
Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150
```

<210> SEQ ID NO 20
<211> LENGTH: 1023
<212> TYPE: DNA
<213> ORGANISM: Artificial Sequence
<220> FEATURE:
<223> OTHER INFORMATION: DNA encoding Human NM23-H7-2 sequence
      optimized for E. coli expression

<400> SEQUENCE: 20

```
atgcatgacg ttaaaaatca ccgtaccttt ctgaaacgca cgaaatatga taatctgcat    60
ctggaagacc tgtttattgg caacaaagtc aatgtgttct ctcgtcagct ggtgctgatc   120
gattatggcg accagtacac cgcgcgtcaa ctgggtagtc gcaaagaaaa aacgctggcc   180
ctgattaaac cggatgcaat ctccaaagct ggcgaaatta tcgaaattat caacaaagcg   240
ggtttcacca tcacgaaact gaaaatgatg atgctgagcc gtaaagaagc cctggatttt   300
catgtcgacc accagtctcg cccgtttttc aatgaactga ttcaattcat caccacgggt   360
ccgattatcg caatggaaat tctgcgtgat gacgctatct gcgaatggaa acgcctgctg   420
ggcccggcaa actcaggtgt tgcgcgtacc gatgccagtg aatccattcg cgctctgttt   480
ggcaccgatg gtatccgtaa tgcagcacat ggtccggact cattcgcatc ggcagctcgt   540
gaaatggaac tgttttttcc cgagctctgg cgttgcggtc cggcaaacac cgccaaattt   600
accaattgta cgtgctgtat tgtcaaaccg cacgcagtgt cagaaggcct gctgggtaaa   660
attctgatgg caatccgtga tgctggcttt gaaatctcgg ccatgcagat gttcaacatg   720
gaccgcgtta acgtcgaaga attctacgaa gtttacaaag gcgtggttac cgaatatcac   780
gatatggtta cggaaatgta ctccggtccg tgcgtcgcga tggaaattca gcaaaacaat   840
gccaccaaaa cgtttcgtga attctgtggt ccggcagatc cggaaatcgc acgtcatctg   900
cgtccgggta ccctgcgcgc aattttggt aaaacgaaaa tccagaacgc tgtgcactgt   960
accgatctgc cggaagacgg tctgctggaa gttcaatact ttttcaaaat tctggataat  1020
tga                                                                1023
```

<210> SEQ ID NO 21  
<211> LENGTH: 340  
<212> TYPE: PRT  
<213> ORGANISM: Artificial Sequence  
<220> FEATURE:  
<223> OTHER INFORMATION: Human NM23-H7-2 sequence optimized for E. coli expression

<400> SEQUENCE: 21

```
Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val
                20                  25                  30

Phe Ser Arg Gln Leu Val Leu Ile Asp Tyr Gly Asp Gln Tyr Thr Ala
            35                  40                  45

Arg Gln Leu Gly Ser Arg Lys Glu Lys Thr Leu Ala Leu Ile Lys Pro
        50                  55                  60

Asp Ala Ile Ser Lys Ala Gly Glu Ile Ile Glu Ile Ile Asn Lys Ala
65                  70                  75                  80

Gly Phe Thr Ile Thr Lys Leu Lys Met Met Met Leu Ser Arg Lys Glu
                85                  90                  95

Ala Leu Asp Phe His Val Asp His Gln Ser Arg Pro Phe Phe Asn Glu
            100                 105                 110

Leu Ile Gln Phe Ile Thr Thr Gly Pro Ile Ile Ala Met Glu Ile Leu
        115                 120                 125

Arg Asp Asp Ala Ile Cys Glu Trp Lys Arg Leu Leu Gly Pro Ala Asn
    130                 135                 140

Ser Gly Val Ala Arg Thr Asp Ala Ser Glu Ser Ile Arg Ala Leu Phe
145                 150                 155                 160

Gly Thr Asp Gly Ile Arg Asn Ala Ala His Gly Pro Asp Ser Phe Ala
                165                 170                 175
```

Ser Ala Ala Arg Glu Met Glu Leu Phe Phe Pro Ser Ser Gly Gly Cys
            180                 185                 190

Gly Pro Ala Asn Thr Ala Lys Phe Thr Asn Cys Thr Cys Ile Val
        195                 200                 205

Lys Pro His Ala Val Ser Glu Gly Leu Leu Gly Lys Ile Leu Met Ala
210                 215                 220

Ile Arg Asp Ala Gly Phe Glu Ile Ser Ala Met Gln Met Phe Asn Met
225                 230                 235                 240

Asp Arg Val Asn Val Glu Glu Phe Tyr Glu Val Tyr Lys Gly Val Val
                245                 250                 255

Thr Glu Tyr His Asp Met Val Thr Glu Met Tyr Ser Gly Pro Cys Val
            260                 265                 270

Ala Met Glu Ile Gln Gln Asn Asn Ala Thr Lys Thr Phe Arg Glu Phe
        275                 280                 285

Cys Gly Pro Ala Asp Pro Glu Ile Ala Arg His Leu Arg Pro Gly Thr
    290                 295                 300

Leu Arg Ala Ile Phe Gly Lys Thr Lys Ile Gln Asn Ala Val His Cys
305                 310                 315                 320

Thr Asp Leu Pro Glu Asp Gly Leu Leu Glu Val Gln Tyr Phe Phe Lys
                325                 330                 335

Ile Leu Asp Asn
            340

<210> SEQ ID NO 22
<211> LENGTH: 399
<212> TYPE: DNA
<213> ORGANISM: Artificial Sequence
<220> FEATURE:
<223> OTHER INFORMATION: DNA encoding Human NME7-A

<400> SEQUENCE: 22
atggaaaaaa cgctagccct aattaaacca gatgcaatat caaaggctgg agaaataatt     60
gaaataataa acaaagctgg atttactata accaaactca aaatgatgat gctttcaagg    120
aaagaagcat tggattttca gtagatcac cagtcaagac ccttttttcaa tgagctgatc    180 cagtttatta caactggtcc tattattgcc atggagattt taagagatga tgctatatgt    240
gaatggaaaa gactgctggg acctgcaaac tctggagtgg cacgcacaga tgcttctgaa    300
agcattagag ccctctttgg aacagatggc ataagaaatg cagcgcatgg ccctgattct    360
tttgcttctg cggccagaga aatggagttg ttttttttga                          399

<210> SEQ ID NO 23
<211> LENGTH: 132
<212> TYPE: PRT
<213> ORGANISM: Artificial Sequence
<220> FEATURE:
<223> OTHER INFORMATION: Human NME7-A

<400> SEQUENCE: 23

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

```
Thr Gly Pro Ile Ile Ala Met Glu Ile Leu Arg Asp Asp Ala Ile Cys
 65                  70                  75                  80

Glu Trp Lys Arg Leu Leu Gly Pro Ala Asn Ser Gly Val Ala Arg Thr
             85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe
        130
```

<210> SEQ ID NO 24
<211> LENGTH: 444
<212> TYPE: DNA
<213> ORGANISM: Artificial Sequence
<220> FEATURE:
<223> OTHER INFORMATION: DNA encoding Human NME7-A1

<400> SEQUENCE: 24

```
atggaaaaaa cgctagccct aattaaacca gatgcaatat caaaggctgg agaaataatt    60
gaaataataa acaaagctgg atttactata accaaactca aatgatgat gctttcaagg   120
aaagaagcat tggattttca tgtagatcac cagtcaagac ccttttttcaa tgagctgatc   180
cagtttatta caactggtcc tattattgcc atggagattt taagagatga tgctatatgt   240
gaatggaaaa gactgctggg acctgcaaac tctggagtgg cacgcacaga tgcttctgaa   300
agcattagag ccctctttgg aacagatggc ataagaaatg cagcgcatgg ccctgattct   360
tttgcttctg cggccagaga aatggagttg tttttttcctt caagtggagg ttgtgggccg   420
gcaaacactg ctaaatttac ttga                                         444
```

<210> SEQ ID NO 25
<211> LENGTH: 147
<212> TYPE: PRT
<213> ORGANISM: Artificial Sequence
<220> FEATURE:
<223> OTHER INFORMATION: Human NME7-A1

<400> SEQUENCE: 25

```
Met Glu Lys Thr Leu Ala Leu Ile Lys Pro Asp Ala Ile Ser Lys Ala
  1               5                  10                  15

Gly Glu Ile Ile Glu Ile Ile Asn Lys Ala Gly Phe Thr Ile Thr Lys
             20                  25                  30

Leu Lys Met Met Met Leu Ser Arg Lys Glu Ala Leu Asp Phe His Val
         35                  40                  45

Asp His Gln Ser Arg Pro Phe Phe Asn Glu Leu Ile Gln Phe Ile Thr
     50                  55                  60

Thr Gly Pro Ile Ile Ala Met Glu Ile Leu Arg Asp Asp Ala Ile Cys
 65                  70                  75                  80

Glu Trp Lys Arg Leu Leu Gly Pro Ala Asn Ser Gly Val Ala Arg Thr
             85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140
```

Lys Phe Thr
145

<210> SEQ ID NO 26
<211> LENGTH: 669
<212> TYPE: DNA
<213> ORGANISM: Artificial Sequence
<220> FEATURE:
<223> OTHER INFORMATION: DNA encoding Human NME7-A2

<400> SEQUENCE: 26

| | | | | | |
|---|---|---|---|---|---|
| atgaatcata | gtgaaagatt | cgttttcatt | gcagagtggt | atgatccaaa | tgcttcactt | 60 |
| cttcgacgtt | atgagctttt | attttaccca | ggggatggat | ctgttgaaat | gcatgatgta | 120 |
| aagaatcatc | gcaccttttt | aaagcggacc | aaatatgata | acctgcactt | ggaagattta | 180 |
| tttataggca | acaaagtgaa | tgtcttttct | cgacaactgg | tattaattga | ctatggggat | 240 |
| caatatacag | ctcgccagct | gggcagtagg | aaagaaaaaa | cgctagccct | aattaaacca | 300 |
| gatgcaatat | caaaggctgg | agaaataatt | gaaataataa | acaaagctgg | atttactata | 360 |
| accaaactca | aaatgatgat | gctttcaagg | aaagaagcat | tggattttca | gtagatcac | 420 |
| cagtcaagac | ccttttttcaa | tgagctgatc | cagtttatta | caactggtcc | tattattgcc | 480 |
| atggagattt | taagagatga | tgctatatgt | gaatggaaaa | gactgctggg | acctgcaaac | 540 |
| tctggagtgg | cacgcacaga | tgcttctgaa | agcattagag | ccctctttgg | aacagatggc | 600 |
| ataagaaatg | cagcgcatgg | ccctgattct | tttgcttctg | cggccagaga | aatggagttg | 660 |
| ttttttttga | | | | | | 669 |

<210> SEQ ID NO 27
<211> LENGTH: 222
<212> TYPE: PRT
<213> ORGANISM: Artificial Sequence
<220> FEATURE:
<223> OTHER INFORMATION: Human NME7-A2

<400> SEQUENCE: 27

Met Asn His Ser Glu Arg Phe Val Phe Ile Ala Glu Trp Tyr Asp Pro
1               5                   10                  15

Asn Ala Ser Leu Leu Arg Arg Tyr Glu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

```
Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe
    210                 215                 220

<210> SEQ ID NO 28
<211> LENGTH: 714
<212> TYPE: DNA
<213> ORGANISM: Artificial Sequence
<220> FEATURE:
<223> OTHER INFORMATION: DNA encoding Human NME7-A3

<400> SEQUENCE: 28
atgaatcata gtgaaagatt cgttttcatt gcagagtggt atgatccaaa tgcttcactt      60
cttcgacgtt atgagctttt atttacccca ggggatggat ctgttgaaat gcatgatgta    120
aagaatcatc gcaccttttt aaagcggacc aaatatgata acctgcactt ggaagattta    180
tttataggca acaaagtgaa tgtctttttct cgacaactgg tattaattga ctatggggat    240
caatatacag ctcgccagct gggcagtagg aagaaaaaa cgctagccct aattaaacca    300
gatgcaatat caaaggctgg agaaataatt gaaataataa acaaagctgg atttactata    360
accaaactca aatgatgat gctttcaagg aaagaagcat tggattttca gtagatcac    420 cagtcaagac cctttttcaa tgagctgatc cagtttatta caactggtcc tattattgcc    480
atggagattt taagagatga tgctatatgt gaatggaaaa gactgctggg acctgcaaac    540
tctggagtgg cacgcacaga tgcttctgaa agcattagag ccctctttgg aacagatggc    600
ataagaaatg cagcgcatgg ccctgattct tttgcttctg cggccagaga aatggagttg    660
ttttttcctt caagtggagg ttgtgggccg gcaaacactg ctaaatttac ttga         714

<210> SEQ ID NO 29
<211> LENGTH: 237
<212> TYPE: PRT
<213> ORGANISM: Artificial Sequence
<220> FEATURE:
<223> OTHER INFORMATION: Human NME7-A3

<400> SEQUENCE: 29

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
```

```
                130               135                140
Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
                180                 185                 190

Arg Ala Leu Phe Gly Thr Asp Gly Ile Arg Asn Ala Ala His Gly Pro
                195                 200                 205

Asp Ser Phe Ala Ser Ala Ala Arg Glu Met Glu Leu Phe Phe Pro Ser
                210                 215                 220

Ser Gly Gly Cys Gly Pro Ala Asn Thr Ala Lys Phe Thr
225                 230                 235
```

```
<210> SEQ ID NO 30
<211> LENGTH: 408
<212> TYPE: DNA
<213> ORGANISM: Artificial Sequence
<220> FEATURE:
<223> OTHER INFORMATION: DNA encoding Human NME7-B

<400> SEQUENCE: 30
atgaattgta cctgttgcat tgttaaaccc catgctgtca gtgaaggact gttgggaaag    60
atcctgatgg ctatccgaga tgcaggtttt gaaatctcag ctatgcagat gttcaatatg   120
gatcgggtta atgttgagga attctatgaa gtttataaag gagtagtgac cgaatatcat   180
gacatggtga cagaaatgta ttctggccct tgtgtagcaa tggagattca acagaataat   240
gctacaaaga catttcgaga attttgtgga cctgctgatc ctgaaattgc ccggcattta   300
cgccctggaa ctctcagagc aatctttggt aaaactaaga tccagaatgc tgttcactgt   360
actgatctgc cagaggatgg cctattagag gttcaatact tcttctga               408
```

```
<210> SEQ ID NO 31
<211> LENGTH: 135
<212> TYPE: PRT
<213> ORGANISM: Artificial Sequence
<220> FEATURE:
<223> OTHER INFORMATION: Human NME7-B

<400> SEQUENCE: 31

Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
                20                  25                  30

Ser Ala Met Gln Met Phe Asn Met Asp Arg Val Asn Val Glu Glu Phe
                35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
                100                 105                 110

Lys Ile Gln Asn Ala Val His Cys Thr Asp Leu Pro Glu Asp Gly Leu
                115                 120                 125

Leu Glu Val Gln Tyr Phe Phe
```

<210> SEQ ID NO 32
<211> LENGTH: 426
<212> TYPE: DNA
<213> ORGANISM: Artificial Sequence
<220> FEATURE:
<223> OTHER INFORMATION: DNA encoding Human NME7-B1

<400> SEQUENCE: 32

```
atgaattgta cctgttgcat tgttaaaccc catgctgtca gtgaaggact gttgggaaag      60
atcctgatgg ctatccgaga tgcaggtttt gaaatctcag ctatgcagat gttcaatatg     120
gatcgggtta atgttgagga attctatgaa gtttataaag gagtagtgac cgaatatcat     180
gacatggtga cagaaatgta ttctggccct tgtgtagcaa tggagattca acagaataat     240
gctacaaaga catttcgaga attttgtgga cctgctgatc ctgaaattgc ccggcattta     300
cgccctggaa ctctcagagc aatctttggt aaaactaaga tccagaatgc tgttcactgt     360
actgatctgc cagaggatgg cctattagag gttcaatact tcttcaagat cttggataat     420
tagtga                                                                426
```

<210> SEQ ID NO 33
<211> LENGTH: 140
<212> TYPE: PRT
<213> ORGANISM: Artificial Sequence
<220> FEATURE:
<223> OTHER INFORMATION: Human NME7-B1

<400> SEQUENCE: 33

```
Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe Lys Ile Leu Asp Asn
    130                 135                 140
```

<210> SEQ ID NO 34
<211> LENGTH: 446
<212> TYPE: DNA
<213> ORGANISM: Artificial Sequence
<220> FEATURE:
<223> OTHER INFORMATION: DNA encoding Human NME7-B2

<400> SEQUENCE: 34

```
atgccttcaa gtggaggttg tgggccggca aacactgcta aatttactaa ttgtacctgt      60
tgcattgtta aacccatgc tgtcagtgaa ggactgttgg gaaagatcct gatggctatc     120
```

```
cgagatgcag gttttgaaat ctcagctatg cagatgttca atatggatcg ggttaatgtt      180
gaggaattct atgaagttta taaggagta gtgaccgaat catgacat ggtgacagaa         240 atgtattctg gcccttgtgt agcaatggag attcaacaga taatgctac aaagacattt       300 cgagaatttt gtggacctgc tgatcctgaa attgcccggc atttacgccc tggaactctc      360
agagcaatct ttggtaaaac taagatccag aatgctgttc actgtactga tctgccagag      420
gatggcctat tagaggttca atactt                                           446
```

```
<210> SEQ ID NO 35
<211> LENGTH: 150
<212> TYPE: PRT
<213> ORGANISM: Artificial Sequence
<220> FEATURE:
<223> OTHER INFORMATION: Human NME7-B2

<400> SEQUENCE: 35

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe
145                 150
```

```
<210> SEQ ID NO 36
<211> LENGTH: 471
<212> TYPE: DNA
<213> ORGANISM: Artificial Sequence
<220> FEATURE:
<223> OTHER INFORMATION: DNA encoding Human NME7-B3

<400> SEQUENCE: 36
atgccttcaa gtggaggttg tgggccggca aacactgcta aatttactaa ttgtacctgt       60
tgcattgtta aaccccatgc tgtcagtgaa ggactgttgg gaaagatcct gatggctatc      120
cgagatgcag gttttgaaat ctcagctatg cagatgttca atatggatcg ggttaatgtt      180
gaggaattct atgaagttta taaggagta gtgaccgaat catgacat ggtgacagaa         240 atgtattctg gcccttgtgt agcaatggag attcaacaga taatgctac aaagacattt       300 cgagaatttt gtggacctgc tgatcctgaa attgcccggc atttacgccc tggaactctc      360
agagcaatct ttggtaaaac taagatccag aatgctgttc actgtactga tctgccagag      420
gatggcctat tagaggttca atacttcttc aagatcttgg ataattagtg a               471
```

```
<210> SEQ ID NO 37
<211> LENGTH: 155
<212> TYPE: PRT
<213> ORGANISM: Artificial Sequence
<220> FEATURE:
<223> OTHER INFORMATION: Human NME7-B3

<400> SEQUENCE: 37

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe Lys Ile Leu Asp Asn
145                 150                 155

<210> SEQ ID NO 38
<211> LENGTH: 864
<212> TYPE: DNA
<213> ORGANISM: Artificial Sequence
<220> FEATURE:
<223> OTHER INFORMATION: DNA encoding Human NME7-AB

<400> SEQUENCE: 38
atggaaaaaa cgctagccct aattaaacca gatgcaatat caaaggctgg agaaataatt       60
gaaataataa acaaagctgg atttactata accaaactca aaatgatgat gctttcaagg      120
aaagaagcat tggattttca gtagatcac cagtcaagac cctttttcaa tgagctgatc      180
cagtttatta caactggtcc tattattgcc atggagattt aagagatga tgctatatgt      240 gaatggaaaa gactgctggg acctgcaaac tctggagtgg cacgcacaga tgcttctgaa      300
agcattagag ccctctttgg aacagatggc ataagaaatg cagcgcatgg ccctgattct      360
tttgcttctg cggccagaga atggagttg tttttttcctt caagtggagg ttgtgggccg      420
gcaaacactg ctaaatttac taattgtacc tgttgcattg ttaaacccca tgctgtcagt      480
gaaggactgt tgggaaagat cctgatggct atccgagatg caggttttga atctcagct      540 atgcagatgt tcaatatgga tcgggttaat gttgaggaat ctatgaagt ttataaagga      600 gtagtgaccg aatatcatga catggtgaca gaaatgtatt ctggccttg tgtagcaatg      660 gagattcaac agaataatgc tacaaagaca tttcgagaat tttgtggacc tgctgatcct      720
gaaattgccc ggcatttacg ccctggaact ctcagagcaa tctttggtaa aactaagatc      780
cagaatgctg ttcactgtac tgatctgcca gaggatggcc tattagaggt tcaatacttc      840
ttcaagatct tggataatta gtga                                             864
```

<210> SEQ ID NO 39
<211> LENGTH: 286
<212> TYPE: PRT
<213> ORGANISM: Artificial Sequence
<220> FEATURE:
<223> OTHER INFORMATION: Human NME7-AB

<400> SEQUENCE: 39

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285
```

<210> SEQ ID NO 40
<211> LENGTH: 846
<212> TYPE: DNA
<213> ORGANISM: Artificial Sequence
<220> FEATURE:
<223> OTHER INFORMATION: DNA encoding Human NME7-AB1

<400> SEQUENCE: 40

```
atggaaaaaa cgctagccct aattaaacca gatgcaatat caaaggctgg agaaataatt      60
gaaataataa acaaagctgg atttactata accaaactca aatgatgat gctttcaagg      120 aaagaagcat tggattttca tgtagatcac cagtcaagac ccttttcaa tgagctgatc      180
```

```
cagtttatta caactggtcc tattattgcc atggagattt taagagatga tgctatatgt    240
gaatggaaaa gactgctggg acctgcaaac tctggagtgg cacgcacaga tgcttctgaa    300
agcattagag ccctctttgg aacagatggc ataagaaatg cagcgcatgg ccctgattct    360
tttgcttctg cggccagaga aatggagttg ttttttcctt caagtggagg ttgtgggccg    420
gcaaacactg ctaaatttac taattgtacc tgttgcattg ttaaacccca tgctgtcagt    480
gaaggactgt tgggaaagat cctgatggct atccgagatg caggttttga aatctcagct    540
atgcagatgt tcaatatgga tcgggttaat gttgaggaat tctatgaagt ttataaagga    600
gtagtgaccg aatatcatga catggtgaca gaaatgtatt ctggcccttg tgtagcaatg    660
gagattcaac agaataatgc tacaaagaca tttcgagaat tttgtggacc tgctgatcct    720
gaaattgccc ggcatttacg ccctggaact ctcagagcaa tctttggtaa aactaagatc    780
cagaatgctg ttcactgtac tgatctgcca gaggatggcc tattagaggt tcaatacttc    840
ttctga                                                              846
```

```
<210> SEQ ID NO 41
<211> LENGTH: 281
<212> TYPE: PRT
<213> ORGANISM: Artificial Sequence
<220> FEATURE:
<223> OTHER INFORMATION: Human NME7-AB1

<400> SEQUENCE: 41

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
                20                  25                  30

Leu Lys Met Met Met Leu Ser Arg Lys Glu Ala Leu Asp Phe His Val
            35                  40                  45

Asp His Gln Ser Arg Pro Phe Phe Asn Glu Leu Ile Gln Phe Ile Thr
        50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240
```

Glu Ile Ala Arg His Leu Arg Pro Gly Thr Leu Arg Ala Ile Phe Gly
            245                 250                 255

Lys Thr Lys Ile Gln Asn Ala Val His Cys Thr Asp Leu Pro Glu Asp
        260                 265                 270

Gly Leu Leu Glu Val Gln Tyr Phe Phe
    275                 280

<210> SEQ ID NO 42
<211> LENGTH: 399
<212> TYPE: DNA
<213> ORGANISM: Artificial Sequence
<220> FEATURE:
<223> OTHER INFORMATION: DNA encoding Human NME7-A sequence optimized
      for E. coli expression

<400> SEQUENCE: 42
atggaaaaaa cgctggccct gattaaaccg gatgcaatct ccaaagctgg cgaaattatc      60
gaaattatca caaagcgggt tttcaccatc acgaaactga aaatgatgat gctgagccgt     120
aaagaagccc tggattttca tgtcgaccac cagtctcgcc cgttttttcaa tgaactgatt    180 caattcatca ccacgggtcc gattatcgca atggaaattc tgcgtgatga cgctatctgc    240
gaatggaaac gcctgctggg cccggcaaac tcaggtgttg cgcgtaccga tgccagtgaa    300
tccattcgcg ctctgtttgg caccgatggt atccgtaatg cagcacatgg tccggactca    360
ttcgcatcgg cagctcgtga atggaactg tttttctga                             399

<210> SEQ ID NO 43
<211> LENGTH: 132
<212> TYPE: PRT
<213> ORGANISM: Artificial Sequence
<220> FEATURE:
<223> OTHER INFORMATION: Human NME7-A sequence optimized for E. coli
      expression

<400> SEQUENCE: 43

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe
    130

<210> SEQ ID NO 44
<211> LENGTH: 444
<212> TYPE: DNA
<213> ORGANISM: Artificial Sequence
<220> FEATURE:

<223> OTHER INFORMATION: DNA encoding Human NME7-A1 sequence optimized
      for E. coli expression

<400> SEQUENCE: 44
atggaaaaaa cgctggccct gattaaaccg gatgcaatct ccaaagctgg cgaaattatc      60
gaaattatca acaaagcggg tttcaccatc acgaaactga aaatgatgat gctgagccgt     120
aaagaagccc tggatttca tgtcgaccac cagtctcgcc cgttttca tgaactgatt       180 caattcatca ccacgggtcc gattatcgca atggaaattc tgcgtgatga cgctatctgc     240
gaatggaaac gcctgctggg cccggcaaac tcaggtgttg cgcgtaccga tgccagtgaa     300
tccattcgcg ctctgtttgg caccgatggt atccgtaatg cagcacatgg tccggactca     360
ttcgcatcgg cagctcgtga atggaactg tttttcccga gctctggcgg ttgcggtccg       420
gcaaacaccg ccaaatttac ctga                                             444

<210> SEQ ID NO 45
<211> LENGTH: 147
<212> TYPE: PRT
<213> ORGANISM: Artificial Sequence
<220> FEATURE:
<223> OTHER INFORMATION: Human NME7-A1 sequence optimized for E. coli
      expression

<400> SEQUENCE: 45

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr
145

<210> SEQ ID NO 46
<211> LENGTH: 669
<212> TYPE: DNA
<213> ORGANISM: Artificial Sequence
<220> FEATURE:
<223> OTHER INFORMATION: DNA encoding Human NME7-A2 sequence optimized
      for E. coli expression

<400> SEQUENCE: 46
atgaatcact ccgaacgctt tgttttatc gccgaatggt atgacccgaa tgcttccctg      60
ctgcgccgct acgaactgct gttttatccg ggcgatggta gcgtggaaat gcatgacgtt    120
aaaaatcacc gtacctttct gaaacgcacg aaatatgata atctgcatct ggaagacctg    180

```
tttattggca  acaaagtcaa  tgtgttctct  cgtcagctgg  tgctgatcga  ttatggcgac     240
cagtacaccg  cgcgtcaact  gggtagtcgc  aaagaaaaaa  cgctggccct  gattaaaccg     300
gatgcaatct  ccaaagctgg  cgaaattatc  gaaattatca  acaaagcggg  tttcaccatc     360
acgaaactga  aaatgatgat  gctgagccgt  aaagaagccc  tggattttca  tgtcgaccac     420
cagtctcgcc  cgttttcaa   tgaactgatt  caattcatca  ccacgggtcc  gattatcgca     480
atggaaattc  tgcgtgatga  cgctatctgc  gaatggaaac  gcctgctggg  cccggcaaac     540
tcaggtgttg  cgcgtaccga  tgccagtgaa  tccattcgcg  ctctgtttgg  caccgatggt     600
atccgtaatg  cagcacatgg  tccggactca  ttcgcatcgg  cagctcgtga  aatggaactg     660
tttttctga                                                                  669
```

<210> SEQ ID NO 47
<211> LENGTH: 222
<212> TYPE: PRT
<213> ORGANISM: Artificial Sequence
<220> FEATURE:
<223> OTHER INFORMATION: Human NME7-A2 sequence optimized for E. coli
      expression

<400> SEQUENCE: 47

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe
    210                 215                 220
```

<210> SEQ ID NO 48
<211> LENGTH: 714
<212> TYPE: DNA
<213> ORGANISM: Artificial Sequence
<220> FEATURE:
<223> OTHER INFORMATION: DNA encoding Human NME7-A3 sequence optimized
      for E. coli expression -continued

<400> SEQUENCE: 48

```
atgaatcact ccgaacgctt tgttttatc gccgaatggt atgacccgaa tgcttccctg      60
ctgcgccgct acgaactgct gttttatccg ggcgatggta gcgtggaaat gcatgacgtt     120
aaaaatcacc gtacctttct gaaacgcacg aaatatgata tctgcatct ggaagacctg      180
tttattggca acaaagtcaa tgtgttctct cgtcagctgg tgctgatcga ttatggcgac     240
cagtacaccg cgcgtcaact gggtagtcgc aagaaaaaa cgctggccct gattaaaccg      300
gatgcaatct ccaaagctgg cgaaattatc gaaattatca acaaagcggg tttcaccatc     360
acgaaactga aaatgatgat gctgagccgt aagaagccc tggattttca tgtcgaccac      420
cagtctcgcc cgttttttcaa tgaactgatt caattcatca ccacgggtcc gattatcgca    480
atggaaattc tgcgtgatga cgctatctgc gaatggaaac gcctgctggg cccggcaaac    540
tcaggtgttg cgcgtaccga tgccagtgaa tccattcgcg ctctgtttgg caccgatggt    600
atccgtaatg cagcacatgg tccggactca ttcgcatcgg cagctcgtga atgggaactg     660
ttttccccga gctctggcgg ttgcggtccg gcaaacaccg ccaaatttac ctga           714
```

<210> SEQ ID NO 49
<211> LENGTH: 237
<212> TYPE: PRT
<213> ORGANISM: Artificial Sequence
<220> FEATURE:
<223> OTHER INFORMATION: Human NME7-A3 sequence optimized for E. coli
      expression

<400> SEQUENCE: 49

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220
```

```
Ser Gly Gly Cys Gly Pro Ala Asn Thr Ala Lys Phe Thr
225                 230                 235
```

<210> SEQ ID NO 50
<211> LENGTH: 408
<212> TYPE: DNA
<213> ORGANISM: Artificial Sequence
<220> FEATURE:
<223> OTHER INFORMATION: DNA encoding Human NME7-B sequence optimized
      for E. coli expression

<400> SEQUENCE: 50

```
atgaattgta cgtgctgtat tgtcaaaccg cacgcagtgt cagaaggcct gctgggtaaa      60
attctgatgg caatccgtga tgctggcttt gaaatctcgg ccatgcagat gttcaacatg     120
gaccgcgtta acgtcgaaga attctacgaa gtttacaaag cgtggttac cgaatatcac     180 gatatggtta cggaaatgta ctccggtccg tgcgtcgcga tggaaattca gcaaaacaat     240
gccaccaaaa cgtttcgtga attctgtggt ccggcagatc cggaaatcgc acgtcatctg     300
cgtccgggta ccctgcgcgc aattttggt aaaacgaaaa tccagaacgc tgtgcactgt     360
accgatctgc cggaagacgg tctgctggaa gttcaatact ttttctga                 408
```

<210> SEQ ID NO 51
<211> LENGTH: 135
<212> TYPE: PRT
<213> ORGANISM: Artificial Sequence
<220> FEATURE:
<223> OTHER INFORMATION: Human NME7-B sequence optimized for E. coli
      expression

<400> SEQUENCE: 51

```
Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe
    130                 135
```

<210> SEQ ID NO 52
<211> LENGTH: 423
<212> TYPE: DNA
<213> ORGANISM: Artificial Sequence
<220> FEATURE:
<223> OTHER INFORMATION: DNA encoding Human NME7-B1 sequence optimized
      for E. coli expression

<400> SEQUENCE: 52

```
atgaattgta cgtgctgtat tgtcaaaccg cacgcagtgt cagaaggcct gctgggtaaa      60
```

```
attctgatgg caatccgtga tgctggcttt gaaatctcgg ccatgcagat gttcaacatg    120
gaccgcgtta acgtcgaaga attctacgaa gtttacaaag gcgtggttac cgaatatcac    180
gatatggtta cggaaatgta ctccggtccg tgcgtcgcga tggaaattca gcaaacaat     240 gccaccaaaa cgtttcgtga attctgtggt ccggcagatc cggaaatcgc acgtcatctg    300
cgtccgggta ccctgcgcgc aattttggt aaaacgaaaa tccagaacgc tgtgcactgt     360
accgatctgc cggaagacgg tctgctggaa gttcaatact ttttcaaaat tctggataat    420
tga                                                                 423
```

<210> SEQ ID NO 53
<211> LENGTH: 140
<212> TYPE: PRT
<213> ORGANISM: Artificial Sequence
<220> FEATURE:
<223> OTHER INFORMATION: Human NME7-B1 sequence optimized for E. coli
      expression

<400> SEQUENCE: 53

```
Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe Lys Ile Leu Asp Asn
    130                 135                 140
```

<210> SEQ ID NO 54
<211> LENGTH: 453
<212> TYPE: DNA
<213> ORGANISM: Artificial Sequence
<220> FEATURE:
<223> OTHER INFORMATION: DNA encoding Human NME7-B2 sequence optimized
      for E. coli expression

<400> SEQUENCE: 54

```
atgccgagct ctggcggttg cggtccggca acaccgcca aatttaccaa ttgtacgtgc     60
tgtattgtca aaccgcacgc agtgtcagaa ggcctgctgg gtaaaattct gatggcaatc    120
cgtgatgctg gctttgaaat ctcggccatg cagatgttca acatggaccg cgttaacgtc    180
gaagaattct acgaagttta caaaggcgtg gttaccgaat atcacgatat ggttacggaa    240
atgtactccg gtccgtgcgt cgcgatggaa attcagcaaa acaatgccac caaaacgttt    300
cgtgaattct gtggtccggc agatccggaa atcgcacgtc atctgcgtcc gggtaccctg    360
cgcgcaattt ttggtaaaac gaaaatccag aacgctgtgc actgtaccga tctgccggaa    420
gacggtctgc tggaagttca atactttttc tga                                453
```

<210> SEQ ID NO 55
<211> LENGTH: 150
<212> TYPE: PRT
<213> ORGANISM: Artificial Sequence
<220> FEATURE:
<223> OTHER INFORMATION: Human NME7-B2 sequence optimized for E. coli
      expression

<400> SEQUENCE: 55

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe
145                 150

<210> SEQ ID NO 56
<211> LENGTH: 468
<212> TYPE: DNA
<213> ORGANISM: Artificial Sequence
<220> FEATURE:
<223> OTHER INFORMATION: DNA encoding Human NME7-B3 sequence optimized
      for E. coli expression

<400> SEQUENCE: 56
atgccgagct ctggcggttg cggtccggca acaccgcca aatttaccaa ttgtacgtgc      60
tgtattgtca aaccgcacgc agtgtcagaa ggcctgctgg gtaaaattct gatggcaatc    120
cgtgatgctg gctttgaaat ctcggccatg cagatgttca acatggaccg cgttaacgtc    180
gaagaattct acgaagttta caaaggcgtg gttaccgaat atcacgatat ggttacggaa    240
atgtactccg gtccgtgcgt cgcgatggaa attcagcaaa acaatgccac caaaacgttt    300
cgtgaattct gtggtccggc agatccggaa atcgcacgtc atctgcgtcc gggtaccctg    360
cgcgcaattt ttggtaaaac gaaaatccag aacgctgtgc actgtaccga tctgccggaa    420
gacggtctgc tggaagttca atactttttc aaaattctgg ataattga                 468

<210> SEQ ID NO 57
<211> LENGTH: 155
<212> TYPE: PRT
<213> ORGANISM: Artificial Sequence
<220> FEATURE:
<223> OTHER INFORMATION: Human NME7-B3 sequence optimized for E. coli
      expression

<400> SEQUENCE: 57

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
50                  55                  60

Glu Val Tyr Lys Gly Val Val Thr Glu Tyr His Asp Met Val Thr Glu
65              70                  75                  80

Met Tyr Ser Gly Pro Cys Val Ala Met Glu Ile Gln Gln Asn Asn Ala
            85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
130                 135                 140

Glu Val Gln Tyr Phe Phe Lys Ile Leu Asp Asn
145                 150                 155

<210> SEQ ID NO 58
<211> LENGTH: 861
<212> TYPE: DNA
<213> ORGANISM: Artificial Sequence
<220> FEATURE:
<223> OTHER INFORMATION: DNA encoding Human NME7-AB sequence optimized
      for E. coli expression

<400> SEQUENCE: 58
atggaaaaaa cgctggccct gattaaaccg gatgcaatct ccaaagctgg cgaaattatc      60
gaaattatca caaagcggg tttcaccatc acgaaactga aatgatgat gctgagccgt      120
aaagaagccc tggatttca gtcgaccac cagtctcgcc cgttttcaa tgaactgatt       180
caattcatca ccacgggtcc gattatcgca atgaaattc tgcgtgatga cgctatctgc      240
gaatggaaac gcctgctggg cccggcaaac tcaggtgttg cgcgtaccga tgccagtgaa      300
tccattcgcg ctctgtttgg caccgatggt atccgtaatg cagcacatgg tccggactca      360
ttcgcatcgg cagctcgtga atggaactg tttttcccga gctctggcgg ttgcggtccg      420
gcaaacaccg ccaaatttac caattgtacg tgctgtattg tcaaaccgca cgcagtgtca      480
gaaggcctgc tgggtaaaat tctgatggca atccgtgatg ctggctttga atctcggcc      540
atgcagatgt tcaacatgga ccgcgttaac gtcgaagaat tctacgaagt ttacaaaggc      600
gtggttaccg aatatcacga tatggttacg gaaatgtact ccggtccgtg cgtcgcgatg      660
gaaattcagc aaaacaatgc caccaaaacg tttcgtgaat ctgtggtcc ggcagatccg      720
gaaatcgcac gtcatctgcg tccgggtacc ctgcgcgcaa tttttggtaa aacgaaaatc      780
cagaacgctg tgcactgtac cgatctgccg gaagacggtc tgctggaagt tcaatacttt      840
ttcaaaattc tggataattg a                                               861

<210> SEQ ID NO 59
<211> LENGTH: 286
<212> TYPE: PRT
<213> ORGANISM: Artificial Sequence
<220> FEATURE:
<223> OTHER INFORMATION: Human NME7-AB sequence optimized for E. coli -continued expression

<400> SEQUENCE: 59

```
Met Glu Lys Thr Leu Ala Leu Ile Lys Pro Asp Ala Ile Ser Lys Ala
1               5                   10                  15
Gly Glu Ile Ile Glu Ile Ile Asn Lys Ala Gly Phe Thr Ile Thr Lys
            20                  25                  30
Leu Lys Met Met Met Leu Ser Arg Lys Glu Ala Leu Asp Phe His Val
        35                  40                  45
Asp His Gln Ser Arg Pro Phe Phe Asn Glu Leu Ile Gln Phe Ile Thr
    50                  55                  60
Thr Gly Pro Ile Ile Ala Met Glu Ile Leu Arg Asp Asp Ala Ile Cys
65                  70                  75                  80
Glu Trp Lys Arg Leu Leu Gly Pro Ala Asn Ser Gly Val Ala Arg Thr
                85                  90                  95
Asp Ala Ser Glu Ser Ile Arg Ala Leu Phe Gly Thr Asp Gly Ile Arg
            100                 105                 110
Asn Ala Ala His Gly Pro Asp Ser Phe Ala Ser Ala Ala Arg Glu Met
        115                 120                 125
Glu Leu Phe Phe Pro Ser Ser Gly Gly Cys Gly Pro Ala Asn Thr Ala
    130                 135                 140
Lys Phe Thr Asn Cys Thr Cys Cys Ile Val Lys Pro His Ala Val Ser
145                 150                 155                 160
Glu Gly Leu Leu Gly Lys Ile Leu Met Ala Ile Arg Asp Ala Gly Phe
                165                 170                 175
Glu Ile Ser Ala Met Gln Met Phe Asn Met Asp Arg Val Asn Val Glu
            180                 185                 190
Glu Phe Tyr Glu Val Tyr Lys Gly Val Val Thr Glu Tyr His Asp Met
        195                 200                 205
Val Thr Glu Met Tyr Ser Gly Pro Cys Val Ala Met Glu Ile Gln Gln
    210                 215                 220
Asn Asn Ala Thr Lys Thr Phe Arg Glu Phe Cys Gly Pro Ala Asp Pro
225                 230                 235                 240
Glu Ile Ala Arg His Leu Arg Pro Gly Thr Leu Arg Ala Ile Phe Gly
                245                 250                 255
Lys Thr Lys Ile Gln Asn Ala Val His Cys Thr Asp Leu Pro Glu Asp
            260                 265                 270
Gly Leu Leu Glu Val Gln Tyr Phe Phe Lys Ile Leu Asp Asn
        275                 280                 285
```

<210> SEQ ID NO 60
<211> LENGTH: 846
<212> TYPE: DNA
<213> ORGANISM: Artificial Sequence
<220> FEATURE:
<223> OTHER INFORMATION: DNA encoding Human NME7-AB1 sequence optimized
      for E. coli expression

<400> SEQUENCE: 60

```
atggaaaaaa cgctggccct gattaaaccg gatgcaatct ccaaagctgg cgaaattatc    60
gaaattatca caaagcgggt tttcaccatc acgaaactga aatgatgat gctgagccgt    120 aaagaagccc tggattttca gtcgaccac cagtctcgcc cgttttttcaa tgaactgatt    180 caattcatca ccacgggtcc gattatcgca atggaaattc tgcgtgatga cgctatctgc    240
gaatggaaac gcctgctggg cccggcaaac tcaggtgttg cgcgtaccga tgccagtgaa    300
```

```
tccattcgcg ctctgtttgg caccgatggt atccgtaatg cagcacatgg tccggactca    360
ttcgcatcgg cagctcgtga aatggaactg ttttccccga gctctggcgg ttgcggtccg    420
gcaaacaccg ccaaatttac caattgtacg tgctgtattg tcaaaccgca cgcagtgtca    480
gaaggcctgc tgggtaaaat tctgatggca atccgtgatg ctggctttga atctcggcc    540 atgcagatgt tcaacatgga ccgcgttaac gtcgaagaat ctacgaagt ttacaaaggc    600 gtggttaccg aatatcacga tatggttacg gaaatgtact ccggtccgtg cgtcgcgatg    660
gaaattcagc aaaacaatgc caccaaaacg tttcgtgaat ctgtggtcc ggcagatccg    720 gaaatcgcac gtcatctgcg tccgggtacc ctgcgcgcaa ttttggtaa aacgaaaatc    780 cagaacgctg tgcactgtac cgatctgccg gaagacggtc tgctggaagt tcaatacttt    840
ttctga                                                               846

<210> SEQ ID NO 61
<211> LENGTH: 281
<212> TYPE: PRT
<213> ORGANISM: Artificial Sequence
<220> FEATURE:
<223> OTHER INFORMATION: Human NME7-AB1 sequence optimized for E. coli
      expression

<400> SEQUENCE: 61

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255
```

```
Lys Thr Lys Ile Gln Asn Ala Val His Cys Thr Asp Leu Pro Glu Asp
            260                 265                 270

Gly Leu Leu Glu Val Gln Tyr Phe Phe
        275                 280

<210> SEQ ID NO 62
<211> LENGTH: 570
<212> TYPE: DNA
<213> ORGANISM: Artificial Sequence
<220> FEATURE:
<223> OTHER INFORMATION: DNA encoding Mouse NME6

<400> SEQUENCE: 62
atgacctcca tcttgcgaag tccccaagct cttcagctca cactagccct gatcaagcct      60
gatgcagttg cccacccact gatcctggag gctgttcatc agcagattct gagcaacaag     120
ttcctcattg tacgaacgag ggaactgcag tggaagctgg aggactgccg gaggttttac     180
cgagagcatg aagggcgttt tttctatcag cggctggtgg agttcatgac aagtgggcca     240
atccgagcct atatccttgc cacaaagat gccatccaac tttggaggac actgatggga     300
cccaccagag tatttcgagc acgctatata gccccagatt caattcgtgg aagtttgggc     360
ctcactgaca cccgaaatac tacccatggc tcagactccg tggtttccgc cagcagagag     420
attgcagcct tcttccctga cttcagtgaa cagcgctggt atgaggagga ggaaccccag     480
ctgcggtgtg gtcctgtgca ctacagtcca ggaggaaggta tccactgtgc agctgaaaca     540
ggaggccaca acaacctaa caaaacctag                                        570

<210> SEQ ID NO 63
<211> LENGTH: 189
<212> TYPE: PRT
<213> ORGANISM: Artificial Sequence
<220> FEATURE:
<223> OTHER INFORMATION: Mouse NME6

<400> SEQUENCE: 63

Met Thr Ser Ile Leu Arg Ser Pro Gln Ala Leu Gln Leu Thr Leu Ala
1               5                  10                  15

Leu Ile Lys Pro Asp Ala Val Ala His Pro Leu Ile Leu Glu Ala Val
            20                  25                  30

His Gln Gln Ile Leu Ser Asn Lys Phe Leu Ile Val Arg Thr Arg Glu
        35                  40                  45

Leu Gln Trp Lys Leu Glu Asp Cys Arg Arg Phe Tyr Arg Glu His Glu
    50                  55                  60

Gly Arg Phe Phe Tyr Gln Arg Leu Val Glu Phe Met Thr Ser Gly Pro
65                  70                  75                  80

Ile Arg Ala Tyr Ile Leu Ala His Lys Asp Ala Ile Gln Leu Trp Arg
                85                  90                  95

Thr Leu Met Gly Pro Thr Arg Val Phe Arg Ala Arg Tyr Ile Ala Pro
            100                 105                 110

Asp Ser Ile Arg Gly Ser Leu Gly Leu Thr Asp Thr Arg Asn Thr Thr
        115                 120                 125

His Gly Ser Asp Ser Val Val Ser Ala Ser Arg Glu Ile Ala Ala Phe
    130                 135                 140

Phe Pro Asp Phe Ser Glu Gln Arg Trp Tyr Glu Glu Glu Pro Gln
145                 150                 155                 160

Leu Arg Cys Gly Pro Val His Tyr Ser Pro Glu Glu Gly Ile His Cys
                165                 170                 175
```

Ala Ala Glu Thr Gly Gly His Lys Gln Pro Asn Lys Thr
            180                 185

<210> SEQ ID NO 64
<211> LENGTH: 585
<212> TYPE: DNA
<213> ORGANISM: Artificial Sequence
<220> FEATURE:
<223> OTHER INFORMATION: DNA encoding Human NME6

<400> SEQUENCE: 64

```
atgacccaga atctggggag tgagatggcc tcaatcttgc gaagccctca ggctctccag    60
ctcactctag ccctgatcaa gcctgacgca gtcgcccatc cactgattct ggaggctgtt   120
catcagcaga ttctaagcaa caagttcctg attgtacgaa tgagagaact actgtggaga   180
aaggaagatt gccagaggtt ttaccgagag catgaagggc gttttttcta tcagaggctg   240
gtggagttca tggccagcgg gccaatccga gcctacatcc ttgcccacaa ggatgccatc   300
cagctctgga gacgctcat gggacccacc agagtgttcc gagcacgcca tgtggcccca   360
gattctatcc gtgggagttt cggcctcact gacacccgca acaccaccca tggttcggac   420
tctgtggttt cagccagcag agagattgca gccttcttcc ctgacttcag tgaacagcgc   480
tggtatgagg aggaagagcc ccagttgcgc tgtggccctg tgctatag cccagaggga   540 ggtgtccact atgtagctgg aacaggaggc ctaggaccag cctga                   585
```

<210> SEQ ID NO 65
<211> LENGTH: 194
<212> TYPE: PRT
<213> ORGANISM: Artificial Sequence
<220> FEATURE:
<223> OTHER INFORMATION: Human NME6

<400> SEQUENCE: 65

Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Gly Leu Gly
            180                 185                 190

Pro Ala

<210> SEQ ID NO 66
<211> LENGTH: 525
<212> TYPE: DNA
<213> ORGANISM: Artificial Sequence
<220> FEATURE:
<223> OTHER INFORMATION: DNA encoding Human NME6 1

<400> SEQUENCE: 66

```
atgacccaga atctggggag tgagatggcc tcaatcttgc gaagccctca ggctctccag      60
ctcactctag ccctgatcaa gcctgacgca gtcgcccatc cactgattct ggaggctgtt     120
catcagcaga ttctaagcaa caagttcctg attgtacgaa tgagagaact actgtggaga     180
aaggaagatt gccagaggtt ttaccgagag catgaagggc gttttttcta tcagaggctg     240
gtggagttca tggccagcgg gccaatccga gcctacatcc ttgcccacaa ggatgccatc     300
cagctctgga ggacgctcat gggacccacc agagtgttcc gagcacgcca tgtggcccca     360
gattctatcc gtgggagttt cggcctcact gacacccgca acaccaccca tggttcggac     420
tctgtggttt cagccagcag agagattgca gccttcttcc ctgacttcag tgaacagcgc     480
tggtatgagg aggaagagcc ccagttgcgc tgtggccctg tgtga                     525
```

<210> SEQ ID NO 67
<211> LENGTH: 174
<212> TYPE: PRT
<213> ORGANISM: Artificial Sequence
<220> FEATURE:
<223> OTHER INFORMATION: Human NME6 1

<400> SEQUENCE: 67

```
Met Thr Gln Asn Leu Gly Ser Glu Met Ala Ser Ile Leu Arg Ser Pro
 1               5                  10                  15

Gln Ala Leu Gln Leu Thr Leu Ala Leu Ile Lys Pro Asp Ala Val Ala
             20                  25                  30

His Pro Leu Ile Leu Glu Ala Val His Gln Gln Ile Leu Ser Asn Lys
         35                  40                  45

Phe Leu Ile Val Arg Met Arg Glu Leu Leu Trp Arg Lys Glu Asp Cys
     50                  55                  60

Gln Arg Phe Tyr Arg Glu His Glu Gly Arg Phe Phe Tyr Gln Arg Leu
 65                  70                  75                  80

Val Glu Phe Met Ala Ser Gly Pro Ile Arg Ala Tyr Ile Leu Ala His
                 85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val
                165                 170
```

<210> SEQ ID NO 68
<211> LENGTH: 468
<212> TYPE: DNA
<213> ORGANISM: Artificial Sequence
<220> FEATURE:

<223> OTHER INFORMATION: DNA encoding Human NME6 2

<400> SEQUENCE: 68

| | | | | | |
|---|---|---|---|---|---|
| atgctcactc | tagccctgat | caagcctgac | gcagtcgccc | atccactgat | tctggaggct | 60 |
| gttcatcagc | agattctaag | caacaagttc | ctgattgtac | gaatgagaga | actactgtgg | 120 |
| agaaaggaag | attgccagag | gttttaccga | gagcatgaag | ggcgttttt | ctatcagagg | 180 |
| ctggtggagt | tcatggccag | cgggccaatc | cgagcctaca | tccttgccca | caaggatgcc | 240 |
| atccagctct | ggaggacgct | catgggaccc | accagagtgt | tccgagcacg | ccatgtggcc | 300 |
| ccagattcta | tccgtgggag | tttcggcctc | actgacaccc | gcaacaccac | ccatggttcg | 360 |
| gactctgtgg | tttcagccag | cagagagatt | gcagccttct | tccctgactt | cagtgaacag | 420 |
| cgctggtatg | aggaggaaga | gccccagttg | cgctgtggcc | ctgtgtga | | 468 |

<210> SEQ ID NO 69
<211> LENGTH: 155
<212> TYPE: PRT
<213> ORGANISM: Artificial Sequence
<220> FEATURE:
<223> OTHER INFORMATION: Human NME6 2

<400> SEQUENCE: 69

```
Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
            20                  25                  30

Val Arg Met Arg Glu Leu Leu Trp Arg Lys Glu Asp Cys Gln Arg Phe
        35                  40                  45

Tyr Arg Glu His Glu Gly Arg Phe Phe Tyr Gln Arg Leu Val Glu Phe
    50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val
145                 150                 155
```

<210> SEQ ID NO 70
<211> LENGTH: 528
<212> TYPE: DNA
<213> ORGANISM: Artificial Sequence
<220> FEATURE:
<223> OTHER INFORMATION: DNA encoding Human NME6 3

<400> SEQUENCE: 70

| | | | | | |
|---|---|---|---|---|---|
| atgctcactc | tagccctgat | caagcctgac | gcagtcgccc | atccactgat | tctggaggct | 60 |
| gttcatcagc | agattctaag | caacaagttc | ctgattgtac | gaatgagaga | actactgtgg | 120 |
| agaaaggaag | attgccagag | gttttaccga | gagcatgaag | ggcgttttt | ctatcagagg | 180 |
| ctggtggagt | tcatggccag | cgggccaatc | cgagcctaca | tccttgccca | caaggatgcc | 240 |
| atccagctct | ggaggacgct | catgggaccc | accagagtgt | tccgagcacg | ccatgtggcc | 300 |

```
ccagattcta tccgtgggag tttcggcctc actgacaccc gcaacaccac ccatggttcg    360
gactctgtgg tttcagccag cagagagatt gcagccttct tccctgactt cagtgaacag    420
cgctggtatg aggaggaaga gccccagttg cgctgtggcc ctgtgtgcta tagcccagag    480
ggaggtgtcc actatgtagc tggaacagga ggcctaggac cagcctga                 528
```

```
<210> SEQ ID NO 71
<211> LENGTH: 175
<212> TYPE: PRT
<213> ORGANISM: Artificial Sequence
<220> FEATURE:
<223> OTHER INFORMATION: Human NME6 3

<400> SEQUENCE: 71

Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
            20                  25                  30

Val Arg Met Arg Glu Leu Leu Trp Arg Lys Glu Asp Cys Gln Arg Phe
        35                  40                  45

Tyr Arg Glu His Glu Gly Arg Phe Phe Tyr Arg Leu Val Glu Phe
    50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val Cys Tyr Ser Pro Glu
145                 150                 155                 160

Gly Gly Val His Tyr Val Ala Gly Thr Gly Gly Leu Gly Pro Ala
                165                 170                 175
```

```
<210> SEQ ID NO 72
<211> LENGTH: 585
<212> TYPE: DNA
<213> ORGANISM: Artificial Sequence
<220> FEATURE:
<223> OTHER INFORMATION: DNA encoding Human NME6 sequence optimized for
      E. coli expression

<400> SEQUENCE: 72
atgacgcaaa atctgggctc ggaaatggca agtatcctgc gctccccgca agcactgcaa    60
ctgaccctgg ctctgatcaa accggacgct gttgctcatc cgctgattct ggaagcggtc   120
caccagcaaa ttctgagcaa caaatttctg atcgtgcgta tgcgcgaact gctgtggcgt   180
aaagaagatt gccagcgttt ttatcgcgaa catgaaggcc gtttcttttta tcaacgcctg   240 gttgaattca tggcctctgg tccgattcgc gcatatatcc tggctcacaa agatgcgatt   300
cagctgtggc gtaccctgat gggtccgacg cgcgtctttc gtgcacgtca tgtggcaccg   360
gactcaatcc gtggctcgtt cggtctgacc gatacgcgca ataccacgca cggtagcgac   420
tctgttgtta gtgcgtcccg tgaaatcgcg gccttttttcc cggacttctc cgaacagcgt   480
```

```
tggtacgaag aagaagaacc gcaactgcgc tgtggcccgg tctgttattc tccggaaggt      540
ggtgtccatt atgtggcggg cacgggtggt ctgggtccgg catga                     585
```

<210> SEQ ID NO 73
<211> LENGTH: 194
<212> TYPE: PRT
<213> ORGANISM: Artificial Sequence
<220> FEATURE:
<223> OTHER INFORMATION: Human NME6 sequence optimized for E. coli
      expression

<400> SEQUENCE: 73

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
                20                  25                  30

His Pro Leu Ile Leu Glu Ala Val His Gln Gln Ile Leu Ser Asn Lys
            35                  40                  45

Phe Leu Ile Val Arg Met Arg Glu Leu Leu Trp Arg Lys Glu Asp Cys
        50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Leu Gly
            180                 185                 190

Pro Ala
```

<210> SEQ ID NO 74
<211> LENGTH: 525
<212> TYPE: DNA
<213> ORGANISM: Artificial Sequence
<220> FEATURE:
<223> OTHER INFORMATION: DNA encoding Human NME6 1 sequence optimized
      for E. coli expression

<400> SEQUENCE: 74

```
atgacgcaaa atctgggctc ggaaatggca agtatcctgc gctccccgca agcactgcaa      60
ctgaccctgg ctctgatcaa accggacgct gttgctcatc cgctgattct ggaagcggtc     120
caccagcaaa ttctgagcaa caaatttctg atcgtgcgta tgcgcgaact gctgtggcgt     180
aaagaagatt gccagcgttt ttatcgcgaa catgaaggcc gtttcttttt tcaacgcctg     240
gttgaattca tggcctctgg tccgattcgc gcatatatcc tggctcacaa agatgcgatt     300
cagctgtggc gtaccctgat gggtccgacg cgcgtctttc gtgcacgtca tgtggcaccg     360
gactcaatcc gtggctcgtt cggtctgacc gatacgcgca ataccacgca cggtagcgac     420
tctgttgtta gtgcgtcccg tgaaatcgcg gcctttttcc cggacttctc cgaacagcgt     480
```
tggtacgaag aagaagaacc gcaactgcgc tgtggcccgg tctga                    525

<210> SEQ ID NO 75
<211> LENGTH: 174
<212> TYPE: PRT
<213> ORGANISM: Artificial Sequence
<220> FEATURE:
<223> OTHER INFORMATION: Human NME6 1 sequence optimized for E. coli
      expression

<400> SEQUENCE: 75

Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val
                165                 170

<210> SEQ ID NO 76
<211> LENGTH: 468
<212> TYPE: DNA
<213> ORGANISM: Artificial Sequence
<220> FEATURE:
<223> OTHER INFORMATION: DNA encoding Human NME6 2 sequence optimized
      for E. coli expression

<400> SEQUENCE: 76
atgctgaccc tggctctgat caaaccggac gctgttgctc atccgctgat tctggaagcg    60
gtccaccagc aaattctgag caacaaattt ctgatcgtgc gtatgcgcga actgctgtgg    120
cgtaaagaag attgccagcg tttttatcgc gaacatgaag ccgtttctt ttatcaacgc    180 ctggttgaat tcatggcctc tggtccgatt cgcgcatata tcctggctca caaagatgcg    240
attcagctgt ggcgtaccct gatgggtccg acgcgcgtct tcgtgcacg tcatgtggca    300 ccggactcaa tccgtggctc gttcggtctg accgatacgc gcaataccac gcacggtagc    360
gactctgttg ttagtgcgtc ccgtgaaatc gcggccttt tcccggactt ctccgaacag    420
cgttggtacg aagaagaaga accgcaactg cgctgtggcc cggtctga               468

<210> SEQ ID NO 77
<211> LENGTH: 155
<212> TYPE: PRT
<213> ORGANISM: Artificial Sequence
<220> FEATURE:
<223> OTHER INFORMATION: Human NME6 2 sequence optimized for E. coli
      expression

<400> SEQUENCE: 77

Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
            20                  25                  30

Val Arg Met Arg Glu Leu Leu Trp Arg Lys Glu Asp Cys Gln Arg Phe
        35                  40                  45

Tyr Arg Glu His Glu Gly Arg Phe Phe Tyr Gln Arg Leu Val Glu Phe
    50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val
145                 150                 155

<210> SEQ ID NO 78
<211> LENGTH: 528
<212> TYPE: DNA
<213> ORGANISM: Artificial Sequence
<220> FEATURE:
<223> OTHER INFORMATION: DNA encoding Human NME6 3 sequence optimized
      for E. coli expression

<400> SEQUENCE: 78
atgctgaccc tggctctgat caaaccggac gctgttgctc atccgctgat tctggaagcg      60
gtccaccagc aaattctgag caacaaattt ctgatcgtgc gtatgcgcga actgctgtgg     120
cgtaaagaag attgccagcg ttttatcgc gaacatgaag ccgtttctt ttatcaacgc       180
ctggttgaat catggcctc tggtccgatt cgcgcatata tcctggctca caaagatgcg      240
attcagctgt ggcgtaccct gatgggtccg acgcgcgtct ttcgtgcacg tcatgtggca     300
ccggactcaa tccgtggctc gttcggtctg accgatacgc gcaataccac gcacggtagc     360
gactctgttg ttagtgcgtc ccgtgaaatc gcggcctttt tcccggactt ctccgaacag     420
cgttggtacg aagaagaaga accgcaactg cgctgtggcc cggtctgtta ttctccggaa     480
ggtggtgtcc attatgtggc gggcacgggt ggtctgggtc cggcatga                  528

<210> SEQ ID NO 79
<211> LENGTH: 175
<212> TYPE: PRT
<213> ORGANISM: Artificial Sequence
<220> FEATURE:
<223> OTHER INFORMATION: Human NME6 3 sequence optimized for E. coli
      expression

<400> SEQUENCE: 79

Met Leu Thr Leu Ala Leu Ile Lys Pro Asp Ala Val Ala His Pro Leu
1               5                   10                  15

```
Ile Leu Glu Ala Val His Gln Gln Ile Leu Ser Asn Lys Phe Leu Ile
             20                  25                  30

Val Arg Met Arg Glu Leu Leu Trp Arg Lys Glu Asp Cys Gln Arg Phe
         35                  40                  45

Tyr Arg Glu His Glu Gly Arg Phe Phe Tyr Gln Arg Leu Val Glu Phe
     50                  55                  60

Met Ala Ser Gly Pro Ile Arg Ala Tyr Ile Leu Ala His Lys Asp Ala
 65                  70                  75                  80

Ile Gln Leu Trp Arg Thr Leu Met Gly Pro Thr Arg Val Phe Arg Ala
                 85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val Cys Tyr Ser Pro Glu
145                 150                 155                 160

Gly Gly Val His Tyr Val Ala Gly Thr Gly Gly Leu Gly Pro Ala
                165                 170                 175

<210> SEQ ID NO 80
<211> LENGTH: 1306
<212> TYPE: DNA
<213> ORGANISM: Artificial Sequence
<220> FEATURE:
<223> OTHER INFORMATION: DNA encoding OriGene-NME7-1 full length

<400> SEQUENCE: 80
gacgttgtat acgactccta tagggcggcc gggaattcgt cgactggatc cggtaccgag     60
gagatctgcc gccgcgatcg ccatgaatca tagtgaaaga ttcgttttca ttgcagagtg    120
gtatgatcca aatgcttcac ttcttcgacg ttatgagctt ttattttacc caggggatgg    180
atctgttgaa atgcatgatg taaagaatca tcgcaccttt ttaaagcgga ccaaatatga    240
taacctgcac ttggaagatt tatttatagg caacaaagtg aatgtcttct ctcgacaact    300
ggtattaatt gactatgggg atcaatatac agctcgccag ctgggcagta ggaaagaaaa    360
aacgctagcc ctaattaaac cagatgcaat atcaaaggct ggagaaataa ttgaaataat    420
aaacaaagct ggatttacta taaccaaact caaaatgatg atgctttcaa ggaaagaagc    480
attggatttt catgtagatc accagtcaag accctttttc aatgagctga tccagtttat    540
tacaactggt cctattattg ccatggagat tttaagagat gatgctatat gtgaatggaa    600
aagactgctg ggacctgcaa actctggagt ggcacgcaca gatgcttctg aaagcattag    660
agccctcttt ggaacagatg gcataagaaa tgcagcgcat ggccctgatt cttttgcttc    720
tgcggccaga gaatggagt tgttttttcc ttcaagtgga ggtgtgggc cggcaaacac    780 tgctaaattt actaattgta cctgttgcat tgttaaaccc catgctgtca gtgaaggact    840
gttgggaaag atcctgatgg ctatccgaga tgcaggtttt gaaatctcag ctatgcagat    900
gttcaatatg gatcgggtta atgttgagga attctatgaa gtttataaag gagtagtgac    960
cgaatatcat gacatggtga cagaaatgta ttctggccct gtgtagcaa tggagattca   1020 acagaataat gctacaaaga catttcgaga attttgtgga cctgctgatc ctgaaattgc   1080
ccggcattta cgcctggaa ctctcagagc aatctttggt aaaactaaga tccagaatgc   1140
tgttcactgt actgatctgc cagaggatgg cctattagag gttcaatact tcttcaagat   1200
```

```
cttggataat acgcgtacgc ggccgctcga gcagaaactc atctcagaag aggatctggc    1260
agcaaatgat atcctggatt acaaggatga cgacgataag gtttaa                  1306
```

<210> SEQ ID NO 81
<211> LENGTH: 407
<212> TYPE: PRT
<213> ORGANISM: Artificial Sequence
<220> FEATURE:
<223> OTHER INFORMATION: OriGene-NME7-1 full length

<400> SEQUENCE: 81

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
    290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
```

```
            340                 345                 350
Ala Val His Cys Thr Asp Leu Pro Glu Asp Gly Leu Leu Glu Val Gln
            355                 360                 365

Tyr Phe Phe Lys Ile Leu Asp Asn Thr Arg Thr Arg Arg Leu Glu Gln
            370                 375                 380

Lys Leu Ile Ser Glu Glu Asp Leu Ala Ala Asn Asp Ile Leu Asp Tyr
385                 390                 395                 400

Lys Asp Asp Asp Lys Val
                405

<210> SEQ ID NO 82
<211> LENGTH: 376
<212> TYPE: PRT
<213> ORGANISM: Artificial Sequence
<220> FEATURE:
<223> OTHER INFORMATION: Abnova NME7-1 Full length

<400> SEQUENCE: 82

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
```

```
                    290                 295                 300
Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
            325                 330                 335

Arg Pro Gly Thr Leu Arg Ala Ile Phe Gly Lys Thr Lys Ile Gln Asn
        340                 345                 350

Ala Val His Cys Thr Asp Leu Pro Glu Asp Gly Leu Leu Glu Val Gln
    355                 360                 365

Tyr Phe Phe Lys Ile Leu Asp Asn
    370                 375

<210> SEQ ID NO 83
<211> LENGTH: 98
<212> TYPE: PRT
<213> ORGANISM: Artificial Sequence
<220> FEATURE:
<223> OTHER INFORMATION: Abnova Partial NME7-B

<400> SEQUENCE: 83

Asp Arg Val Asn Val Glu Glu Phe Tyr Glu Val Tyr Lys Gly Val Val
1               5                   10                  15

Thr Glu Tyr His Asp Met Val Thr Glu Met Tyr Ser Gly Pro Cys Val
            20                  25                  30

Ala Met Glu Ile Gln Gln Asn Asn Ala Thr Lys Thr Phe Arg Glu Phe
        35                  40                  45

Cys Gly Pro Ala Asp Pro Glu Ile Ala Arg His Leu Arg Pro Gly Thr
    50                  55                  60

Leu Arg Ala Ile Phe Gly Lys Thr Lys Ile Gln Asn Ala Val His Cys
65                  70                  75                  80

Thr Asp Leu Pro Glu Asp Gly Leu Leu Glu Val Gln Tyr Phe Phe Lys
                85                  90                  95

Ile Leu

<210> SEQ ID NO 84
<211> LENGTH: 27
<212> TYPE: DNA
<213> ORGANISM: Artificial Sequence
<220> FEATURE:
<223> OTHER INFORMATION: DNA encoding Histidine Tag

<400> SEQUENCE: 84
ctcgagcacc accaccacca ccactga                                          27

<210> SEQ ID NO 85
<211> LENGTH: 36
<212> TYPE: DNA
<213> ORGANISM: Artificial Sequence
<220> FEATURE:
<223> OTHER INFORMATION: DNA encoding Strept II Tag

<400> SEQUENCE: 85
accggttgga gccatcctca gttcgaaaag taatga                                36

<210> SEQ ID NO 86
<211> LENGTH: 32
<212> TYPE: DNA
<213> ORGANISM: Artificial Sequence
<220> FEATURE:
<223> OTHER INFORMATION: Primer
```

<400> SEQUENCE: 86
atcgatcata tggccaactg tgagcgtacc tt                          32

<210> SEQ ID NO 87
<211> LENGTH: 31
<212> TYPE: DNA
<213> ORGANISM: Artificial Sequence
<220> FEATURE:
<223> OTHER INFORMATION: Primer

<400> SEQUENCE: 87
gtggtgctcg agttcataga tccagttctg a                           31

<210> SEQ ID NO 88
<211> LENGTH: 30
<212> TYPE: DNA
<213> ORGANISM: Artificial Sequence
<220> FEATURE:
<223> OTHER INFORMATION: Primer

<400> SEQUENCE: 88
gcaggaacat tatacatggc ggtgattctg                             30

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
gccatgtata atgttcctgc caacttgtat                             30

<210> SEQ ID NO 90
<211> LENGTH: 29
<212> TYPE: DNA
<213> ORGANISM: Artificial Sequence
<220> FEATURE:
<223> OTHER INFORMATION: Primer

<400> SEQUENCE: 90
tcggggagac caactctgca gactccaag                              29

<210> SEQ ID NO 91
<211> LENGTH: 29
<212> TYPE: DNA
<213> ORGANISM: Artificial Sequence
<220> FEATURE:
<223> OTHER INFORMATION: Primer

<400> SEQUENCE: 91
cttggagtct gcagagttgg tctccccga                              29

<210> SEQ ID NO 92
<211> LENGTH: 33
<212> TYPE: DNA
<213> ORGANISM: Artificial Sequence
<220> FEATURE:
<223> OTHER INFORMATION: Primer

<400> SEQUENCE: 92
atcgatcata tggccaactg tgagcgtacc ttc                         33

<210> SEQ ID NO 93
<211> LENGTH: 33

<212> TYPE: DNA
<213> ORGANISM: Artificial Sequence
<220> FEATURE:
<223> OTHER INFORMATION: Primer

<400> SEQUENCE: 93
gtggtgaccg gtatagatcc agttctgagc aca        33

<210> SEQ ID NO 94
<211> LENGTH: 33
<212> TYPE: DNA
<213> ORGANISM: Artificial Sequence
<220> FEATURE:
<223> OTHER INFORMATION: Primer

<400> SEQUENCE: 94
atcgatcata tggccaactg tgagcgtacc ttc        33

<210> SEQ ID NO 95
<211> LENGTH: 33
<212> TYPE: DNA
<213> ORGANISM: Artificial Sequence
<220> FEATURE:
<223> OTHER INFORMATION: Primer

<400> SEQUENCE: 95
gtggtgaccg gtgatccagt tctgagcaca gct        33

<210> SEQ ID NO 96
<211> LENGTH: 33
<212> TYPE: DNA
<213> ORGANISM: Artificial Sequence
<220> FEATURE:
<223> OTHER INFORMATION: Primer

<400> SEQUENCE: 96
atcgatcata tggccaactg tgagcgtacc ttc        33

<210> SEQ ID NO 97
<211> LENGTH: 35
<212> TYPE: DNA
<213> ORGANISM: Artificial Sequence
<220> FEATURE:
<223> OTHER INFORMATION: Primer

<400> SEQUENCE: 97
gtggtgaccg gtagcacagc tcgtgtaatc tacca      35

<210> SEQ ID NO 98
<211> LENGTH: 51
<212> TYPE: PRT
<213> ORGANISM: Artificial Sequence
<220> FEATURE:
<223> OTHER INFORMATION: histidine-tagged MUC1* extra cellular domain
      peptide

<400> SEQUENCE: 98

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala His His His
        35                  40                  45

His His His
    50

```
<210> SEQ ID NO 99
<211> LENGTH: 38
<212> TYPE: DNA
<213> ORGANISM: Artificial Sequence
<220> FEATURE:
<223> OTHER INFORMATION: Primer

<400> SEQUENCE: 99
agagcctcga gattatccag aattttgaaa aagtattg                            38

<210> SEQ ID NO 100
<211> LENGTH: 30
<212> TYPE: DNA
<213> ORGANISM: Artificial Sequence
<220> FEATURE:
<223> OTHER INFORMATION: Primer

<400> SEQUENCE: 100
atcgatcata tgcatgacgt taaaaatcac                                     30

<210> SEQ ID NO 101
<211> LENGTH: 38
<212> TYPE: DNA
<213> ORGANISM: Artificial Sequence
<220> FEATURE:
<223> OTHER INFORMATION: Primer

<400> SEQUENCE: 101
agagcctcga gattatccag aattttgaaa aagtattg                            38

<210> SEQ ID NO 102
<211> LENGTH: 42
<212> TYPE: DNA
<213> ORGANISM: Artificial Sequence
<220> FEATURE:
<223> OTHER INFORMATION: Primer

<400> SEQUENCE: 102
atcgacatat ggaaaaaacg ctggccctga ttaaaccgga tg                       42

<210> SEQ ID NO 103
<211> LENGTH: 43
<212> TYPE: DNA
<213> ORGANISM: Artificial Sequence
<220> FEATURE:
<223> OTHER INFORMATION: Primer

<400> SEQUENCE: 103
actgcctcga ggaaaaacag ttccatttca cgagctgccg atg                      43

<210> SEQ ID NO 104
<211> LENGTH: 42
<212> TYPE: DNA
<213> ORGANISM: Artificial Sequence
<220> FEATURE:
<223> OTHER INFORMATION: Primer

<400> SEQUENCE: 104
atcgacatat ggaaaaaacg ctggccctga ttaaaccgga tg                       42

<210> SEQ ID NO 105
<211> LENGTH: 38
<212> TYPE: DNA
<213> ORGANISM: Artificial Sequence
<220> FEATURE:
```

<223> OTHER INFORMATION: Primer

<400> SEQUENCE: 105
agagcctcga gattatccag aattttgaaa aagtattg                          38

<210> SEQ ID NO 106
<211> LENGTH: 42
<212> TYPE: DNA
<213> ORGANISM: Artificial Sequence
<220> FEATURE:
<223> OTHER INFORMATION: Primer

<400> SEQUENCE: 106
atcgacatat ggaaaaaacg ctggccctga ttaaaccgga tg                     42

<210> SEQ ID NO 107
<211> LENGTH: 38
<212> TYPE: DNA
<213> ORGANISM: Artificial Sequence
<220> FEATURE:
<223> OTHER INFORMATION: Primer

<400> SEQUENCE: 107
agagcaccgg tattatccag aattttgaaa aagtattg                          38

<210> SEQ ID NO 108
<211> LENGTH: 35
<212> TYPE: DNA
<213> ORGANISM: Artificial Sequence
<220> FEATURE:
<223> OTHER INFORMATION: Primer

<400> SEQUENCE: 108
atcgacatat gacgcaaaat ctgggctcgg aaatg                             35

<210> SEQ ID NO 109
<211> LENGTH: 34
<212> TYPE: DNA
<213> ORGANISM: Artificial Sequence
<220> FEATURE:
<223> OTHER INFORMATION: Primer

<400> SEQUENCE: 109
actgcctcga gtgccggacc cagaccaccc gtgc                              34

<210> SEQ ID NO 110
<211> LENGTH: 35
<212> TYPE: DNA
<213> ORGANISM: Artificial Sequence
<220> FEATURE:
<223> OTHER INFORMATION: Primer

<400> SEQUENCE: 110
atcgacatat gacgcaaaat ctgggctcgg aaatg                             35

<210> SEQ ID NO 111
<211> LENGTH: 35
<212> TYPE: DNA
<213> ORGANISM: Artificial Sequence
<220> FEATURE:
<223> OTHER INFORMATION: Primer

<400> SEQUENCE: 111
actgcaccgg ttgccggacc cagaccaccc gtgcg                             35

-continued

```
<210> SEQ ID NO 112
<211> LENGTH: 41
<212> TYPE: PRT
<213> ORGANISM: Artificial Sequence
<220> FEATURE:
<223> OTHER INFORMATION: PSMGFR N-10 peptide

<400> SEQUENCE: 112

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala His His His His His His
        35                  40

<210> SEQ ID NO 113
<211> LENGTH: 376
<212> TYPE: PRT
<213> ORGANISM: Artificial Sequence
<220> FEATURE:
<223> OTHER INFORMATION: A domain of NME7

<400> SEQUENCE: 113

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270
```

```
Met Phe Asn Met Asp Arg Val Asn Val Glu Glu Phe Tyr Glu Val Tyr
            275                 280                 285

Lys Gly Val Val Thr Glu Tyr His Asp Met Val Thr Glu Met Tyr Ser
        290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn
        370                 375

<210> SEQ ID NO 114
<211> LENGTH: 35
<212> TYPE: DNA
<213> ORGANISM: Artificial Sequence
<220> FEATURE:
<223> OTHER INFORMATION: Primer

<400> SEQUENCE: 114
atcgacatat gacgcaaaat ctgggctcgg aaatg                              35

<210> SEQ ID NO 115
<211> LENGTH: 34
<212> TYPE: DNA
<213> ORGANISM: Artificial Sequence
<220> FEATURE:
<223> OTHER INFORMATION: Primer

<400> SEQUENCE: 115
actgcctcga gtgccggacc cagaccaccc gtgc                               34

<210> SEQ ID NO 116
<211> LENGTH: 27
<212> TYPE: DNA
<213> ORGANISM: Artificial Sequence
<220> FEATURE:
<223> OTHER INFORMATION: Primer

<400> SEQUENCE: 116
atcgatcata tgaatcactc cgaacgc                                       27

<210> SEQ ID NO 117
<211> LENGTH: 585
<212> TYPE: DNA
<213> ORGANISM: Homo sapiens

<400> SEQUENCE: 117
atgacccaga atctggggag tgagatggcc tcaatcttgc gaagccctca ggctctccag   60
ctcactctag ccctgatcaa gcctgacgca gtcgcccatc cactgattct ggaggctgtt  120
catcagcaga ttctaagcaa caagttcctg attgtacgaa tgagagaact actgtggaga  180
aaggaagatt gccagaggtt ttaccgagag catgaagggc gttttttcta tcagaggctg  240
gtggagttca tggccagcgg gccaatccga gcctacatcc ttgcccacaa ggatgccatc  300
cagctctgga ggacgctcat gggacccacc agagtgttcc gagcacgcca tgtgccccca  360
gattctatcc gtgggagttt cggcctcact gacacccgca acaccaccca tgtggtggcgac  420
```

```
tctgtggttt cagccagcag agagattgca gccttcttcc ctgacttcag tgaacagcgc    480
tggtatgagg aggaagagcc ccagttgcgc tgtggccctg tgtgctatag cccagaggga    540
ggtgtccact atgtagctgg aacaggaggc ctaggaccag cctga                   585
```

```
<210> SEQ ID NO 118
<211> LENGTH: 194
<212> TYPE: PRT
<213> ORGANISM: Homo sapiens

<400> SEQUENCE: 118

Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Gly Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val Cys Tyr
                165                 170                 175

Ser Pro Glu Gly Gly Val His Tyr Val Ala Gly Thr Gly Gly Leu Gly
            180                 185                 190

Pro Ala
```

```
<210> SEQ ID NO 119
<211> LENGTH: 585
<212> TYPE: DNA
<213> ORGANISM: Homo sapiens

<400> SEQUENCE: 119
atgacccaga atctggggag tgagatggcc tcaatcttgc gaagccctca ggctctccag    60
ctcactctag ccctgatcaa gcctgacgca gtcgcccatc cactgattct ggaggctgtt    120
catcagcaga ttctaagcaa caagttcctg attgtacgaa tgagagaact actgtggaga    180
aaggaagatt gccagaggtt ttaccgagag catgaagggc gttttttcta tcagaggctg    240
gtggagttca tggccagcgg gccaatccga gcctacatcc ttgcccacaa ggatgccatc    300
cagctctgga gacgctcat gggacccacc agagtgttcc gagcacgcca tgtggcccca    360
gattctatcc gtgggagttt cggcctcact gacacccgca acaccaccca tggtgccgac    420
tctgatgctt cagccagcag agagattgca gccttcttcc ctgacttcag tgaacagcgc    480
tggtatgagg aggaagagcc ccagttgcgc tgtggccctg tgtgctatag cccagaggga    540
ggtgtccact atgtagctgg aacaggaggc ctaggaccag cctga                   585
```

<210> SEQ ID NO 120
<211> LENGTH: 194
<212> TYPE: PRT
<213> ORGANISM: Homo sapiens

<400> SEQUENCE: 120

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ala Asp Ser Asp Ala Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Leu Gly
            180                 185                 190

Pro Ala
```

<210> SEQ ID NO 121
<211> LENGTH: 585
<212> TYPE: DNA
<213> ORGANISM: Artificial Sequence
<220> FEATURE:
<223> OTHER INFORMATION: NME-6 S139G

<400> SEQUENCE: 121

```
atgacgcaaa atctgggctc ggaaatggca agtatcctgc gctccccgca agcactgcaa      60
ctgaccctgg ctctgatcaa accggacgct gttgctcatc cgctgattct ggaagcggtc     120
caccagcaaa ttctgagcaa caaatttctg atcgtgcgta tgcgcgaact gctgtggcgt     180
aaagaagatt gccagcgttt ttatcgcgaa catgaaggcc gtttcttta tcaacgcctg      240 gttgaattca tggcctctgg tccgattcgc gcatatatcc tggctcacaa agatgcgatt     300
cagctgtggc gtaccctgat gggtccgacg cgcgtctttc gtgcacgtca tgtggcaccg     360
gactcaatcc gtggctcgtt cggtctgacc gatacgcgca ataccacgca cggtggcgac     420
tctgttgtta gtgcgtcccg tgaaatcgcg gccttttcc cggacttctc cgaacagcgt      480
tggtacgaag aagaagaacc gcaactgcgc tgtggcccgg tctgttattc tccggaaggt     540
ggtgtccatt atgtgcgggg cacgggtggt ctgggtccgg catga                     585
```

<210> SEQ ID NO 122

```
<211> LENGTH: 194
<212> TYPE: PRT
<213> ORGANISM: Artificial Sequence
<220> FEATURE:
<223> OTHER INFORMATION: NME-6 S139G sequence optimized for E. coli
      expression

<400> SEQUENCE: 122
```

Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Gly Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Leu Gly
            180                 185                 190

Pro Ala

```
<210> SEQ ID NO 123
<211> LENGTH: 585
<212> TYPE: DNA
<213> ORGANISM: Artificial Sequence
<220> FEATURE:
<223> OTHER INFORMATION: NME-6 HutoS sequence optimized for E. coli
      expression

<400> SEQUENCE: 123
atgacgcaaa atctgggctc ggaaatggca agtatcctgc gctccccgca agcactgcaa    60
ctgaccctgg ctctgatcaa accggacgct gttgctcatc cgctgattct ggaagcggtc   120
caccagcaaa ttctgagcaa caaatttctg atcgtgcgta tgcgcgaact gctgtggcgt   180
aaagaagatt gccagcgttt ttatcgcgaa catgaaggcc gttttctttta tcaacgcctg   240 gttgaattca tggcctctgg tccgattcgc gcatatatcc tggctcacaa agatgcgatt   300
cagctgtggc gtaccctgat gggtccgacg cgcgtctttc gtgcacgtca tgtggcaccg   360
gactcaatcc gtggctcgtt cggtctgacc gatacgcgca ataccacgca cggtgccgac   420
tctgatgcta gtgcgtcccg tgaaatcgcg gccttttttcc cggacttctc cgaacagcgt   480
tggtacgaag aagaagaacc gcaactgcgc gtggcccggg tctgttattc tccggaaggt   540
ggtgtccatt atgtggcggg cacgggtggt ctgggtccgg catga              585
```

```
<210> SEQ ID NO 124
<211> LENGTH: 194
<212> TYPE: PRT
<213> ORGANISM: Artificial Sequence
<220> FEATURE:
<223> OTHER INFORMATION: NME-6 HutoS sequence optimized for E. coli
      expression

<400> SEQUENCE: 124

Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65              70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ala Asp Ser Asp Ala Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Gly Leu Gly
            180                 185                 190

Pro Ala
```

MEDIA FOR STEM CELL PROLIFERATION AND INDUCTION

BACKGROUND OF THE INVENTION

1. Field of the Invention

The present application relates to stem cell growth media. The present application also relates to media used to induce mature or somatic cells to revert to less mature state.

2. General Background and State of the Art

Stem cell therapy holds the promise of being able to not only treat but cure many acquired diseases, heritable conditions and consequences of traumatic injury. However, there are a number of gaps in current scientific knowledge as well as technical and regulatory barriers that need to be overcome before the promise of stem cell therapies can become reality. The first problem involves regulatory issues. FDA will impose guidelines to ensure patient safety and product reproducibility, which are expected to be modeled after those required for traditional drugs. This would mean that any therapeutic cell that began as a stem cell would need to be generated, from day-1, using defined, quantifiable reagents and under reproducible conditions. In the case of stem cell derived cells for therapy, this has not been possible. Both human embryonic stem (ES) cells as well as human induced pluripotent stem (iPS) cells have traditionally been propagated in vitro using complex mixtures of largely undefined components. Current practice is still to culture ES and iPS cells over a layer of fibroblast feeder cells that are usually of murine origin (mouse embryonic fibroblasts: MEFs) although human feeder cells have also been used. The use of cells from another species is considered by many to be unsafe. In addition to the issue of a different animal species, the requirement for a layer of feeder cells introduces another layer of irreproducibility into the system; the growth of the stem cells requires factors that are secreted by the fibroblast feeder cells. These required factors have not been identified or quantified. In an attempt to get away from the use of feeder cells, stem cells have been grown over a layer of Matrigel, which is a mixture of undefined and unquantifiable factors derived from mouse sarcoma cells. Stem cells can be grown over a layer of Matrigel, however, only if conditioned media from the feeder cells is added. Thus, the Matrigel method does not provide defined conditions for generating cells.

Conventionally known growth factor that enables human stem cell growth is basic fibroblast growth factor (bFGF also called FGF-2, or simply FGF). In an effort to develop stem cell growth conditions that could meet expected FDA regulations for human stem cell therapeutics, a recent research article reported that human embryonic stem cells and iPS cells could be grown using a defined media, called "E8," which does not contain animal components but that contains extremely high levels of bFGF (100 ng/mL compared to standard 4 ng/mL) plus TGF-beta. The major problem with this media and all other FGF-based media is that true pluripotent stem cells, called "ground" state or "naive" state cells, are unstable in FGF (J. Hanna, A. W. Cheng, K. Saha et al., *Proc Natl Acad Sci USA* 107 (20), 9222 (2010), Jacob H. Hanna, Krishanu Saha, and Rudolf Jaenisch, *Cell* 143 (4), 508 (2010), J. Nichols and A. Smith, *Cell Stem Cell* 4 (6), 487 (2009)). These reports conclude that the use of FGF or bFGF drives human stem cells from the naïve state into a "primed" state. "Primed" is a misnomer. Although primed stem cells have already undergone a degree of differentiation, this does not "prime" them or set them up to differentiate into functional human cells. The opposite is true. Scientific studies now show that primed stem cells are not able to differentiate into any cell in the human body, which is required for the use of stem cells for most if not all therapeutic applications (FGF signaling inhibits neural induction in human embryonic stem cells. Boris Greber, Philippe Coulon, Miao Zhang, Soren Moritz, Stefan Frank, Arnoldo Jose´ Muller-Molina, Marcos J Arauzo-Bravo, Dong Wook Han, Hans-Christian Pape and Hans R Scholer. *The EMBO* Journal (2011) 30, 4874-4884). For example, FGF grown stem cells can not differentiate into all types of neuronal cells required for treatment for neurodegenerative diseases like Parkinson's or Alzheimer's or for traumatic spinal cord injury. In addition, researchers have not been able to make human stem cells differentiate in a coordinated way, so they randomly differentiate into many cell types whereas for therapeutics, one wants a single type of cell required for that therapy. Researchers do not have these problems when working with mouse stem cells because they are in the naïve state. Another problem with the E8 media is the unusually high levels of bFGF and TGF-beta, which are considered not to be physiologically relevant, and therefore calls into question whether or not these unnaturally high levels of growth factors will cause another unforeseen problem.

In summary, the body of recent research, into differences between primed and naïve or ground state stem cells, concludes that FGF is not the natural growth factor that makes the true pluripotent human stem cells grow. The fact that human stem cells that are in the true pluripotent state (ground state or naive) cannot be maintained in the presence of FGF indicates that there is a need in the art to identify and use the real growth factor that supports the growth of the truly pluripotent human naive stem cells for generating or maintaining human stem cells for human therapeutics. The true growth factor for naïve stem cells should be able to work in a variety of media and culture conditions, including those expected to be required by drug regulatory agencies.

SUMMARY OF THE INVENTION

In one aspect, the present invention is directed to a cell culture media for growth, maintenance and induction of reversion to a less mature state of a cell comprising a MUC1* activating ligand. The cell may be stem or progenitor cell in the case where the cell is desired to be proliferated without differentiation occurring, or the cell may be somatic, mature or progenitor cell in which the mature or progenitor cell is desired to be induced to be a pluripotent cell. Preferably, the cell may be human cell. Preferably the media may be free of bFGF, TGF-beta or both. Further, in another aspect, the media may be free of serum. The media may further include insulin, selenium, transferrin, 1-ascorbic acid or non-essential amino acids.

In another aspect, the MUC1* ligand may be an NME family protein. Preferably, the NME family protein may be NME1. The NME1 may exist as two monomers dimerized or engineered as a single chain having two subunits. Alternatively, NME family protein may be NME7 or NME6.

In another aspect, the cell culture media may include an inhibitor of a rho associated kinase. The cell culture media may include an inhibitor of a guanine exchange factor. The inhibitor of the guanine exchange factor may be NME1 in hexamer form or a peptide derived from NME1.

In further other aspect, the cell culture media may further include other growth factors, such as without limitation FGF-2 or TGF-beta.

In another aspect, the invention is directed to a method that includes contacting cells with cell culture media of NME family protein to stimulate growth of stem or progenitor cells or to induce cells to revert to a less mature state.

In this method, the cells may be stem or progenitor cells in the case where the cells are desired to be proliferated without differentiation occurring, or the cells may be somatic, mature or progenitor cells in which the mature or progenitor cells are desired to be induced to be pluripotent. Preferably, the cells may be human cells. Preferably the media may be free of bFGF, TGF-beta or both. Further, in another aspect, the media may be free of serum. The media may further include insulin, selenium, transferrin, 1-ascorbic acid or non-essential amino acids.

Preferably, the NME family protein may be NME1. The NME1 may exist as two monomers dimerized or engineered as a single chain having two subunits. Alternatively, NME family protein may be NME7 or NME6.

In another aspect of the inventive method, the cell culture media may include an inhibitor of a rho associated kinase. The cell culture media may include an inhibitor of a guanine exchange factor. The inhibitor of the guanine exchange factor may be NME1 in hexamer form or a peptide derived from NME1. In further other aspect, the cell culture media may further include other growth factors, such as without limitation FGF-2 or TGF-beta.

In yet another aspect, the invention is directed to a cell culture media of NME family protein, plus a base media and non-essential amino acids for the growth or maintenance of stem cells or induction to pluripotency of mature cells.

In another aspect, the invention is directed to a method that includes contacting cells with cell culture media of NME family protein in serum-free minimal media to stimulate growth of stem or progenitor cells or to induce cells to revert to a less mature state.

In yet another aspect, the invention is directed to a composition that includes a stem cell population, in which the composition further includes a serum-free culture media that includes NME family of proteins.

In yet another aspect, the invention is directed to a method of growing stem cells on a surface on which are ligands that bind to the progenitor or stem cells, comprising contacting the cells with media that includes NME family of proteins.

In another aspect, the present invention is directed to a method of making a pure population of naïve stem cells, comprising: (i) contacting cells with cell culture media comprising NME family protein so as to obtain a single colony of naïve stem cells; (ii) isolating the single colony of naïve stem cells; and (iii) contacting the colony with cell culture media comprising NME family protein to obtain a pure population of naïve stem cells. In step (i) above, about 25 to 60%, or 30 to 50% of the cells in naïve state may be obtained. In the method above, in step (iii), the purity of the population of naïve stem cell may be at least about 80%, 90%, 95%, 99%, or 100%.

In another aspect, the invention is directed to a method of making a pure population of naïve stem cells from induced pluripotent stem cells, comprising: (i) contacting mature or progenitor cells with cell culture media comprising NME family protein so as to obtain a single colony of naïve stem cells; (ii) isolating the single colony of naïve stem cells; and (iii) contacting the colony with cell culture media comprising NME family protein to obtain a pure population of naïve stem cells. The mature cells may be transfected with pluripotency genes in step (i). The mature or progenitor cells may be somatic cells, dermablasts or fibroblasts. In step (i) above, about 25 to 60%, or 30 to 50% of the cells in naïve state may be obtained. In the method above, in step (iii), the purity of the population of naïve stem cell may be at least about 80%, 90%, 95%, 99%, or 100%.

In one aspect, the cell media and the method of using the cell media indicated above may include cell culture media that includes NME7, which has molecular weight of approximately 25 kDa or approximately 30 kDa. The NME7 protein may be NME7-AB. The cell culture media may include an inhibitor of a rho associated kinase, or an activator of signaling proteins in the PI3K or RAC pathway preferably in the absence of a rho kinase inhibitor. Or, the cell culture media may further comprise nucleic acids that suppress expression of NME1 or NME2.

In yet another aspect, the present invention is directed to a method of generating human embryonic stem cell lines comprising: (i) contacting cells derived from a blastocyst with cell culture media comprising NME family protein; (ii) isolating outgrowths having stem-like morphology; (iii) contacting the isolated outgrowths with cell culture media comprising NME family protein; and (iv) and isolating clones that have the desired karyotype and express levels of pluripotency and naïve genes that indicate the cells are pluripotent. In this method, the NME family member may be NME7. The NME7 may be NME7-AB. The media containing the NME family member preferably may not contain FGF. The above method may include the step of suppressing NME1 and NME2 in the cells.

In another aspect, the invention is directed to a method of generating human induced pluripotent stem cell lines comprising: (i) contacting cells derived from a donor or patient with cell culture media comprising NME family protein; (ii) contacting the cells with agents that induce expression of pluripotency genes OCT4, SOX2, NANOG, KLF4, c-Myc or LIN28; (iii) isolating cells having stem cell-like morphology; (iv) contacting the isolated cells with cell culture media comprising NME family protein; (v) isolating clones that have the desired karyotype and express levels of pluripotency genes that indicate the cells are pluripotent; and (vi) and propagating clones in a media comprising an NME family member. In this method, the NME family member may be NME7. The NME7 may be NME7-AB. The media containing the NME family member preferably may not contain FGF. The above method may include the step of suppressing NME1 and NME2 in the cells.

In another aspect, the present invention includes syncing the differentiation time of the stem cells. In particular, the cells may be induced to turn into stem cells, and then at an appropriate point, the cells may be caused to differentiate at the same time.

In yet another aspect, the invention is directed to a stem cell line that has been passaged more than four times, which conventionally has not been done before. Further, the present invention is drawn to a population of naïve cells concentrated so as to be effective.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1 shows magnified photographic images of fully confluent undifferentiated human stem cells cultured in Minimal Stem Cell Media, "MM", with NM23 as the only growth factor plus a Rho kinase inhibitor, Y27632, on a Vitronectin surface as described.

FIG. 2 shows magnified photographic images of partially confluent undifferentiated human stem cells cultured in Minimal Stem Cell Media, "MM", with NM23 as the only growth factor without the Rho kinase inhibitor, Y27632, on a Vitronectin surface as described.

FIG. 3 shows magnified photographic images of fully confluent undifferentiated human stem cells cultured in Minimal Stem Cell Media with bFGF, 50% conditioned media from human feeder cells, HS27, plus the Rho kinase inhibitor, Y27632, on a Vitronectin surface as described.

FIG. 4 shows magnified photographic images of partially confluent undifferentiated human stem cells cultured in Minimal Stem Cell Media with bFGF, 50% conditioned media from human feeder cells, HS27, without the Rho kinase inhibitor, Y27632, on a Vitronectin surface as described.

FIG. 5 shows magnified photographic images of confluent undifferentiated human stem cells cultured in completely defined stem cell media, "MN6", with NM23 as the only growth factor plus a Rho kinase inhibitor, Y27632, on a Vitronectin surface as described.

FIG. 6 shows magnified photographic images of partially confluent undifferentiated human stem cells cultured in completely defined stem cell media, "MN6", with NM23 as the only growth factor without the Rho kinase inhibitor, Y27632, on a Vitronectin surface as described.

FIG. 7 shows magnified photographic images of partially confluent undifferentiated human stem cells cultured in a minimal completely defined stem cell media, "MN2", with NM23 as the only growth factor plus a Rho kinase inhibitor, Y27632, on a Vitronectin surface as described.

FIG. 9 shows magnified photographic images of partially confluent undifferentiated human stem cells cultured in completely defined stem cell media, "E8", which is MN6 plus bFGF at 100 ng/mL and TGF-beta plus a Rho kinase inhibitor, Y27632, on a Vitronectin surface as described.

FIG. 10 shows magnified photographic images of poorly attached and differentiating human stem cells cultured in completely defined stem cell media, "E8", which is MN6 plus bFGF at 100 ng/mL and TGF-beta without the Rho kinase inhibitor, Y27632, on a Vitronectin surface as described.

FIGS. 11A-11D show magnified photographic images of fully confluent undifferentiated human stem cells cultured in Minimal Stem Cell Media, "MM", A,C or MN6 media B,D both with NM23, as the only growth factor plus a Rho kinase inhibitor, Y27632, on an anti-MUC1* antibody surface.

FIGS. 13A-13D show graphs of RT-PCR measurements of pluripotency genes and as well as naïve and primed genes for stem cells cultured in FGF-based media compared to NME-based media on feeder cells, Matrigel, Vitronectin or anti-MUC1* coated surfaces.

FIG. 25.1 is a non-reducing SDS-PAGE gel from NME7-1 and NME7-2 expression and purification over an NTA-Ni column, showing little or no protein expression at the expected molecular weight of ~40 kDa.

FIG. 25.2 is a Western blot of the eluate of NME7-1 and NME7-2 purification over an NTA-Ni column, showing some expression of NME7-1 and of NME7-2 at the expected molecular weight of ~40 kDa.

FIG. 27 (A) is an elution profile of size exclusion chromatography purification of NME7-AB; (B) is non-reducing SDS-PAGE gel from NME7-AB peak fractions; (C) is the elution profile of size exclusion chromatography of the purified NME7-AB.

FIGS. 33A-33C show photographs of nanoparticle binding assays wherein a MUC1* extra cellular domain peptide is immobilized onto SAM-coated nanoparticles and NME proteins are added free in solution. A color change from pink to blue indicates that the protein free in solution can simultaneously bind to two peptides on two different nanoparticles.

FIG. 35 shows photographs of human embryonic stem (ES) cells grown in a NME1 (NM23-S120G dimers) media then stained for DAPI, OCT4 and H3K27me3 that stains Histone-3 which is condensed in the nucleus (red dot) if the cell has inactivated an X chromosome, indicating it is no longer completely naïve.

FIG. 41C shows a table of cell counts for the cloning efficiency assay.

FIGS. 55A-55C show photographs of Western blots showing expression of NME7 species in stem cell lysates (A,C) and stem cell conditioned media (B).

FIG. 57 shows photograph of an SDS-PAGE gel where proteins obtained from an NME7 pull down assay were separated on a gel, bands excised and analyzed by mass spectrometry. Mass spec showed that lower molecular weight species pulled down by NME7 antibody, ~23 kDa, were also NME7 but peptide sequences in that NME7 species all mapped to the NDPK A domain of NME7.

DETAILED DESCRIPTION OF THE PREFERRED EMBODIMENTS

Definitions

Figure 8:
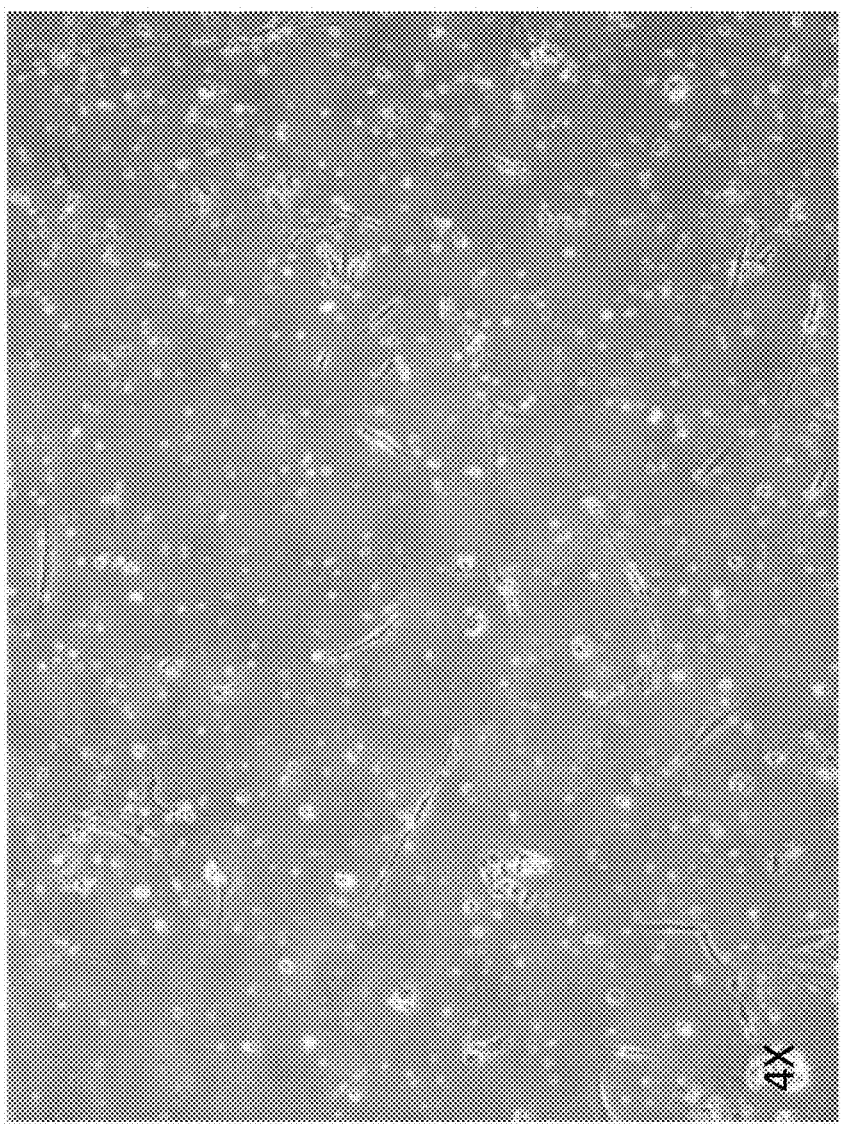
FIG. 8 shows magnified photographic images of poorly attached and differentiating human stem cells cultured in a minimal completely defined stem cell media, "MN2", with NM23 as the only growth factor without the Rho kinase inhibitor, Y27632, on a Vitronectin surface as described.

The MUC1* extra cellular domain is defined primarily by the PSMGFR sequence (GTINVHDVETQFNQYKTEAAS-RYNLTISDVSVSDVPFPFSAQSGA (SEQ ID NO:6)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

NME family proteins, numbered 1-10, are proteins grouped together because they all have at least one NDPK (nucleotide diphosphate kinase) domain. In some cases, the NDPK domain is not functional in terms of being able to catalyze the conversion of ATP to ADP. NME proteins were formally known as NM23 proteins, numbered H1, H2 and so on. Herein, the terms NM23 and NME are interchangeable. Herein, terms NME1, NME2, NME6 and NME7 are used to refer to the native protein as well as NME variants. In some cases these variants are more soluble, express better in E. coli or are more soluble than the native sequence protein. For example, NME7 as used in the specification can mean the native protein or a variant, such as NME7-AB that has superior commercial applicability because variations allow high yield expression of the soluble, properly folded protein in E. coli. "NME1" as referred to herein is interchangeable with "NM23-H1". It is also intended that the invention not be limited by the exact sequence of the NME proteins. The mutant NME1-S120G, also called NM23-S120G, are used interchangeably throughout the application. The S120G mutants and the P96S mutant are preferred because of their preference for dimer formation, but may be referred to herein as NM23 dimers or NME1 dimers.

NME7 as referred to herein is intended to mean native NME7, or variants that increase yield, solubility or other characteristics that make the NME7 more effective or commercially more viable.

As used herein, FGF, FGF-2 or bFGF refer to fibroblast growth factor.

As used herein, Rho associated kinase inhibitors may be small molecules, peptides or proteins (Rath N, Olson M F. Rho-associated kinases in tumorigenesis: re-considering ROCK inhibition for cancer therapy. EMBO Rep. 2012; 13(10):900-8). Examples of rho kinase inhibitors are Y27632, HA-1077, also called Fasudil, H-1152 and thiazovivin (Olson M F. Applications for ROCK kinase inhibition. Curr Opin Cell Biol. 2008; 20(2):242-8; Watanabe K, Ueno M, Kamiya D, et al. A ROCK inhibitor permits survival of dissociated human embryonic stem cells. Nat Biotechnol. 2007; 25(6):681-6; Breitenlechner C, Gassel M, Hidaka H, et al. Protein kinase A in complex with Rho-kinase inhibitors Y-27632, Fasudil, and H-1152P: structural basis of selectivity. Structure. 2003; 11(12):1595-607; Lin T, Ambasudhan R, Yuan X, et al. A chemical platform for improved induction of human iPSCs. Nat Methods. 2009; 6(11):805-8). In addition to Rho kinase inhibitors, the invention envisions using inhibitors of related pathways in place of the Rho kinase inhibitors. For example, in the same pathway, guanine exchange factors (GEFs) are upstream of Rho kinase. The GEFs activate the Rho kinases. Therefore, instead of using rho kinase inhibitors, the invention envisions using GEF inhibitors. Since rho kinase is in the inactive state when bound to GDP, any agent that increases the amount of GDP present in a cell, such as RAD, GEM, and RhoE as well as others, can be used in place of rho kinase inhibitors to aid in stem cell growth, survival and attachment to surfaces (Riento K, Guasch R M, Garg R, Jin B, Ridley A J (2003) RhoE binds to ROCKI and inhibits downstream signaling. *Mol Cell Biol* 23: 4219-4229; Komander D, Garg R, Wan P T, Ridley A J, Barford D (2008) Mechanism of multi-site phosphorylation from a ROCK-I: RhoE complex structure. *EMBO J* 27: 3175-3185; Ward Y, Yap S F, Ravichandran V, Matsumura F, Ito M, Spinelli B, Kelly K (2002) The GTP binding proteins Gem and Rad are negative regulators of the Rho-Rho kinase pathway. *J Cell Biol* 157: 291-302), in their place. Myosin is also in the same pathway as Rho kinases. Myosin is indirectly activated by Rho kinase and as such is downstream of rho kinase in the same pathway. Therefore, myosin inhibitors can also be used in place of rho kinase inhibitors according to methods of the invention to aid in stem cell survival and/or to aid in stem cell attachment to surfaces. Blebbistatin is a myosin inhibitor and can be used in place of any rho kinase inhibitor used according to methods of the invention (Ohgushi M, Matsumura M, Eiraku M, Murakami K, Aramaki T, Nishiyama A, et al. Molecular pathway and cell state responsible for dissociation-induced apoptosis in human pluripotent stem cells. Cell Stem Cell 2010; 7:225-39; Ohata H, Ishiguro T, Aihara Y, et al. Induction of the Stem-like Cell Regulator CD44 by Rho Kinase Inhibition Contributes to the Maintenance of Colon Cancer-Initiating Cells. Cancer Res. 2012; 72(19):5101-10).

Rho kinase inhibitors are abbreviated here and elsewhere as ROCi or ROCKi. The use of specific rho kinase inhibitors are meant to be exemplary and can be substituted for any other rho kinase inhibitor.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
                                                (SEQ ID NO: 1)
MTPGTQSPFF LLLLLTVLTV VTGSGHASST PGGEKETSAT

QRSSVPSSTE KNAVSMTSSV LSSHSPGSGS STTQGQDVTL

APATEPASGS AATWGQDVTS VPVTRPALGS TTPPAHDVTS

APDNKPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDNRPALGS TAPPVHNVTS

ASGSASGSAS TLVHNGTSAR ATTTPASKST PFSIPSHHSD

TPTTLASHST KTDASSTHHS SVPPLTSSNH STSPQLSTGV

SFFFLSFHIS NLQFNSSLED PSTDYYQELQ RDISEMFLQI

YKQGGFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL
``` describes full-length MUC1 Receptor (Mucin 1 precursor, Genbank Accession number: P15941).

MTPGTQSPFFLLLLLTVLT (SEQ ID NO: 2)

MTPGTQSPFFLLLLLTVLT VVTA (SEQ ID NO: 3)

MTPGTQSPFFLLLLLTVLT VVTG (SEQ ID NO: 4)

SEQ ID NOS:2, 3 and 4 describe N-terminal MUC-1 signaling sequence for directing MUC1 receptor and truncated isoforms to cell membrane surface. Up to 3 amino acid residues may be absent at C-terminal end as indicated by variants in SEQ ID NOS:2, 3 and 4.

(SEQ ID NO: 5)
GTINVHDVETQFNQYKTEAASRYNLTISDVSVSDVPFPFSAQSGAGVPGW

GIALLVLVCVLVALAIVYLIALAVCQCRRKNYGQLDIFPARDTYHPMSEY

PTYHTHGRYVPPSSTDRSPYEKVSAGNGGSSLSYTNPAVAAASANL describes a truncated MUC1 receptor isoform having nat-PSMGFR at its N-terminus and including the transmembrane and cytoplasmic sequences of a full-length MUC1 receptor.

(SEQ ID NO: 6)
GTINVHDVETQFNQYKTEAASRYNLTISDVSVSDVPFPFSAQSGA describes Native Primary Sequence of the MUC1 Growth Factor Receptor (nat-PSMGFR—an example of "PSMGFR"):

(SEQ ID NO: 7)
TINVHDVETQFNQYKTEAASRYNLTISDVSVSDVPFPFSAQSGA describes Native Primary Sequence of the MUC1 Growth Factor Receptor (nat-PSMGFR—An example of "PSMGFR"), having a single amino acid deletion at the N-terminus of SEQ ID NO:6).

(SEQ ID NO: 8)
GTINVHDVETQFNQYKTEAASPYNLTISDVSVSDVPFPFSAQSGA describes "SPY" functional variant of the native Primary Sequence of the MUC1 Growth Factor Receptor having enhanced stability (var-PSMGFR—An example of "PSMGFR").

(SEQ ID NO: 9)
TINVHDVETQFNQYKTEAASPYNLTISDVSVSDVPFPFSAQSGA describes "SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO:8).

(SEQ ID NO: 10)
tgtcagtgccgccgaaagaactacgggcagctggacatcttccagcccg ggatacctaccatcctatgagcgagtaccccacctaccacacccatggc gctatgtgcccctagcagtaccgatcgtagccctatgagaaggtttct gcaggtaacggtggcagcagcctctcttacacaaacccagcagtggcagc cgcttctgccaacttg describes MUC1 cytoplasmic domain nucleotide sequence.

(SEQ ID NO: 11)
CQCRRKNYGQLDIFPARDTYHPMSEYPTYHTHGRYVPPSSTDRSPYEKVS

AGNGGSSLSYTNPAVAAASANL describes MUC 1 cytoplasmic domain amino acid sequence.

(SEQ ID NO: 12)
gagatcctgagacaatgaatcatagtgaaagattcgttttcattgcagag tggtatgatccaaatgcttcacttcttcgacgttatgagcttttattta cccaggggatggatctgttgaaatgcatgatgtaaagaatcatcgcacct ttttaaagcggaccaaatatgataacctgcacttggaagatttatttata ggcaacaaagtgaatgtcttttctcgacaactggtattaattgactatgg ggatcaatatacagctcgccagctgggcagtaggaaagaaaaaacgctag ccctaattaaaccagatgcaatatcaaaggctggagaaataattgaaata ataaacaaagctggatttactataaccaaactcaaaatgatgatgctttc aaggaaagaagcattggattttcatgtagatcaccagtcaagacccttt tcaatgagctgatccagtttattacaactggtcctattattgccatggag atttaagagatgatgctatatgtgaatggaaaagactgctgggacctgc aaactctggagtggcacgcacagatgcttctgaaagcattagagccctct ttggaacagatggcataagaaatgcagcgcatggccctgattcttttgct tctgcggccagagaaatggagttgttttttccttcaagtggaggttgtgg gccggcaaacactgctaaatttactaattgtacctgttgcattgttaaac cccatgctgtcagtgaaggtatgttgaatacactatattcagtacatttt gttaataggagagcaatgtttattttcttgatgtactttatgtatagaaa ataa describes NME7 nucleotide sequence (NME7: GENBANK ACCESSION AB209049).

(SEQ ID NO: 13)
DPETMNHSERFVFIAEWYDPNASLLRRYELLFYPGDGSVEMHDVKNHRTF

LKRTKYDNLHLEDLFIGNKVNVFSRQLVLIDYGDQYTARQLGSRKEKTLA

LIKPDAISKAGEIIEIINKAGFTITKLKMMMLSRKEALDFHVDHQSRPFF

NELIQFITTGPIIAMEILRDDAICEWKRLLGPANSGVARTDASESIRALF

GTDGIRNAAHGPDSFASAAREMELFFPSSGGCGPANTAKFTNCTCCIVKP

HAVSEGMLNTLYSVHFVNRRAMFIFLMYFMYRK describes NME7 amino acid sequence (NME7: GENBANK ACCESSION AB209049).

(SEQ ID NO: 14)
atggtgctactgtctactttagggatcgtctttcaaggcgaggggcctcc tatctcaagctgtgatacaggaaccatggccaactgtgagcgtaccttca ttgcgatcaaaccagatggggtccagcggggtcttgtgggagagattatc aagcgttttgagcagaaaggattccgccttgttggtctgaaattcatgca agcttccgaagatcttctcaaggaacactacgttgacctgaaggaccgtc cattctttgccggcctggtgaaatacatgcactcagggccggtagttgcc

```
atggtctgggaggggctgaatgtggtgaagacgggccgagtcatgctcgg ggagaccaaccctgcagactccaagcctgggaccatccgtggagacttct gcatacaagttggcaggaacattatacatggcagtgattctgtggagagt gcagagaaggagatcggcttgtggtttcaccctgaggaactggtagatta cacgagctgtgctcagaactggatctatgaatga
``` describes NM23-H1 nucleotide sequence (NM23-H1: GEN-BANK ACCESSION AF487339).

(SEQ ID NO: 15)
```
MVLLSTLGIVFQGEGPPISSCDTGTMANCERTFIAIKPDGVQRGLVGEII

KRFEQKGFRLVGLKFMQASEDLLKEHYVDLKDRPFFAGLVKYMHSGPVVA

MVWEGLNVVKTGRVMLGETNPADSKPGTIRGDFCIQVGRNIIHGSDSVES

AEKEIGLWFHPEELVDYTSCAQNWIYE NM23-H1
``` describes amino acid sequence (NM23-H1: GENBANK ACCESSION AF487339).

(SEQ ID NO: 16)
```
atggtgctactgtctactttagggatcgtctttcaaggcgaggggcctcc tatctcaagctgtgatacaggaaccatggccaactgtgagcgtaccttca ttgcgatcaaaccagatggggtccagcggggtcttgtgggagagattatc aagcgttttgagcagaaaggattccgccttgttggtctgaaattcatgca agcttccgaagatcttctcaaggaacactacgttgacctgaaggaccgtc cattctttgccggcctggtgaaatacatgcactcagggccggtagttgcc atggtctgggaggggctgaatgtggtgaagacgggccgagtcatgctcgg ggagaccaaccctgcagactccaagcctgggaccatccgtggagacttct gcatacaagttggcaggaacattatacatggcggtgattctgtggagagt gcagagaaggagatcggcttgtggtttcaccctgaggaactggtagatta cacgagctgtgctcagaactggatctatgaatga
``` describes NM23-H1 S120G mutant nucleotide sequence (NM23-H1: GENBANK ACCESSION AF487339).

(SEQ ID NO: 17)
```
MVLLSTLGIVFQGEGPPISSCDTGTMANCERTFIAIKPDGVQRGLVGEII

KRFEQKGFRLVGLKFMQASEDLLKEHYVDLKDRPFFAGLVKYMHSGPVVA

MVWEGLNVVKTGRVMLGETNPADSKPGTIRGDFCIQVGRNIIHGGDSVES

AEKEIGLWFHPEELVDYTSCAQNWIYE
``` describes NM23-H1 S120G mutant amino acid sequence (NM23-H1: GENBANK ACCESSION AF487339).

(SEQ ID NO: 18)
```
atggccaacctggagcgcaccttcatcgccatcaagccggacggcgtgca gcgcggcctggtgggcgagatcatcaagcgcttcgagcagaagggattcc gcctcgtggccatgaagttcctccgggcctctgaagaacacctgaagcag cactacattgacctgaaagaccgaccattcttccctgggctggtgaagta catgaactcagggccggttgtggccatggtctgggaggggctgaacgtgg tgaagacaggccgagtgatgcttggggagaccaatccagcagattcaaag ccaggcaccattcgtggggacttctgcattcaggttggcaggaacatcat tcatggcagtgattcagtaaaaagtgctgaaaaagaaatcagcctatggt ttaagcctgaagaactggttgactacaagtcttgtgctcatgactgggtc tatgaataa
``` describes NM23-H2 nucleotide sequence (NM23-H2: GENBANK ACCESSION AK313448).

(SEQ ID NO: 19)
```
MANLERTFIAIKPDGVQRGLVGEIIKRFEQKGFRLVAMKFLRASEEHLKQ

HYIDLKDRPFFPGLVKYMNSGPVVAMVWEGLNVVKTGRVMLGETNPADSK

PGTIRGDFCIQVGRNIIHGSDSVKSAEKEISLWFKPEELVDYKSCAHDWV

YE
``` describes NM23-H2 amino acid sequence (NM23-H2: GENBANK ACCESSION AK313448).

Human NM23-H7-2 Sequence Optimized for *E. coli* Expression:

(DNA)

(SEQ ID NO: 20)
```
atgcatgacgttaaaaatcaccgtacctttctgaaacgcacgaaatatga taatctgcatctggaagacctgtttattggcaacaaagtcaatgtgttct ctcgtcagctggtgctgatcgattatggcgaccagtacaccgcgcgtcaa ctgggtagtcgcaaagaaaaaacgctggccctgattaaaccggatgcaat ctccaaagctggcgaaattatcgaaattatcaacaaagcgggtttcacca tcacgaaactgaaaatgatgatgctgagccgtaaagaagccctggatttt catgtcgaccaccagtctcgcccgttttttcaatgaactgattcaattcat caccacgggtccgattatcgcaatggaaattctgcgtgatgacgctatct gcgaatggaaacgcctgctgggccgcaaactcaggtgttgcgcgtacc gatgccagtgaatccattcgcgctctgtttggcaccgatggtatccgtaa tgcagcacatggtccggactcattcgcatcggcagctcgtgaaatggaac tgtttttcccgagctctggcggttgcggtccggcaaacaccgccaaattt accaattgtacgtgctgtattgtcaaaccgcacgcagtgtcagaaggcct gctgggtaaaattctgatggcaatccgtgatgctggctttgaaatctcgg ccatgcagatgttcaacatggaccgcgttaacgtcgaagaattctacgaa gtttacaaaggcgtggttaccgaatatcacgatatggttacggaaatgta ctccggtccgtgcgtcgcgatggaaattcagcaaaacaatgccaccaaaa cgtttcgtgaattctgtggtccggcagatccggaaatcgcacgtcatctg cgtccgggtaccctgcgcgcaattttttggtaaaacgaaaatccagaacgc tgtgcactgtaccgatctgccggaagacggtctgctggaagttcaatact ttttcaaaattctggataattga
```

(Amino Acids)

(SEQ ID NO: 21)
MHDVKNHRTFLKRTKYDNLHLEDLFIGNKVNVFSRQLVLIDYGDQYTARQ
LGSRKEKTLALIKPDAISKAGEIIEIINKAGFTITKLKMMMLSRKEALDF
HVDHQSRPFFNELIQFITTGPIIAMEILRDDAICEWKRLLGPANSGVART
DASESIRALFGTDGIRNAAHGPDSFASAAREMELFFPSSGGCGPANTAKF
TNCTCCIVKPHAVSEGLLGKILMAIRDAGFEISAMQMFNMDRVNVEEFYE
VYKGVVTEYHDMVTEMYSGPCVAMEIQQNNATKTFREFCGPADPEIARHL
RPGTLRAIFGKTKIQNAVHCTDLPEDGLLEVQYFFKILDN-

Human NME7-A:
(DNA)

(SEQ ID NO: 22)
atggaaaaaacgctagccctaattaaaccagatgcaatatcaaaggctgg
agaaataattgaataataaacaaagctggatttactataaccaaactca
aaatgatgatgctttcaaggaaagaagcattggattttcatgtagatcac
cagtcaagaccctttttcaatgagctgatccagtttattacaactggtcc
tattattgccatggagattttaagagatgatgctatatgtgaatggaaaa
gactgctgggacctgcaaactctggagtggcacgcacagatgcttctgaa
agcattagagccctcttggaacagatggcataagaaatgcagcgcatgg
ccctgattcttttgcttctgcggccagagaaatggagttgttttttttga (Amino Acids)

(SEQ ID NO: 23)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFF-

Human NME7-A1:
(DNA)

(SEQ ID NO: 24)
atggaaaaaacgctagccctaattaaaccagatgcaatatcaaaggctgg
agaaataattgaataataaacaaagctggatttactataaccaaactca
aaatgatgatgctttcaaggaaagaagcattggattttcatgtagatcac
cagtcaagaccctttttcaatgagctgatccagtttattacaactggtcc
tattattgccatggagattttaagagatgatgctatatgtgaatggaaaa
gactgctgggacctgcaaactctggagtggcacgcacagatgcttctgaa
agcattagagccctcttggaacagatggcataagaaatgcagcgcatgg
ccctgattcttttgcttctgcggccagagaaatggagttgttttttcctt
caagtggaggttgtgggccggcaaacactgctaaatttacttga (Amino Acids)

(SEQ ID NO: 25)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFFPSSGGCGPANTAKFT-

Human NME7-A2:
(DNA)

(SEQ ID NO: 26)
atgaatcatagtgaaagattcgttttcattgcagagtggtatgatccaaa
tgcttcacttcttcgacgttatgagcttttattttacccaggggatggat
ctgttgaaatgcatgatgtaaagaatcatcgcaccttttaaagcggacc
aaatatgataacctgcacttggaagatttatttataggcaacaaagtgaa
tgtcttttctcgacaactggtattaattgactatgggatcaatatacag
ctcgccagctgggcagtaggaaagaaaaaacgctagccctaattaaacca
gatgcaatatcaaaggctggagaaataattgaataataaacaaagctgg
atttactataaccaaactcaaaatgatgatgcttcaaggaaagaagcat
tggattttcatgtagatcaccagtcaagacccttttcaatgagctgatc
cagtttattacaactggtcctattattgccatggagattttaagagatga
tgctatatgtgaatggaaaagactgctgggacctgcaaactctggagtgg
cacgcacagatgcttctgaaagcattagagccctcttggaacagatggc
ataagaaatgcagcgcatggccctgattcttttgcttctgcggccagaga
aatggagttgttttttttga (Amino Acids)

(SEQ ID NO: 27)
MNHSERFVFIAEWYDPNASLLRRYELLFYPGDGSVEMHDVKNHRTFLKRT
KYDNLHLEDLFIGNKVNVFSRQLVLIDYGDQYTARQLGSRKEKTLALIKP
DAISKAGEIIEIINKAGFTITKLKMMMLSRKEALDFHVDHQSRPFFNELI
QFITTGPIIAMEILRDDAICEWKRLLGPANSGVARTDASESIRALFGTDG
IRNAAHGPDSFASAAREMELFF-

Human NME7-A3:
(DNA)

(SEQ ID NO: 28)
atgaatcatagtgaaagattcgttttcattgcagagtggtatgatccaa
atgcttcacttcttcgacgttatgagcttttattttacccaggggatgg
atctgttgaaatgcatgatgtaaagaatcatcgcaccttttaaagcgg
accaaatatgataacctgcacttggaagatttatttataggcaacaaag
tgaatgtcttttctcgacaactggtattaattgactatgggatcaata
tacagctcgccagctgggcagtaggaaagaaaaaacgctagccctaatt
aaaccagatgcaatatcaaaggctggagaaataattgaataataaaca
aagctggatttactataaccaaactcaaaatgatgatgctttcaaggaa
agaagcattggattttcatgtagatcaccagtcaagaccctttttcaat
gagctgatccagtttattacaactggtcctattattgccatggagattt
taagagatgatgctatatgtgaatggaaaagactgctgggacctgcaaa
ctctggagtggcacgcacagatgcttctgaaagcattagagccctcttt -continued
ggaacagatggcataagaaatgcagcgcatggccctgattcttttgctt
ctgcggccagagaaatggagttgttttttccttcaagtggaggttgtgg
gccggcaaacactgctaaatttacttga (Amino Acids)

(SEQ ID NO: 29)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFFPSSGGCGPANTAKFT-

Human NME7-B:
(DNA)

(SEQ ID NO: 30)
atgaattgtacctgttgcattgttaaacccatgctgtcagtgaaggac
tgttgggaaagatcctgatggctatccgagatgcaggttttgaaatctc
agctatgcagatgttcaatatggatcgggttaatgttgaggaattctat
gaagtttataaaggagtagtgaccgaatatcatgacatggtgacagaaa
tgtattctggcccttgtgtagcaatggagattcaacagaataatgctac
aaagacatttcgagaattttgtggacctgctgatcctgaaattgcccgg
catttacgccctggaactctcagagcaatctttggtaaaactaagatcc
agaatgctgttcactgtactgatctgccagaggatggcctattagaggt
tcaatacttcttctga (Amino Acids)

(SEQ ID NO: 31)
MNCTCCIVKPHAVSEGLLGKILMAIRDAGFEISAMQMFNMDRVNVEEFY
EVYKGVVTEYHDMVTEMYSGPCVAMEIQQNNATKTFREFCGPADPEIAR
HLRPGTLRAIFGKTKIQNAVHCTDLPEDGLLEVQYFF-

Human NME7-B1:
(DNA)

(SEQ ID NO: 32)
atgaattgtacctgttgcattgttaaacccatgctgtcagtgaaggac
tgttgggaaagatcctgatggctatccgagatgcaggttttgaaatctc
agctatgcagatgttcaatatggatcgggttaatgttgaggaattctat
gaagtttataaaggagtagtgaccgaatatcatgacatggtgacagaaa
tgtattctggcccttgtgtagcaatggagattcaacagaataatgctac
aaagacatttcgagaattttgtggacctgctgatcctgaaattgcccgg
catttacgccctggaactctcagagcaatctttggtaaaactaagatcc
agaatgctgttcactgtactgatctgccagaggatggcctattagaggt
tcaatacttcttcaagatcttggataattagtga (Amino Acids)

(SEQ ID NO: 33)
MNCTCCIVKPHAVSEGLLGKILMAIRDAGFEISAMQMFNMDRVNVEEFY
EVYKGVVTEYHDMVTEMYSGPCVAMEIQQNNATKTFREFCGPADPEIAR
HLRPGTLRAIFGKTKIQNAVHCTDLPEDGLLEVQYFFKILDN-

Human NME7-B2:
(DNA)

(SEQ ID NO: 34)
atgccttcaagtggaggttgtgggccggcaaacactgctaaatttacta
attgtacctgttgcattgttaaacccatgctgtcagtgaaggactgtt
gggaaagatcctgatggctatccgagatgcaggttttgaaatctcagct
atgcagatgttcaatatggatcgggttaatgttgaggaattctatgaag
tttataaaggagtagtgaccgaatatcatgacatggtgacagaaatgta
ttctggcccttgtgtagcaatggagattcaacagaataatgctacaaag
acatttcgagaattttgtggacctgctgatcctgaaattgcccggcatt
tacgccctggaactctcagagcaatctttggtaaaactaagatccagaa
tgctgttcactgtactgatctgccagaggatggcctattagaggttcaa
tacttcttctga (Amino Acids)

(SEQ ID NO: 35)
MPSSGGCGPANTAKFTNCTCCIVKPHAVSEGLLGKILMAIRDAGFEIS
AMQMFNMDRVNVEEFYEVYKGVVTEYHDMVTEMYSGPCVAMEIQQNNAT
KTFREFCGPADPEIARHLRPGTLRAIFGKTKIQNAVHCTDLPEDGLLEV
QYFF-

Human NME7-B3:
(DNA)

(SEQ ID NO: 36)
atgccttcaagtggaggttgtgggccggcaaacactgctaaatttacta
attgtacctgttgcattgttaaacccatgctgtcagtgaaggactgtt
gggaaagatcctgatggctatccgagatgcaggttttgaaatctcagct
atgcagatgttcaatatggatcgggttaatgttgaggaattctatgaag
tttataaaggagtagtgaccgaatatcatgacatggtgacagaaatgta
ttctggcccttgtgtagcaatggagattcaacagaataatgctacaaag
acatttcgagaattttgtggacctgctgatcctgaaattgcccggcatt
tacgccctggaactctcagagcaatctttggtaaaactaagatccagaa
tgctgttcactgtactgatctgccagaggatggcctattagaggttcaa
tacttcttcaagatcttggataattagtga (Amino Acids)

(SEQ ID NO: 37)
MPSSGGCGPANTAKFTNCTCCIVKPHAVSEGLLGKILMAIRDAGFEIS
AMQMFNMDRVNVEEFYEVYKGVVTEYHDMVTEMYSGPCVAMEIQQNNAT
KTFREFCGPADPEIARHLRPGTLRAIFGKTKIQNAVHCTDLPEDGLLEV
QYFFKILDN--

Human NME7-AB:
(DNA)

(SEQ ID NO: 38)
atggaaaaaacgctagccctaattaaaccagatgcaatatcaaaggctg gagaaataattgaaataataaacaaagctggatttactataaccaaact caaaatgatgatgcttttcaaggaaagaagcattggattttcatgtagat caccagtcaagaccttttcaatgagctgatccagtttattacaactg gtcctattattgccatggagattttaagagatgatgctatatgtgaatg gaaaagactgctgggacctgcaaactctggagtggcacgcacagatgct tctgaaagcattagagccctctttggaacagatggcataagaaatgcag cgcatggccctgattcttttgcttctgcggccagagaaatggagttgtt ttttccttcaagtggaggttgtgggccggcaaacactgctaaatttact aattgtacctgttgcattgttaaaccccatgctgtcagtgaaggactgt tgggaaagatcctgatggctatccgagatgcaggttttgaaatctcagc tatgcagatgttcaatatggatcgggttaatgttgaggaattctatgaa gtttataaaggagtagtgaccgaatatcatgacatggtgacagaaatgt attctggcccttgtgtagcaatggagattcaacagaataatgctacaaa gacatttcgagaattttgtggacctgctgatcctgaaattgcccggcat ttacgccctggaactctcagagcaatctttggtaaaactaagatccaga atgctgttcactgtactgatctgccagaggatggcctattagaggttcaa atacttcttcaagatcttggataattagtga (Amino Acids)

(SEQ ID NO: 39)
MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFFKILDN--

Human NME7-AB 1:
(DNA)

(SEQ ID NO: 40)
atggaaaaaacgctagccctaattaaaccagatgcaatatcaaaggctg gagaaataattgaaataataaacaaagctggatttactataaccaaact caaaatgatgatgcttttcaaggaaagaagcattggattttcatgtagat caccagtcaagaccttttcaatgagctgatccagtttattacaactg gtcctattattgccatggagattttaagagatgatgctatatgtgaatg gaaaagactgctgggacctgcaaactctggagtggcacgcacagatgct tctgaaagcattagagccctctttggaacagatggcataagaaatgcag cgcatggccctgattcttttgcttctgcggccagagaaatggagttgtt ttttccttcaagtggaggttgtgggccggcaaacactgctaaatttact aattgtacctgttgcattgttaaaccccatgctgtcagtgaaggactgt tgggaaagatcctgatggctatccgagatgcaggttttgaaatctcagc tatgcagatgttcaatatggatcgggttaatgttgaggaattctatgaa gtttataaaggagtagtgaccgaatatcatgacatggtgacagaaatgt attctggcccttgtgtagcaatggagattcaacagaataatgctacaaa gacatttcgagaattttgtggacctgctgatcctgaaattgcccggcat ttacgccctggaactctcagagcaatctttggtaaaactaagatccaga atgctgttcactgtactgatctgccagaggatggcctattagaggttcaa tacttcttctga (Amino Acids)

(SEQ ID NO: 41)
MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFF-

Human NME7-A Sequence Optimized for *E. coli* Expression:
(DNA)

(SEQ ID NO: 42)
atggaaaaaacgctggccctgattaaaccggatgcaatctccaaagctg gcgaaattatcgaaattatcaacaaagcgggtttcaccatcacgaaact gaaaatgatgatgctgagccgtaaagaagccctggattttcatgtcgac caccagtctcgcccgttttcaatgaactgattcaattcatcaccacgg gtccgattatcgcaatggaaattctgcgtgatgacgctatctgcgaatg gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt tttctga (Amino Acids)

(SEQ ID NO: 43)
MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFF-

Human NME7-A1 Sequence Optimized for *E. coli* Expression:
(DNA)

(SEQ ID NO: 44)
atggaaaaaacgctggccctgattaaaccggatgcaatctccaaagctg gcgaaattatcgaaattatcaacaaagcgggtttcaccatcacgaaact -continued

```
gaaaatgatgatgctgagccgtaaagaagccctggattttcatgtcgac caccagtctcgcccgttttcaatgaactgattcaattcatcaccacgg gtccgattatcgcaatggaaattctgcgtgatgacgctatctgcgaatg gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt tttcccgagctctggcggttgcggtccggcaaacaccgccaaatttacc tga
```

(Amino Acids)

(SEQ ID NO: 45)
MEKTLALIKPDAISKAGEIIEIINKAGFTITKLKMMMLSRKEALDFHVD
HQSRPFFNELIQFITTGPIIAMEILRDDAICEWKRLLGPANSGVARTDA
SESIRALFGTDGIRNAAHGPDSFASAAREMELFFPSSGGCGPANTAKFT-

Human NME7-A2 Sequence Optimized for *E. coli* Expression:
(DNA)

(SEQ ID NO: 46)
```
atgaatcactccgaacgctttgttttatcgccgaatggtatgacccga atgcttccctgctgcgccgctacgaactgctgttttatccgggcgatgg tagcgtggaaatgcatgacgttaaaaatcaccgtacctttctgaaacgc acgaaatatgataatctgcatctggaagacctgtttattggcaacaaag tcaatgtgttctctcgtcagctggtgctgatcgattatggcgaccagta caccgcgcgtcaactgggtagtcgcaaagaaaaaacgctggccctgatt aaaccggatgcaatctccaaagctggcgaaattatcgaaattatcaaca aagcgggtttccaccatcacgaaactgaaaatgatgatgctgagccgtaa agaagccctggattttcatgtcgaccaccagtctcgcccgttttcaat gaactgattcaattcatcaccacgggtccgattatcgcaatggaaattc tgcgtgatgacgctatctgcgaatggaaacgcctgctgggcccggcaaa ctcaggtgttgcgcgtaccgatgccagtgaatccattcgcgctctgttt ggcaccgatggtatccgtaatgcagcacatggtccggactcattcgcat cggcagctcgtgaaatggaactgtttttctga
```

(Amino Acids)

(SEQ ID NO: 47)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFF-

Human NME7-A3 Sequence Optimized for *E. coli* Expression:
(DNA)

(SEQ ID NO: 48)
```
atgaatcactccgaacgctttgttttatcgccgaatggtatgacccga atgcttccctgctgcgccgctacgaactgctgttttatccgggcgatgg tagcgtggaaatgcatgacgttaaaaatcaccgtacctttctgaaacgc acgaaatatgataatctgcatctggaagacctgtttattggcaacaaag tcaatgtgttctctcgtcagctggtgctgatcgattatggcgaccagta caccgcgcgtcaactgggtagtcgcaaagaaaaaacgctggccctgatt aaaccggatgcaatctccaaagctggcgaaattatcgaaattatcaaca aagcgggtttccaccatcacgaaactgaaaatgatgatgctgagccgtaa agaagccctggattttcatgtcgaccaccagtctcgcccgttttcaat gaactgattcaattcatcaccacgggtccgattatcgcaatggaaattc tgcgtgatgacgctatctgcgaatggaaacgcctgctgggcccggcaaa ctcaggtgttgcgcgtaccgatgccagtgaatccattcgcgctctgttt ggcaccgatggtatccgtaatgcagcacatggtccggactcattcgcat cggcagctcgtgaaatggaactgtttttcccgagctctggcggttgcgg tccggcaaacaccgccaaatttacctga
```

(Amino Acids)

(SEQ ID NO: 49)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFFPSSGGCGPANTAKFT-

Human NME7-B Sequence Optimized for *E. coli* Expression:
(DNA)

(SEQ ID NO: 50)
```
atgaattgtacgtgctgtattgtcaaaccgcacgcagtgtcagaaggcc tgctgggtaaaattctgatggcaatccgtgatgctggctttgaaatctc ggccatgcagatgttcaacatggaccgcgttaacgtcgaagaattctac gaagtttacaaaggcgtggttaccgaatatcacgatatggttacggaaa tgtactccggtccgtgcgtcgcgatggaaattcagcaaaacaatgccac caaaacgtttcgtgaattctgtggtccggcagatccggaaatcgcacgt catctgcgtccgggtaccctgcgcgcaattttttggtaaaacgaaaat ccagaacgctgtgcactgtaccgatctgccggaagacggtctgctggaa gttcaatacttttctga
```

(Amino Acids)

(SEQ ID NO: 51)
MNCTCCIVKPHAVSEGLLGKILMAIRDAGFEISAMQMFNMDRVNVEEFY
EVYKGVVTEYHDMVTEMYSGPCVAMEIQQNNATKTFREFCGPADPEIAR
HLRPGTLRAIFGKTKIQNAVHCTDLPEDGLLEVQYFF-

Human NME7-B1 Sequence Optimized for *E. coli* Expression:
(DNA)

(SEQ ID NO: 52)
atgaattgtacgtgctgtattgtcaaaccgcacgcagtgtcagaaggcc
tgctgggtaaaattctgatggcaatccgtgatgctggctttgaaatctc
ggccatgcagatgttcaacatggaccgcgttaacgtcgaagaattctac
gaagtttacaaaggcgtggttaccgaatatcacgatatggttacggaaa
tgtactccggtccgtgcgtcgcgatggaaattcagcaaaacaatgccac
caaaacgtttcgtgaattctgtggtccggcagatccggaaatcgcacgt
catctgcgtccgggtaccctgcgcgcaattttttggtaaaacgaaaatcc
agaacgctgtgcactgtaccgatctgccggaagacggtctgctggaagt
tcaatactttttcaaaattctggataattga (Amino Acids)

(SEQ ID NO: 53)
MNCTCCIVKPHAVSEGLLGKILMAIRDAGFEISAMQMFNMDRVNVEEFY
EVYKGVVTEYHDMVTEMYSGPCVAMEIQQNNATKTFREFCGPADPEIAR
HLRPGTLRAIFGKTKIQNAVHCTDLPEDGLLEVQYFFKILDN-

Human NME7-B2 Sequence Optimized for *E. coli* Expression:
(DNA)

(SEQ ID NO: 54)
atgccgagctctggcggttgcggtccggcaaacaccgccaaatttacca
attgtacgtgctgtattgtcaaaccgcacgcagtgtcagaaggcctgct
gggtaaaattctgatggcaatccgtgatgctggctttgaaatctcggcc
atgcagatgttcaacatggaccgcgttaacgtcgaagaattctacgaag
tttacaaaggcgtggttaccgaatatcacgatatggttacggaaatgta
ctccggtccgtgcgtcgcgatggaaattcagcaaaacaatgccaccaaa
acgtttcgtgaattctgtggtccggcagatccggaaatcgcacgtcatc
tgcgtccgggtaccctgcgcgcaattttttggtaaaacgaaaatccagaa
cgctgtgcactgtaccgatctgccggaagacggtctgctggaagttcaa
tactttttctga (Amino Acids)

(SEQ ID NO: 55)
MPSSGGCGPANTAKFTNCTCCIVKPHAVSEGLLGKILMAIRDAGFEISA
MQMFNMDRVNVEEFYEVYKGVVTEYHDMVTEMYSGPCVAMEIQQNNATK
TFREFCGPADPEIARHLRPGTLRAIFGKTKIQNAVHCTDLPEDGLLEVQ
YFF-

Human NME7-B3 Sequence Optimized for *E. coli* Expression:
(DNA)

(SEQ ID NO: 56)
atgccgagctctggcggttgcggtccggcaaacaccgccaaatttacca
attgtacgtgctgtattgtcaaaccgcacgcagtgtcagaaggcctgct
gggtaaaattctgatggcaatccgtgatgctggctttgaaatctcggcc
atgcagatgttcaacatggaccgcgttaacgtcgaagaattctacgaag
tttacaaaggcgtggttaccgaatatcacgatatggttacggaaatgta
ctccggtccgtgcgtcgcgatggaaattcagcaaaacaatgccaccaaa
acgtttcgtgaattctgtggtccggcagatccggaaatcgcacgtcatc
tgcgtccgggtaccctgcgcgcaattttttggtaaaacgaaaatccagaa
cgctgtgcactgtaccgatctgccggaagacggtctgctggaagttcaa
tactttttcaaaattctggataattga (Amino Acids)

(SEQ ID NO: 57)
MPSSGGCGPANTAKFTNCTCCIVKPHAVSEGLLGKILMAIRDAGFEISA
MQMFNMDRVNVEEFYEVYKGVVTEYHDMVTEMYSGPCVAMEIQQNNATK
TFREFCGPADPEIARHLRPGTLRAIFGKTKIQNAVHCTDLPEDGLLEVQ
YFFKILDN-

Human NME7-AB Sequence Optimized for *E. coli* Expression:
(DNA)

(SEQ ID NO: 58)
atggaaaaaacgctggccctgattaaaccggatgcaatctccaaagctgg
cgaaattatcgaaattatcaacaaagcgggtttcaccatcacgaaactga
aaatgatgatgctgagccgtaaagaagccctggattttcatgtcgaccac
cagtctcgcccgttttttcaatgaactgattcaattcatcaccacgggtcc
gattatcgcaatggaaattctgcgtgatgacgctatctgcgaatggaaac
gcctgctgggcccggcaaactcaggtgttgcgcgtaccgatgccagtgaa
tccattcgcgctctgtttggcaccgatggtatccgtaatgcagcacatgg
tccggactcattcgcatcggcagctcgtgaaatggaactgttttttcccga
gctctggcggttgcggtccggcaaacaccgccaaatttaccaattgtacg
tgctgtattgtcaaaccgcacgcagtgtcagaaggcctgctgggtaaaat
tctgatggcaatccgtgatgctggctttgaaatctcggccatgcagatgt
tcaacatggaccgcgttaacgtcgaagaattctacgaagtttacaaaggc
gtggttaccgaatatcacgatatggttacggaaatgtactccggtccgtg
cgtcgcgatggaaattcagcaaaacaatgccaccaaaacgtttcgtgaat
tctgtggtccggcagatccggaaatcgcacgtcatctgcgtccgggtacc
ctgcgcgcaattttttggtaaaacgaaaatccagaacgctgtgcactgtac -continued
cgatctgccggaagacggtctgctggaagttcaatactttttcaaaattc tggataattga (Amino Acids)

(SEQ ID NO: 59)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFFPSSGGCGPANTAKFTNCT
CCIVKPHAVSEGLLGKILMAIRDAGFEISAMQMFNMDRVNVEEFYEVYKG
VVTEYHDMVTEMYSGPCVAMEIQQNNATKTFREFCGPADPEIARHLRPGT
LRAIFGKTKIQNAVHCTDLPEDGLLEVQYFFKILDN-

Human NME7-AB 1 Sequence Optimized for *E. coli* Expression:
(DNA)

(SEQ ID NO: 60)
Atggaaaaaacgctggccctgattaaaccggatgcaatctccaaagctgg
cgaaattatcgaaattatcaacaaagcgggtttccaccatcacgaaactga
aaatgatgatgctgagccgtaaagaagccctggattttcatgtcgaccac
cagtctcgcccgttttcaatgaactgattcaattcatcaccacgggtcc
gattatcgcaatggaaattctgcgtgatgacgctatctgcgaatggaaac
gcctgctgggcccggcaaactcaggtgttgcgcgtaccgatgccagtgaa
tccattcgcgctctgtttggcaccgatggtatccgtaatgcagcacatgg
tccggactcattcgcatcggcagctcgtgaaatggaactgttttttcccga
gctctggcggttgcggtccggcaaacaccgccaaatttaccaattgtacg
tgctgtattgtcaaaccgcacgcagtgtcagaaggcctgctgggtaaaat
tctgatggcaatccgtgatgctggctttgaaatctcggccatgcagatgt
tcaacatggaccgcgttaacgtcgaagaattctacgaagtttacaaaggc
gtggttaccgaatatcacgatatggttacggaaatgtactccggtccgtg
cgtcgcgatggaaattcagcaaaacaatgccaccaaaacgtttcgtgaat
tctgtggtccggcagatccggaaatcgcacgtcatctgcgtccgggtacc
ctgcgcgcaatttttggtaaaacgaaaatccagaacgctgtgcactgtac
cgatctgccggaagacggtctgctggaagttcaatactttttctga (Amino Acids)

(SEQ ID NO: 61)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFFPSSGGCGPANTAKFTNCT
CCIVKPHAVSEGLLGKILMAIRDAGFEISAMQMFNMDRVNVEEFYEVYKG
VVTEYHDMVTEMYSGPCVAMEIQQNNATKTFREFCGPADPEIARHLRPGT
LRAIFGKTKIQNAVHCTDLPEDGLLEVQYFF-

Mouse NME6
(DNA)

(SEQ ID NO: 62)
Atgacctccatcttgcgaagtccccaagctcttcagctcacactagccct
gatcaagcctgatgcagttgcccacccactgatcctggaggctgttcatc
agcagattctgagcaacaagttcctcattgtacgaacgagggaactgcag
tggaagctggaggactgccggaggttttaccgagagcatgaagggcgttt
ttctatcagcggctggtggagttcatgacaagtgggccaatccgagcct
atatccttgcccacaaagatgccatccaactttggaggacactgatggga
cccaccagagtatttcgagcacgctatatagccccagattcaattcgtgg
aagtttgggcctcactgacacccgaaatactacccatggctcagactccg
tggtttccgccagcagagagattgcagccttcttccctgacttcagtgaa
cagcgctggtatgaggaggaggaaccccagctgcggtgtggtcctgtgca
ctacagtccagaggaaggtatccactgtgcagctgaaacaggaggccaca
aacaacctaacaaaacctag (Amino Acids)

(SEQ ID NO: 63)
MTSILRSPQALQLTLALIKPDAVAHPLILEAVHQQILSNKFLIVRTRELQ
WKLEDCRRFYREHEGRFFYQRLVEFMTSGPIRAYILAHKDAIQLWRTLMG
PTRVFRARYIAPDSIRGSLGLTDTRNTTHGSDSVVSASREIAAFFPDFSE
QRWYEEEEPQLRCGPVHYSPEEGIHCAAETGGHKQPNKT-

Human NME6:
(DNA)

(SEQ ID NO: 64)
Atgacccagaatctggggagtgagatggcctcaatcttgcgaagccctca
ggctctccagctcactctagccctgatcaagcctgacgcagtcgcccatc
cactgattctggaggctgttcatcagcagattctaagcaacaagttcctg
attgtacgaatgagagaactactgtggagaaaggaagattgccagaggtt
ttaccgagagcatgaagggcgttttttctatcagaggctggtggagttca
tggccagcgggccaatccgagcctacatccttgcccacaaggatgccatc
cagctctggaggacgctcatgggacccaccagagtgttccgagcacgcca
tgtggcccagattctatccgtgggagtttcggcctcactgacacccgca
acaccacccatggttcggactctgtggtttcagccagcagagagattgca
gccttcttccctgacttcagtgaacagcgctggtatgaggaggaagagcc
ccagttgcgctgtggccctgtgtgctatagcccagagggaggtgtccact
atgtagctggaacaggaggcctaggaccagcctga (Amino Acids)

(SEQ ID NO: 65)
MTQNLGSEMASILRSPQALQLTLALIKPDAVAHPLILEAVHQQILSNKFL
IVRMRELLWRKEDCQRFYREHEGRFFYQRLVEFMASGPIRAYILAHKDAI
QLWRTLMGPTRVFRARHVAPDSIRGSFGLTDTRNTTHGSDSVVSASREIA
AFFPDFSEQRWYEEEEPQLRCGPVCYSPEGGVHYVAGTGGLGPA-

Human NME6 1:
(DNA)

(SEQ ID NO: 66)
Atgacccagaatctggggagtgagatggcctcaatcttgcgaagccctca ggctctccagctcactctagccctgatcaagcctgacgcagtcgcccatc cactgattctggaggctgttcatcagcagattctaagcaacaagttcctg attgtacgaatgagagaactactgtggagaaaggaagattgccagaggtt ttaccgagagcatgaagggcgttttttctatcagaggctggtggagttca tggccagcgggccaatccgagcctacatccttgcccacaaggatgccatc cagctctggaggacgctcatgggacccaccagagtgttccgagcacgcca tgtggccccagattctatccgtgggagtttcggcctcactgacacccgca acaccacccatggttcggactctgtggtttcagccagcagagagattgca gccttcttccctgacttcagtgaacagcgctggtatgaggaggaagagcc ccagttgcgctgtggccctgtgtga (Amino Acids)

(SEQ ID NO: 67)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGSDSVVSASREIA

AFFPDFSEQRWYEEEEPQLRCGPV-

Human NME6 2:
(DNA)

(SEQ ID NO: 68)
Atgctcactctagccctgatcaagcctgacgcagtcgcccatccactgat tctggaggctgttcatcagcagattctaagcaacaagttcctgattgtac gaatgagagaactactgtggagaaaggaagattgccagaggttttaccga gagcatgaagggcgttttttctatcagaggctggtggagttcatggccag cgggccaatccgagcctacatccttgcccacaaggatgccatccagctct ggaggacgctcatgggacccaccagagtgttccgagcacgccatgtggcc ccagattctatccgtgggagtttcggcctcactgacacccgcaacaccac ccatggttcggactctgtggtttcagccagcagagagattgcagccttct ccctgacttcagtgaacagcgctggtatgaggaggaagagccccagttg cgctgtggccctgtgtga (Amino Acids)

(SEQ ID NO: 69)
MLTLALIKPDAVAHPLILEAVHQQILSNKFLIVRMRELLWRKEDCQRFYR

EHEGRFFYQRLVEFMASGPIRAYILAHKDAIQLWRTLMGPTRVFRARHVA

PDSIRGSFGLTDTRNTTHGSDSVVSASREIAAFFPDFSEQRWYEEEEPQL

RCGPV-

Human NME6 3:
(DNA)

(SEQ ID NO: 70)
Atgctcactctagccctgatcaagcctgacgcagtcgcccatccactgat tctggaggctgttcatcagcagattctaagcaacaagttcctgattgtac gaatgagagaactactgtggagaaaggaagattgccagaggttttaccga gagcatgaagggcgttttttctatcagaggctggtggagttcatggccag cgggccaatccgagcctacatccttgcccacaaggatgccatccagctct ggaggacgctcatgggacccaccagagtgttccgagcacgccatgtggcc ccagattctatccgtgggagtttcggcctcactgacacccgcaacaccac ccatggttcggactctgtggtttcagccagcagagagattgcagccttct ccctgacttcagtgaacagcgctggtatgaggaggaagagccccagttg cgctgtggccctgtgtgctatagcccagagggaggtgtccactatgtagc tggaacaggaggcctaggaccagcctga (Amino Acids)

(SEQ ID NO: 71)
MLTLALIKPDAVAHPLILEAVHQQILSNKFLIVRMRELLWRKEDCQRFYR

EHEGRFFYQRLVEFMASGPIRAYILAHKDAIQLWRTLMGPTRVFRARHVA

PDSIRGSFGLTDTRNTTHGSDSVVSASREIAAFFPDFSEQRWYEEEEPQL

RCGPVCYSPEGGVHYVAGTGGLGPA-

Human NME6 Sequence Optimized for *E. coli* Expression:
(DNA)

(SEQ ID NO: 72)
Atgacgcaaaatctgggctcggaaatggcaagtatcctgcgctccccgca agcactgcaactgaccctggctctgatcaaaccggacgctgttgctcatc cgctgattctggaagcggtccaccagcaaattctgagcaacaaatttctg atcgtgcgtatgcgcgaactgctgtggcgtaaagaagattgccagcgttt ttatcgcgaacatgaaggcgttttcttttatcaacgcctggttgaattca tggcctctggtccgattcgcgcatatatcctggctcacaaagatgcgatt cagctgtggcgtaccctgatgggtccgacgcgcgtctttcgtgcacgtca tgtggcaccggactcaatccgtggctcgttcggtctgaccgatacgcgca ataccacgcacggtagcgactctgttgttagtgcgtcccgtgaaatcgcg gcctttttcccggacttctccgaacagcgttggtacgaagaagaagaacc gcaactgcgctgtggcccggtctgttattctccggaaggtggtgtccatt atgtggcgggcacgggtggtctgggtccggcatga (Amino Acids)

(SEQ ID NO: 73)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGSDSVVSASREIA

AFFPDFSEQRWYEEEEPQLRCGPVCYSPEGGVHYVAGTGGLGPA-

Human NME6 1 Sequence Optimized for *E. coli* Expression:

(DNA)

(SEQ ID NO: 74)
Atgacgcaaaatctgggctcggaaatggcaagtatcctgcgctccccgca agcactgcaactgaccctggctctgatcaaaccggacgctgttgctcatc cgctgattctggaagcggtccaccagcaaattctgagcaacaaattctg atcgtgcgtatgcgcgaactgctgtggcgtaaagaagattgccagcgttt ttatcgcgaacatgaaggccgtttcttttatcaacgcctggttgaattca tggcctctggtccgattcgcgcatatatcctggctcacaaagatgcgatt cagctgtggcgtaccctgatgggtccgacgcgcgtctttcgtgcacgtca tgtggcaccggactcaatccgtggctcgttcggtctgaccgatacgcgca ataccacgcacggtagcgactctgttgttagtgcgtcccgtgaaatcgcg gccttttcccggacttctccgaacagcgttggtacgaagaagaagaacc gcaactgcgctgtggcccggtctga (Amino Acids)

(SEQ ID NO: 75)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGSDSVVSASREIA

AFFPDFSEQRWYEEEEPQLRCGPV-

Human NME6 2 Sequence Optimized for *E. coli* Expression:

(DNA)

(SEQ ID NO: 76)
Atgctgaccctggctctgatcaaaccggacgctgttgctcatccgctgat tctggaagcggtccaccagcaaattctgagcaacaaatttctgatcgtgc gtatgcgcgaactgctgtggcgtaaagaagattgccagcgttttttatcgc gaacatgaaggccgtttcttttatcaacgcctggttgaattcatggcctc tggtccgattcgcgcatatatcctggctcacaaagatgcgattcagctgt ggcgtaccctgatgggtccgacgcgcgtctttcgtgcacgtcatgtggca ccggactcaatccgtggctcgttcggtctgaccgatacgcgcaataccac gcacggtagcgactctgttgttagtgcgtcccgtgaaatcgcggccttttt tcccggacttctccgaacagcgttggtacgaagaagaagaaccgcaactg cgctgtggcccggtctga (Amino Acids)

(SEQ ID NO: 77)
MLTLALIKPDAVAHPLILEAVHQQILSNKFLIVRMRELLWRKEDCQRFYR

EHEGRFFYQRLVEFMASGPIRAYILAHKDAIQLWRTLMGPTRVFRARHVA

PDSIRGSFGLTDTRNTTHGSDSVVSASREIAAFFPDFSEQRWYEEEEPQL

RCGPV-

Human NME6 3 Sequence Optimized for *E. coli* Expression:

(DNA)

(SEQ ID NO: 78)
Atgctgaccctggctctgatcaaaccggacgctgttgctcatccgctgat tctggaagcggtccaccagcaaattctgagcaacaaatttctgatcgtgc gtatgcgcgaactgctgtggcgtaaagaagattgccagcgttttttatcgc gaacatgaaggccgtttcttttatcaacgcctggttgaattcatggcctc tggtccgattcgcgcatatatcctggctcacaaagatgcgattcagctgt ggcgtaccctgatgggtccgacgcgcgtctttcgtgcacgtcatgtggca ccggactcaatccgtggctcgttcggtctgaccgatacgcgcaataccac gcacggtagcgactctgttgttagtgcgtcccgtgaaatcgcggccttttt tcccggacttctccgaacagcgttggtacgaagaagaagaaccgcaactg cgctgtggcccggtctgttattctccggaaggtggtgtccattatgtggc gggcacgggtggtctgggtccggcatga (Amino Acids)

(SEQ ID NO: 79)
MLTLALIKPDAVAHPLILEAVHQQILSNKFLIVRMRELLWRKEDCQRFYR

EHEGRFFYQRLVEFMASGPIRAYILAHKDAIQLWRTLMGPTRVFRARHVA

PDSIRGSFGLTDTRNTTHGSDSVVSASREIAAFFPDFSEQRWYEEEEPQL

RCGPVCYSPEGGVHYVAGTGGLGPA-

OriGene-NME7-1 Full Length
(DNA)

(SEQ ID NO: 80)
gacgttgtatacgactcctatagggcggccgggaattcgtcgactggatc cggtaccgaggagatctgccgccgcgatcgccatgaatcatagtgaaaga ttcgttttcattgcagagtggtatgatccaaatgcttcacttcttcgacg ttatgagcttttattttacccaggggatggatctgttgaaatgcatgatg taaagaatcatcgcaccttttttaaagcggaccaaatatgataacctgcac ttggaagatttatttataggcaacaaagtgaatgtcttctctcgacaact ggtattaattgactatggggatcaatatacagctcgccagctgggcagta ggaaagaaaaaacgctagccctaattaaaccagatgcaatatcaaaggct ggagaaataattgaaataaacaaagctggatttactataaccaaact caaaatgatgatgctttcaaggaaagaagcattggattttcatgtagatc accagtcaagacccttttttcaatgagctgatccagtttattacaactggt cctattattgccatggagattttaagagatgatgctatatgtgaatggaa aagactgctgggacctgcaaactctggagtggcacgcacagatgcttctg aaagcattagagccctcttttggaacagatggcataagaaatgcagcgcat ggccctgattcttttgcttctgcggccagagaaatggagttgttttttcc ttcaagtggaggttgtgggccggcaaacactgctaaatttactaattgta cctgttgcattgttaaaccccatgctgtcagtgaaggactgttgggaaag atcctgatggctatccgagatgcaggttttgaaatctcagctatgcagat -continued gttcaatatggatcgggttaatgttgaggaattctatgaagtttataaag gagtagtgaccgaatatcatgacatggtgacagaaatgtattctggccct tgtgtagcaatggagattcaacagaataatgctacaaagacatttcgaga attttgtggacctgctgatcctgaaattgcccggcatttacgccctggaa ctctcagagcaatctttggtaaaactaagatccagaatgctgttcactgt actgatctgccagaggatggcctattagaggttcaatacttcttcaagat cttggataatacgcgtacgcggccgctcgagcagaaactcatctcagaag aggatctggcagcaaatgatatcctggattacaaggatgacgacgataag gtttaa (Amino Acids)

(SEQ ID NO: 81)
MNHSERFVFIAEWYDPNASLLRRYELLFYPGDGSVEMHDVKNHRTFLKRT

KYDNLHLEDLFIGNKVNVFSRQLVLIDYGDQYTARQLGSRKEKTLALIKP

DAISKAGEIIEIINKAGFTITKLKMMMLSRKEALDFHVDHQSRPFFNELI

QFITTGPIIAMEILRDDAICEWKRLLGPANSGVARTDASESIRALFGTDG

IRNAAHGPDSFASAAREMELFFPSSGGCGPANTAKFTNCTCCIVKPHAVS

EGLLGKILMAIRDAGFEISAMQMFNMDRVNVEEFYEVYKGVVTEYHDMVT

EMYSGPCVAMEIQQNNATKTFREFCGPADPEIARHLRPGTLRAIFGKTKI

QNAVHCTDLPEDGLLEVQYFFKILDNTRTRRLEQKLISEEDLAANDILDY

KDDDDKV

Abnova NME7-1 Full Length (Amino Acids)

(SEQ ID NO: 82)
MNHSERFVFIAEWYDPNASLLRRYELLFYPGDGSVEMHDVKNHRTFLKRT

KYDNLHLEDLFIGNKVNVFSRQLVLIDYGDQYTARQLGSRKEKTLALIKP

DAISKAGEIIEIINKAGFTITKLKMMMLSRKEALDFHVDHQSRPFFNELI

QFITTGPIIAMEILRDDAICEWKRLLGPANSGVARTDASESIRALFGTDG

IRNAAHGPDSFASAAREMELFFPSSGGCGPANTAKFTNCTCCIVKPHAVS

EGLLGKILMAIRDAGFEISAMQMFNMDRVNVEEFYEVYKGVVTEYHDMVT

EMYSGPCVAMEIQQNNATKTFREFCGPADPEIARHLRPGTLRAIFGKTKI

QNAVHCTDLPEDGLLEVQYFFKILDN

NME6 S139G (Human)
(DNA)

(SEQ ID NO: 117)
atgacccagaatctggggagtgagatggcctcaatcttgcgaagccctca ggctctccagctcactctagccctgatcaagcctgacgcagtcgcccatc cactgattctggaggctgttcatcagcagattctaagcaacaagttcctg attgtacgaatgagagaactactgtggagaaaggaagattgccagaggtt ttaccgagagcatgaagggcgttttttctatcagaggctggtggagttca tggccagcgggccaatccgagcctacatccttgcccacaaggatgccatc cagctctggaggacgctcatgggacccaccagagtgttccgagcacgcca tgtggccccagattctatccgtgggagtttcggcctcactgacacccgca acaccacccatggtggcgactctgtggtttcagccagcagagagattgca gccttcttccctgacttcagtgaacagcgctggtatgaggaggaagagcc ccagttgcgctgtggccctgtgtgctatagcccagagggaggtgtccact atgtagctggaacaggaggcctaggaccagcctga (Amino Acids)

(SEQ ID NO: 118)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGGDSVVSASREIA

AFFPDFSEQRWYEEEEPQLRCGPVCYSPEGGVHYVAGTGGLGPA*

NME6 HutoS (Human)
(DNA)

(SEQ ID NO: 119)
Atgacccagaatctggggagtgagatggcctcaatcttgcgaagccctca ggctctccagctcactctagccctgatcaagcctgacgcagtcgcccatc cactgattctggaggctgttcatcagcagattctaagcaacaagttcctg attgtacgaatgagagaactactgtggagaaaggaagattgccagaggtt ttaccgagagcatgaagggcgttttttctatcagaggctggtggagttca tggccagcgggccaatccgagcctacatccttgcccacaaggatgccatc cagctctggaggacgctcatgggacccaccagagtgttccgagcacgcca tgtggccccagattctatccgtgggagtttcggcctcactgacacccgca acaccacccatggtgccgactctgatgcttcagccagcagagagattgca gccttcttccctgacttcagtgaacagcgctggtatgaggaggaagagcc ccagttgcgctgtggccctgtgtgctatagcccagagggaggtgtccact atgtagctggaacaggaggcctaggaccagcctga (Amino Acids)

(SEQ ID NO: 120)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGADSDASASREIA

AFFPDFSEQRWYEEEEPQLRCGPVCYSPEGGVHYVAGTGGLGPA*

NME-6 S139G Sequence Optimized for *E. coli* Expression
(DNA)

(SEQ ID NO: 121)
atgacgcaaaatctgggctcggaaatggcaagtatcctgcgctccccgca agcactgcaactgaccctggctctgatcaaaccggacgctgttgctcatc cgctgattctggaagcggtccaccagcaaattctgagcaacaaatttctg atcgtgcgtatgcgcgaactgctgtggcgtaaagaagattgccagcgttt -continued ttatcgcgaacatgaaggccgtttcttttatcaacgcctggttgaattca tggcctctggtccgattcgcgcatatatcctggctcacaaagatgcgatt cagctgtggcgtaccctgatgggtccgacgcgcgtctttcgtgcacgtca tgtggcaccggactcaatccgtggctcgttcggtctgaccgatacgcgca ataccacgcacggtggcgactctgttgttagtgcgtcccgtgaaatcgcg gccttttcccggacttctccgaacagcgttggtacgaagaagaagaacc gcaactgcgctgtggcccggtctgttattctccggaaggtggtgtccatt atgtggcgggcacgggtggtctgggtccggcatga (Amino Acids)

(SEQ ID NO: 122)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGGDSVVSASREIA

AFFPDFSEQRWYEEEEPQLRCGPVCYSPEGGVHYVAGTGGLGPA*

NME-6 HutoS Sequence Optimized for *E. coli* Expression
(DNA)

(SEQ ID NO: 123)
Atgacgcaaaatctgggctcggaaatggcaagtatcctgcgctccccgca agcactgcaactgaccctggctctgatcaaaccggacgctgttgctcatc cgctgattctggaagcggtccaccagcaaattctgagcaacaaatttctg atcgtgcgtatgcgcgaactgctgtggcgtaaagaagattgccagcgttt ttatcgcgaacatgaaggccgtttcttttatcaacgcctggttgaattca tggcctctggtccgattcgcgcatatatcctggctcacaaagatgcgatt cagctgtggcgtaccctgatgggtccgacgcgcgtctttcgtgcacgtca tgtggcaccggactcaatccgtggctcgttcggtctgaccgatacgcgca ataccacgcacggtgccgactctgatgctagtgcgtcccgtgaaatcgcg gccttttcccggacttctccgaacagcgttggtacgaagaagaagaacc gcaactgcgctgtggcccggtctgttattctccggaaggtggtgtccatt atgtggcgggcacgggtggtctgggtccggcatga (Amino Acids)

(SEQ ID NO: 124)
MTQNLGSEMASILRSPQALQLTLALIKPDAVAHPLILEAVHQQILSNKFL

IVRMRELLWRKEDCQRFYREHEGRFFYQRLVEFMASGPIRAYILAHKDAI

QLWRTLMGPTRVFRARHVAPDSIRGSFGLTDTRNTTHGADSDASASREIA

AFFPDFSEQRWYEEEEPQLRCGPVCYSPEGGVHYVAGTGGLGPA*

Abnova Partial NME7-B
(Amino Acids)

(SEQ ID NO: 83)
DRVNVEEFYEVYKGVVTEYHDMVTEMYSGPCVAMEIQQNNATKTFREF

CGPADPEIARHLRPGTLRAIFGKTKIQNAVHCTDLPEDGLLEVQYFFKIL

Histidine Tag
(ctcgag)caccaccaccaccaccactga (SEQ ID NO:84)
Strept II Tag (SEQ ID NO: 85)
(accggt)tggagccatcctcagttcgaaaagtaatga Ligands of MUC1*

The inventors previously disclosed that ligands of the MUC1* receptor can function as growth factors, and in particular are growth factors for stem and progenitor cells. NME family proteins (previously called NM23) are ligands of MUC1*. NME proteins are grouped together because they all have an NDPK (nucleotide diphosphate kinase) domain. NME1 or NME2 expressed or purified such that a significant population exists as a dimer, support the growth of embryonic or induced pluripotent stem cells in the absence of feeder cells, their extracts, serum or any other cytokine. Herein, we report that NME7 is also a ligand of MUC1* and also supports the growth of embryonic or induced pluripotent stem cells in the absence of feeder cells, their extracts, serum or any other cytokine. NME6, NME1 and NME2 all have a single NDPK domain and are of similar molecular weight. NME7 is twice their molecular weight and contains two NDPK domains. NME6 can exist as a dimer, like NME1. Therefore, NME1, NME2 and NME6 in dimeric form and NME7 are preferred NME family proteins for the growth of stem or progenitor cells, which included but are not limited to mesenchymal stem cells, hematopoietic stem cells, pluripotent stem cells and naïve state stem cells, as well as for the maintenance or induction of pluripotency. Especially preferred are NME1 and NME7. Still more preferred are NME1 in dimeric form and NME7. It is not intended that the invention be restricted to the natural forms of the proteins. For commercial advantage, the proteins may be made as recombinant proteins that may bear mutations, truncations or additional sequences. Herein, this NME7 variant is referred to simply as NME7 since the invention is not meant to be limited by specific variants that may increase the yield of expressed recombinant protein, solubility and the like. Further, the invention envisions the use of single chain variants of NME1 or NME6, wherein the single chain protein is comprised of two connected monomers, wherein each monomer may consist of a single NDPK A or B domain.

Induced Pluripotency

Forced expression of combinations of the transcription factors, Oct4, Sox2, Klf4 and c-Myc or Oct4, Sox2, Nanog and Lin28 have been shown to cause mature cells to revert to the pluripotent state (Takahashi and Yamanaka, 2006). Each of the transcription factors that induce pluripotency regulates the transcription of about a dozen genes. Among these were several that the inventor has identified as being MUC1-associated factors. OCT4 and SOX2 bind to the MUC1 promoter itself. Pluripotency proteins SOX2 and NANOG bind to the NME7 promoter, underscoring its importance for pluripotency of stem cells. NM23 (also known as NME) was previously identified, by the present inventor, as the activating ligand of MUC1* (Mahanta et al., 2008). NME7 is an activating ligand of MUC1*. OCT4 and SOX2 both bind to the promoter for MMP16 which we disclose herein is a cleavage enzyme of MUC1. OCT4, SOX2 or NANOG also bind to promoter sites for cleavage enzymes MMP2, MMP9, MMP10, ADAM TSL-1, ADAM TS-4, ADAM-17 (a MUC1 cleavage enzyme), ADAM-TS16, ADAM-19 and ADAM-28. Some or all of these cleavage enzymes may be upregulated to enhance the cleavage of MUC1 to the MUC1* form to induce pluripotency or maintain it (Boyer et al, 2005). Taken together, it is clear that MUC1* (cleaved form) and its ligand NME7 are activators of pluripotency, since the key pluripotency proteins, SOX2 and NANOG bind to the NME7 promoter and OCT4 and SOX2 bind to the MUC1 promoter, and turn on expression of these genes.

Figure 15:
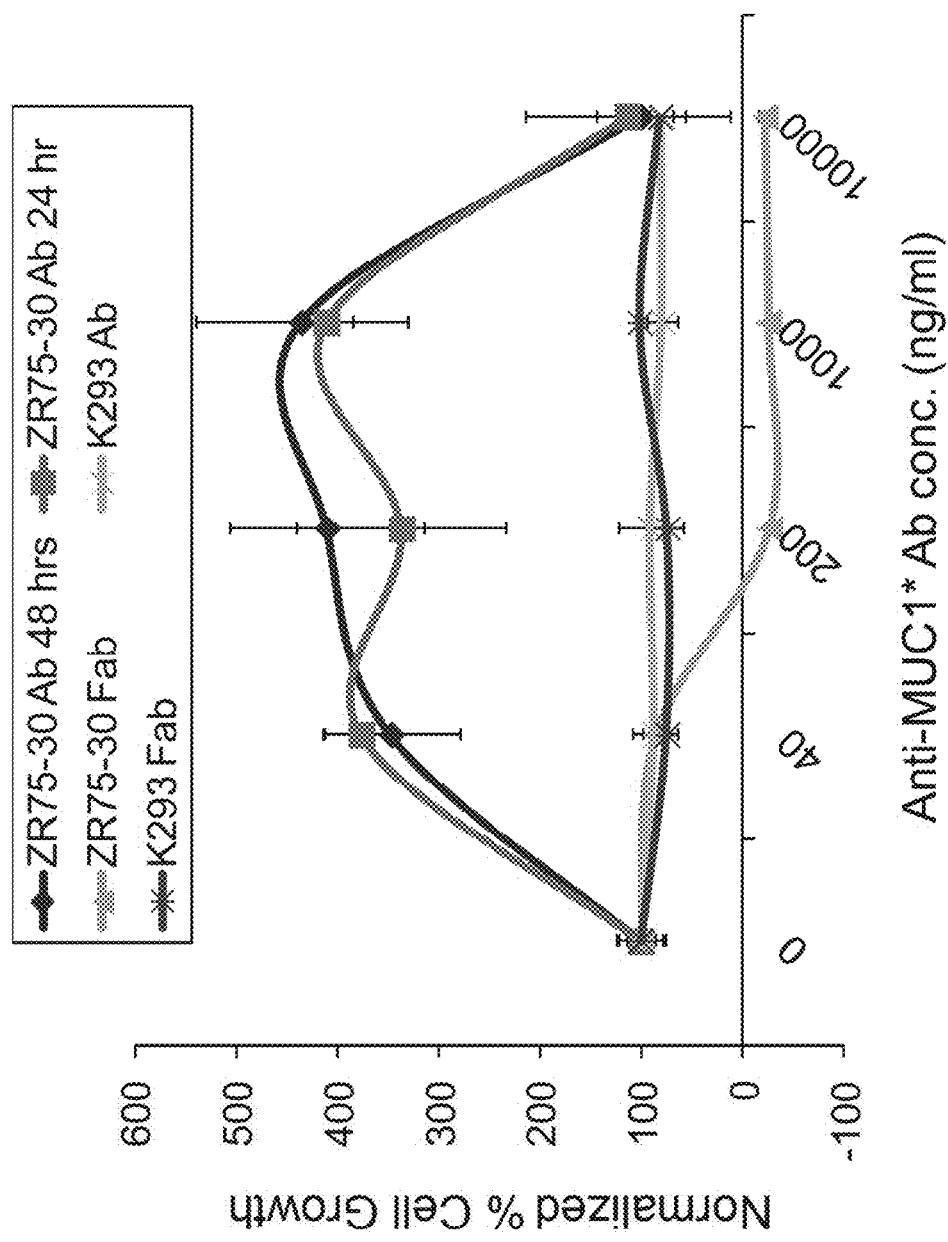
FIG. 15 is a graph of cancer cell growth measured as a function of bivalent or monovalent antibody concentration, showing that it is dimerization of the MUC1* receptor that stimulates growth. The growth of MUC1-positive breast cancer cells, ZR-75-30, was stimulated by the addition of bivalent (Ab) Anti-MUC1* and inhibited by the addition of the monovalent Fab. The addition of bivalent antibody produces the characteristic bell-shaped growth curve indicative of growth factor receptor dimerization. The growth of MUC1-negative HEK 293 cells was not impacted by either the bivalent or monovalent Fab Anti-MUC1*. When the bivalent antibody was added in excess, there is one bivalent antibody bound to each receptor rather than one bivalent antibody dimerizing every two receptors and thus inhibits growth.

Our previous work with embryonic stem cells, which only express the cleaved form of MUC1, MUC1*, showed that dimerization of its extracellular domain stimulate growth and inhibit differentiation (Hikita et al., 2008). These effects were achieved by dimerizing the MUC1* extracellular domain using either a bivalent Anti-MUC1* antibody (FIG. 15), recombinant NM23, or a mutant NM23 (S120G) that preferentially forms dimers (Kim et al., 2003). Inhibition of MUC1* extracellular domain using the monovalent Anti-MUC1* Fab was lethal within hours.

Surface Plasmon Resonance (SPR) experiments were performed that show that only NME1 dimers bind to the MUC1* extra cellular domain peptide. FIG. 17A shows photographs of non-reducing gels of NM23-WT, NM23-S120G-mixed, NM23-S120G-hexamer and NM23-S120G-dimer, which show the multimerization state of the wild type protein and the three different preparations of the S120G mutant. FIG. 17B shows an overlay of Surface Plasmon Resonance (SPR) measurements showing the ability of the four different NM23s to bind to a MUC1* extra cellular domain peptide (PSMGFR) attached to the SPR chip surface. Results show that the amount of binding of NM23 to its cognate receptor, MUC1*, is a function of how much dimer is present in the sample. SPR measures protein mass at the chip-solution interface, so if the hexamer bound to the MUC1* peptide surface, it would yield an SPR signal 3-times greater than if a dimer bound. FIG. 17C shows photograph of a nanoparticle experiment that shows that only NM23 dimers bind to the cognate receptor MUC1*. MUC1* extra cellular domain peptide was immobilized onto gold nanoparticles. To each aliquot of nanoparticles, either NM23-WT, NM23-S120G-dimer or NM23-S120G-hexamer was added. If the NM23 bound to the nanoparticle immobilized MUC1* peptide, it would cause the nanoparticles to become drawn close together which causes the solution to change from pink to blue. The experiment shows that only the NM23-S120G-dimer bound to the MUC1* peptide. The addition of an anti-MUC1* Fab competitively inhibited binding of NM23-S120G-dimers in solution to the MUC1* peptide on the nanoparticles. FIGS. 17D-G show different NM23 multimers tested for their ability to support pluripotent stem cell growth. Human ES (embryonic stem) cells were cultured in either FIG. 17D-NM23-S120G-dimer, FIG. 17E-NM23-S120G-hexamer, FIG. 17F-NM23-WT, or FIG. 17G-NM23-S120G-dimer plus the MUC1* extra cellular domain peptide (PSMGFR) to competitively inhibit binding of the NM23 dimer to the MUC1* receptor on the stem cell surface. Induction of differentiation is readily observed (colony thickening, darkening) in (G), (E), and (F in that order, showing that inhibition of the NM23-dimer-MUC1* interaction induces differentiation as does culturing the cell in NM23 hexamers that do not bind to MUC1*. Only the dimer preparation of NM23-S120G (D) was able to support undifferentiated stem cell growth.

Figure 18:
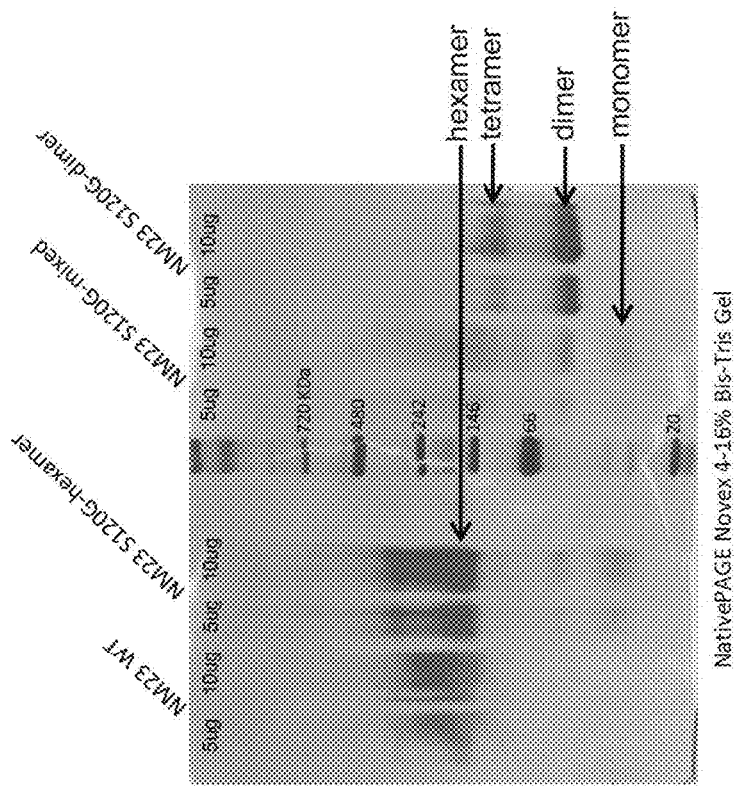
FIG. 18 shows a native, non-denaturing gel that shows the multimerization state of NM23-WT versus three different preparations of recombinant NM23-S120G.

FIG. 18 shows a native, non-denaturing gel that shows the multimerization state of NM23-WT versus three different preparations of recombinant NM23-S120G.

Figure 19:
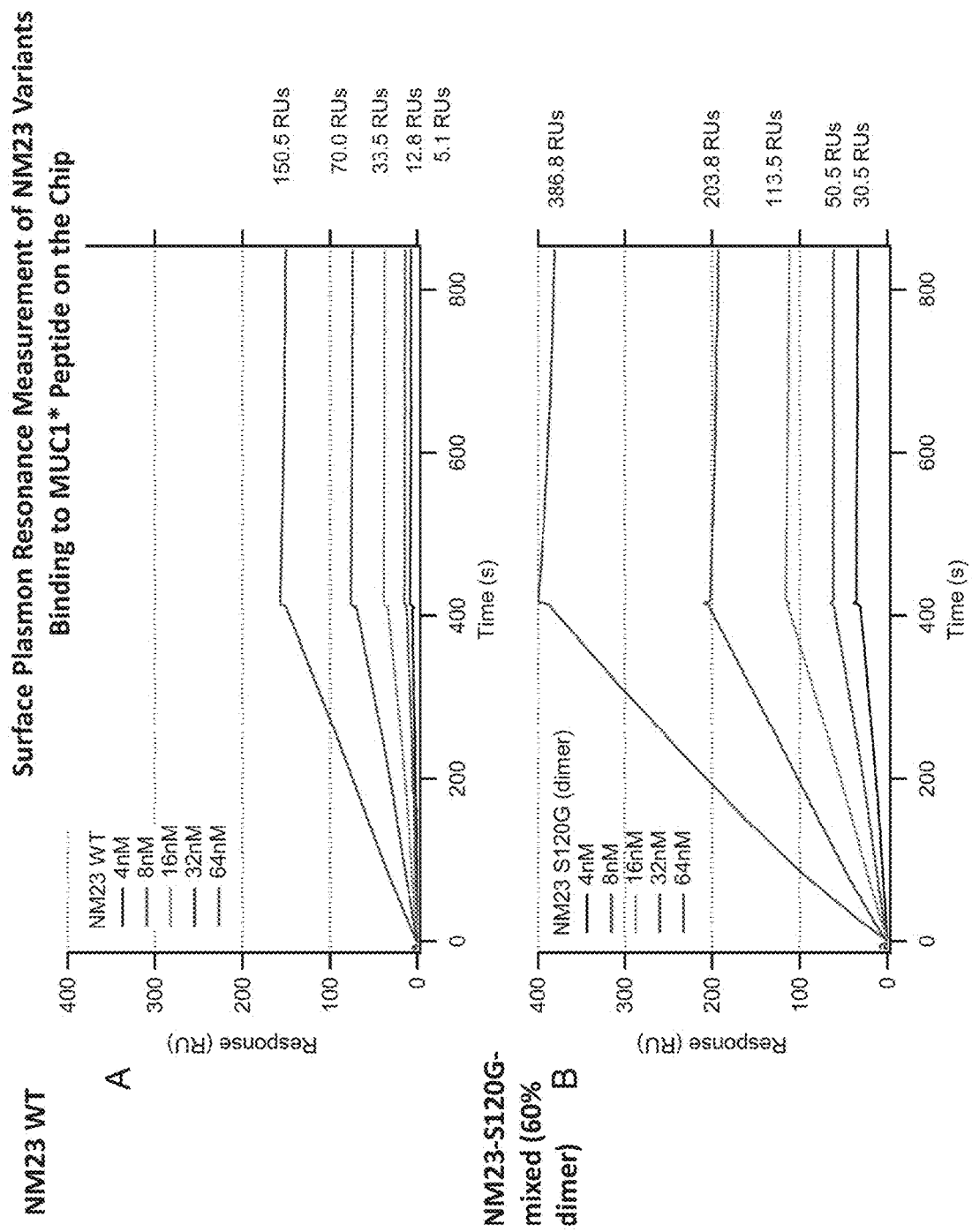
FIG. 19 shows SPR measurements of A) NM23 wild type (WT) and B) a preparation of NM23-S120G-"mixed" that produced 60% dimer.

FIG. 19 shows SPR measurements of A) NM23 wild type (WT) and B) a preparation of NM23-S120G-"mixed" that produced 60% dimer. Protein was injected at five different concentrations. Results show that 8-times more NM23-S120G-mixed protein bound to a MUC1* extra cellular domain peptide surface than NM23-WT. Because the wild type protein is a hexamer, the number of RUs must be divided by 3 to compare to the amount of dimer that bound. Although both wild type and S120G-dimer show a concentration dependence in binding, the amount of wild type hexamer that bound is so small that it may still be within the noise range of the system.

These findings indicate that MUC1* is a significant "stemness" factor. In addition, OCT4 and SOX2 bind to the MUC1 gene promoter and also to the promoter of its cleavage enzymes. SOX2 and NANOG bind to the NM23 (NME7) promoter. Since blocking the extracellular domain of MUC1* is lethal to hES cells, it follows that the pluripotency genes, OCT4, SOX2, and NANOG, bind to the promoter sites of MUC1, its cleavage enzymes and its activating ligand NME7 and induce their expression of MUC1. One or more of the genes or gene products that have already been shown to induce pluripotency can be replaced by transfecting the gene or introducing the gene product for MUC1* alone or in addition to its cleavage enzymes and/or activating ligands, NME7, NME-H1, NME-H2 or an antibody that dimerizes the PSMGFR epitope of MUC1 or MUC1*.

Experiments were performed to test the efficiency of induction of pluripotency in somatic cells using the standard protocol that uses FGF-based media or an altered protocol that uses NME-based media.

The conventionally used standard protocol is to first plate dermablasts or fibroblasts (human foreskin fibroblast-neonatal, "hFFn": #PC501A-hFF, System Biosciences, Mountain View, Calif.) on plastic and culture them in fibroblast media (FM), changed every 24 hours. After 5 days, the cells are transferred to a surface coated with inactivated fibroblast feeder cells, which can be mouse (MEFs) or human (HS27). For the next 2 days, cells remain in FM. On Day 7 the media is changed to bFGF-based media and media is changed every 24 hours. ~2-4 weeks post initial plating, colonies (clones) that have embryonic stem (ES) cell-like morphology are selected and individually plated into new wells coated with inactivated feeder cells (MEFs or HS27s) and sequentially passaged every 3-4 days. Wells that continue to grow as ES-like cells are propagated and tested for the presence of pluripotency markers.

Figure 31:
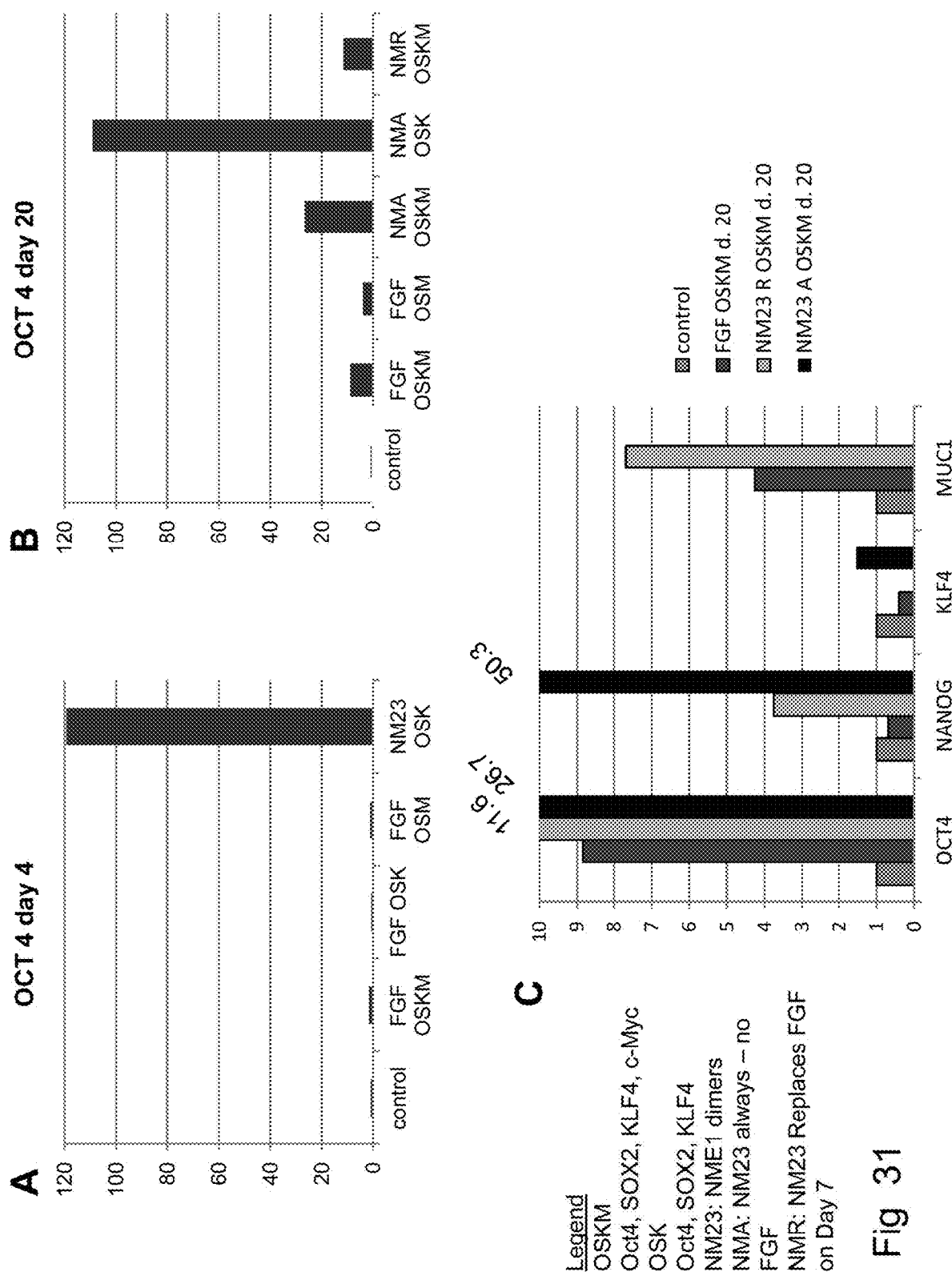
FIG. 31A-31G show graphs and photographs of somatic cells undergoing induction of pluripotency in either FGF-based media or NME-based media. A-C are graphs showing RT-PCR measurements of pluripotency markers at Day 4 and Day 20 of the pluripotency induction process. D-G show photographs of confocal microscope images of representative cells induced to be pluripotent using standard method using standard FGF media or omitting one pluripotency gene and culturing cells in NME1 dimer media.

Contrary to the conventionally used standard protocol, we cultured the somatic cells in NME media always (NME1 dimers: "NM23-MM-A"). In addition, we either plated the cells over a layer of fibroblast feeder cells or over a layer of anti-MUC1* antibody (C3 or C8 that recognize the N-10 PSMGFR peptide. RT-PCR measurements were performed to quantify the amount of Oct4 expressed under a variety of conditions by Day 4 (FIG. 31A) or by day 20 (FIG. 31B). By Day 4, the only condition that resulted in an induction of pluripotency, as measured by expression levels of Oct4, was for fibroblasts transfected with OCT4, SOX2 and KLF4 ("OSK") (no c-Myc) and cultured in NME1 dimers in minimal media ("MM"). For those cells Oct4 was 119-times greater than the starting cells and nearly 200-times greater than identical cells that were instead cultured in fibroblast media. By Day 20, cells transfected with only three genes, OSK and cultured in NM23-MM-A expressed Oct4 at 109-times greater than the control. Cells that had been transfected with OSKM and cultured in NM23-MM always had Oct4 expression that was 3-times greater than identical cells cultured in fibroblast media (FM) then switched to bFGF media (standard), while cells cultured in FM then switched to NM23-MM only had Oct4 expression that was 1.3-times greater than cells cultured in FM then bFGF-M (FIG. 31C) Immunocytochemical staining of the cells at Day 20 for pluripotency marker Tra 1-60 shows the major advantage of inducing pluripotency in cells using an NME-based media. Cells that were transfected with OCT4, SOX2 and KLF4 and cultured in NME1 dimers in minimal media and in the absence of added FGF had a vast increase in efficiency of induction of pluripotency (FIG. 31F,G) compared to cells transfected with all four pluripotency genes OCT4, SOX2, KLF4 and c-Myc and cultured according to standard protocol in FGF-media (FIG. 31D,E). Cells that were transfected with three pluripotency genes, OCT4, SOX2 and KLF4, did not have detectable pluripotency markers and lacked stem-like morphology.

In a preferred embodiment, NM23 (NM23-H1, NM23-H2, or NME7) is introduced to cells, as the gene that encodes it, as the protein itself or as a protein bearing a leader sequence such as a poly-arginine tract, to facilitate entry into the cell, to aid in the induction or maintenance of pluripotency. The inventors recently showed that when NM23 is secreted by pluripotent stem cells (and cancer cells), it is an activating ligand of the cleaved form of MUC1-MUC1*—and triggers the MAP kinase proliferation pathway. NM23 stimulation of MUC1* was shown to promote the growth of pluripotent hESCs and inhibited their differentiation (Hikita et al., 2008). NM23 also induces the transcription of c-MYC (Dexheimer at al., 2009) and replaces the need for c-MYC. NM23 is added exogenously either in its native state to activate the MUC1* growth factor receptor or with a poly arginine tract to facilitate entry into the cell and nucleus where it induces C-MYC expression. NM23 (NME) may be added as the encoding nucleic acid, or as the expressed protein with or without a modification that facilitates entry into the cell. NME1 or NME2 can be used in their native state or in mutant forms that favor the dimeric state, such as the S120G mutation or NME7.

In another aspect of the invention, a bivalent antibody that binds to the extracellular domain of MUC1* (PSMGFR) or a dimeric MUC1* ligand, such as NM23, or genes encoding them are added to MUC1*-expressing cells to induce pluripotency, increase the efficiency of the induction of pluripotency, to maintain pluripotency or to inhibit differentiation. The cells to which these MUC 1 or MUC1* interacting proteins are added may be naturally occurring cells or those into which genes to induce stem cell-like characteristics have been added, or have already entered the differentiation process or may be stem cells.

Genes for inducing pluripotency may be introduced on the same or different plasmids, which may be lenti viral vector driven or adenovirus vectors or any integrating or non-integrating viral or non-viral vector, or any other system that facilitates introduction of these genes into the desired cells.

In many cases, it is preferential to achieve the effects of pluripotency-inducing proteins by introducing the proteins themselves rather than the nucleic acids or genes that encode them. The invention encompasses genes disclosed here for the induction of stem-like characteristics or pluripotency that can be replaced by the gene products, the proteins, either in their native state or modified with leader sequences such as poly-arginine tracts to allow entry into the cells. The products of these genes, i.e. proteins, or other proteins which interact with one or more of the products of the transfected genes are introduced to cells to induce or maintain pluripotency or other stem-cell like characteristics.

NM23 protein such as, but not limited to, NME-H1, NME-H2, NME6 or NME-7 enhances the induction or maintenance of pluripotency. NM23 is introduced along with one or more of the previously identified pluripotency factors, including but not limited to OCT4, SOX2, KLF4, as well as others disclosed herein.

NM23 Family Proteins

NM23 exists as a family of proteins wherein the commonality among these proteins is the presence of a nucleoside diphosphate kinase (NDPK) domain that catalyzes the conversion of ATP to ADP. NM23 has previously been known as Tumor Metastasis Factor. With the recent identification of ten NM23 family members, they are now also known as NME proteins 1-10 (Boissan et al., Mol Cell Biochem (2009) 329:51-62, "The mammalian Nm23/NDPK family: from metastasis control to cilia movement,").

Scientists first isolated a differentiation inhibition factor from human leukemia cells and showed that the addition of this factor blocked chemically induced differentiation of certain types of leukemia and myeloid cells (Okabe-Kado, 1985, Cancer Research 45, 4848-4852, "Characterization of a Differentiation-inhibitory Activity from Nondifferentiating Mouse Myeloid Leukemia Cells); this inhibitory factor was later identified as NME1 (NM23-H1) (Okabe-Kado, 1992, "Identity of a differentiation inhibiting factor for mouse myeloid leukemia cells with NM23/nucleoside diphosphate kinase", Biochem Biophys Res Comm, 182 No. 3 987-994). Leukemia cells are blood cells that are blocked from terminal differentiation. Interestingly, the ability to inhibit differentiation of leukemia cells was shown to be independent of its catalytic domain. Mutations in the NDPK domain that abrogated its enzymatic activity had no effect on the protein's ability to block differentiation of some types of leukemia cells. However, the scientific literature of the following decades paints a picture of total confusion as to whether NM23 inhibits differentiation, accelerates differentiation or has no effect at all.

Many research articles provided evidence indicating that NM23 induces differentiation. Rosengard et al, 1989, Dearolf et al 1993, and Timmons et al 1993 reported that in vivo the *Drosophila* NM23 homologue, awd, is required for proper differentiation. Lakso et al 1992 reported that NM23 (mouse in vivo) increases with initiation of tissue differentiation, implying that it induces differentiation. Yamashiro et al 1994 reported that in vitro NM23 levels increase during differentiation of human erythroleukemia cells. Lombardi et al 1995 concluded that NM23 (mouse in vitro) increases with initiation of cellular differentiation, again indicating that NM23 induces differentiation. Gervasi 1996, reported that overexpression of NM23 (rat in vitro) induced neuronal differentiation and down regulation of NM23 with anti-sense DNA inhibited differentiation. Amendola et al 1997 showed that transfection of NM23 in human neuroblastoma cells increased differentiation.

In direct contradiction to the many research articles that reported that NM23 induced differentiation, an equal number of papers published in the same time frame reported the opposite: that NM23 inhibited differentiation. Munoz-Dorado et al 1990 found that ndk (Myxococcus NM23 homologue, in vivo) was essential for growth but was down regulated during development, implying that its presence would inhibit differentiation. Okabe-Kado 1992 showed that in vitro a differentiation inhibitory factor (later identified by same group as NM23) inhibited differentiation of mouse leukemia. Yamashiro et al 1994 reported that NM23 levels decrease during differentiation of human megakaryoblasts, consistent with NM23 inhibiting differentiation. Okabe- Kado 1995 showed that recombinant NM23 inhibited erythroid differentiation of leukemia cell lines HEL, KU812, and K562 but not monocyte or granulocyte differentiation of progenitors HL60, U937, or HEL/S cells. Venturelli et al 1995 reported that NM23 overexpression inhibited G-CSF dependent granulocyte differentiation of human hematopoietic progenitors. Willems et al 1998 found that NM23 expression decreases as human CD34$^+$ hematopoietic progenitors from the bone marrow cells differentiate. In 2002, Willems et al showed that NM23 had no effect on cell proliferation, did not induce or inhibit differentiation but skewed differentiation of CD34+ cells toward the erythroid lineage.

In a 2000 review article, Lombardi summarized these and other contradictory results pertaining to the role of NM23 in differentiation and concluded, "Although the role of the NM23 genes in the control of cell differentiation is widely under investigation, the functional connection between NM23 expression levels and such processes remains to be completely elucidated." In other words, the functional connection between NM23 and differentiation was not understood.

The inventors previously discovered that the growth factor receptor function of a MUC 1 cleavage product, MUC1*, is activated by ligand induced dimerization of its extra cellular domain and that the ligand of MUC1* was NM23. The inventors further demonstrated that it was the dimer form of NM23 that inhibits differentiation and supports the growth of stem and progenitor cells. In addition, the inventors discovered that NM23 species induce pluripotency. We have now discovered that several NM23 family members have this stem-related function. NME1 (NM23-H1) promotes stem cell growth and inhibits differentiation when it is a dimer only. NME6 is roughly the same molecular weight as NME1 and in sea sponge (Suberites domuncula) it is reported to exist as a dimer (Perina et al, 2011, "Characterization of Nme6-like gene/protein from marine sponge Suberites domuncula" Naunyn-Schmiedeberg's Arch Pharmacol, 384:451-460). Although NME7 (NM23-H7) is a monomeric protein, the inventors have discovered that it functions like a dimer. It contains two NDPK catalytic domains, is approximately twice the molecular weight of an NME1 or NME6 monomer and is expressed and secreted by human embryonic stem (ES) and induced pluripotent stem (iPS) cells (see FIG. 23 and FIG. 24). Depletion of NME7 and NME1 from stem cells caused the cells to differentiate (data not shown). In a sandwich ELISA assay, recombinant NME7 (NME7-AB) simultaneously bound to two MUC1* extra cellular domain peptides, wherein both peptides were the full PSMGFR sequence. The first peptide was coupled to ovalbumin via a C-terminal Cysteine and was coated onto an ELISA plate. The addition of recombinant NME7 resulted in significant specific binding with little or no background. NME7 was then added to the peptide surface to saturation. The second PSMGFR peptide bore either a histidine tag or a biotin molecule. Then, either HRP labeled anti-His-tag antibody or streptavidin was added, which showed robust and concentration dependent binding of the second MUC1* peptide to the NME7. The results show that monomeric NME7 is able to dimerize MUC1* on a cell surface.

NME7 can also exist as a smaller protein of molecular weight ~25 kDa. Pull down assays of stem cell lysates and supernatants were performed followed by mass spectrometry. The smaller molecular weight forms of NME7 all contained peptide sequences from its NDPK A domain, but not from the B domain. This may be an alternative splice isoform or a cleavage product. Like NME1, this smaller A domain NME7 may dimerize.

NME family proteins are differentially expressed at different times of cell and tissue development. Whereas we detect NME6, NME7 and NME1 in embryonic stem cells, only NME1 and NME2 are routinely expressed in adult cells or adult stem cells. Because NME1 forms hexamers which induce rather than inhibit stem cell differentiation, it follows that NME6 and NME7 are expressed earlier in embryogenesis and in true pluripotent stem cells because they cannot form the hexamers.

In the earliest stages of embryogenesis, growth and inhibition of differentiation would be the default, with the regulatory function of the hexamer being important in later stages when one wants to initiate differentiation when a certain density of stem cells is reached. In support of our findings, Boyer et al (Boyer et al, 2005, "Core Transcriptional Regulatory Circuitry in Human Embryonic Stem Cells", Cell, Vol. 122, 947-956) reported that pluripotency inducing proteins SOX2 and NANOG bind to the promoter of NME7 but not other NME family members, indicating that it is the first NME protein expressed and is consistent with the notion that it can induce or maintain pluripotency but cannot form the hexamers that turn it off. Boyer et al also report that pluripotency inducing proteins SOX2 and OCT4 bind to the promoter of MUC1, the target receptor of NME7 following cleavage to MUC1*. SOX2 and OCT4 also bind to the promoter of the MUC1 cleavage enzyme MMP-16. The fact that these pluripotency inducing proteins redundantly bind to the promoters of MUC1, its cleavage enzyme and its ligand, NME7 argue that this subset of proteins is important to pluripotency and that NME7 is the first of the pluripotency proteins expressed in the developing embryo. NME7 is highly expressed by human stem cells if they are cultured in NM23 variants that prefer dimer formation.

Example 7 describes an experiment in which BGO1v human embryonic stem cells are grown in either NM23-S120G, which has been refolded and purified to exist primarily as a dimer (FIGS. 16-17), over a coating of anti-MUC1* monoclonal antibody MN-C3 or cultured in bFGF over mouse fibroblast feeder cells. Western blots of the resultant cells show that NME7 is highly expressed in stem cells that have been cultured in NM23-S120G dimers (FIG. 23 Part I. C—Lane 1) but only weakly expressed in stem cells cultured in bFGF (Lane 2). These results imply that stem cells cultured in NM23 dimers revert to a more pluripotent state also called the naïve state, whereas culturing stem cells in bFGF drives stem cells into a more differentiated state called the "primed" state. Research indicates that stem cells in the primed state are not capable of differentiating into any cell type the way true pluripotent stem cells should be able to.

Jaenisch and colleagues reported a set of markers of the naïve state and a second set of markers that are characteristic of the primed state (J. Hanna, A. W. Cheng, K. Saha et al., Proc Natl Acad Sci USA 107 (20), 9222 (2010), Jacob H. Hanna, Krishanu Saha, and Rudolf Jaenisch, Cell 143 (4), 508 (2010)). Experiments were performed in which human embryonic stem (ES) or induced pluripotent stem (iPS) cells were cultured in NME1 dimers or in NME7 in a variety of minimal media or they were cultured in FGF-based media. The surfaces upon which the stem cells were plated was also varied. RT-PCR measurements were then performed to measure expression levels of the naïve genes versus the primed genes for cells cultured in NME-based media compared to FGF-based media. In all cases, NME-based media generated stem cells that were in a more naïve state than cells cultured in FGF-based media. For example, cells grown in FGF in minimal media (MM) grown over MEF feeder cells had higher expression of the primed markers and lower expression of the naïve markers than the same source cells grown in NME1 dimers in minimal media (MM) wherein cells were plated over plasticware coated with an anti-MUC1* antibody. Another FGF-based media called mTeSR fared even worse with very high levels of the primed genes and lower levels of the naïve ones (FIG. 13). As stem cells that had previously been cultured in FGF were transitioned to NME-based media, there was a trend toward expressing higher levels of the naïve genes and lower levels of the primed genes with successive passage number. For one example of this trend, see Example 13C. These results are consistent with measurement of Histone-3 in the nucleus which is a more stringent determinant of the naïve state. Histone-3 is detected as a condensed dot in the nucleus of primed stem cells but not in the nucleus of naïve stem cells. 100% of FGF-grown cells are in the primed state and have condensed Histone-3 in their nucleus. By the $6^{th}$ passage in NME1 dimers or NME7, about 25-30% of the stem cells, which had previously been grown in FGF, had transitioned to the full naïve state, which is pre-X-inactivation. By the $10^{th}$ passage, the percentage in the true naïve state had increased to 50-60%. For several examples of this see FIGS. 34-40. These results are consistent with the findings shown in FIG. 23 Part I. C. Comparing Lane 1 to Lane 2, NME7 is expressed to a greater degree in the desirable naïve stem cells, which are able to differentiate into any cell type in the human body. Therefore, strategies that increase expression of NME7 in a cell, for example via introduction of nucleic acids capable of causing expression of NME7 or methods that add NME7 protein, or NME1 mutants or variants that prefer dimer formation are strategies that maintain pluripotency, maintain the naïve stem cell state in embryonic or induced pluripotent stem cells, and/or induce pluripotency in more mature cell types, including somatic cells, dermablasts and fibroblasts. These strategies may include ectopic expression of one or more of the pluripotency genes Oct4, Sox2, Nanog, Klf4 or c-myc in addition to NME7 or NME1 dimer forming or dimer mimicking variants.

Figure 23:
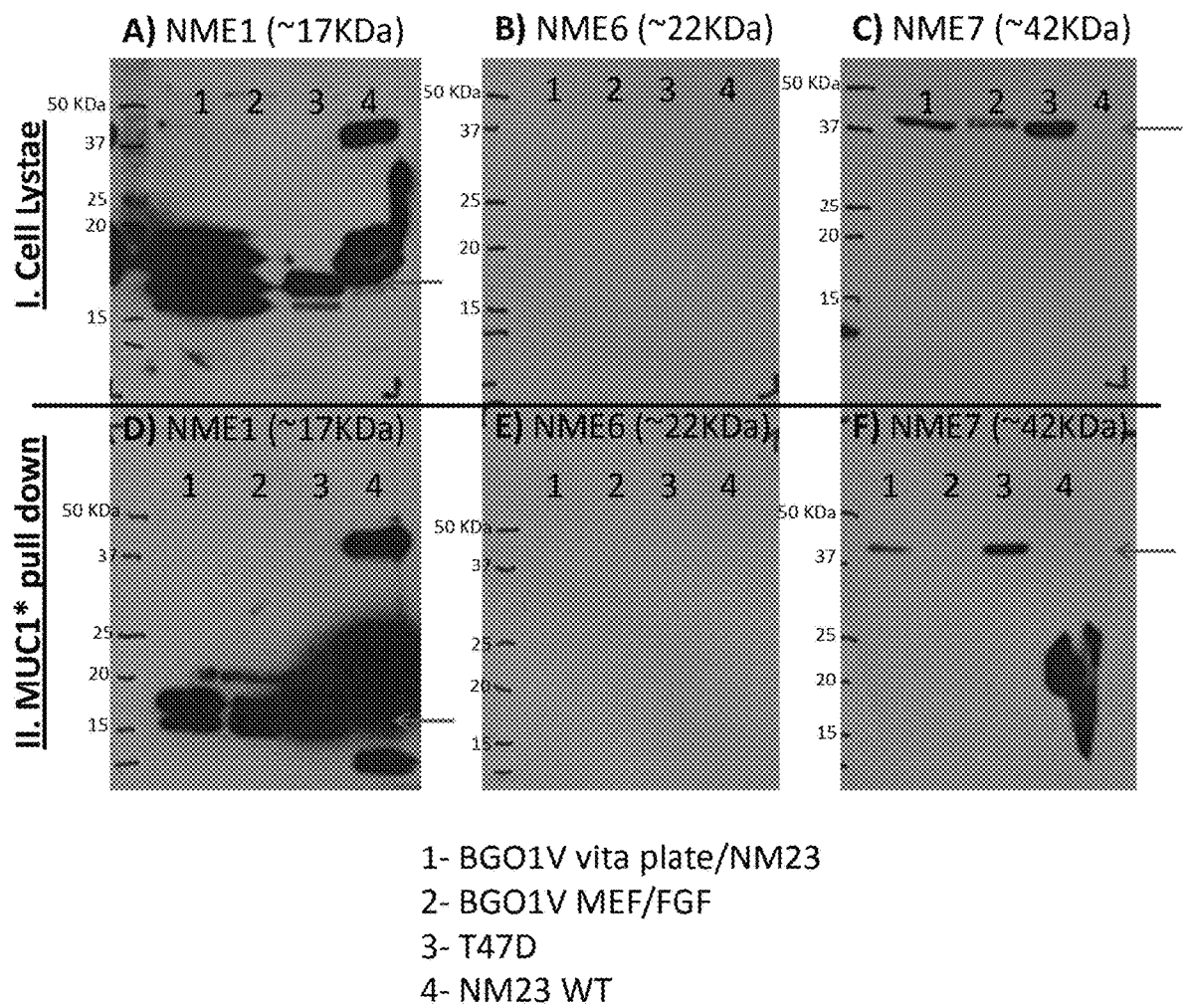
FIG. 23 shows photographs of Western blots detecting the presence of NME1 (A,D), NME6 (B,E) or NME7 (C,F) in human stem cells cultured in NM23-S120G dimers, cultured in bFGF over MEFs or human breast cancer cells or the presence of the NME isoforms in a MUC1* pull-down assay.

NME7 exists as a single protein but structurally is comprised of two monomers and so functions as a dimer. NME7 contains two NDPK domains, portions of which bind to the MUC1* growth factor receptor. Example 7 also describes a binding experiment called a pull-down assay. In this experiment, the MUC1* extra cellular domain peptide was attached to beads which were then incubated with lysates from BGO1v human embryonic stem cells. After wash steps and release from the beads, species capture by interaction with the MUC1* peptide were separated on an SDS-PAGE gel then probed with an anti-NME7 antibody. FIG. 23 Part II. F)—Lane 1 shows that NME7 binds to the MUC1* extra cellular domain. Portions of the double NDPK domains in NME7 bind to MUC1* growth factor receptor and dimerize it which activates pathways that maintain pluripotency, induce pluripotency and inhibit differentiation of stem and progenitor cells.

NME6 exists as a dimer, and resists formation of higher order multimers. NME6 dimers bind to MUC1* growth factor receptor and dimerize it which activates pathways that maintain pluripotency, induce pluripotency and inhibit differentiation of stem and progenitor cells. Like NME1 mutants and variants that prefer dimer formation, both NME6 and NME7 are capable of maintaining and inducing pluripotency and inhibiting differentiation of stem and progenitor cells, including iPS cells.

Like NME1 mutants and variants that prefer dimer formation, NME6 and NME7 can be added exogenously to stem cells (embryonic or induced pluripotent) or progenitor cells to induce growth, maintain them in an undifferentiated state or inhibit their differentiation. NME6 and NME7 can be added exogenously to stem or progenitor cells to induce pluripotency. In addition, nucleic acids encoding NME1 mutants and variants that prefer dimer formation, NME6 and/or NME7, or variants thereof, including single chain variants that behave as dimers, can be introduced into cells to induce the cells to revert to a less differentiated state or to maintain cells in a less mature state.

Because NME is highly conserved among all species, the methods described herein are not intended to be limited to human NME species nor limited to use with human cells.

In another aspect of the invention, we have discovered that the addition of exogenous NME7 fully maintains stem cell growth and pluripotency, inhibits differentiation and is also able to induce pluripotency. NME7 is a monomeric protein that has two NDPK domains, A and B. Until now, its function has not been elucidated. It was previously only known that NME7 was expressed in testes, ovary and brain. NME7 is suspected to be involved in the motility of flagella and is thought not to have NDPK activity because of the lack of certain key residues.

NME7 expressed in *E. coli* and secreted as a soluble protein was added to human stem cells in culture in a minimal stem cell media devoid of any other growth factor, feeder cells or their conditioned media. The stem cells were adsorbed onto the cell culture plate by adhering to a layer of an antibody that recognizes a stem cell surface antigen. In this way, interference by growth factors and other cytokines present in surface coatings such as Matrigel were avoided.

As a comparison, stem cells from the same source were cultured side-by-side but instead of adding exogenous recombinant NME7, recombinant NM23-H1 (also known as NME1) that had been refolded and purified as a population of dimers was added (See Examples 9 and 10 and FIGS. 25-30). In both NME7 and NM23-H1 dimers, stem cells proliferated without differentiating. FIGS. 27-30 show that the cells have stem cell morphology in that they are growing as a single layer of cells that have a high nucleus to cytoplasm ratio. In addition, immunocytochemistry and quantitative PCR showed that the resultant cells both expressed pluripotency markers but did not express differentiation markers such as FOXa2 and miR-145. A cell count showed that stem cells cultured in NME7 produced 1.4-times more cells than those cultured in NM23-H1 dimers. This represents a significant improvement over the state of the art because the NM23-H1 isoform can exist as a dimer, tetramer or hexamer, wherein only the dimer is the active form and the hexamer induces differentiation. Thus, it is advantageous to add the NME form that only activates, such as NME7. From a commercial standpoint, it is more cost-effective to produce NME7 since it is active as a monomer, expressed in *E. coli* and secreted as the soluble protein. This eliminates the problems and expense of denaturing, refolding, inducing to form dimers and isolating as stable populations of dimers. NME7 can also be added exogenously to induce cells to revert to a less mature state in vitro or in vivo or to induce pluripotency in somatic cells. In some cases it could be advantageous to suppress expression of NM23-H1 (NME1), using siRNA, anti-sense nucleic acids, or any other method for suppressing gene expression, while adding exogenous NME7. As we have demonstrated, NM23-H1 (NME1) forms tetramers and hexamers as its concentration increases, which then induce differentiation. Thus, it is yet another aspect of the invention that NME1 hexamers are added exogenously or NME1 is genetically induced to be expressed within a stem cell, when it is desired to have a cell differentiate to a more mature state.

To aid in protein expression and purification, several NME7 constructs were made and tested. Although it has been previously reported that NME7 can be expressed in in vitro expression systems using wheat germ cell extracts (MW 36.52 kDa) and in human HEK293 cells (MW 38 kDa), we found that a smaller construct containing essentially just the NDPK A and B domains can be expressed in E. coli as a soluble protein with very high yields. We made NME7-AB with either a histidine tag or a strep tag, however it can be made without an affinity tag or with any other affinity tag. NME7-AB promoted pluripotency and inhibited differentiation of human stem cells as well as or better than NME1 (NM23-H1) dimers that had previously been shown by us to fully support stem cell growth, maintenance of pluripotency, able to induce pluripotency and inhibit differentiation. Our experiments show that NME7 can substitute for NME1 dimers without the threat of hexamer formation over time and in a more cost-effective and commercially applicable way.

NME family proteins are highly conserved across all species, including plants. Therefore, sequences of NME family members, isoforms and variants of the invention, especially NME1, NME6 and NME7 constructs, may be comprised of sequences from any species or combinations of sequences from different species, with mammalian species being preferred, mouse species still more preferred, and human species most preferred. Such NME family members, isoforms and variants can be used for the propagation of, self-renewal, maintenance of pluripotency, induction of pluripotency or inhibition of differentiation in any species, wherein mammalian species are preferred, mouse species more preferred and human species most preferred.

NME1 in dimeric form or NME7 can also be used for the maintenance of naïve human stem cells or for the induction of naïve stem cells from stem cells in the primed state or for making naïve stem cells from somatic cells in the process of generating iPS cells. Stem cells in the naïve state are characterized by high expression levels of the pluripotency genes OCT4, KLF2 and NANOG or KLF4 and low expression levels of FOXa2, OTX, LHX and XIST compared to stem cells grown in bFGF-containing media. An even more stringent indicator of the naïve state is that the cells have not yet undergone X-inactivation. High levels of XIST are indicators of inactivation of one of the X chromosomes, but a more definite determinant is immunocytochemical staining of Histone 3. If X-inactivation has occurred, Histone 3 is condensed and can be visualized as a discrete mass in the cell's nucleus. If X has not yet been inactivated, Histone 3 is either undetected or is dispersed throughout the nucleus, sometimes referred to as a "cloud."

Both embryonic stem cells (ES) and induced pluripotent stem (iPS) cells, cultured in NME1 dimers or in NME7 gave rise to stem cells that had reduced levels of FOXa2, OTX, LHX and XIST, compared to cells cultured in FGF and also did not have detectable or condensed Histone 3 in the nucleus of ~50% of the cells, after at least 8-10 passages in the NME-based media. Cells cultured in NME-based media for 6 passages had only 25% of the cells that were pre-X-inactivation, which is a hallmark of the naïve state. Researchers (J. Hanna, A. W. Cheng, K. Saha et al., Proc Natl Acad Sci USA 107 (20), 9222 (2010), Jacob H. Hanna, Krishanu Saha, and Rudolf Jaenisch, Cell 143 (4), 508 (2010)) who were able to temporarily revert primed stem cells to a naïve state by treating the cells with a variety of biochemicals and inhibitors in addition to ectopically expressing genes, reported about 1 in 10,000 cells were in a naïve state. By using single cell cloning techniques they were able to isolate pure populations of naïve human stem cells, but they were unstable and could only be maintained in the naïve state for a few passages, which was less than 5 passages in most cases. Another indicator of stem cells being in the naïve state is that the cells have a higher cloning efficiency, which is calculated as the number of discrete colonies that can be counted per a specified number of cells plated. The cloning efficiency of mouse stem cells, which unlike human stem cells, are easily maintained in the naïve state by culturing in media containing mLIF (murine leukemia inducing factor), is ~30%. By stark contrast, the cloning efficiency of human stem cells cultured in FGF-based media is ~1%. ES cells cultured in NME1 dimers had a cloning efficiency of 18% and the same cells cultured in NME7 had a cloning efficiency of 23%. However, these were cell populations that only had about 50% of the cells in the naïve state by Histone-3 staining. Therefore, the actual cloning efficiency of the naïve cells in that population is at least 2-times the measured 20%, which is about 40% cloning efficiency which is above that of mouse naïve stem cells. Taken together, these data show that stem cells cultured in NME1 or NME7 revert from the primed state to a naïve state and are maintained in a naïve state.

The invention also envisions the use of NME1 or NME7 to generate populations of stem cells that are essentially 100% pluripotent and in the naïve state. By merely culturing currently commercially available ES or iPS cells in media containing NME1 dimers or NME7, populations of cells are generated that are about 50% in the completely naïve state. Using cloning techniques, known to those skilled in the art, such as limiting dilution, on mixed population of naïve and primed stem cells, populations of stem cells that are all in the naïve state are generated. In yet another aspect of the invention new stem cell lines are generated. ES cell lines are generated using previously described techniques (Embryonic Stem Cell Lines Derived from Human Blastocysts. James A. Thomson, Joseph Itskovitz-Eldor, Sander S. Shapiro, Michelle A. Waknitz, Jennifer J. Swiergiel, Vivienne S. Marshall, Jeffrey M. Jones et al. Science 282, 1145 (1998); DOI: 10.1126/science.282.5391.1145; Isolation of Embryonic Stem (ES) Cells in Media Supplemented with Recombinant Leukemia Inhibitory Factor (LIF). Shirley Pease, Paola Braghetta, J David Gearing, Dianne Grail, and R. Lindsay Williams Developmental Biology 141, 344-352 (1990)) with the exception that instead of culturing cells in FGF, which drives the naturally naïve cells into the primed state, cells are cultured in media containing NME7 or NME1 wherein at least some of the NME1 protein is in the dimeric state, more preferably wherein at least 25% of the protein is in the dimeric state and still more preferably wherein at least 50% of the protein is a dimer. In one aspect, cells are derived from the inner cell mass of a human blastcyst and cultured in a media containing NME7 or NME1 dimers. In another aspect of the invention, somatic cells, such as dermablasts or fibroblasts are induced to revert to a less mature state by culturing in a media containing NME7 or NME1 dimers. In yet another aspect of the invention, iPS cell lines are generated by transducing somatic cells, dermablasts or fibroblasts with one or more of the pluripotency genes Oct4, Sox2, Klf4, Nanog, c-Myc, or LIN28 or by treating the cells with the products of those genes, i.e., the proteins or with agents that cause the proteins to be produced and doing so in the presence of a media that contains NME1 dimers or NME7. More generally, the invention envisions generating new iPS cell lines, which are produced with greater efficiency or are in a more naïve state than iPS cells generated by traditional methods that include the use of FGF, using any method that induces a cell to revert to a less mature state, including a pluripotent state, by culturing the cells in the presence of NME1 dimers or NME7. In a preferred embodiment, the use of FGF is eliminated. In another preferred embodiment, cells undergoing the process of generating iPS cells are not transferred onto fibroblast feeder cells.

Surfaces for Growing Stem Cells

Figure 20:
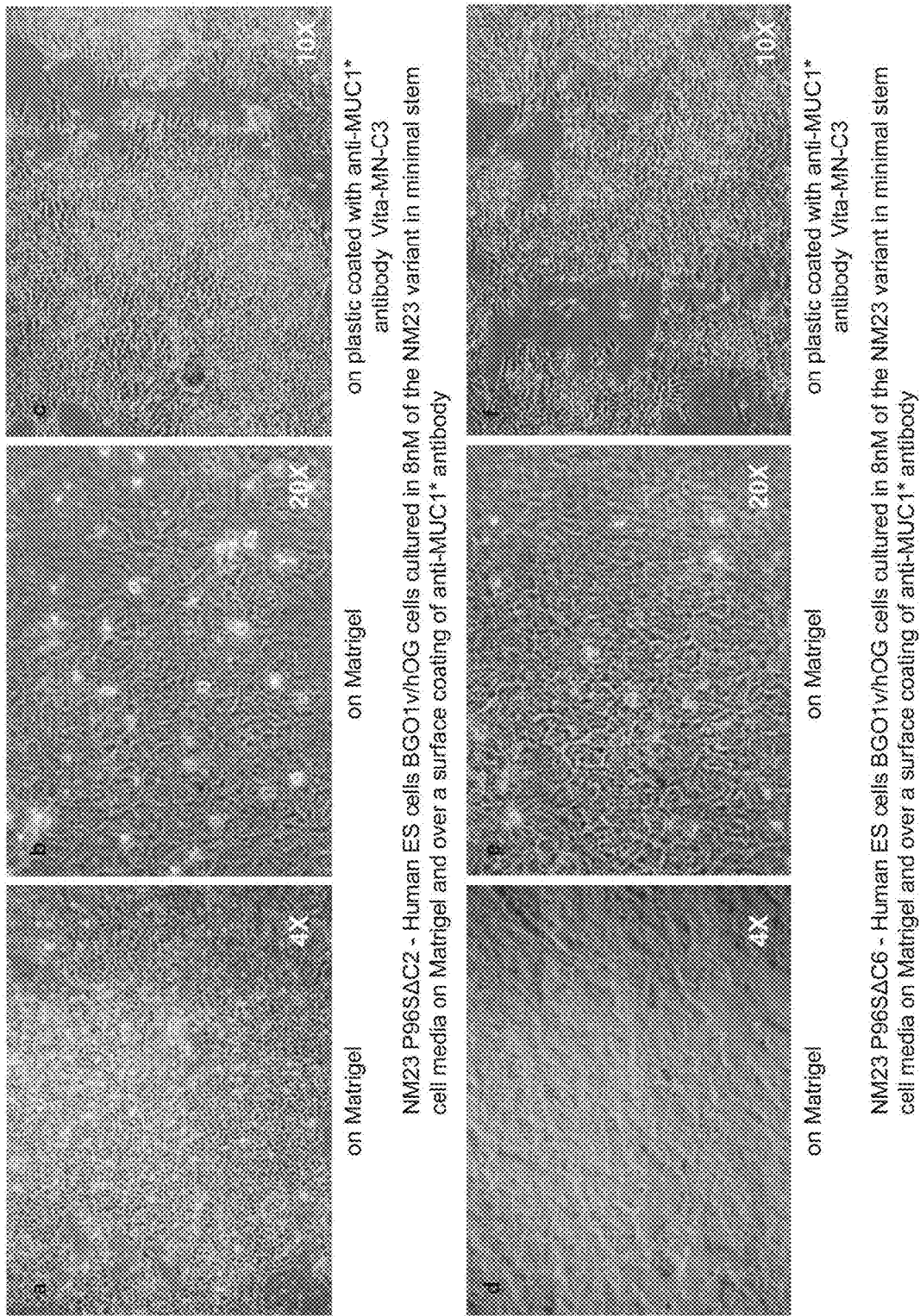
FIG. 20 shows photographs of human ES cells, BGO1v/hOG line, that were cultured in 8 nM of an NM23 variant in minimal stem cell media on Matrigel (a, b, d, e) and on a cell culture plate coated with anti-MUC1* antibody, MN-C3 (c, f); (a-c) variant is P96SΔC2; (d-f) variant is P96SΔC6. These variants were not refolded or purified, showing that they do not need to be refolded or purified before use.
Figure 21:
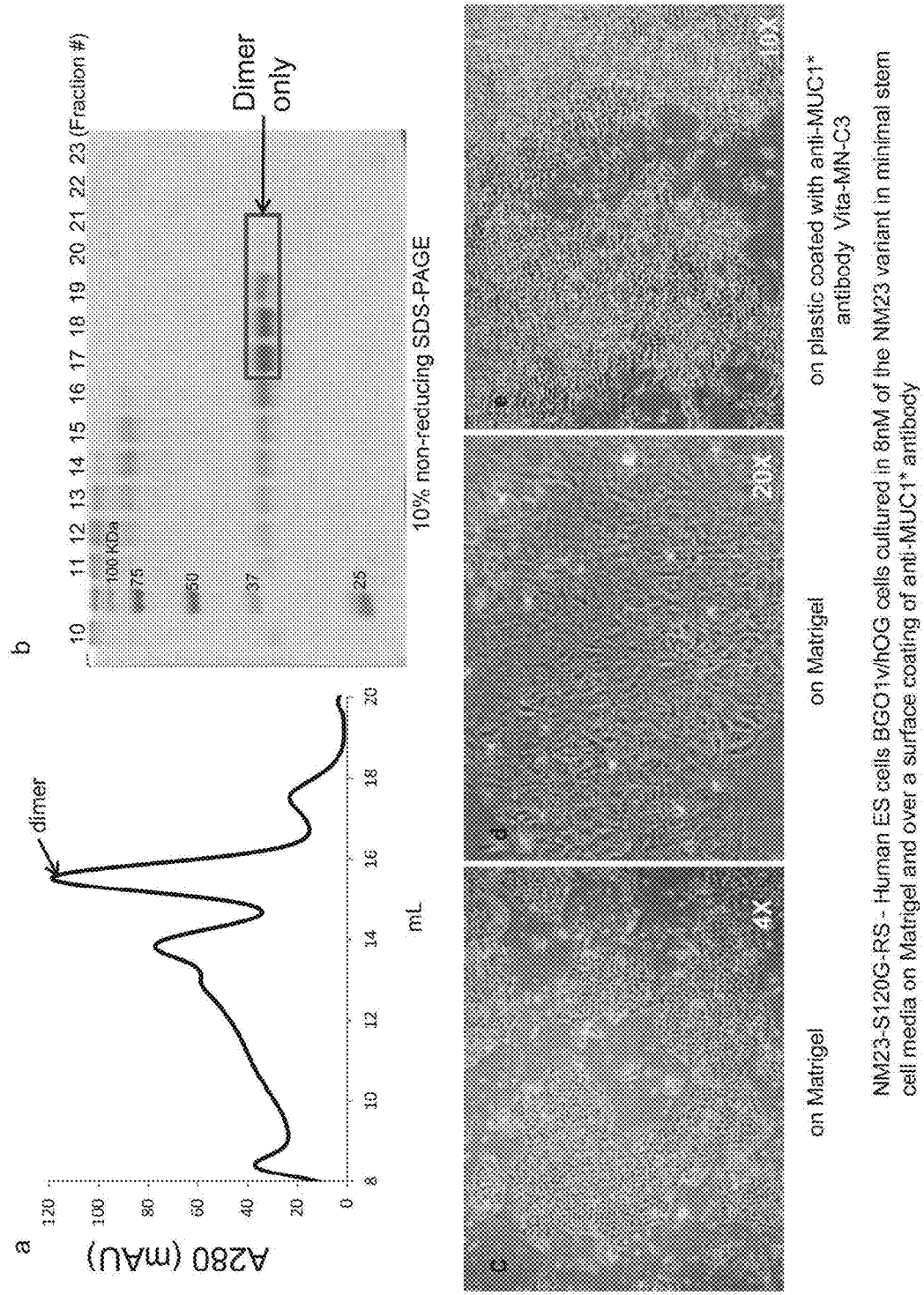
FIG. 21 shows that the major population of NM23-S120G (refolded, "RS") exists as a dimer as shown in the FPLC trace (a) and verified by a non-reducing PAGE (b). Dimer only fractions purified by FPLC were pooled and used at 8 nM in minimal stem cell media to grow human ES cells, BGO1v/hOG line. (c-e) photographs of the human stem cells show that cultured in 8 nM of the NM23 variant produces pluripotent stem cells whether on Matrigel (c, d) or on a cell culture plate coated with anti-MUC1* antibody, MN-C3 (e).

It is not intended that the invention be limited by the nature of the surface upon which the stem cells or the cells undergoing induction of pluripotency are grown. Any suitable surface for stem cell growth or induction of pluripotency can be used with media containing NME1, NME6, or NME7. Such surfaces include but are not limited to feeder cells, Matrigel, hydrogels, integrins and integrin derivatives, E-cadherin and E-cadherin derivatives, vitronectin, antibodies to cell surface receptors, antibodies that recognize the MUC1* extra cellular domain, antibodies that recognize the PSMGFR sequence, Vita™ brand plates (ThermoFisher), VITA™ plates coated with an anti-MUC1* antibody and the like. NME1 mutants and variants that can form stable dimers (P96S, S120G mutants and a single chain construct) were added to minimal stem cell media (MM) and used to propagate stem cells that were growing over a Matrigel surface or an anti-MUC1* antibody coated surface. The growth of the stem cells and their ability to resist spontaneous differentiation was essentially equal in all three media and on both surfaces (FIG. 20, FIG. 21). Some surfaces negatively impact the quality of the stem cells grown on them. Feeder cells secrete as yet unknown factors that result in primed state stem cells. Integrins, such as vitronectin, bind to cognate receptors on the cell surface and generate a biological signal, which may or may not be desirable for the maintenance of naïve state stem cells. Measurement of markers of the naïve and primed state showed that stem cells attached to an adhesion layer of vitronectin, even when cultured in NME1 dimers, had an increase in the primed markers and a decrease in the expression of naïve markers. In a preferred embodiment, the surface, which may be a plastic, biodegradable, mesh or solid, planar or particle-like, is coated with an antibody that recognizes the MUC1* extra cellular domain, consisting primarily of the PSMGFR sequence. In a yet more preferred embodiment, the surface is a VITA™ brand plate coated with an antibody that recognizes the PSMGFR peptide. In a still more preferred embodiment the anti-MUC1* antibody recognizes the N-terminal portion of the PSMGFR peptide, including the N-terminal 15 amino acids.

In some cases, a rho kinase inhibitor is used to enhance adhesion of the cells to the surface. Many rho kinase inhibitors, including but not limited to HA100, Y27632, and thiozivincan be used to aid in enhancing adhesion of stem cells to surfaces, particularly to the surfaces that are plastic coated with anti-MUC1* antibodies. For most stem cell lines currently available, a rho kinase inhibitor is added for the first 24-48 hours only.

Alternatively, inhibitors of guanine exchange factors (GEFs) are added to the media instead of rho kinase inhibitor for at least a portion of the culture period, to enhance adhesion to surfaces that are not cells or comprised of complex cell mixtures such as Matrigel Inhibitors of GEFs are used in some cases instead of rho kinase inhibitors to enhance the attachment of stem cells to surfaces that are coated with anti-MUC1* antibodies. In one aspect of the invention, the guanine exchange factor inhibitor is NME1 in hexameric form. In another aspect of the invention, the guanine exchange factor inhibitor is a peptide that is derived from NME1.

Inhibitors of rho kinase or guanine exchange factor may be required for maximal adhesion of primed stem cells or mixed populations of primed and naïve stem cells to certain surfaces, such as plates coated with anti-MUC1* antibodies. However, pure populations of naïve stem cells do not require the use of rho kinase inhibitors or guanine exchange factor inhibitors. In one aspect of the invention, pure populations of naïve stem cells are cultured in the absence of FGF or a rho kinase inhibitor.

Rho kinase inhibitors are agents that inhibit rho kinase I or II. They may be small molecules, peptides or proteins Rath N, Olson M F. Rho-associated kinases in tumorigenesis: re-considering ROCK inhibition for cancer therapy. EMBO Rep. 2012; 13(10):900-8. Examples of rho kinase inhibitors are Y27632, HA-1077, also called Fasudil, H-1152, and thiazovivin (Olson M F. Applications for ROCK kinase inhibition. Curr Opin Cell Biol. 2008; 20(2): 242-8; Watanabe K, Ueno M, Kamiya D, et al. A ROCK inhibitor permits survival of dissociated human embryonic stem cells. Nat Biotechnol. 2007; 25(6):681-6; Breitenlechner C, Gassel M, Hidaka H, et al. Protein kinase A in complex with Rho-kinase inhibitors Y-27632, Fasudil, and H-1152P: structural basis of selectivity. Structure. 2003; 11(12):1595-607; Lin T, Ambasudhan R, Yuan X, et al. A chemical platform for improved induction of human iPSCs. Nat Methods. 2009; 6(11):805-8). In addition to Rho kinase inhibitors, the invention envisions using inhibitors of related pathways in place of the Rho kinase inhibitors. For example, in the same pathway, guanine exchange factors (GEFs) are upstream of Rho kinase. The GEFs activate the Rho kinases. Therefore instead of using rho kinase inhibitors, the invention envisions using GEF inhibitors. Since rho kinase is in the inactive state when bound to GDP, any agent that increases the amount of GDP present in a cell, such as RAD, GEM, and RhoE as well as others, can be used in place of rho kinase inhibitors to aid in stem cell growth, survival and attachment to surfaces (Riento K, Guasch R M, Garg R, Jin B, Ridley A J (2003) RhoE binds to ROCKI and inhibits downstream signaling. Mol Cell Biol 23: 4219-4229; Komander D, Garg R, Wan P T, Ridley A J, Barford D (2008) Mechanism of multi-site phosphorylation from a ROCK-I: RhoE complex structure. EMBO J 27: 3175-3185; Ward Y, Yap S F, Ravichandran V, Matsumura F, Ito M, Spinelli B, Kelly K (2002) The GTP binding proteins Gem and Rad are negative regulators of the Rho-Rho kinase pathway. J Cell Biol 157: 291-302), in their place. Myosin is also in the same pathway as Rho kinases. Myosin is indirectly activated by Rho kinase and as such is downstream of rho kinase in the same pathway. Therefore, myosin inhibitors can also be used in place of rho kinase inhibitors according to methods of the invention to aid in stem cell survival and/or to aid in stem cell attachment to surfaces. Blebbistatin is a myosin inhibitor and can be used in place of any rho kinase inhibitor used according to methods of the invention (Ohgushi M, Matsumura M, Eiraku M, Murakami K, Aramaki T, Nishiyama A, et al. Molecular pathway and cell state responsible for dissociation-induced apoptosis in human pluripotent stem cells. Cell Stem Cell 2010; 7:225-39; Ohata H, Ishiguro T, Aihara Y, et al. Induction of the Stem-like Cell Regulator CD44 by Rho Kinase Inhibition Contributes to the Maintenance of Colon Cancer-Initiating Cells. Cancer Res. 2012; 72(19):5101-10). Another alternative to using a rho associated kinase inhibitor, is to activate or inhibit any target that results in increased cell migration. Activation of modulators of the RAC pathway, that increases cell migration include PI3K, CDC42, PAK, N-WASP as well as RAC1, and lamellipodium. Agents that enhance their expression levels in the cell or increase their activity are used to enhance stem cell survival and attachment to surfaces. RAC1 GTPase expression decreases as stem cells dissociate and conversely Rho associated kinases increase, which leads to loss of cell migration and apoptosis (Ohgushi M, Matsumura M, Eiraku M, et al. Molecular pathway and cell state responsible for dissociation-induced apoptosis in human pluripotent stem cells. Cell Stem Cell. 2010; 7(2):225-39.) Therefore inhibitors of the PI3k or RAC pathway should be suppressed, or activators of RAC pathway increased in order to enhance stem cell survival and attachment to surfaces, such as to antibody coatings wherein the antibody binds to a stem cell surface protein, such as MUC1*. NME1 in hexamer form and NME2, likely also in hexamer form, bind to GEF Tiam1 and Dbl-1 to inhibit GTPases RAC1 and CDC42 GTPase, respectively ((Ohgushi M, Matsumura M, Eiraku M, et al. Molecular pathway and cell state responsible for dissociation-induced apoptosis in human pluripotent stem cells. Cell Stem Cell. 2010; 7(2):225-39; Murakami M, Meneses P I, Knight J S, Lan K, Kaul R, Verma S C, Robertson E S. Nm23-H1 modulates the activity of the guanine exchange factor Dbl-1. Int J Cancer. 2008; 123:500-10; Miyamoto M, Iwashita S, Yamaguchi S, Ono Y. Role of nm23 in the regulation of cell shape and migration via Rho family GTPase signals. Mol Cell Biochem. 2009; 329:175-9). Therefore, inhibition of RAC and CDC42 modulated by NME1 and NME2 hexamers decrease cell migration and limit stem cell attachment and survival. We have suppressed NME1 and NME2 in embryonic and induced pluripotent stem cells in culture in NME7 media and observe no ill effects. Suppression of NME1 and NME2 in stem and progenitor cells that are cultured in NME6 or NME7 containing media are preferred methods for enhancing stem and progenitor cell survival and attachment to surfaces for in vitro culture. In a preferred embodiment, embryonic stem cells or iPS cells are cultured in a media that contains NME7 and siRNA to suppress NME1 and NME2. In a preferred embodiment the nucleic acids that suppress NME1 and NME2 are siRNA molecules derivatized with cholesterol moieties to enable entry into the cells (Darmicon). In a more preferred embodiment the stem cells are not contacted with a rho kinase (ROCK1) inhibitor such as Y27632.

Alternatively, stem cells cultured in media containing NME1, NME6 or NME7, are grown in suspension. A number of techniques for cell growth in suspension are known to those skilled in the art. Wave bags, roller bottles, and the like can be used in association with NME-containing media for stem cell growth or for the induction of pluripotency in more mature cells such as somatic cells, dermablast or fibroblasts. In a preferred embodiment, the NME protein is NME1 in dimer form. In a still more preferred embodiment the NME protein is NME7.

It is not intended that the invention be limited by the nature of the media to which NME1, NME6 or NME7 is added. NME family proteins can be added to any media suitable for stem or progenitor cell growth or any media suitable for the induction of pluripotency. A base media such as DMEM, DMEM/F12, or similar further containing knockout serum replacement or similar and non-essential amino acids are preferred. In a preferred embodiment, the base media contains 60-80% DMEM-like base and 20-40% knockout serum replacement or similar, plus concentrated non-essential amino acids. In other cases the base media contains a DMEM-like base plus insulin, selenium, and transferrin. In cases where the resultant cells are destined for use in a human, the preferred species of the protein components is human.

Ligands of the MUC1* growth factor receptor, in particular NME family proteins, promote the growth of, and maintenance of pluripotency of stem and progenitor cells. MUC1* ligands in a media also support the process of making induced pluripotent stem (iPS) cells and support the process of inducing cells to revert to a less mature state. In addition, MUC1* ligands themselves induce cells to revert to a less mature state in the absence of other factors such as transfection or transduction of pluripotency genes including OCT4, SOX2, KLF4, NANOG or c-Myc.

The inventors previously disclosed that ligands of the MUC1* receptor can function as growth factors. Ligands that dimerize the MUC1* extra cellular domain were shown to increase the growth of MUC1-positive cancer cells and also stem and progenitor cells that expressed MUC1*. The present application discloses that NME7 is also a ligand of the MUC1* growth factor receptor. NME7 is secreted by stem cells. NME7 in a base media devoid of any other cytokines fully supports the growth of embryonic or induced pluripotent stem cells. NME7 functions to promote growth of and maintain pluripotency of stem cells in a manner very similar to NME1 dimers. NME1, expressed or purified such that a significant population exists as a dimer, fully supports the growth of embryonic or induced pluripotent stem cells and does not require serum or any other cytokines. NME1 in dimeric form and NME7 also induce pluripotency in cells that are in a more mature state than the naïve or ground state stem cells. Whereas growth of human stem cells in FGF containing media produce stem cells in the "primed" state, growth of human stem cells in NME1 dimers or NME7 induces those cells to revert to an earlier state called the "naive" or "ground" state. Recent research provides evidence that stem cells in the primed state cannot develop into all the cell types in the human body the way that naïve stem cells can. Therefore, stem cells cultured in NME1 or NME7 that are in a more naïve state are ideally suited for use in human therapies because the naïve state is the natural state of human stem cells and it is those naïve stem cells that are able to develop into any cell in the human body. In a preferred embodiment, stem cells cultured in NME1 or NME7 are used for any and all human stem cell therapies.

The present application discloses that NM23 as a component of a defined, xeno-free media supports stem cell growth, including both embryonic and induced pluripotent and further can be used as the media in which to reprogram somatic, progenitor, or somewhat mature cells such that they become pluripotent stem cells, which are also referred to as iPS cells.

The addition of NM23 to base media DMEM/F12 (or similar) plus insulin (human preferred), selenium, transferrin, 1-ascorbic acid, with pH adjusted using NaHCO$_3$ fully supported ES and iPS cell growth when cells were attached to Vitronectin-coated surfaces or anti-MUC1* coated surfaces. The use of Rho kinase inhibitors HA100 or Y27632 for at least the first 24 hours greatly improved stem cell surface attachment. Especially preferred are NM23 and NM23 variants that can be expressed and/or isolated as dimers. Other growth factors such as FGF-2 or TGF-beta may optionally be added to NM23 in this media. In addition, cells may be grown under hypoxic conditions for improved performance.

The addition of NM23 to base media DMEM/F12 (or similar) plus insulin (human preferred), selenium, transferrin, 1-ascorbic acid, with pH adjusted using NaHCO₃ fully supported ES and iPS cell growth when cells were attached to Vitronectin-coated surfaces, anti-MUC1* coated surfaces, Matrigel and other surfaces to which stem cells attach. The use of Rho kinase inhibitors HA100 or Y27632 for at least the first 24 hours greatly improved stem cell surface attachment. Addition of any Rho kinase inhibitor (ROCKi) changes cell shape and attachment properties and can be used in media containing NM23 to enhance the attachment of stem cells, progenitor cells and other non-adherent cells to surfaces. In the presence of a rho kinase inhibitor, cells transition within 24 to 48 hours from a rounded shape with weak surface attachments to a more flattened shape with many surface attachments. Although the use of Rho kinase inhibitors has been previously described for use with stem cells to enhance survival, Rho kinase inhibitors do not increase survival in NME based media. For that reason, it is only used to make cells flatten out and form greater attachments to surface.

The use of rho kinase inhibitors have been previously described for use with bFGF-based media, also to increase survival. Herein, we describe the use of Rho kinase inhibitors to aid in attachment to surfaces when NME1, NME6 or NME7 are used in a media. Especially preferred are NM23 and NM23 variants that can be expressed and/or isolated as dimers as well as NME7, which is a monomer that has two NDPK domains. Although these NDPK domains until now have only been known to have enzymatic activity, the inventors have discovered that a portion of the NDPK domain contains a motif that binds to the MUC1* extra cellular domain.

Figure 14:
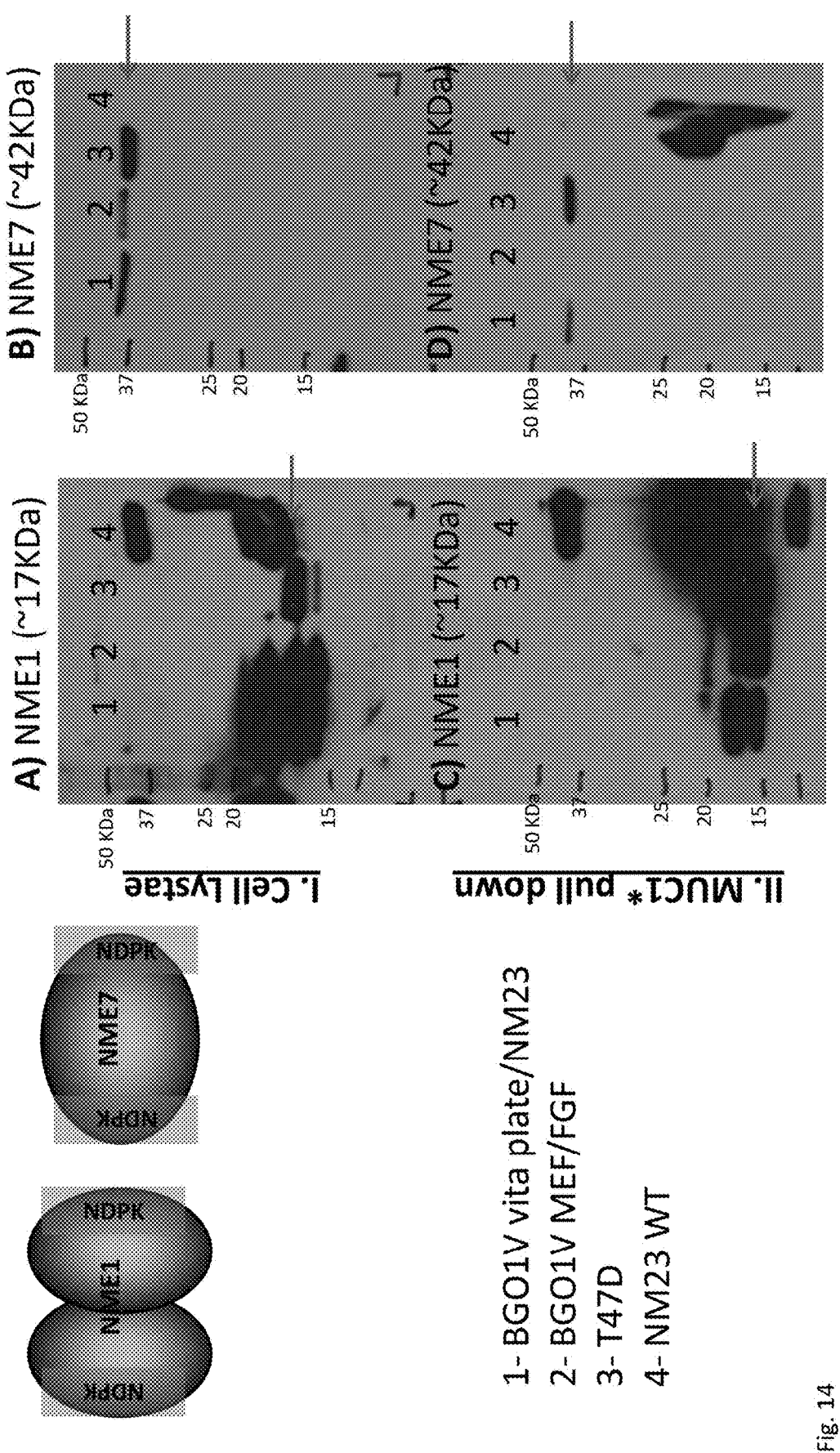
FIGS. 14A-D shows Western blots of a pull-down assay wherein NME7 from human stem cells and cancer cells bound to a synthetic peptide having the sequence of the PSMGFR peptide.

FIG. 14 shows that in a pull-down assay, NME7 from human stem cells bound to a synthetic peptide having the sequence of the PSMGFR peptide. The inventors have shown that: 1) only NME1 dimers (not hexamers) support pluripotent stem cell growth; 2) NME1 dimers (not hexamers) bind to two or more MUC1* extra cellular domain peptides in a nanoparticle assay; and 3) MUC1*'s pluripotency activity and growth factor receptor activity occurs after ligand-induced dimerization of its extra cellular domain; a bivalent anti-MUC1* antibody results in a bell-shaped curve of growth as a function of antibody concentration which shows that it is dimerization of the extra cellular domain that causes the growth factor receptor function.

We have also shown that NME7 functions similarly to NME1 dimers in their ability to support pluripotent stem cell growth and inhibit differentiation. NME7 via NDPK domains, binds to the MUC1* receptor's extra cellular domain to promote pluripotent, naïve stem cell growth and inhibits differentiation. In particular, NME7 binds to the PSMGFR peptide which is a part of the MUC1* extra cellular domain.

NM23-H1, which is also known as NME1, is active as it is a stem or progenitor cell growth factor only when in dimer form. NME1 can exist as a dimer, tetramer or hexamer as a function of concentration as well as its sequence. Mutations such as the S120G or P96S with or without C-terminus deletions prefer dimer formation and are somewhat resistant to hexamer formation so are preferred as stem or progenitor cell growth factors. NME6 exists as a dimer and is also preferred for use as a growth factor, like NME1 dimers, for the maintenance and induction of pluripotency and for inhibition of differentiation. NME7 is a monomer but may bind like a dimer with its two NDPK domains. In pull-down assays NME7 binds to MUC1* extra cellular domain peptide, indicating that portions of at least one NDPK domain binds to the MUC1* receptor, and like NME1 dimers, results in the maintenance or induction of pluripotency while inhibiting differentiation. In a sandwich assay, NME7 was shown to simultaneously bind to two MUC1* extra cellular domain peptides (PSMGFR), indicating that the NME7-AB protein can dimerize MUC1* on the cell surface. NME1 also binds to the MUC1* extra cellular domain peptide and the MUC1* receptor on cells. NME1 hexamers do not bind to the MUC1* receptor and do not maintain or induce pluripotency. NME1 dimers, NME6 dimers, or NME7 for the growth, maintenance, induction of pluripotency and inhibition of differentiation can be used in many different base media that are suitable for culture of stem or progenitor cells. The composition of compatible base media can vary. In some cases, other growth factors or cytokines may be added into the media along with NME protein. Other growth factors such as FGF-2 or TGF-beta may optionally be added to NM23 in this media. In a most preferred embodiment, NME1 dimers, NME6 dimers or NME7 is added to a base media that does not contain other growth factors or cytokines. Cells may be grown under hypoxic conditions for improved performance.

The methods of the invention can act to provide the cells with a growth factor to stimulate the proliferation of a specific population of cells, which may carry a genetic mutation or correction. In one embodiment, an NME family protein is encoded in a nucleic acid sequence that may be contained within a plasmid that is introduced into a cell. The nucleic acid sequence that encodes the NME family protein can be part of a plasmid, or expression vector that also carries the sequence of a gene whose expression is desirable. The gene may be a corrected gene or gene to be expressed. The invention also envisions introducing a nucleic acid encoding an NME family member into a stem cell such that the cell constitutively expresses its own growth factor, simplifying culturing because it would only require a minimal solution for growth. In a preferred embodiment, the nucleic acid is an expression plasmid, which may have an inducible or controllable promoter. In a preferred embodiment the NME family member is NME1, NME6 or NME7. In a still more preferred embodiment the NME family member is NME7. In the most preferred embodiment, the NME family is NME7-AB. The invention also includes the use of these methods, in patients, in cells destined for transplant in patients, in blastocysts and embryos as well as in fertilized or unfertilized eggs, which may be used for in vitro fertilization.

The invention additionally envisions the use of NME-based media for the generation of new stem cell lines that may be embryonic in origin or induced from more mature cells. In a preferred embodiment, the NME-based media is a minimal media containing recombinant NME7. Yet more preferred is a media containing NME7-AB.

New stem cell lines are established as follows: Human cells are harvested from the inner mass of a blastocyst or the entire blastocyst can be used. The cells of the blastocyst are maintained and cultured in a media containing NME7. In a preferred embodiment, the media is free of other growth factors or cytokines. The harvested cells may be plated over a layer of feeder cells, which may be fibroblasts or may be MUC 1-positive cancer cells, or over an antibody layer. In a preferred embodiment, the antibody is an anti-MUC1* antibody. Still more preferred is an antibody that binds to the N-10 PSMGFR peptide. Alternatively the cells may be cultured or maintained in suspension in an NME7 containing media. A variety of techniques known to those skilled in the art can then be used to isolate stem-like cells, which can then be cloned to obtain clones that have the desired karyotype, and the desired gene expression profile. In a preferred embodiment, clones are isolated and proliferated that have gene expression indicative of the naïve state and not the primed state and further have not undergone X-inactivation if the cells are female. In a typical stem cell derivation method, the blastocyst or cells from the blastocyst are plated onto a surface and cultured for some period of time until blast outgrowths are observed that appear stem-like. These are harvested, grown and clones having the desired characteristics are isolated and maintained. Standard cloning techniques are performed to isolate clones that are positive for pluripotency markers as well as naïve markers and having low or no expression of primed markers such as FOXA2, OTX, LHX or sometimes XIST or lack of condensed Histone-3 in the nucleus. Clones are maintained and propagated in minimal media containing NME7 and optionally maintained in the naïve state by growing the cells over a layer of anti-MUC1* antibodies. In an alternative method, the cells are cultured in suspension. A Rho kinase inhibitor may be added to the NME7 containing media. In a preferred embodiment, the media is free of FGF.

It has been demonstrated, in mouse and human, that somatic cells can be reprogrammed by ectopic expression of transcription factors (Lowry et al., 2008; Maherali et al., 2007; Nakagawa et al., 2008; Okita et al., 2007; Park et al., 2008; Takahashi et al., 2006; Takahashi and Yamanaka, 2006; Wernig et al., 2007; Yu et al., 2006) to become pluripotent. The generation of induced pluripotent stem (iPS) cells holds great promise for the realization of truly personalized regenerative medicine (Yamanaka, 2007; Jaenish and Young, 2008) because stem cells derived from a patient's own skin cell can be used to generate cells and tissues to repair damage caused by disease or aging. Forced expression of combinations of the transcription factors, Oct4, Sox2, Klf4 and c-Myc or Oct4, Sox2, Nanog and Lin28 have been shown to cause mature cells to revert to the pluripotent state. However, these methods use FGF-based media throughout the process, which likely slows or corrupts the process of iPS generation.

An improvement over the known technique is to generated iPS cell lines as follows: Somatic cells, dermablasts or fibroblasts which may be from a donor or a patient are cultured in a media containing an NME family protein. In a preferred embodiment the NME family protein is NME1 dimer, NME6, or NME7. In a more preferred embodiment, the NME family member is NME7, wherein NME7-AB is especially preferred. The cells can be treated with nucleic acids, small molecules, or proteins that result in an increase in levels of pluripotency genes or proteins in the cells, wherein the pluripotency genes or gene products are chosen from OCT4, NANOG, KLF4, c-Myc, LIN28, and NME7. In a preferred embodiment, the starting cells are transfected with Oct4, SOX2 and Klf4. The starting cells that are somatic cells, dermablasts, fibroblasts or other cell are initially plated onto plastic multi-well plates in a minimal media containing roughly 2-50 nM NME7, more preferred is 8-16 nM. Media is changed every 24-72 hours as is typical. As cells begin to lose their adhesion to the plastic, they can be moved to a surface to which they will adhere, such as a surface of inactivated fibroblasts, inactivated cancer cells or a surface coated with an antibody to a stem cell surface protein, wherein an anti-MUC1* antibody is preferred. A rho kinase inhibitor may be added to the media in addition to the NME family member. After approximately 2-3 weeks, stem-like cells will have emerged and can be isolated and cloned. Clones with desired karyotype and gene expression profiles are selected and proliferated as stable self-renewing cell lines. In a preferred embodiment, clones that are naïve are selected. Human cells are preferred for these methods of generating new stem cell lines.

It is not intended that the invention be limited by the type of stem or progenitor cell for which the methods of the invention are useful. Essentially any stem or progenitor cells that expresses the cleaved for of MUC1, i.e. MUC1* can be used along with media and methods of the invention.

For a variety of reasons, including FDA compliance, totally defined and xeno-free media are desirable for the growth of human stem cells destined for therapeutic uses. The examples and figures herein demonstrate that NME1 dimers and NME7 fully support pluripotent, naïve stem cell growth and inhibit differentiation and these functions are independent of base media components. Virtually any base media that is suitable for stem cell growth will suffice. Preferred are base media that do not contain other growth factors or cytokines.

Researchers recently reported a base media, called E8, that includes DMEM/F12, insulin, selenium, transferrin, 1-ascorbic acid, and $NaHCO_3$ for pH adjustment, plus bFGF and TGF-beta as the growth factors, which is a defined and xeno-free media for human stem cell growth (Chen G, Gulbranson D, Hou Z et al, "Chemically defined conditions for human iPSC derivation and culture" Nature Methods, Vol. 8. No. 5, 2011 pgs 424-431). This base media, devoid of bFGF and TGF-beta, but with NME1 or NME6 dimers or NME7, that we called "MN6", was shown to fully support human and mouse pluripotent stem cell growth, inhibited differentiation and also supported the induction of pluripotency during iPS generation. NME1 or NME6 dimers, or NME7 in MN2 media which is a base media and non-essential amino acids only (see Example 1), somewhat supported pluripotent stem cell growth. These findings underscore the fact that NME1 dimers and NME7 are the natural growth factors of human stem cells and can be used in a variety of media suitable for stem or progenitor cell growth. Similar to the E8 media, media suitable for use with NME1 dimers and NME7 is comprised of a base media such as DMEM/F12 or DME/F12/Glutamax I, L-ascorbic acid, sodium selenium, insulin, transferrin and an agent to adjust pH such as sodium bicarbonate. In another aspect of the invention, the base media to which NME1 dimers or NME7 is added is comprised of DME/F12/Glutamax I, a serum replacement such as Knockout serum replacement (LifeTechnologies/Invitrogen), amino acids, such as non-essential amino acid solution (LifeTechnologies/Invitrogen), and optionally beta-mercaptoethanol. Media containing components from each of these base media are also envisioned. In fact, any base media suitable for stem or progenitor cell growth can be used with NME1 dimers and NME7 for the growth of stem or progenitor cells, to inhibit differentiation even to the primed state, and to induce pluripotency in more mature cells, which may be somatic cells, dermablasts, fibroblasts or progenitor cells.

A variety of media supported stem cell growth and inhibited differentiation when mixed with NME1 dimers or NME7. The concentration of NME1 dimers, NME6 dimers, or NME7 can vary. In one aspect the NME concentration is between 1 nM and 100 nM (based on the molecular weight of the monomer). In a preferred embodiment, the concentration of NME1 dimers, NME6 dimers, or NME7 is from 2 nM to 64 nM. In a still more preferred embodiment, the concentration of NME1 dimers, NME6 dimers, or NME7 is 4 nM to 32 nM.

One media called Minimal Media "MM" that when mixed with NME1 dimers or NME7, at 8 nM-16 nM, fully supported human stem cell growth and mouse stem cell growth and made human primed stem cells revert to the naïve state was comprised of:

400 ml DME/F12/GlutaMAX I (Invitrogen #10565-018),
100 ml Knockout Serum Replacement (KO-SR, Invitrogen #10828-028),
5 ml 100× MEM Non-essential Amino Acid Solution (Invitrogen #11140-050), and
0.9 ml (0.1 mM) β-mercaptoethanol (55 mM stock, Invitrogen #21985-023).

Another media that worked similarly when NME1 dimers or NME7 was added at 8 nM-16 nM was "MN6", comprised of:

DMEM/F12,
L-Ascorbic acid 64 mg/L,
Sodium selenium 14 ug/L,
Insulin 19.4 mg/L,
Sodium Bicarb 543 mg/L, and
Transferrin 10.7 mg/L Another media that was tested with NME1 dimers or NME7 was added at 8 nM-16 nM was "MN2" comprised of:

400 ml DME/F12/GlutaMAX I (Invitrogen #10565-018), and
5 ml 100×MEM Non-essential Amino Acid Solution (Invitrogen #11140-050)

NME1 dimers and NME7 in "MM" or "MN6" support human stem cell growth as well as or better than the FGF-containing media "E8" or mTeSR. The experiments shown in FIGS. 1-10 were carried out by plating stem cells on a layer of Vitronectin while the experiments of FIGS. 11 and 12 were carried out by plating stem cells onto a layer of anti-MUC1* antibody. NME1 dimers or NME7 in any minimal or defined media promotes pluripotency and inhibits differentiation. Any surface or base media that is suitable for stem cell growth are compatible with growth in NME1, NME6, or NME7. The methods of the invention are not limited to use with embryonic stem cells. NME1 dimers or NME7 also fully supported the growth of human ES cells and iPS cells as well as mouse ES and iPS cells. In addition, NME1 dimers or NME7 supported the induction of pluripotency in somatic cells and in fact increased the efficiency of iPS generation.

In addition to using NM23 in this defined and xeno free media for the growth and maintenance of ES and iPS cells, it is also used in the process of making iPS cells from progenitors or mature somatic cells such as dermablasts.

Cell Culture Media

Any cell culture may be used so long as a MUC1* ligand is either added to the media or is expressed by the cell. In particular, minimal media is preferred that includes MUC1* ligand such as NM23 family of proteins added to the media or expressed by the cell. A minimal media was made that included only DMEM/F12, insulin (human preferred), selenium, transferrin, 1-ascorbic acid, with pH adjusted using NaHCO₃ was made; we called this media "MN6", see detailed formula below. Another minimal media was made that included only 400 ml DME/F12/GlutaMAX I (Invitrogen #10565-018) and 5 ml 100×MEM Non-essential Amino Acid Solution (Invitrogen #11140-050); we called this media MN2, see detailed formula below. NME7, NME6 or NME1 (NM23-S120G) in Another base media called minimal stem cell media or "MM" is comprised of MN2 media plus 100 ml Knockout Serum Replacement (KO-SR, Invitrogen #10828-028) and 0.9 ml (0.1 mM) β-mercaptoethanol (55 mM stock, Invitrogen #21985-023). To these three base media were added 8 nM-16 nM NME7, NME6 or NME1 (NM23-S120G), wherein NME1 was refolded and purified such that the population was essentially all dimers. In some cases a Rho kinase inhibitor (ROCi) such as Y27632 was added. The presence of NME1, NME6 or NME7 in any of these media, promoted pluripotent stem cell growth and inhibited differentiation.

A previously reported media of MN6 plus FGF-2 and TGF-beta, "E8" (G. Chen, D. R. Gulbranson, Z. Hou et al., Nat Methods 8 (5), 424 (2011)), plus/minus Y27632, was compared to NME-based media. In addition, as another control, FGF-2 (also called bFGF) plus 50% MEF conditioned media was used as the media.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Media

Example 1.1

Components of Minimal Stem Cell Media ("MM") (500 mls)

400 ml DME/F12/GlutaMAX I (Invitrogen #10565-018)
100 ml Knockout Serum Replacement (KO-SR, Invitrogen #10828-028)
5 ml 100×MEM Non-essential Amino Acid Solution (Invitrogen #11140-050)
0.9 ml (0.1 mM) β-mercaptoethanol (55 mM stock, Invitrogen #21985-023)

Example 1.2

Components of E8 Media

DMEM/F12
L-Ascorbic acid 64 mg/L
Sodium selenium 14 ug/L
Insulin 19.4 mg/L
Sodium Bicarb 543 mg/L
Transferrin 10.7 mg/L
TGFbeta 1 2 ug/L
FGF2 100 ug/L Example 1.3

Components of MN7 is E8 Media, Minus the bFGF

Example 1.4

Components of MN6 Media

DMEM/F12
L-Ascorbic acid 64 mg/L
Sodium selenium 14 ug/L

Insulin 19.4 mg/L
Sodium Bicarb 543 mg/L
Transferrin 10.7 mg/L

Example 1.5

Components of MN2 Media 400 ml DME/F12/GlutaMAX I (Invitrogen #10565-018)
5 ml 100×MEM Non-essential Amino Acid Solution (Invitrogen #11140-050)
Examples 1-3 and FIGS. 1-14 are from 70124

Example 1.6

Human ES cells (H9s) were plated onto either a layer of Vitronectin or a layer of anti-MUC1* antibody (MN-C3) on 6-well cell culture plates. For each condition, a Rho kinase inhibitor, Y27632, was present or absent. The presence of the Rho kinase inhibitor for at least the first 24 hours improved cell attachment and performance but was not absolutely essential for undifferentiated stem cell growth.

The results were that NM23 in the dimer form fully supported pluripotent stem cell growth in the 6-component defined and xeno-free media as well as the controls and as well as or better than the combination of FGF-2 and TGF-beta. FIGS. 1-10 are photographic images of the stem cells in culture Day 4 post-plating.

Figure 12:
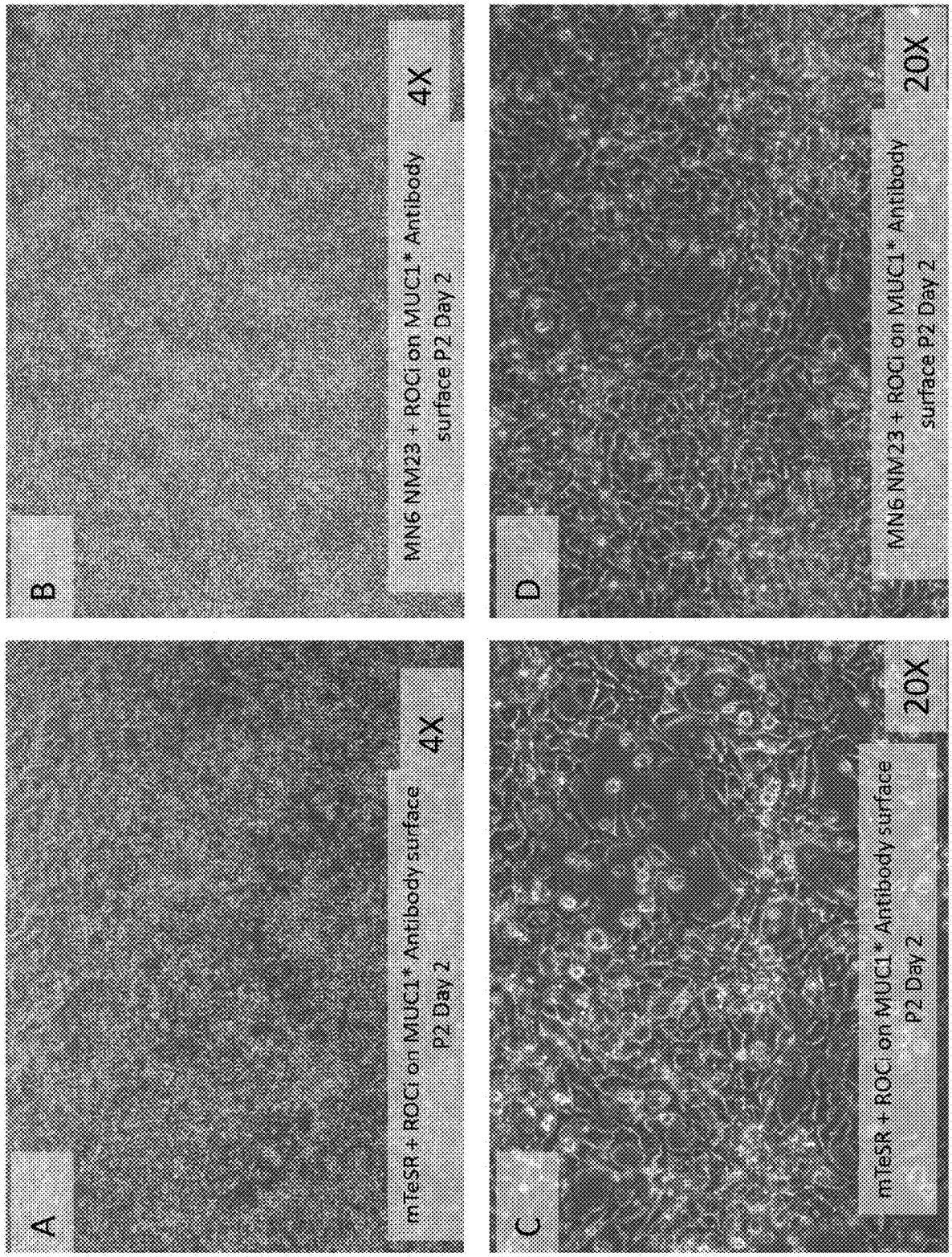
FIGS. 12A-12D show magnified photographic images of fully confluent undifferentiated human stem cells cultured in mTeSR A,C or MN6 media with NM23 B,D both with a Rho kinase inhibitor, Y27632, on an anti-MUC1* antibody surface.

FIGS. 11 and 12 show human ES cells (H9s) plated onto a layer of anti-MUC1* antibody (MN-C3). The source cells had previously been cultured according to standard protocols in bFGF at 4 ng/mL on mouse feeder cells (MEFs) for 55 passages. FIG. 11 shows the stem cells on the first passage (P1) onto the anti-MUC1* antibody surface on Day 4 post-plating (D4), wherein A, C have been cultured in NM23 dimers at 8 nM in Minimal Stem Cell media, "MM", and B, D have been cultured in NM23 dimers at 8 nM in MN6 fully defined and xeno-free media. As can be seen, there is no difference between the confluency or pluripotency of the resultant stem cells based on different base media. FIG. 12 shows the same source stem cells after two passages (P2) on Day 2 post-plating (D2), wherein A, C were cultured in mTeSR media and B, D were cultured in MN6 media plus 8 nM dimeric NM23. As can be seen, NM23 in MN6 media performed as well or better than mTeSR in terms of confluency and pluripotency of the resultant stem cells based on different base media. All media were supplemented with a Rho kinase inhibitor, Y27632 at 10 uM for the first 48 hours only, for each passage. FIG. 13 compares growth rates for the same cells on anti-MUC1* antibody surface or on Vitronectin but cultured in different media.

In addition to the NM23-S120G refolded and purified as dimers, a single chain NM23 construct that included two NM23 monomer sub-units connected by a flexible linker of $G_4S_1$ repeated 2-times—NM23-GS2 and a single chain NM23 construct that included 2 NM23 monomers connected by a longer linker—NM23-X4 were tested and performed as well as the naturally dimerized NM23-S120G.

Example 2

Induction of Pluripotency Using NME-Based Media in the Absence of FGF

The conventionally used standard protocol is to first plate dermablasts or fibroblasts (human foreskin fibroblast-neonatal, "hFFn": #PC501A-hFF, System Biosciences, Mountain View, Calif.) on plastic and culture them in fibroblast media (FM), changed every 24 hours. After 5 days, the cells are transferred to a surface coated with inactivated fibroblast feeder cells, which can be mouse (MEFs) or human (HS27). For the next 2 days, cells remain in FM. On Day 7 the media is changed to bFGF-based media and media is changed every 24 hours. ~2-4 weeks post initial plating, colonies (clones) that have embryonic stem (ES) cell-like morphology are selected and individually plated into new wells coated with inactivated feeder cells (MEFs or HS27s) and sequentially passaged every 3-4 days. Wells that continue to grow as ES-like cells are propagated and tested for the presence of pluripotency markers.

Contrary to the conventionally used standard protocol, we cultured the somatic cells in NME media always (NME1 dimers: "NM23-MM-A"). In addition, we either plated the cells over a layer of fibroblast feeder cells or over a layer of anti-MUC1* antibody (C3 or C8 that recognize the N-10 PSMGFR peptide. RT-PCR measurements were performed to quantify the amount of Oct4 expressed under a variety of conditions by Day 4 (FIG. 31A) or by day 20 (FIG. 31B). By Day 4, the only condition that resulted in an induction of pluripotency, as measured by expression levels of Oct4, was for fibroblasts transfected with OCT4, SOX2 and KLF4 ("OSK") (no c-Myc) and cultured in NME1 dimers in minimal media ("MM"). For those cells Oct4 was 119-times greater than the starting cells and nearly 200-times greater than identical cells that were instead cultured in fibroblast media. By Day 20, cells transfected with only three genes, OSK and cultured in NM23-MM-A expressed Oct4 at 109-times greater than the control. Cells that had been transfected with OSKM and cultured in NM23-MM always had Oct4 expression that was 3-times greater than identical cells cultured in fibroblast media (FM) then switched to bFGF media (standard), while cells cultured in FM then switched to NM23-MM only had Oct4 expression that was 1.3-times greater than cells cultured in FM then bFGF-M (FIG. 31C) Immunocytochemical staining of the cells at Day 20 for pluripotency marker Tra 1-60 shows the major advantage of inducing pluripotency in cells using an NME-based media. Cells that were transfected with OCT4, SOX2 and KLF4 and cultured in NME1 dimers in minimal media and in the absence of added FGF had a vast increase in efficiency of induction of pluripotency (FIG. 31F,G) compared to cells transfected with all four pluripotency genes OCT4, SOX2, KLF4 and c-Myc and cultured according to standard protocol in FGF-media (FIG. 31D,E). Cells that were transfected with three pluripotency genes, OCT4, SOX2 and KLF4, did not have detectable pluripotency markers and lacked stem-like morphology.

Example 3

In this series of experiments, we probed the expression of NME6 and NME7 in stem cells and cancer cells. In addition, we identified MUC1* as the target of NME7. We first performed Western blot assays on cell lysates to determine the presence or absence of NME1 and NME7. In FIG. 14A, lysates from BGO1v human embryonic stem cells that had been cultured in NME1 dimers over a surface coated with anti-MUC1* antibodies (Lane 1), or cultured in bFGF over MEFs (Lane 2) or T47D human breast cancer cell lysates (Lane 3) or NME1-wt as a positive control, were separated by SDS-PAGE then probed with an anti-NME1 specific antibody. The results show that NME1 is strongly expressed in human ES cells whether cultured in NME1 dimers or bFGF, and in T47D cancer cells. In FIG. 14B, the same cell lysates are separated by SDS-PAGE and then probed with an anti-NME7 specific antibody. The results show that NME7 is strongly expressed in human ES cells cultured in NME1 dimers over an anti-MUC1* antibody surface (Lane 1), weakly expressed in the same ES cells that were cultured in bFGF over MEFs (Lane 2), and strongly expressed in breast cancer cells (Lane 3). Lane 4 in which NME1 was added is blank indicating that the NME7 antibody does not cross react with NME1. The fact that NME7 is expressed to a greater degree in stem cells cultured in NME1 dimers, which we have shown express markers indicating that they are in a more naïve state than cells cultured in bFGF, means that NME7 is expressed at a higher level in naïve cells, compared to its expression in primed cells.

To determine whether NME7 also functions as a growth factor with MUC1* as its target receptor, we performed pull-down assays. In these experiments, a synthetic MUC1* extra cellular domain peptide (His-tagged PSMGFR sequence) was immobilized on NTA-Ni magnetic beads. These beads were incubated with the cell lysates of BGO1v human embryonic stem cells that had been cultured in NME1 dimers over a surface coated with anti-MUC1* antibodies (Lane 1), or cultured in bFGF over MEFs (Lane 2) or T47D human breast cancer cell lysates (Lane 3). Beads were rinsed and captured proteins were released by addition of imidazole. Proteins were separated by SDS-PAGE and then probed with either an anti-NME1 antibody (FIG. 14C) or an NME7 antibody (FIG. 14D). The results show that NME7 binds to the MUC1* extra cellular domain peptide. This means that in stem cells and cancer cells, NME7 via its portions of its two NDPK domains, activates pluripotency pathways by dimerizing the MUC1* extra cellular domain.

Example 4

Generation of Protein Constructs

Example 4.1

NM23-WT

NM23 wt was amplified by polymerase chain reaction (PCR) using the following primers:

```
Forward
                                     (SEQ ID NO: 86)
5'-atcgatcatatggccaactgtgagcgtaccttt-3'

Reverse
                                     (SEQ ID NO: 87)
5'-gtggtgctcgagttcatagatccagttctga-3'
```

The fragment was then purified, digested (NdeI, XhoI) and cloned between NdeI and XhoI restriction sites of the expression vector pET21b.

Example 4.2

NM23-S120G

Figure 16:
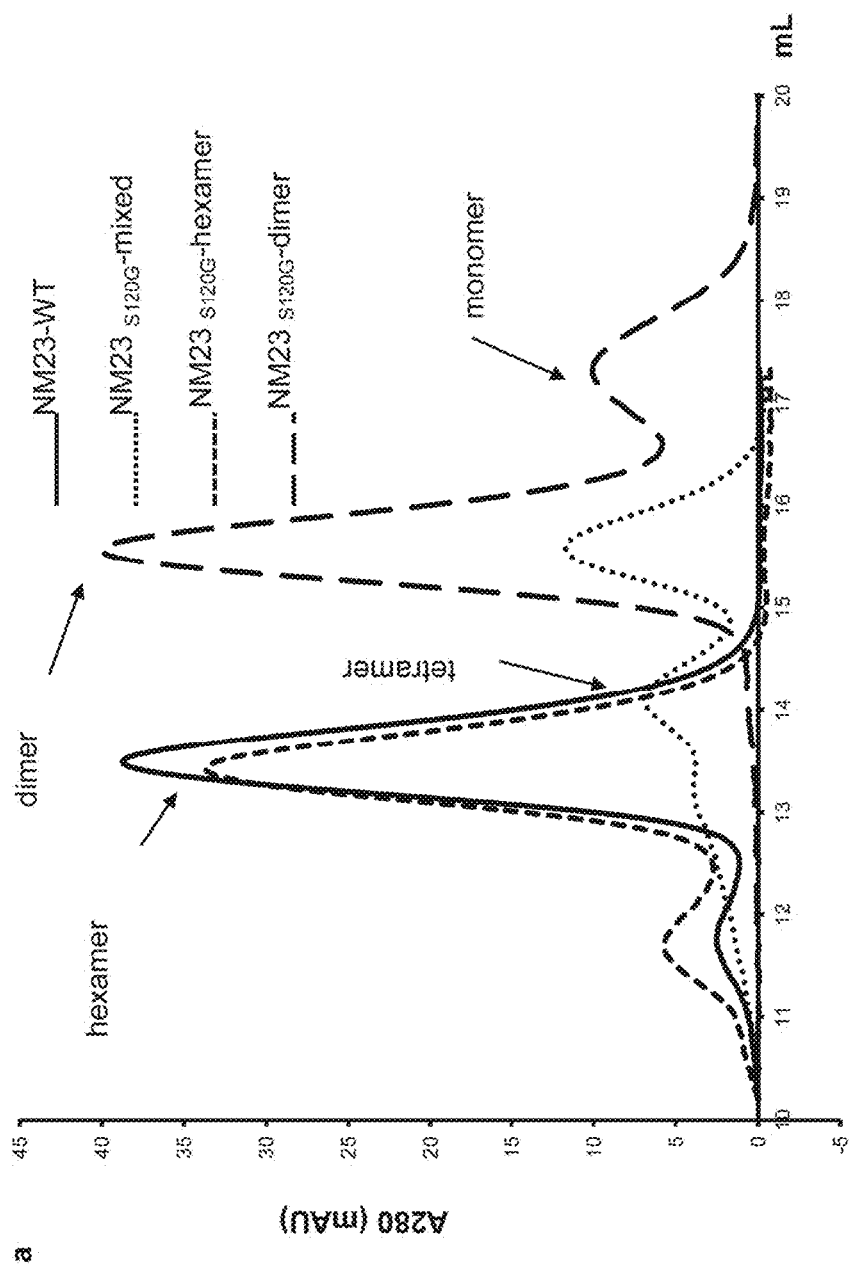
FIG. 16 shows an overlay of FPLC traces that characterize the different multimerization states of either wild type NM23 (WT) or three different preparations of mutant NM23-S120G. The wild type NM23 shows a single peak that corresponds to the molecular weight of the hexamer and a shoulder corresponding to higher order multimers. One preparation of NM23-S120G (labeled "mixed") that was not refolded, has the dominant peak that corresponds to the dimer and a lesser peak of tetramers. Another preparation of NM23-S120G ("hexamer") that was also not refolded has the major peak of hexamers with shoulder of higher order multimers. A refolded preparation of NM23-S120G ("dimer") is comprised mostly of dimers.
Figure 17:
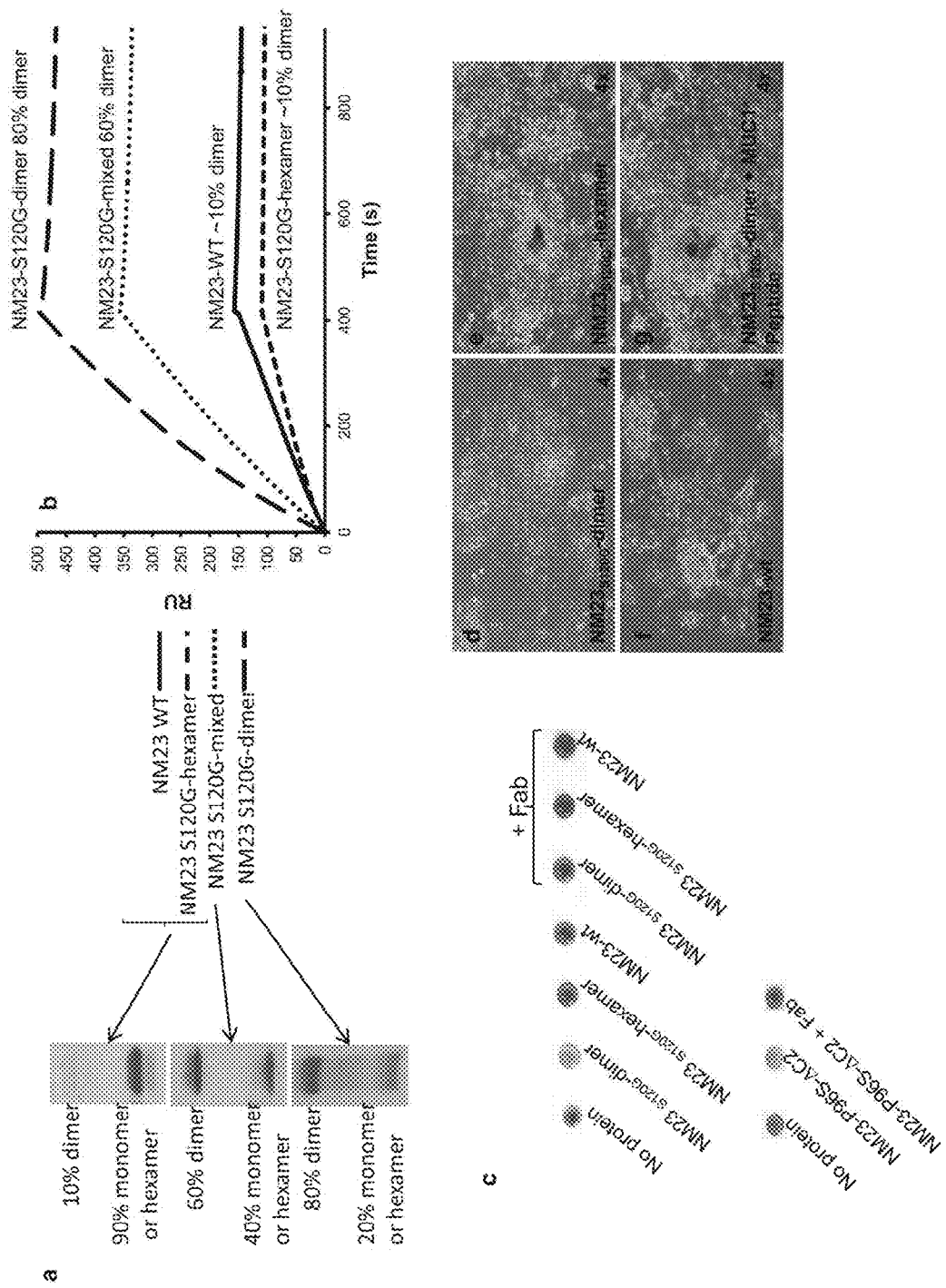
FIG. 17A shows photographs of non-reducing gels of NM23-WT, NM23-S120G-mixed, NM23-S120G-hexamer and NM23-S120G-dimer, showing the multimerization state of the wild type protein and the three different preparations of the S120G mutant.
FIG. 17B shows Surface Plasmon Resonance (SPR) measurements of different NM23 multimers binding to MUC1* extra cellular domain peptide (PSMGFR) attached to the SPR chip surface.
FIG. 17C shows photograph of a nanoparticle experiment showing that only NM23 dimers bind to the cognate receptor MUC1*. MUC1* extra cellular domain peptide was immobilized onto gold nanoparticles.
FIGS. 17D-G show different NM23-H1 multimers tested for their ability to support pluripotent stem cell growth.

NM23-H1 mutant S120G (serine #120 mutated to a glycine) was made using the GeneTailor™ Site-directed mutagenesis system (Life Technologies) following the manufacturer instructions using the following primers: 5'-gcaggaacattatacatggcggtgattctg-3' (SEQ ID NO:88) and 5'-gccatgtataatgttcctgccaacttgtat-3' (SEQ ID NO:89). FIG. 16 shows overlay of FPLC traces comparing multimerization state of the wild type protein to the non-refolded S120G mutant and the refolded S120G. FIGS. 17-19 show that only the dimeric form of the protein binds to MUC1* (not the hexamer) and only the dimer is able to support pluripotent stem cell growth. FIG. 21 shows non-reducing SDS-PAGE characterization and corresponding FPLC trace for the expressed and refolded protein as well as photographs of human stem cells, showing the NM23-S120G ability to support pluripotent stem cell growth.

Example 4.3

NM23 P96S and Deletion Constructs

We generated the NM23-H1 mutant P96S (proline #96 mutated to a serine) using the QuickChange site-directed mutagenesis kit (Agilent) following the manufacturer instructions using the following primers: 5'-tcggggagac-caactctgcagactccaag-3' (SEQ ID NO:90) and 5'-cttg-gagtctgcagagttggtctccccga-3' (SEQ ID NO:91). The template used for the PCR reaction was NM23 wild type cloned between NdeI and XhoI restriction sites. After sequence confirmation, the deletion constructs were generated by PCR. NM23 P96S ΔC1 was amplified using the following primers: 5'-atcgatcatatggccaactgtgagcgtaccttc-3' (SEQ ID NO:92) and 5'-gtggtgaccggtatagatccagttctgagcaca-3' (SEQ ID NO:93). NM23 P96S ΔC2 was amplified using the following primers: 5'-atcgatcatatggccaactgtgagcgtaccttc-3' (SEQ ID NO:94) and 5'-gtggtgaccggtgatccagttctgagcacagct-3' (SEQ ID NO:95). NM23 P96S ΔC6 was amplified using the following primers: 5'-atcgatcatatggccaactgtgagcgtaccttc-3' (SEQ ID NO:96) and 5'-gtggtgaccggtagcacagctcgtgtaatc-tacca-3' (SEQ ID NO:97). The resulting fragments were purified, digested (NdeI, AgeI) and cloned between NdeI and AgeI restriction sites of the expression vector pET21b. The pET21b was previously modified by replacing the XhoI restriction by AgeI using an overlap PCR method. Optimal dimer formation was observed when NM23-P96S was cloned between NdeI and XhoI. Optimal dimer formation for all deletion mutants was observed when cloned between NdeI and AgeI. FIG. 20 shows their ability to support pluripotent stem cell growth.

Example 5

Expression and Refolding of Mutant and Variant NME1 Species

Example 5.1

Protein Expression and Optional Refolding/Purification

LB broth (Luria-Bertani broth) was inoculated with ¹/₁₀ of an overnight culture and cultured at 37° C. until OD600 reached ~0.5. At this point, recombinant protein expression was induced with 0.4 mM Isopropyl-β-D-thio-galactoside (IPTG, Gold Biotechnology) and culture was stopped after 5 h. After harvesting the cells by centrifugation (6000 rpm for 10 min at 4° C.), cell pellet was resuspended with running buffer: PBS pH7.4, 360 mM NaCl and 80 mM imidazole. Then lysozyme (1 mg/mL, Sigma), $MgCl_2$ (0.5 mM) and DNAse (0.5 ug/mL, Sigma) was added. Cell suspension was incubated on a rotating platform (275 rpm) for 30 min at 37° C. and sonicated on ice for 5 min. Insoluble cell debris was removed by centrifugation (20000 rpm for 30 min at 4° C.). The cleared lysate was then applied to a Ni-NTA column (Qiagen) equilibrated with the running buffer. The column was washed (8 CV) before eluting the protein off the column with the running buffer (6 CV) supplemented with 420 mM imidazole.

Example 5.2

Optional Protein Denaturation for Subsequent Refolding

For protein denaturation, the elution fractions were pooled and denatured by adding 1 vol of 100 mM Tris pH 8.0+8M urea, the solution was concentrated by half and another vol of 100 mM Tris pH 8.0+8M urea was added. This cycle was repeated until final urea concentration was ~7M. The protein was then refolded by dialysis.

Example 6

Cross Species Function

NM23 supports proliferation of mouse ES cells with pluripotent colony morphology.

Mouse ES cells (129/S6, EMD Millipore, Billerica, Mass.) were cultured on inactivated MEF feeder cell layers for two days in mouse ES cell minimal medium (mESC-MM) supplemented with either 1,000 U/mL recombinant mLIF (a, c) (EMD Millipore) or 16 nM NM23-S120G-RS (b, d), and photographed at low magnification under phase-contrast illumination. Size bars indicate 500 microns. In both cases, single cells and colonies consisting of just a few cells on day 1 give rise to larger multicellular oval colonies with bright, defined edges typical of pluripotent mouse ES cells. mESC-MM consists of KnockOut D-MEM basal medium, 15% KnockOut Serum Replacement, 1× GlutaMax I, 1× OptiMEM non-essential amino acids, 0.1 mM B-ME (Life Technologies, Carlsbad, Calif.), and 1× Penicillin/Streptomycin (Lonza, Allendale, N.J.).

Figure 22:
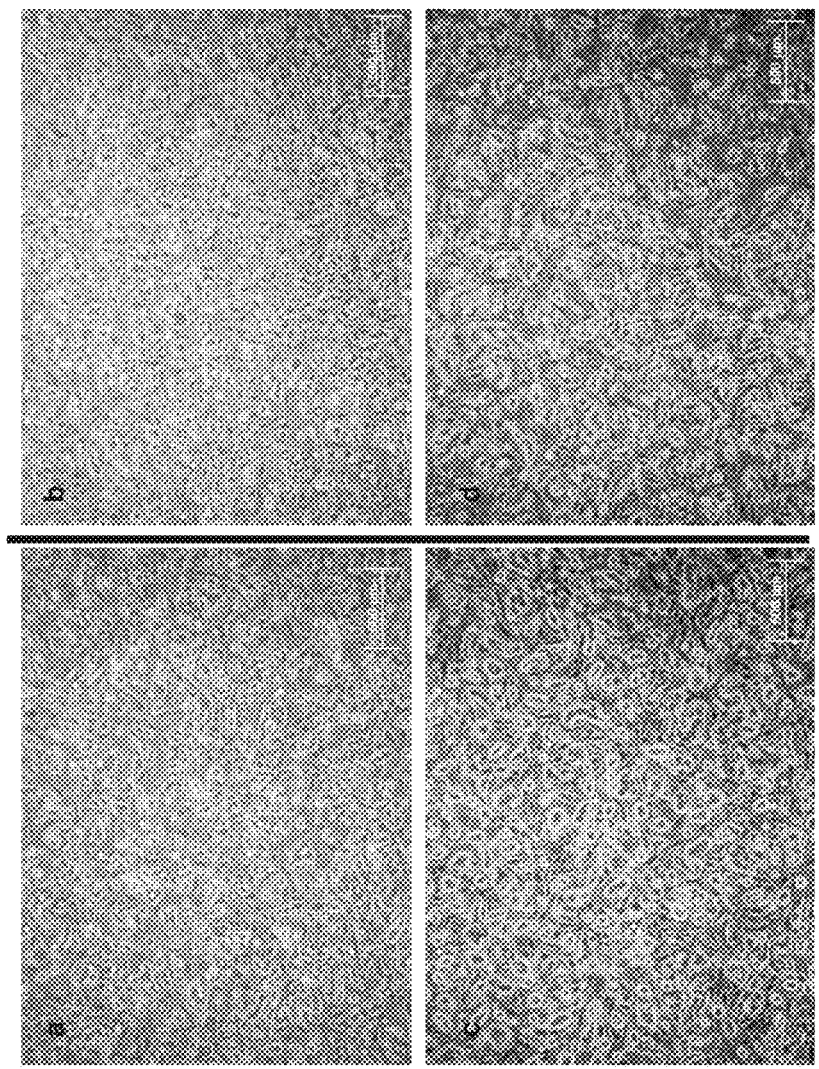
FIG. 22 shows photographs of mouse embryonic stem (ES) cells that have been cultured in on inactivated MEF feeder cell layers for two days in mouse ES cell minimal medium supplemented with either mLIF or NM23-S120G-RS. The images show that mouse ES cells grow as well using NM23 dimers as the only growth factor as they do in the standard mouse stem cell media with m LIF as the basic growth factor.

Results are shown in FIG. 22 and demonstrate that mouse stem cells grow equally well in NM23 (human) as they do in mouse stem cell media with mouse LIF as the growth factor. Therefore, NM23 variants described herein can be used in mouse cell systems and mouse NM23 and NM23 variants can be used in human cell systems.

Example 7

To determine whether or not human stem cells express NME6 or NME7 in addition to NME1 (H1) and NME2 (H2), we performed Western blot analysis on lysates and supernatant from various human stem cell lines. Human embryonic stem cell line BGO1v cells were cultured either in a) NM23-S120G in dimer form only on a cell culture plate coated with anti-MUC1* monoclonal antibody MN-C3; or b) bFGF at 4 ng/mL on mouse feeder cells (MEFs). After 3 days in culture, the stem cells were harvested and lysed, then analyzed by Western blot using antibodies to probe for the presence of NME1, NME6 and NME7. For comparison, the same analysis was done in parallel on T47D MUC1*-positive breast cancer cells. As a control, recombinant NM23-H1 wild type (NM23-wt) protein was loaded onto the gel and also probed with antibodies that recognize the 3 different NMEs. Note that the gel is a denaturing gel so that the apparent molecular weight of the NM23-S120G dimer and the wild type hexamer will both appear to be the weight of a monomer. The antibodies used to probe the gel were: for NME1: nm23-H1 (C-20); NME6: nm23-H6 (L-17) and NME7: nm23-H7 (B9) (all purchased from Santa Cruz Biotechnology, Inc):

FIG. 23 shows photos of 6 Western blot gels. Part I. A-C shows the Western blots wherein the cell lysate was separated by gel electrophoresis and then probed with antibodies for: A) NME1, B) NME6 and C) NME7. In each panel, Lane 1 corresponds to BGO1v stem cells cultured in NM23-S120G (in dimer form) on a cell culture plate coated with anti-MUC1* monoclonal antibody MN-C3; Lane 2 corresponds to BGO1v stem cells cultured in bFGF on MEFs; Lane 3 corresponds to T47D breast cancer cells; Lane 4 corresponds to purified recombinant NM23-H1 wild type (NM23-wt).

FIG. 23(A) shows that NME1 is present in BGO1v human embryonic stem cells, whether cultured in NM23 in dimer form on an anti-MUC1* antibody surface (Lane 1) or cultured in bFGF on a surface of mouse feeder cells (MEFs) (Lane 2). NME1 is also present in human breast cancer cells (Lane 3). And the positive control, Lane 4, shows that the antibody used does in fact recognize NME1 purified protein.

FIG. 23(B) shows that NME6 is not present in any of the samples tested, using these antibodies.

FIG. 23(C) shows that NME7 is strongly expressed in human stem cells if they are cultured in NM23 (dimers) on an anti-MUC1* surface (Lane 1) but only weakly expressed in stem cells cultured in bFGF on MEF feeder cells (Lane 2). NME7 is also strongly expressed human breast cancer cells (Lane 3), but is not recognized by the C-20 antibody purportedly specific for the H1 isoform.

One of the conclusions of this experiment is that NME7 is an earlier form of NM23 that is expressed in a more naïve stem cell. We have already shown that NM23 in dimer form induces stem cells to revert to a more pluripotent state often called the naïve state. Our experiments and those of others have shown that culturing stem cells in bFGF or culturing stem cells over a layer of mouse fibroblast feeder cells (MEFs) drives or maintains stem cells in the less pluripotent state called the "primed" state. Referring to FIG. 23(C), these primed stem cells express much less NME7, consistent with the idea that NME7 is associated with a more naïve and thus truly pluripotent stem cell state. Since the naïve state human stem cells are predicted to be better able to differentiate into functional adult cells, the naïve stem cells are the desired cells for research as well as for therapeutic use. Thus, strategies that involve inducing expression of NME7 are desired to obtain cells for therapeutic uses. Conversely, strategies that decrease expression of NME7 in cancers would be anti-cancer therapies.

FIGS. 23(D-F) show photos of Western blots of pull-down assays to determine which NMEs bound to the MUC1* extra cellular domain peptide. Here, a histidine-tagged MUC1* extra cellular domain peptide (GTINVHD-VETQFNQYKTEAAS-RYNLTISDVSVSDVPFPFSAQSGA-HHHHHH (SEQ ID NO:98)) was attached to NTA-Ni agarose beads and then incubated with the same cell lysates as in Part I of FIG. 23. After 1 hour incubation at 4 degrees C., beads were centrifuged for 5 minutes at 15000 RPMs. Supernatant was discarded and beads were washed with PBS to remove species bound by non-specific binding. Imidazole was added to release the complex from the beads. After centrifugation, the supernatant was separated by gel electrophoresis and analyzed as in FIG. 23, Part I with antibodies against NME1 (D), NME6 (E) and NME7 (F). FIG. 23(D) shows that NME1 in stem cells, whether cultured in NM23 (dimers) (Lane 1) or in bFGF (Lane 2), binds to MUC1* extra cellular domain peptide, as the inventor has previously shown. Lane 3 shows that NME1 in breast cancer cell lysates also binds to MUC1* extra cellular domain peptide and Lane 4 shows that the C-20 NME1 specific antibody binds to the purified recombinant wild type NME1. E) This gel shows that NME6, which in Part I of FIG. 23 was shown not to be in these cell lysates, was also not pulled down by the MUC1* peptide. FIG. 23(F) importantly shows that NME7 binds to the MUC1* extra cellular domain peptide. NME7 from stem cells cultured in NM23 dimers and over a MUC1* antibody surface expressed greater amounts of NME7 than stem cells cultured in bFGF over MEFs. Consistent with Part I of FIG. 23, NME7 was shown to bind to MUC1* peptide and was pulled down in the assay by that interaction (Lane 1). However, NME7 does not appear in Lane 2, which is likely due to the reduced expression in cells cultured in bFGF. Lane 3 shows that NME7 expressed in breast cancer cells binds to MUC1* and Lane 4 shows no protein because the NME7 antibody does not recognize the NME1 isotype. NME7 likely binds to two MUC1* peptides to dimerize MUC1* receptors on cells, thus stimulating pluripotency, growth and inhibiting differentiation.

Example 8

Figure 24:
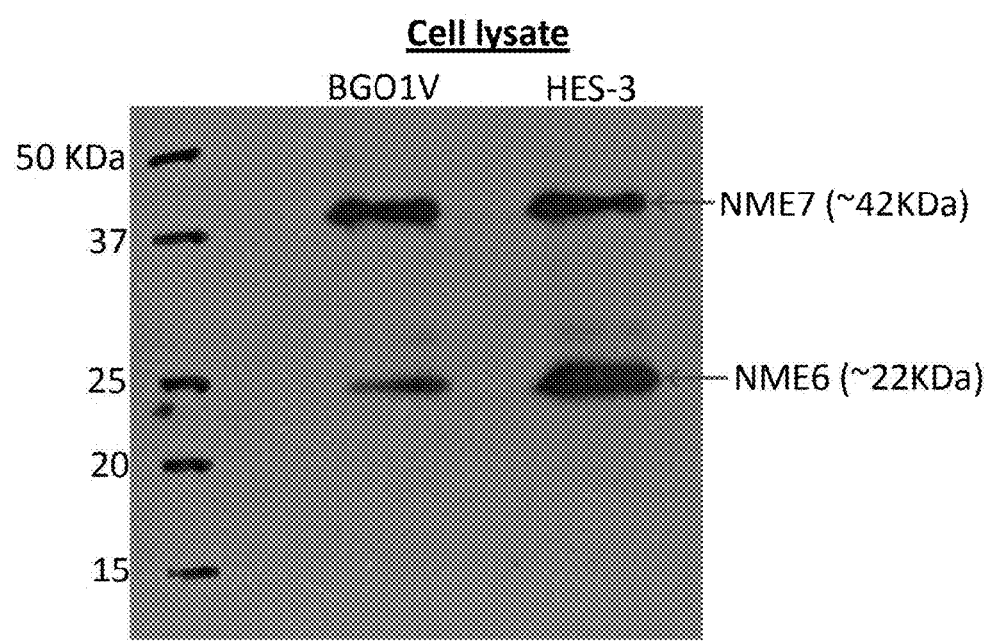
FIG. 24 is a photograph of a Western blot of human embryonic stem cell lysates probed with an antibody specific for NME7.

Western blot analysis of human stem cell lines BGO1v and HES-3 cells shows that an NME antibody, purportedly specific for NME7 recognized NME7 (nm23-H7B9 from Santa Cruz Biotechnology, Inc) and another species that is the same molecular weight as NME6 (anti-NME6 from Abnova) (FIG. 24).

Example 9

Figure 25:
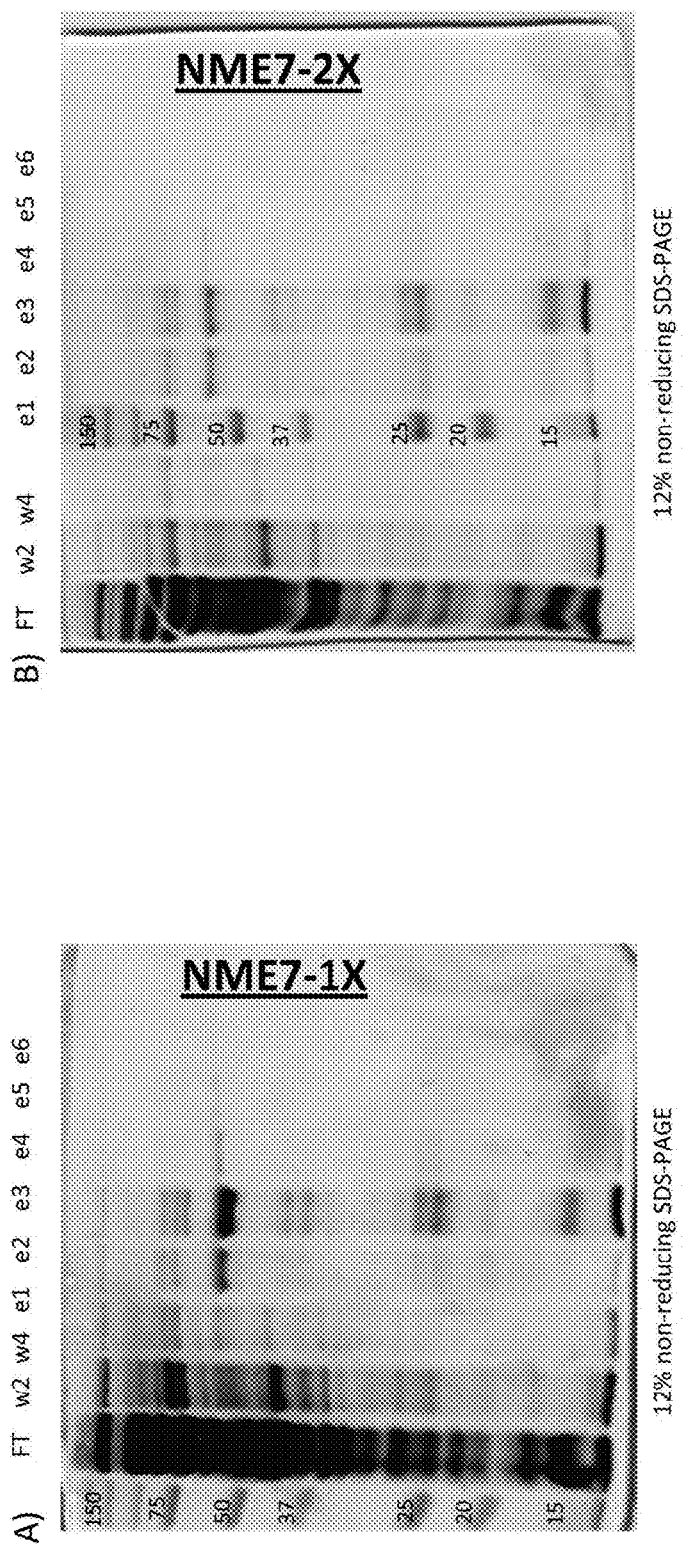
FIG. 25 shows photographs of SDS-PAGE of NME7-1 (A) and NME7-2 (B) expressed in E. coli.
Figure 26:
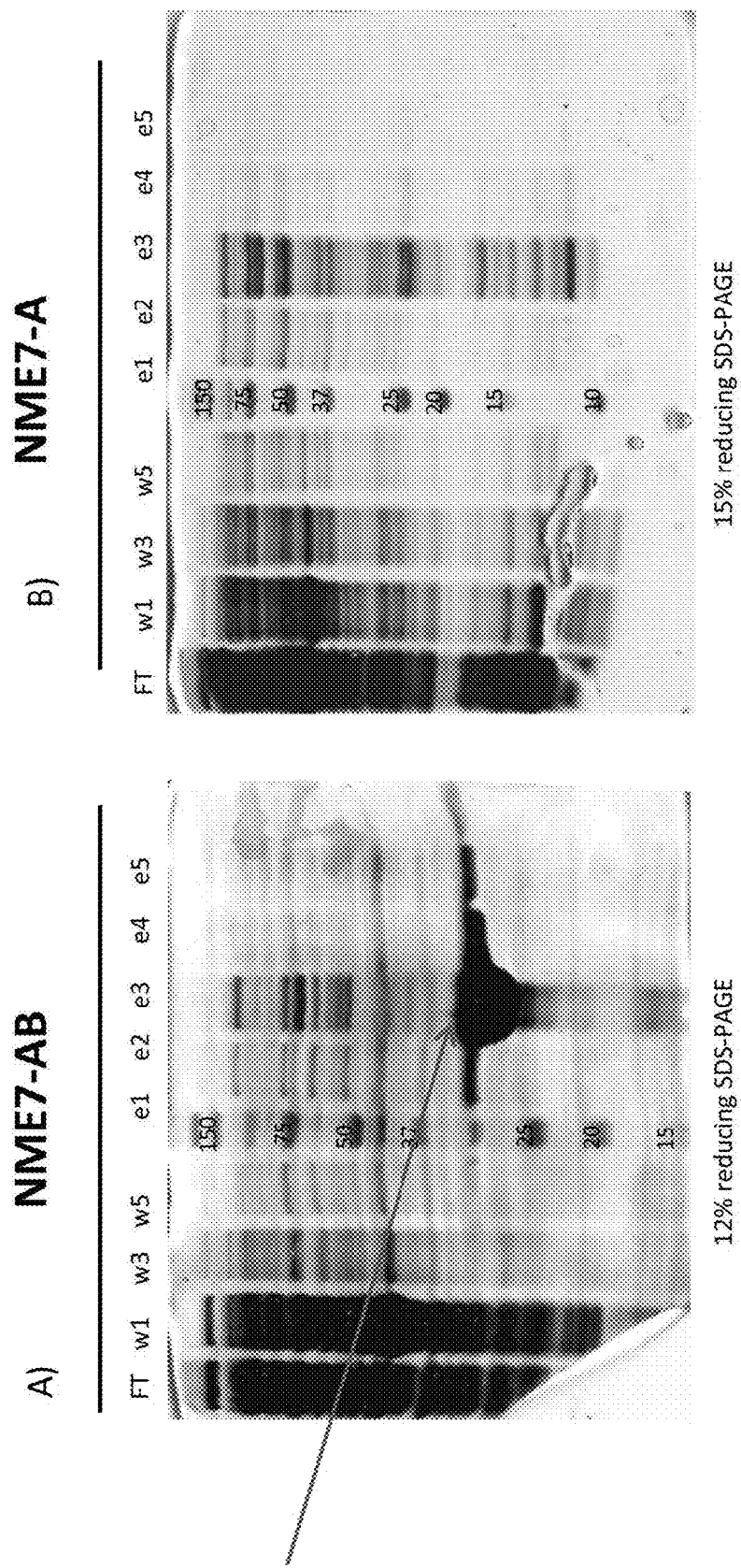
FIG. 26 is a non-reducing SDS-PAGE gel from NME7-AB and NME7-A expression and purification over an NTA-Ni column, showing good expression at the expected molecular weight of ~30 kDa for NME7-AB (A) but not for NME7-A at the expected molecular weight of ~14 kDa (B).
Figure 28:
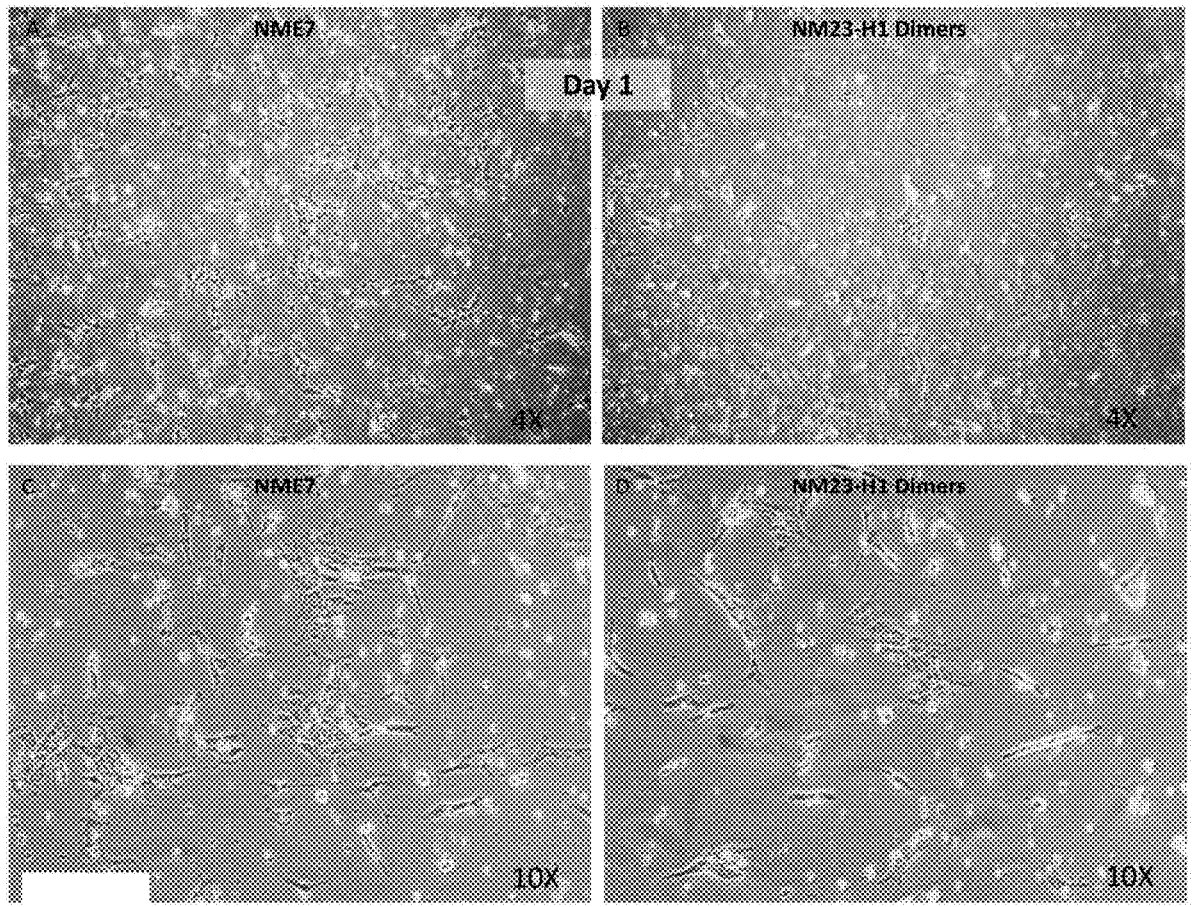
FIGS. 28A-28D are magnified photographs of human iPS stem cells cultured in either recombinant NME7-AB, or recombinant NM23 (NME1) purified dimers on Day 1 post-plating.
Figure 29:
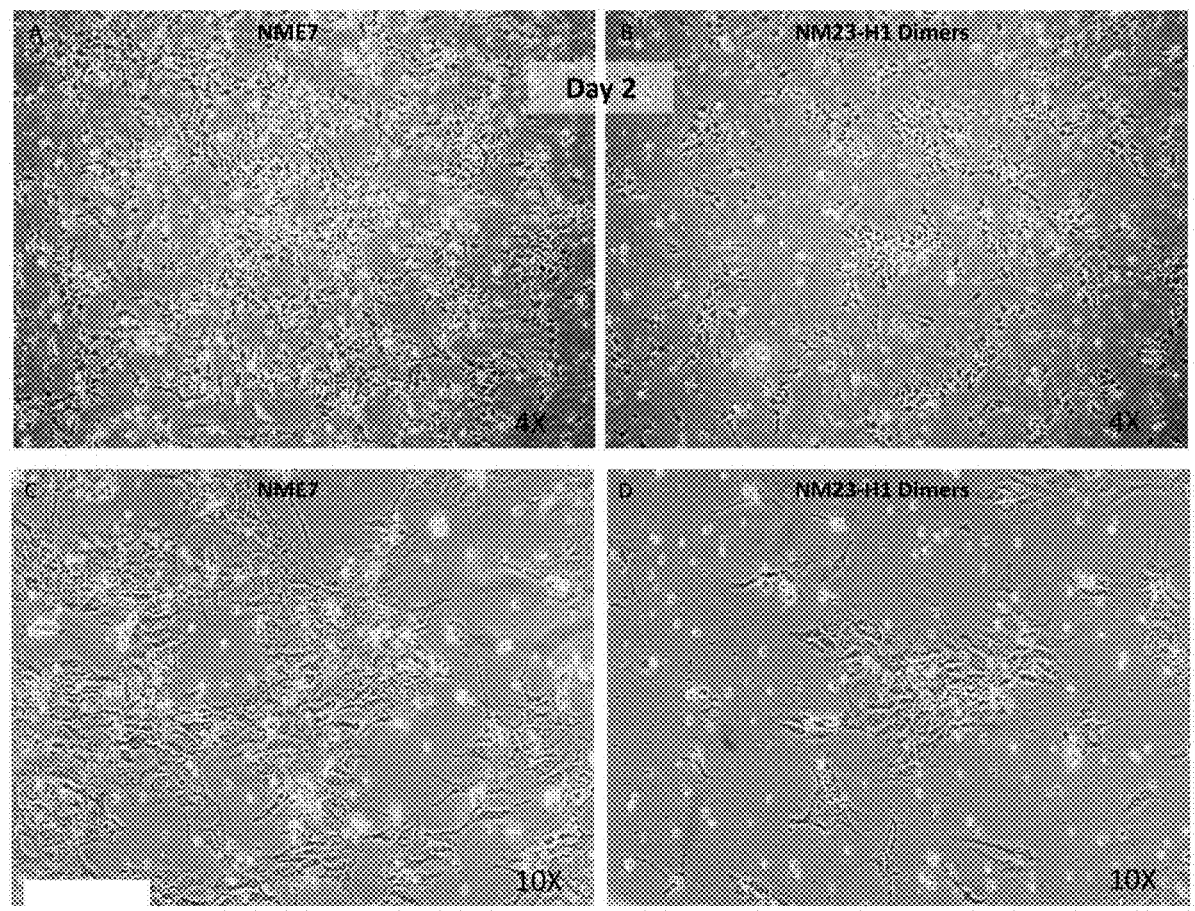
FIGS. 29A-29D are magnified photographs of human iPS stem cells cultured in either recombinant NME7-AB, or recombinant NM23 (NME1) purified dimers on Day 2 post-plating.
Figure 30:
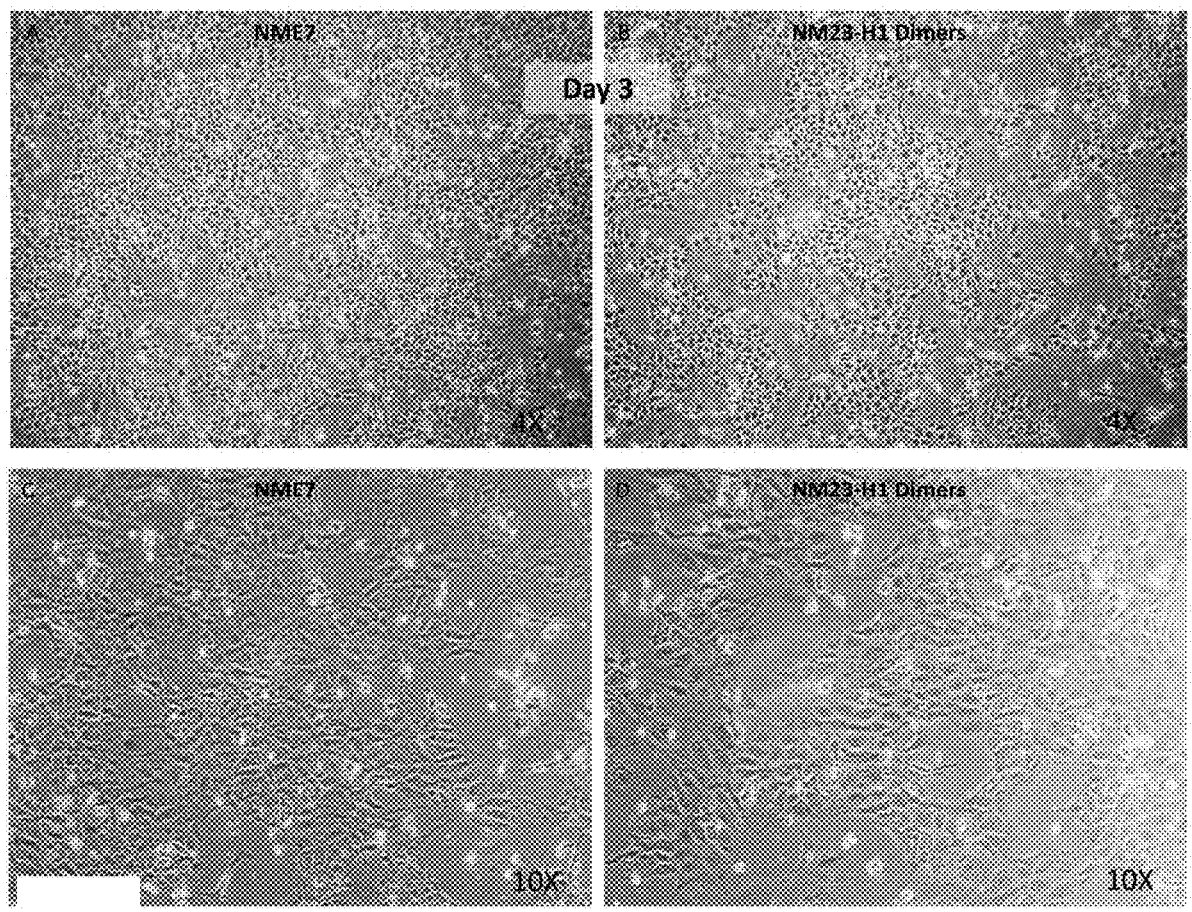
FIGS. 30A-30D are magnified photographs of human iPS stem cells cultured in either recombinant NME7-AB, or recombinant NM23 (NME1) purified dimers on Day 3 post-plating.

Generating recombinant NME7—First constructs were made to make a recombinant NME7 that could be expressed efficiently and in soluble form. The first approach was to make a construct that would encode the native NME7 (-1) or an alternative splice variant NME7 (-2), which has an N-terminal deletion. In some cases, the constructs carried a histidine tag or a strep tag to aid in purification. NME7-1 expressed poorly in *E. coli* (FIGS. 25A, 25.1A, 25.2A) and NME7-2 did not express at all in *E. coli* (FIGS. 25B, 25.1B, 25.2B). However, a novel construct was made in which the targeting sequence was deleted and the NME7 comprised essentially the NDPK A and B domains having a calculated molecular weight of 31 kDa. This novel NME7-AB expressed very well in *E. coli* and existed as the soluble protein (FIG. 26 A). A construct in which a single NDPK domain was expressed, NME-A, did not express in *E. coli* (FIG. 26 B). NME7-AB was first purified over an NTA-Ni column (FIG. 27 A) and then further purified by size exclusion chromatography (FPLC) over a Sephadex 200 column (FIG. 27 B). The purified NME7-AB protein was then tested for its ability to promote pluripotency and inhibit differentiation of stem cells.

Example 10

Testing recombinant NME7 for ability to maintain pluripotency and inhibit differentiation. A soluble variant of NME7, NME7-AB, was generated and purified as described in Example 9. Human stem cells (iPS cat #SC101a-1, System Biosciences) were grown per the manufacturer's directions in 4 ng/ml bFGF over a layer of mouse fibroblast feeder cells for four passages. These source stem cells were then plated into 6-well cell culture plates (Vita™, Thermo Fisher) that had been coated with 12.5 ug/well of a monoclonal anti-MUC1* antibody, MN-C3. Cells were plated at a density of 300,000 cells per well. The base media was Minimal Stem Cell Media consisting of: 400 ml DME/F12/ GlutaMAX I (Invitrogen #10565-018), 100 ml Knockout Serum Replacement (KO-SR, Invitrogen #10828-028), 5 ml 100×MEM Non-essential Amino Acid Solution (Invitrogen #11140-050) and 0.9 ml (0.1 mM) β-mercaptoethanol (55 mM stock, Invitrogen #21985-023). The base media can be any media. In a preferred embodiment, the base media is free of other growth factors and cytokines. To the base media was added either 8 nM of NME7-AB or 8 nM NM23-H1 refolded and purified as stable dimers. Media was changed every 48 hours and due to accelerated growth had to be harvested and passaged at Day 3 post-plating. FIGS. 27-30 document the day by day comparison of growth in NM23-H1 dimers to growth in NME7 monomers. NME7 and NM23-H1 (NME1) dimers both grew pluripotently and had no differentiation even when 100% confluent. As can be seen in the photos, NME7 cells grew faster than the cells grown in NM23-H1 dimers. Cell counts at the first harvest verified that culture in NME7 produced 1.4-times more cells than culture in NM23-H1 dimers.

Example 11

The following novel NME6 and NME7 variants were designed and generated:

Human NM23-H7-2 sequence optimized for *E. coli* expression:

(DNA)

```
                                        (SEQ ID NO: 20)
atgcatgacgttaaaaatcaccgtacctttctgaaacgcacgaaatatga taatctgcatctggaagacctgtttattggcaacaaagtcaatgtgttct ctcgtcagctggtgctgatcgattatggcgaccagtacaccgcgcgtcaa ctgggtagtcgcaaagaaaaaacgctggccctgattaaaccggatgcaat ctccaaagctggcgaaattatcgaaattatcaacaaagcgggtttcacca tcacgaaactgaaaatgatgatgctgagccgtaaagaagccctggatttt catgtcgaccaccagtctcgcccgttttttcaatgaactgattcaattcat caccacgggtccgattatcgcaatggaaattctgcgtgatgacgctatct gcgaatggaaacgcctgctgggccggcaaactcaggtgttgcgcgtacc gatgccagtgaatccattcgcgctctgtttggcaccgatggtatccgtaa tgcagcacatggtccggactcattcgcatcggcagctcgtgaaatggaac tgttttcccgagctctggcggttgcggtccggcaaacaccgccaaattt accaattgtacgtgctgtattgtcaaaccgcacgcagtgtcagaaggcct gctgggtaaaattctgatggcaatccgtgatgctggctttgaaatctcgg ccatgcagatgttcaacatggaccgcgttaacgtcgaagaattctacgaa gtttacaaaggcgtggttaccgaatatcacgatatggttacggaaatgta ctccggtccgtgcgtcgcgatggaaattcagcaaaacaatgccaccaaaa cgtttcgtgaattctgtggtccggcagatccggaaatcgcacgtcatctg
```

-continued
```
cgtccgggtaccctgcgcgcaattttttggtaaaacgaaaatccagaacgc
tgtgcactgtaccgatctgccggaagacggtctgctggaagttcaatact
ttttcaaaattctggataattga
```

(Amino Acids)

(SEQ ID NO: 21)
MHDVKNHRTFLKRTKYDNLHLEDLFIGNKVNVFSRQLVLIDYGDQYTAR
QLGSRKEKTLALIKPDAISKAGEIIEIINKAGFTITKLKMMMLSRKEAL
DFHVDHQSRPFFNELIQFITTGPIIAMEILRDDAICEWKRLLGPANSGV
ARTDASESIRALFGTDGIRNAAHGPDSFASAAREMELFFPSSGGCGPAN
TAKFTNCTCCIVKPHAVSEGLLGKILMAIRDAGFEISAMQMFNMDRVNV
EEFYEVYKGVVTEYHDMVTEMYSGPCVAMEIQQNNATKTFREFCGPADP
EIARHLRPGTLRAIFGKTKIQNAVHCTDLPEDGLLEVQYFFKILDN-

Human NME7-A:
(DNA)

(SEQ ID NO: 22)
```
atggaaaaaacgctagccctaattaaaccagatgcaatatcaaaggctgg
agaaataattgaaataaaacaaagctggatttactataaccaaactca
aaatgatgatgctttcaaggaaagaagcattggattttcatgtagatcac
cagtcaagaccttttcaatgagctgatccagtttattacaactggtcc
tattattgccatggagattttaagagatgatgctatatgtgaatggaaaa
gactgctgggacctgcaaactctggagtggcacgcacagatgcttctgaa
agcattagagccctctttggaacagatggcataagaaatgcagcgcatgg
ccctgattcttttgcttctgcggccagagaaatggagttgtttttttga
```

(Amino Acids)

(SEQ ID NO: 23)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFF-

Human NME7-A1:
(DNA)

(SEQ ID NO: 24)
```
atggaaaaaacgctagccctaattaaaccagatgcaatatcaaaggctgg
agaaataattgaaataaaacaaagctggatttactataaccaaactca
aaatgatgatgctttcaaggaaagaagcattggattttcatgtagatcac
cagtcaagaccttttcaatgagctgatccagtttattacaactggtcc
tattattgccatggagattttaagagatgatgctatatgtgaatggaaaa
gactgctgggacctgcaaactctggagtggcacgcacagatgcttctgaa
agcattagagccctctttggaacagatggcataagaaatgcagcgcatgg
ccctgattcttttgcttctgcggccagagaaatggagttgtttttttcctt
caagtggaggttgtgggccggcaaacactgctaaatttacttga
```

(Amino Acids)

(SEQ ID NO: 25)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFFPSSGGCGPANTAKFT-

Human NME7-A2:
(DNA)

(SEQ ID NO: 26)
```
atgaatcatagtgaaagattcgttttcattgcagagtggtatgatccaaa
tgcttcacttcttcgacgttatgagcttttattttacccaggggatggat
ctgttgaaatgcatgatgtaaagaatcatcgcaccttttaaagcggacc
aaatatgataacctgcacttggaagatttatttataggcaacaaagtgaa
tgtcttttctcgacaactggtattaattgactatggggatcaatatacag
ctcgccagctgggcagtaggaaagaaaaaacgctagccctaattaaacca
gatgcaatatcaaaggctggagaaataattgaaataataaacaaagctgg
atttactataaccaaactcaaaatgatgatgctttcaaggaaagaagcat
tggattttcatgtagatcaccagtcaagaccttttcaatgagctgatc
cagtttattacaactggtcctattattgccatggagattttaagagatga
tgctatatgtgaatggaaaagactgctgggacctgcaaactctggagtgg
cacgcacagatgcttctgaaagcattagagccctctttggaacagatggc
ataagaaatgcagcgcatggccctgattcttttgcttctgcggccagaga
aatggagttgttttttga
```

(Amino Acids)

(SEQ ID NO: 27)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFF-

Human NME7-A3:
(DNA)

(SEQ ID NO: 28)
```
atgaatcatagtgaaagattcgttttcattgcagagtggtatgatccaaa
tgcttcacttcttcgacgttatgagcttttattttacccaggggatggat
ctgttgaaatgcatgatgtaaagaatcatcgcaccttttaaagcggacc
aaatatgataacctgcacttggaagatttatttataggcaacaaagtgaa
tgtcttttctcgacaactggtattaattgactatggggatcaatatacag
ctcgccagctgggcagtaggaaagaaaaaacgctagccctaattaaacca
gatgcaatatcaaaggctggagaaataattgaaataataaacaaagctgg
atttactataaccaaactcaaaatgatgatgctttcaaggaaagaagcat
tggattttcatgtagatcaccagtcaagaccttttcaatgagctgatc
```

-continued
```
cagtttattacaactggtcctattattgccatggagattttaagagatga
tgctatatgtgaatggaaaagactgctgggacctgcaaactctggagtgg
cacgcacagatgcttctgaaagcattagagccctctttggaacagatggc
ataagaaatgcagcgcatggccctgattcttttgcttctgcggccagaga
aatggagttgttttttccttcaagtggaggttgtgggccggcaaacactg
ctaaatttacttga
```

(Amino Acids)

(SEQ ID NO: 29)
```
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFFPSSGGCGPANTAKFT-
```

Human NME7-B:
(DNA)

(SEQ ID NO: 30)
```
atgaattgtacctgttgcattgttaaacccatgctgtcagtgaaggact
gttgggaaagatcctgatggctatccgagatgcaggttttgaaatctcag
ctatgcagatgttcaatatggatcgggttaatgttgaggaattctatgaa
gtttataaaggagtagtgaccgaatatcatgacatggtgacagaaatgta
ttctggcccttgtgtagcaatggagattcaacagaataatgctacaaaga
catttcgagaattttgtggacctgctgatcctgaaattgcccggcattta
cgccctggaactctcagagcaatctttggtaaaactaagatccagaatgc
tgttcactgtactgatctgccagaggatggcctattagaggttcaatact
tcttctga
```

(Amino Acids)

(SEQ ID NO: 31)
```
MNCTCCIVKPHAVSEGLLGKILMAIRDAGFEISAMQMFNMDRVNVEEFY
EVYKGVVTEYHDMVTEMYSGPCVAMEIQQNNATKTFREFCGPADPEIAR
HLRPGTLRAIFGKTKIQNAVHCTDLPEDGLLEVQYFF-
```

Human NME7-B1:
(DNA)

(SEQ ID NO: 32)
```
atgaattgtacctgttgcattgttaaacccatgctgtcagtgaaggact
gttgggaaagatcctgatggctatccgagatgcaggttttgaaatctcag
ctatgcagatgttcaatatggatcgggttaatgttgaggaattctatgaa
gtttataaaggagtagtgaccgaatatcatgacatggtgacagaaatgta
ttctggcccttgtgtagcaatggagattcaacagaataatgctacaaaga
catttcgagaattttgtggacctgctgatcctgaaattgcccggcattta
cgccctggaactctcagagcaatctttggtaaaactaagatccagaatgc
tgttcactgtactgatctgccagaggatggcctattagaggttcaatact
tcttcaagatcttggataattagtga
```

(Amino Acids)

(SEQ ID NO: 33)
```
MNCTCCIVKPHAVSEGLLGKILMAIRDAGFEISAMQMFNMDRVNVEEFY
EVYKGVVTEYHDMVTEMYSGPCVAMEIQQNNATKTFREFCGPADPEIAR
HLRPGTLRAIFGKTKIQNAVHCTDLPEDGLLEVQYFFKILDN-
```

Human NME7-B2:
(DNA)

(SEQ ID NO: 34)
```
atgccttcaagtggaggttgtgggccggcaaacactgctaaatttactaa
ttgtacctgttgcattgttaaacccatgctgtcagtgaaggactgttgg
gaaagatcctgatggctatccgagatgcaggttttgaaatctcagctatg
cagatgttcaatatggatcgggttaatgttgaggaattctatgaagttta
taaaggagtagtgaccgaatatcatgacatggtgacagaaatgtattctg
gcccttgtgtagcaatggagattcaacagaataatgctacaaagacattt
cgagaattttgtggacctgctgatcctgaaattgcccggcatttacgccc
tggaactctcagagcaatctttggtaaaactaagatccagaatgctgttc
actgtactgatctgccagaggatggcctattagaggttcaatacttcttc
tga
```

(Amino Acids)

(SEQ ID NO: 35)
```
MPSSGGCGPANTAKFTNCTCCIVKPHAVSEGLLGKILMAIRDAGFEISAM
QMFNMDRVNVEEFYEVYKGVVTEYHDMVTEMYSGPCVAMEIQQNNATKTF
REFCGPADPEIARHLRPGTLRAIFGKTKIQNAVHCTDLPEDGLLEVQ
YFF-
```

Human NME7-B3:
(DNA)

(SEQ ID NO: 36)
```
atgccttcaagtggaggttgtgggccggcaaacactgctaaatttactaa
ttgtacctgttgcattgttaaacccatgctgtcagtgaaggactgttgg
gaaagatcctgatggctatccgagatgcaggttttgaaatctcagctatg
cagatgttcaatatggatcgggttaatgttgaggaattctatgaagttta
taaaggagtagtgaccgaatatcatgacatggtgacagaaatgtattctg
gcccttgtgtagcaatggagattcaacagaataatgctacaaagacattt
cgagaattttgtggacctgctgatcctgaaattgcccggcatttacgccc
tggaactctcagagcaatctttggtaaaactaagatccagaatgctgttc
actgtactgatctgccagaggatggcctattagaggttcaatacttcttc
aagatcttggataattagtga
```

(Amino Acids)

(SEQ ID NO: 37)
MPSSGGCGPANTAKFTNCTCCIVKPHAVSEGLLGKILMAIRDAGFEISAM
QMFNMDRVNVEEFYEVYKGVVTEYHDMVTEMYSGPCVAMEIQQNNATKTF
REFCGPADPEIARHLRPGTLRAIFGKTKIQNAVHCTDLPEDGLLEVQYFF
KILDN--

Human NME7-AB:
(DNA)

(SEQ ID NO: 38)
atggaaaaaacgctagccctaattaaaccagatgcaatatcaaaggctgg
agaaataattgaaataataaacaaagctggatttactataaccaaactca
aaatgatgatgctttcaaggaaagaagcattggattttcatgtagatcac
cagtcaagacccttttcaatgagctgatccagtttattacaactggtcc
tattattgccatggagattttaagagatgatgctatatgtgaatggaaaa
gactgctgggacctgcaaactctggagtggcacgcacagatgcttctgaa
agcattagagccctctttggaacagatggcataagaaatgcagcgcatgg
ccctgattcttttgcttctgcggccagagaaatggagttgttttttcctt
caagtggaggttgtgggccggcaaacactgctaaatttactaattgtacc
tgttgcattgttaaaccccatgctgtcagtgaaggactgttgggaaagat
cctgatggctatccgagatgcaggttttgaaatctcagctatgcagatgt
tcaatatggatcgggttaatgttgaggaattctatgaagtttataaagga
gtagtgaccgaatatcatgacatggtgacagaaatgtattctggcccttg
tgtagcaatggagattcaacagaataatgctacaaagacatttcgagaat
tttgtggacctgctgatcctgaaattgcccggcatttacgccctggaact
ctcagagcaatctttggtaaaactaagatccagaatgctgttcactgtac
tgatctgccagaggatggcctattagaggttcaatacttcttcaagatct
tggataattagtga (Amino Acids)

(SEQ ID NO: 39)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFFPSSGGCGPANTAKFTNCT
CCIVKPHAVSEGLLGKILMAIRDAGFEISAMQMFNMDRVNVEEFYEVYKG
VVTEYHDMVTEMYSGPCVAMEIQQNNATKTFREFCGPADPEIARHLRPGT
LRAIFGKTKIQNAVHCTDLPEDGLLEVQYFFKILDN--

Human NME7-AB 1:
(DNA)

(SEQ ID NO: 40)
atggaaaaaacgctagccctaattaaaccagatgcaatatcaaaggctgg
agaaataattgaaataataaacaaagctggatttactataaccaaactca
aaatgatgatgctttcaaggaaagaagcattggattttcatgtagatcac
cagtcaagacccttttcaatgagctgatccagtttattacaactggtcc
tattattgccatggagattttaagagatgatgctatatgtgaatggaaaa
gactgctgggacctgcaaactctggagtggcacgcacagatgcttctgaa
agcattagagccctctttggaacagatggcataagaaatgcagcgcatgg
ccctgattcttttgcttctgcggccagagaaatggagttgttttttcctt
caagtggaggttgtgggccggcaaacactgctaaatttactaattgtacc
tgttgcattgttaaaccccatgctgtcagtgaaggactgttgggaaagat
cctgatggctatccgagatgcaggttttgaaatctcagctatgcagatgt
tcaatatggatcgggttaatgttgaggaattctatgaagtttataaagga
gtagtgaccgaatatcatgacatggtgacagaaatgtattctggcccttg
tgtagcaatggagattcaacagaataatgctacaaagacatttcgagaat
tttgtggacctgctgatcctgaaattgcccggcatttacgccctggaact
ctcagagcaatctttggtaaaactaagatccagaatgctgttcactgtac
tgatctgccagaggatggcctattagaggttcaatacttcttctga (Amino Acids)

(SEQ ID NO: 41)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFFPSSGGCGPANTAKFTNCT
CCIVKPHAVSEGLLGKILMAIRDAGFEISAMQMFNMDRVNVEEFYEVYKG
VVTEYHDMVTEMYSGPCVAMEIQQNNATKTFREFCGPADPEIARHLRPGT
LRAIFGKTKIQNAVHCTDLPEDGLLEVQYFF-

Human NME7-a Sequence Optimized for *E. coli* Expression:
(DNA)

(SEQ ID NO: 42)
atggaaaaaacgctggccctgattaaaccggatgcaatctccaaagctgg
cgaaattatcgaaattatcaacaaagcgggtttcaccatcacgaaactga
aaatgatgatgctgagccgtaaagaagccctggattttcatgtcgaccac
cagtctcgcccgttttcaatgaactgattcaattcatcaccacgggtcc
gattatcgcaatggaaattctgcgtgatgacgctatctgcgaatggaaac
gcctgctgggcccggcaaactcaggtgttgcgcgtaccgatgccagtgaa
tccattcgcgctctgtttggcaccgatggtatccgtaatgcagcacatgg
tccggactcattcgcatcggcagctcgtgaaatggaactgttttctga (Amino Acids)

(SEQ ID NO: 43)
MEKTLALIKPDAISKAGEIIEIINKAGFTITKLKMMMLSRKEALDFHVDH
QSRPFFNELIQFITTGPIIAMEILRDDAICEWKRLLGPANSGVARTDASE
SIRALFGTDGIRNAAHGPDSFASAAREMELFF-

Human NME7-A1 Sequence Optimized for *E. coli* Expression:
(DNA)

(SEQ ID NO: 44)
atggaaaaaacgctggccctgattaaaccggatgcaatctccaaagctgg
cgaaattatcgaaattatcaacaaagcgggtttcaccatcacgaaactga
aaatgatgatgctgagccgtaaagaagccctggattttcatgtcgaccac
cagtctcgcccgttttcaatgaactgattcaattcatcaccacgggtcc
gattatcgcaatggaaattctgcgtgatgacgctatctgcgaatggaaac
gcctgctgggcccggcaaactcaggtgttgcgcgtaccgatgccagtgaa
tccattcgcgctctgtttggcaccgatggtatccgtaatgcagcacatgg
tccggactcattcgcatcggcagctcgtgaaatggaactgttttttcccga
gctctggcggttgcggtccggcaaacaccgccaaatttacctga (Amino Acids)

(SEQ ID NO: 45)
MEKTLALIKPDAISKAGEIIEIINKAGFTITKLKMMMLSRKEALDFHVD
HQSRPFFNELIQFITTGPIIAMEILRDDAICEWKRLLGPANSGVARTDA
SESIRALFGTDGIRNAAHGPDSFASAAREMELFFPSSGGCGPANTAKFT-

Human NME7-A2 Sequence Optimized for *E. coli* Expression:
(DNA)

(SEQ ID NO: 46)
atgaatcactccgaacgctttgttttatcgccgaatggtatgacccga
atgcttccctgctgcgccgctacgaactgctgttttatccgggcgatgg
tagcgtggaaatgcatgacgttaaaaatcaccgtacctttctgaaacgc
acgaaatatgataatctgcatctggaagacctgtttattggcaacaaag
tcaatgtgttctctcgtcagctggtgctgatcgattatggcgaccagta
caccgcgcgtcaactgggtagtcgcaaagaaaaaacgctggccctgatt
aaaccggatgcaatctccaaagctggcgaaattatcgaaattatcaaca
aagcgggtttcaccatcacgaaactgaaaatgatgatgctgagccgtaa
agaagccctggattttcatgtcgaccaccagtctcgcccgttttcaat
gaactgattcaattcatcaccacgggtccgattatcgcaatggaaattc
tgcgtgatgacgctatctgcgaatggaaacgcctgctgggcccggcaaa
ctcaggtgttgcgcgtaccgatgccagtgaatccattcgcgctctgttt
ggcaccgatggtatccgtaatgcagcacatggtccggactcattcgcat
cggcagctcgtgaaatggaactgttttttctga (Amino Acids)

(SEQ ID NO: 47)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFF-

Human NME7-A3 Sequence Optimized for *E. coli* Expression:
(DNA)

(SEQ ID NO: 48)
atgaatcactccgaacgctttgttttatcgccgaatggtatgacccga
atgcttccctgctgcgccgctacgaactgctgttttatccgggcgatgg
tagcgtggaaatgcatgacgttaaaaatcaccgtacctttctgaaacgc
acgaaatatgataatctgcatctggaagacctgtttattggcaacaaag
tcaatgtgttctctcgtcagctggtgctgatcgattatggcgaccagta
caccgcgcgtcaactgggtagtcgcaaagaaaaaacgctggccctgatt
aaaccggatgcaatctccaaagctggcgaaattatcgaaattatcaaca
aagcgggtttcaccatcacgaaactgaaaatgatgatgctgagccgtaa
agaagccctggattttcatgtcgaccaccagtctcgcccgttttcaat
gaactgattcaattcatcaccacgggtccgattatcgcaatggaaattc
tgcgtgatgacgctatctgcgaatggaaacgcctgctgggcccggcaaa
ctcaggtgttgcgcgtaccgatgccagtgaatccattcgcgctctgttt
ggcaccgatggtatccgtaatgcagcacatggtccggactcattcgcat
cggcagctcgtgaaatggaactgttttttcccgagctctggcggttgcgg
tccggcaaacaccgccaaatttacctga (Amino Acids)

(SEQ ID NO: 49)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFFPSSGGCGPANTAKFT-

Human NME7-B Sequence Optimized for *E. coli* Expression:
(DNA)

(SEQ ID NO: 50)
atgaattgtacgtgctgtattgtcaaaccgcacgcagtgtcagaaggcc
tgctgggtaaaattctgatggcaatccgtgatgctggctttgaaatctc
ggccatgcagatgttcaacatggaccgcgttaacgtcgaagaattctac
gaagtttacaaaggcgtggttaccgaatatcacgatatggttacggaaa
tgtactccggtccgtgcgtcgcgatggaaattcagcaaaacaatgccac
caaaacgtttcgtgaattctgtggtccggcagatccggaaatcgcacgt
catctgcgtccgggtaccctgcgcgcaattttttggtaaaacgaaaatcc
agaacgctgtgcactgtaccgatctgccggaagacggtctgctggaagt
tcaatactttttctga (Amino Acids)

(SEQ ID NO: 51)
MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIAR

HLRPGTLRAIFGKTKIQNAVHCTDLPEDGLLEVQYFF-

Human NME7-B1 Sequence Optimized for *E. coli* Expression:
(DNA)

(SEQ ID NO: 52)
atgaattgtacgtgctgtattgtcaaaccgcacgcagtgtcagaaggcc tgctgggtaaaattctgatggcaatccgtgatgctggctttgaaatctc ggccatgcagatgttcaacatggaccgcgttaacgtcgaagaattctac gaagtttacaaaggcgtggttaccgaatatcacgatatggttacggaaa tgtactccggtccgtgcgtcgcgatggaaattcagcaaaacaatgccac caaaacgtttcgtgaattctgtggtccggcagatccggaaatcgcacgt catctgcgtccgggtaccctgcgcgcaattttggtaaaacgaaatcc agaacgctgtgcactgtaccgatctgccggaagacggtctgctggaagt tcaatacttttcaaaattctggataattga (Amino Acids)

(SEQ ID NO: 53)
MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIAR

HLRPGTLRAIFGKTKIQNAVHCTDLPEDGLLEVQYFFKILDN-

Human NME7-B2 Sequence Optimized for *E. coli* Expression:
(DNA)

(SEQ ID NO: 54)
atgccgagctctggcggttgcggtccggcaaacaccgccaaatttacca attgtacgtgctgtattgtcaaaccgcacgcagtgtcagaaggcctgct gggtaaaattctgatggcaatccgtgatgctggctttgaaatctcggcc atgcagatgttcaacatggaccgcgttaacgtcgaagaattctacgaag tttacaaaggcgtggttaccgaatatcacgatatggttacggaaatgta ctccggtccgtgcgtcgcgatggaaattcagcaaaacaatgccaccaaa acgtttcgtgaattctgtggtccggcagatccggaaatcgcacgtcatc tgcgtccgggtaccctgcgcgcaattttggtaaaacgaaatccagaa cgctgtgcactgtaccgatctgccggaagacggtctgctggaagttcaa tacttttctga (Amino Acids)

(SEQ ID NO: 55)
MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKT

FREFCGPADPEIARHLRPGTLRAIFGKTKIQNAVHCTDLPEDGLLEVQY

FF-

Human NME7-B3 Sequence Optimized for *E. coli* Expression:
(DNA)

(SEQ ID NO: 56)
atgccgagctctggcggttgcggtccggcaaacaccgccaaatttacca attgtacgtgctgtattgtcaaaccgcacgcagtgtcagaaggcctgct gggtaaaattctgatggcaatccgtgatgctggctttgaaatctcggcc atgcagatgttcaacatggaccgcgttaacgtcgaagaattctacgaag tttacaaaggcgtggttaccgaatatcacgatatggttacggaaatgta ctccggtccgtgcgtcgcgatggaaattcagcaaaacaatgccaccaaa acgtttcgtgaattctgtggtccggcagatccggaaatcgcacgtcatc tgcgtccgggtaccctgcgcgcaattttggtaaaacgaaatccagaa cgctgtgcactgtaccgatctgccggaagacggtctgctggaagttcaa tacttttcaaaattctggataattga (Amino Acids)

(SEQ ID NO: 57)
MPSSGGCGPANTAKFTNCTCCIVKPHAVSEGLLGKILMAIRDAGFEISA

MQMFNMDRVNVEEFYEVYKGVVTEYHDMVTEMYSGPCVAMEIQQNNATK

TFREFCGPADPEIARHLRPGTLRAIFGKTKIQNAVHCTDLPEDGLLEVQ

YFFKILDN-

Human NME7-AB Sequence Optimized for *E. coli* Expression:
(DNA)

(SEQ ID NO: 58)
atggaaaaaacgctggccctgattaaaccggatgcaatctccaaagctg gcgaaattatcgaaattatcaacaaagcgggtttcaccatcacgaaact gaaaatgatgatgctgagccgtaaagaagccctggattttcatgtcgac caccagtctcgcccgttttttcaatgaactgattcaattcatcaccacgg gtccgattatcgcaatggaaattctgcgtgatgacgctatctgcgaatg gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt ttttcccgagctctggcggttgcggtccggcaaacaccgccaaatttacc aattgtacgtgctgtattgtcaaaccgcacgcagtgtcagaaggcctgc tgggtaaaattctgatggcaatccgtgatgctggctttgaaatctcggc catgcagatgttcaacatggaccgcgttaacgtcgaagaattctacgaa gtttacaaaggcgtggttaccgaatatcacgatatggttacggaaatgt actccggtccgtgcgtcgcgatggaaattcagcaaaacaatgccaccaa aacgtttcgtgaattctgtggtccggcagatccggaaatcgcacgtcat ctgcgtccgggtaccctgcgcgcaattttggtaaaacgaaatccaga -continued
acgctgtgcactgtaccgatctgccggaagacggtctgctggaagttca atacttttcaaaattctggataattga (Amino Acids)

(SEQ ID NO: 59)
MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFFKILDN-

Human NME7-AB 1 Sequence Optimized for *E. coli* Expression:
(DNA)

(SEQ ID NO: 60)
Atggaaaaaacgctggccctgattaaaccggatgcaatctccaaagctg gcgaaattatcgaaattatcaacaaagcgggtttcaccatcacgaaact gaaaatgatgatgctgagccgtaaagaagccctggattttcatgtcgac caccagtctcgcccgttttcaatgaactgattcaattcatcaccacgg gtccgattatcgcaatggaaattctgcgtgatgacgctatctgcgaatg gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt tttcccgagctctggcggttgcggtccggcaaacaccgccaaatttacc aattgtacgtgctgtattgtcaaaccgcacgcagtgtcagaaggcctgc tgggtaaaattctgatggcaatccgtgatgctggctttgaaatctcggc catgcagatgttcaacatggaccgcgttaacgtcgaagaattctacgaa gtttacaaaggcgtggttaccgaatatcacgatatggttacggaaatgt actccggtccgtgcgtcgcgatggaaattcagcaaaacaatgccaccaa aacgtttcgtgaattctgtggtccggcagatccggaaatcgcacgtcat ctgcgtccgggtaccctgcgcgcaatttttggtaaaacgaaaatccaga acgctgtgcactgtaccgatctgccggaagacggtctgctggaagttca atacttttctga (Amino Acids)

(SEQ ID NO: 61)
MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFF-

Mouse NME6
(DNA)

(SEQ ID NO: 62)
Atgacctccatcttgcgaagtccccaagctcttcagctcacactagccc tgatcaagcctgatgcagttgcccacccactgatcctggaggctgttca tcagcagattctgagcaacaagttcctcattgtacgaacgagggaactg cagtggaagctggaggactgccggaggttttaccgagagcatgaaggc gttttttctatcagcggctggtggagttcatgacaagtgggccaatccg agcctatatccttgcccacaaagatgccatccaactttggaggacactg atgggacccaccagagtatttcgagcacgctatatagccccagattcaa ttcgtggaagtttgggcctcactgacacccgaaatactacccatggctc agactccgtggtttccgccagcagagagattgcagccttcttccctgac ttcagtgaacagcgctggtatgaggaggaggaaccccagctgcggtgtg gtcctgtgcactacagtccagaggaaggtatccactgtgcagctgaaac aggaggccacaaacaacctaacaaaacctag (Amino Acids)

(SEQ ID NO: 63)
MTSILRSPQALQLTLALIKPDAVAHPLILEAVHQQILSNKFLIVRTREL

QWKLEDCRRFYREHEGRFFYQRLVEFMTSGPIRAYILAHKDAIQLWRTL

MGPTRVFRARYIAPDSIRGSLGLTDTRNTTHGSDSVVSASREIAAFFPD

FSEQRWYEEEEPQLRCGPVHYSPEEGIHCAAETGGHKQPNKT-

Human NME6:
(DNA)

(SEQ ID NO: 64)
Atgacccagaatctggggagtgagatggcctcaatcttgcgaagccctc aggctctccagctcactctagccctgatcaagcctgacgcagtcgccca tccactgattctggaggctgttcatcagcagattctaagcaacaagttc ctgattgtacgaatgagagaactactgtggagaaggaagattgccaga ggttttaccgagagcatgaaggcgttttttctatcagaggctggtgga gttcatggccagcgggccaatccgagcctacatccttgcccacaaggat gccatccagctctggaggacgctcatgggacccaccagagtgttccgag cacgccatgtggccccagattctatccgtgggagtttcggcctcactga cacccgcaacaccaccatggttcggactctgtggtttcagccagcaga gagattgcagccttcttccctgacttcagtgaacagcgctggtatgagg aggaagagccccagttgcgctgtggccctgtgtgctatagcccagaggg aggtgtccactatgtagctggaacaggaggcctaggaccagcctga (Amino Acids)

(SEQ ID NO: 65)
MTQNLGSEMASILRSPQALQLTLALIKPDAVAHPLILEAVHQQILSNKF

LIVRMRELLWRKEDCQRFYREHEGRFFYQRLVEFMASGPIRAYILAHKD

-continued

AIQLWRTLMGPTRVFRARHVAPDSIRGSFGLTDTRNTTHGSDSVVSASR

EIAAFFPDFSEQRWYEEEEPQLRCGPVCYSPEGGVHYVAGTGGLGPA-

Human NME6 1:
(DNA)

(SEQ ID NO: 66)
Atgacccagaatctggggagtgagatggcctcaatcttgcgaagccctc aggctctccagctcactctagccctgatcaagcctgacgcagtcgccca tccactgattctggaggctgttcatcagcagattctaagcaacaagttc ctgattgtacgaatgagagaactactgtggagaaaggaagattgccaga ggttttaccgagagcatgaagggcgttttttctatcagaggctggtgga gttcatggccagcgggccaatccgagcctacatccttgcccacaaggat gccatccagctctggaggacgctcatgggacccaccagagtgttccgag cacgccatgtggccccagattctatccgtgggagtttcggcctcactga caccccgcaacaccacccatggttcggactctgtggtttcagccagaga gagattgcagccttcttccctgacttcagtgaacagcgctggtatgagg aggaagagccccagttgcgctgtggccctgtgtga (Amino Acids)

(SEQ ID NO: 67)
MTQNLGSEMASILRSPQALQLTLALIKPDAVAHPLILEAVHQQILSNKF

LIVRMRELLWRKEDCQRFYREHEGRFFYQRLVEFMASGPIRAYILAHKD

AIQLWRTLMGPTRVFRARHVAPDSIRGSFGLTDTRNTTHGSDSVVSASR

EIAAFFPDFSEQRWYEEEEPQLRCGPV-

Human NME6 2:
(DNA)

(SEQ ID NO: 68)
Atgctcactctagccctgatcaagcctgacgcagtcgcccatccactga ttctggaggctgttcatcagcagattctaagcaacaagttcctgattgt acgaatgagagaactactgtggagaaaggaagattgccagaggttttac cgagagcatgaagggcgttttttctatcagaggctggtggagttcatgg ccagcgggccaatccgagcctacatccttgcccacaaggatgccatcca gctctggaggacgctcatgggacccaccagagtgttccgagcacgccat gtggccccagattctatccgtgggagtttcggcctcactgacacccgca acaccacccatggttcggactctgtggtttcagccagcagagagattgc agccttcttccctgacttcagtgaacagcgctggtatgaggaggaagag ccccagttgcgctgtggccctgtgtga (Amino Acids)

(SEQ ID NO: 69)
MLTLALIKPDAVAHPLILEAVHQQILSNKFLIVRMRELLWRKEDCQRFY

REHEGRFFYQRLVEFMASGPIRAYILAHKDAIQLWRTLMGPTRVFRARH

VAPDSIRGSFGLTDTRNTTHGSDSVVSASREIAAFFPDFSEQRWYEEEE

PQLRCGPV-

Human NME6 3:
(DNA)

(SEQ ID NO: 70)
Atgctcactctagccctgatcaagcctgacgcagtcgcccatccactga ttctggaggctgttcatcagcagattctaagcaacaagttcctgattgt acgaatgagagaactactgtggagaaaggaagattgccagaggttttac cgagagcatgaagggcgttttttctatcagaggctggtggagttcatgg ccagcgggccaatccgagcctacatccttgcccacaaggatgccatcca gctctggaggacgctcatgggacccaccagagtgttccgagcacgccat gtggccccagattctatccgtgggagtttcggcctcactgacacccgca acaccacccatggttcggactctgtggtttcagccagcagagagattgc agccttcttccctgacttcagtgaacagcgctggtatgaggaggaagag ccccagttgcgctgtggccctgtgtgctatagcccagagggaggtgtcc actatgtagctggaacaggaggcctaggaccagcctga (Amino Acids)

(SEQ ID NO: 71)
MLTLALIKPDAVAHPLILEAVHQQILSNKFLIVRMRELLWRKEDCQRFY

REHEGRFFYQRLVEFMASGPIRAYILAHKDAIQLWRTLMGPTRVFRARH

VAPDSIRGSFGLTDTRNTTHGSDSVVSASREIAAFFPDFSEQRWYEEEE

PQLRCGPVCYSPEGGVHYVAGTGGLGPA-

Human NME6 Sequence Optimized for *E. coli* Expression:
(DNA)

(SEQ ID NO: 72)
Atgacgcaaaatctgggctcggaaatggcaagtatcctgcgctccccgc aagcactgcaactgaccctggctctgatcaaaccggacgctgttgctca tccgctgattctggaagcggtccaccagcaaattctgagcaacaaattt ctgatcgtgcgtatgcgcgaactgctgtggcgtaaagaagattgccagc gtttttatcgcgaacatgaaggccgtttcttttatcaacgcctggttga attcatggcctctggtccgattcgcgcatatatcctggctcacaaagat gcgattcagctgtggcgtaccctgatgggtcgacgcgtctttcgtg cacgtcatgtggcaccggactcaatccgtggctcgttcggtctgaccga tacgcgcaataccacgcacggtagcgactctgttgttagtgcgtcccgt gaaatcgcggccttttcccggacttctccgaacagcgttggtacgaag aagaagaaccgcaactgcgctgtggcccggtctgttattctccggaagg tggtgtccattatgtggcgggcacgggtggtctgggtccggcatga (Amino Acids)

(SEQ ID NO: 73)
MTQNLGSEMASILRSPQALQLTLALIKPDAVAHPLILEAVHQQILSNKF

LIVRMRELLWRKEDCQRFYREHEGRFFYQRLVEFMASGPIRAYILAHKD

AIQLWRTLMGPTRVFRARHVAPDSIRGSFGLTDTRNTTHGSDSVVSASR

EIAAFFPDFSEQRWYEEEEPQLRCGPVCYSPEGGVHYVAGTGGLGPA-

Human NME6 1 Sequence Optimized for *E. coli* Expression:
(DNA)

(SEQ ID NO: 74)
```
Atgacgcaaaatctgggctcggaaatggcaagtatcctgcgctccccgc aagcactgcaactgaccctggctctgatcaaaccggacgctgttgctca tccgctgattctggaagcggtccaccagcaaattctgagcaacaaattt ctgatcgtgcgtatgcgcgaactgctgtggcgtaaagaagattgccagc gtttttatcgcgaacatgaaggccgtttcttttatcaacgcctggttga attcatggcctctggtccgattcgcgcatatatcctggctcacaaagat gcgattcagctgtggcgtaccctgatgggtccgacgcgcgtctttcgtg cacgtcatgtggcaccggactcaatccgtggctcgttcggtctgaccga tacgcgcaataccacgcacggtagcgactctgttgttagtgcgtcccgt gaaatcgcggcttttccccggacttctccgaacagcgttggtacgaag aagaagaaccgcaactgcgctgtggcccggtctga
```

(Amino Acids)

(SEQ ID NO: 75)
MTQNLGSEMASILRSPQALQLTLALIKPDAVAHPLILEAVHQQILSNKF

LIVRMRELLWRKEDCQRFYREHEGRFFYQRLVEFMASGPIRAYILAHKD

AIQLWRTLMGPTRVFRARHVAPDSIRGSFGLTDTRNTTHGSDSVVSASR

EIAAFFPDFSEQRWYEEEEPQLRCGPV-

Human NME6 2 Sequence Optimized for *E. coli* Expression:
(DNA)

(SEQ ID NO: 76)
```
Atgctgaccctggctctgatcaaaccggacgctgttgctcatccgctga ttctggaagcggtccaccagcaaattctgagcaacaaatttctgatcgt gcgtatgcgcgaactgctgtggcgtaaagaagattgccagcgttttat cgcgaacatgaaggccgtttcttttatcaacgcctggttgaattcatgg cctctggtccgattcgcgcatatatcctggctcacaaagatgcgattca gctgtggcgtaccctgatgggtccgacgcgcgtctttcgtgcacgtcat gtggcaccggactcaatccgtggctcgttcggtctgaccgatacgcgca ataccacgcacggtagcgactctgttgttagtgcgtcccgtgaaatcgc ggcttttcccggacttctccgaacagcgttggtacgaagaagaagaa ccgcaactgcgctgtggcccggtctga
```

(Amino Acids)

(SEQ ID NO: 77)
MLTLALIKPDAVAHPLILEAVHQQILSNKFLIVRMRELLWRKEDCQRFY

REHEGRFFYQRLVEFMASGPIRAYILAHKDAIQLWRTLMGPTRVFRARH

VAPDSIRGSFGLTDTRNTTHGSDSVVSASREIAAFFPDFSEQRWYEEEE

PQLRCGPV-

Human NME6 3 Sequence Optimized for *E. coli* Expression:
(DNA)

(SEQ ID NO: 78)
```
Atgctgaccctggctctgatcaaaccggacgctgttgctcatccgctga ttctggaagcggtccaccagcaaattctgagcaacaaatttctgatcgt gcgtatgcgcgaactgctgtggcgtaaagaagattgccagcgttttat cgcgaacatgaaggccgtttcttttatcaacgcctggttgaattcatgg cctctggtccgattcgcgcatatatcctggctcacaaagatgcgattca gctgtggcgtaccctgatgggtccgacgcgcgtctttcgtgcacgtcat gtggcaccggactcaatccgtggctcgttcggtctgaccgatacgcgca ataccacgcacggtagcgactctgttgttagtgcgtcccgtgaaatcgc ggcttttcccggacttctccgaacagcgttggtacgaagaagaagaa ccgcaactgcgctgtgcccggtctgttattctccggaaggtggtgtcc attatgtggcgggcacgggtggtctgggtccggcatga
```

(Amino Acids)

(SEQ ID NO: 79)
MLTLALIKPDAVAHPLILEAVHQQILSNKFLIVRMRELLWRKEDCQRFY

REHEGRFFYQRLVEFMASGPIRAYILAHKDAIQLWRTLMGPTRVFRARH

VAPDSIRGSFGLTDTRNTTHGSDSVVSASREIAAFFPDFSEQRWYEEEE

PQLRCGPVCYSPEGGVHYVAGTGGLGPA-

NME6 and NME7 as well as novel variants may be expressed with any affinity tag but were expressed with the following tags:

Histidine Tag (ctcgag)caccaccaccaccaccactga (SEQ ID NO: 84)

Strept II Tag (SEQ ID NO: 85)
(accggt)tggagccatcctcagttcgaaaagtaatga

Example 12

NME6 and NME7 Construct Generation

Example 12.1

Human NME7-1 Sequence Optimized for *E. coli* Expression

NME7 wt-cDNA, codon optimized for expression in *E. coli* was generated per our request by Genscript (NJ). NME7-1 was amplified by polymerase chain reaction (PCR) using the following primers:

Forward (SEQ ID NO: 116)
5'-atcgatcatatgaatcactccgaacgc-3'

Reverse (SEQ ID NO: 99)
5'-agagcctcgagattatccagaattttgaaaaagtattg-3'

The fragment was then purified, digested (NdeI, XhoI) and cloned between NdeI and XhoI restriction sites of the expression vector pET21b.

Example 12.2

Human NME7-2 Sequence Optimized for *E. coli* Expression

NME7-2 was amplified by polymerase chain reaction (PCR) using the following primers:

Forward (SEQ ID NO: 100)
5'-atcgatcatatgcatgacgttaaaaatcac-3'

Reverse (SEQ ID NO: 101)
5'-agagcctcgagattatccagaattttgaaaaagtattg-3'

The fragment was then purified, digested (NdeI, XhoI) and cloned between NdeI and XhoI restriction sites of the expression vector pET21b.

Example 12.3

Human NME7-a Sequence Optimized for *E. coli* Expression

NME7-A was amplified by polymerase chain reaction (PCR) using the following primers:

Forward (SEQ ID NO: 102)
5'-atcgacatatggaaaaaacgctggccctgattaaaccggatg-3'

Reverse (SEQ ID NO: 103)
5'-actgcctcgaggaaaaacagttccatttcacgagctgccgatg-3'

The fragment was then purified, digested (NdeI, XhoI) and cloned between NdeI and XhoI restriction sites of the expression vector pET21b.

Example 12.4

Human NME7-AB Sequence Optimized for *E. coli* Expression

NME7-AB was amplified by polymerase chain reaction (PCR) using the following primers:

Forward (SEQ ID NO: 104)
5'-atcgacatatggaaaaaacgctggccctgattaaaccggatg-3'

Reverse (SEQ ID NO: 105)
5'-agagcctcgagattatccagaattttgaaaaagtattg-3'

The fragment was then purified, digested (NdeI, XhoI) and cloned between NdeI and XhoI restriction sites of the expression vector pET21b. The protein is expressed with a C-Term His Tag.

NME7-AB was amplified by polymerase chain reaction (PCR) using the following primers:

Forward (SEQ ID NO: 106)
5'-atcgacatatggaaaaaacgctggccctgattaaaccggatg-3'

Reverse (SEQ ID NO: 107)
5'-agagcaccggtattatccagaattttgaaaaagtattg-3'

The fragment was then purified, digested (NdeI, AgeI) and cloned between NdeI and AgeI restriction sites of the expression vector pET21b where XhoI was replaced by AgeI followed by the Strep Tag II and two stop codon before the His Tag. The protein is expressed with a C-Term Strep Tag II.

Example 12.5

Human NME6 Sequence Optimized for *E. coli* Expression

NME6 was amplified by polymerase chain reaction (PCR) using the following primers:

Forward (SEQ ID NO: 108)
5'-atcgacatatgacgcaaaatctgggctcggaaatg-3'

Reverse (SEQ ID NO: 109)
5'-actgcctcgagtgccggacccagaccacccgtgc-3'

The fragment was then purified, digested (NdeI, XhoI) and cloned between NdeI and XhoI restriction sites of the expression vector pET21b. The protein is expressed with a C-Term His Tag.

NME6 was amplified by polymerase chain reaction (PCR) using the following primers:

Forward (SEQ ID NO: 110)
5'-atcgacatatgacgcaaaatctgggctcggaaatg-3'

Reverse (SEQ ID NO: 111)
5'-actgcaccggttgccggacccagaccacccgtgcg-3'

The fragment was then purified, digested (NdeI, AgeI) and cloned between NdeI and AgeI restriction sites of the expression vector pET21b where XhoI was replaced by AgeI followed by the Strep Tag II and two stop codon before the His Tag. The protein is expressed with a C-Term Strep Tag II.

Example 12.6

Generating Recombinant NME7-AB

LB broth (Luria-Bertani broth) is inoculated with 1/10 of an overnight culture and cultured at 37° C. until OD600 reached ~0.5. At this point, recombinant protein expression is induced with 0.4 mM Isopropyl-β-D-thio-galactoside (IPTG, Gold Biotechnology) and culture is stopped after 5 h. After harvesting the cells by centrifugation (6000 rpm for 10 min at 4° C.), cell pellet is resuspended with running buffer: PBS pH7.4, 360 mM NaCl and 80 mM imidazole. Then lysozyme (1 mg/mL, Sigma), $MgCl_2$ (0.5 mM) and DNAse (0.5 ug/mL, Sigma) is added. Cell suspension is incubated on a rotating platform (275 rpm) for 30 min at 37° C. and sonicated on ice for 5 min. Insoluble cell debris are removed by centrifugation (20000 rpm for 30 min at 4° C.). The cleared lysate is then applied to a Ni-NTA column (Qiagen) equilibrated with the running buffer. The column was washed with 4 CV of running buffer, then 4 CV of running buffer supplemented with 30 mM imidazole before eluting the protein off the column with the running buffer (6 CV) supplemented with 70 mM imidazole followed by a second elution with the running buffer (4 CV) supplemented with 490 mM imidazole. NME7-AB is further purified by size exclusion chromatography (Superdex 200) "FPLC".

Example 12.7

Generating Recombinant NME6

LB broth (Luria-Bertani broth) is inoculated with 1/10 of an overnight culture and cultured at 37° C. until OD600 reached ~0.5. At this point, recombinant protein expression is induced with 0.4 mM Isopropyl-β-D-thio-galactoside (IPTG, Gold Biotechnology) and culture is stopped after 5 h. After harvesting the cells by centrifugation (6000 rpm for 10 min at 4° C.), cell pellet is resuspended with running buffer: PBS pH7.4, 360 mM NaCl and 80 mM imidazole. Then lysozyme (1 mg/mL, Sigma), $MgCl_2$ (0.5 mM) and DNAse (0.5 ug/mL, Sigma) is added. Cell suspension is incubated on a rotating platform (275 rpm) for 30 min at 37° C. and sonicated on ice for 5 min. Insoluble cell debris are removed by centrifugation (20000 rpm for 30 min at 4° C.). The cleared lysate is then applied to a Ni-NTA column (Qiagen) equilibrated with the running buffer. The column is washed (8 CV) before eluting the protein off the column with the running buffer (6 CV) supplemented with 420 mM imidazole. NME6 is further purified by size exclusion chromatography (Superdex 200) "FPLC".

Example 13

Quantitative PCR Analysis of Naïve and Primed Genes in Stem Cells Cultured in NME-Base Media Compared to bFGF-Based Media Human ES H9 cells (WICELL) were cultured for the indicated number of passages in either 4 ng/mL bFGF (Peprotech) over MEF feeder cells, or in mTeSR (Stem Cell Technologies) over Matrigel, or in 8 nM NM23 (NME1 S120G dimers) in minimal media "MM" wherein cells were plated onto a VITA™ plate (ThermoFisher) that was coated with 12.5 ug/mL C3 anti-MUC1* mab, abbreviated in FIG. 13 as "NM23/MUC1* Ab". RNA was isolated using the Trizol® Reagent (Invitrogen) and cDNA was reverse transcribed with Random Hexamers (Invitrogren) using Super Script II (Invitrogen) and subsequently assayed for the genes FOXA2, XIST, KLF2, KLF4, NANOG and OCT4, using Applied Biosystems gene expression assays (OCT4 P/N Hs00999634_gH, Nanog P/N Hs02387400_g1, KLF2 P/N Hs00360439_g1, KLF4 P/N Hs00358836_m1, FOXa2 P/N Hs00232764_m1, OTX2 P/N Hs00222238_ml, LHX2 P/N Hs00180351_m1, XIST P/N Hs01079824_m1 and GAPDH P/N 4310884E), on an Applied Biosystems 7500 real-time instrument. A) Cells were cultured in bFGF over MEFs, in mTeSR over Matrigel, or in NM23 over anti-MUC1* C3 antibody. Each sample was run in triplicate. Gene expression was normalized to GAPDH. Data are expressed as a fold change relative to the bFGF/MEF control. B) H9 cells are cultured in mTeSR over Matrigel for the indicated number of passages and gene expression is measured as described above. Data are expressed as a fold change relative to the bFGF/MEF control. C) H9 cells are cultured in 8 nM NM23 (H1 S120G dimers) over a layer of anti-MUC1* C3 mab for the indicated number of passages and gene expression is measured as described above. Data are expressed as a fold change relative to the bFGF/MEF control. D) H9 cells that had previously been cultured in bFGF over MEFs were cultured for a single passage in either NM23, bFGF or mTeSR as described above except that the cells were plated over a layer of human Vitronectin. For comparison, cells were cultured in NM23 over anti-MUC1* antibody. Gene expression is measured as described above. Data are expressed as a fold change relative to the bFGF/MEF control. Panel A shows that most of the pluripotency genes (OCT4, NANOG, KLF4 and KLF2) are expressed at higher levels when cells are cultured in NM23 over a layer of MUC1* antibody, compared to culture in either the standard FGF-based media or in another FGF-based media mTeSR. Most strikingly, the primed markers FOXA2 and XIST are significantly higher when stem cells are cultured in FGF-based media (standard or mTeSR). Panel B shows that as a function of passage number, growth in mTeSR may trend toward an increase in the already elevated expression levels of the primed genes. Panel C shows the opposite, that as a function of passage number, growth in NM23 over MUC1* antibody trends toward decreasing expression of the primed (undesirable) genes. Panel D shows that growth over a Vitronectin surface negatively impacts the gene expression signature wherein high OCT4, NANOG, KLF4 and KLF2 along with low expression of FOXA2 and XIST are desirable and considered characteristic of the naïve state.

Example 14

Figure 32:
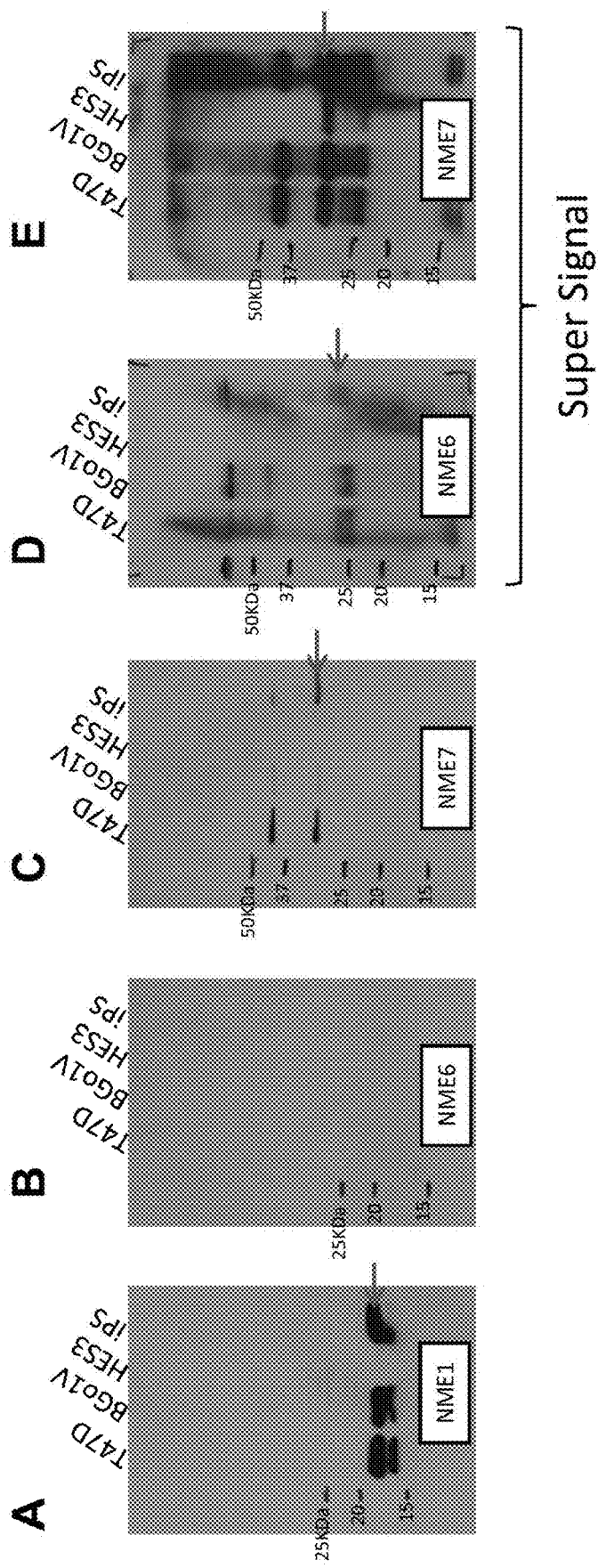
FIGS. 32A-32E show Western blots resulting from a MUC1* pull-down assay of cancer cells and stem cells, wherein species that were pulled down by a MUC1* antibody were probed with antibodies against NME1, NME6 and NME7.

A MUC1 Pull Down Assay Shows that NME1, NME6 and NME7 Bind to a MUC1 Species Protein A pull down assay using an antibody to the MUC1* cytoplasmic tail (Ab-5) was performed on a panel of cells. The proteins pulled down by the MUC 1 antibody were separated by SDS-PAGE then probed with antibodies specific for NME1, NME6 and NME7, using Western blot technique. MUC1*-positive breast cancer cell line T47D cells (ATCC), human embryonic stem cell line BGO1v (LifeTechnologies), human ES cells (HES-3, BioTime Inc.) and human iPS cells (SC101A-1, System Biosciences Inc.) T47D cancer cells were grown according to ATCC protocol in RPMI-1640 (ATCC) plus 10% FBS (VWR). All stem cells were cultured in minimal stem cell media "MM" with 8 nM NM23-RS (recombinant NME1 S120G dimers). Stem cells were grown on plasticware coated with 12.5 ug/mL anti-MUC1* C3 mab. Cells were lysed with 200 uL RIPA buffer for 10 min on ice. After removal of cell debris by centrifugation, the supernatant was used in a co-immunoprecipitation assay. MUC1* was pulled down using the Ab-5 antibody (anti-MUC-1 Ab-5, Thermo Scientific), which recognizes the MUC1 cytoplasmic tail, coupled to Dynabeads protein G (Life Technologies). The beads were washed twice with RIPA buffer and resuspended in reducing buffer. A sample of the supernatant was subjected to a reducing SDS-PAGE followed by transfer of the protein to a PVDF membrane. FIG. 32 shows that the membrane was then probed with: A) an anti-NM23-H1 (NME1) Antibody (C-20, Santa Cruz Biotechnology); B) anti-NME6 (Abnova); or C)

anti NM23-H7 Antibody (B-9, Santa Cruz Biotechnology); D) the staining of NME6 was enhanced using Supersignal (Pierce); and E) the staining of NME7 was enhanced using Supersignal. After incubation with their respective secondary antibody coupled to HRP, the proteins were detected by chemiluminescence, (see FIG. 32, A-E). The photos show that native NME1, NME6 and NME7 are present in MUC1*-positive breast cancer cells, in human ES cells and in human iPS cells and that they bind to MUC1*. Note that the number of cells present in the HES-3 pellet was less than the number present in the other samples.

Example 15

Recombinant NM23 (S120G Mutant 111 Dimers), NME7-AB, as Well as Native NME7 Bind to the MUC1* Extra Cellular Domain Peptide and can Induce Receptor Dimerization Gold nanoparticles of a diameter of 30.0 nm were coated with an NTA-SAM surface according to Thompson et al. (ACS Appl. Mater. Interfaces, 2011, 3 (8), pp 2979-2987). The NTA-SAM coated gold nanoparticles were then activated with an equal volume of 180 uM $NiSO_4$, incubated for 10 min at room temperature, washed, and resuspended in a 10 mM phosphate buffer (pH 7.4). The gold nanoparticles were then loaded with PSMGFR N-10 peptide (QFNQYK-TEAASRYNLTISDVSVSDVPFPFSAQSGAHHHHHH (SEQ ID NO:112)) at 0.5 uM final concentration, and incubated at room temperature for 10 min. Recombinant NME7-AB protein expressed and purified from E. coli was added free in solution at the concentrations indicated. When particle-immobilized proteins bind to each other, or simultaneously bind to two different peptides on two different particles, the particle solution color changes from pink/red to purple/blue. If the protein added free in solution causes particle aggregation, it is strong evidence that the free protein dimerizes the cognate peptide, since binding to a single peptide would not induce two or more particles to be brought into close proximity to each other.

FIG. 33(A) shows NTA-Ni-SAM coated nanoparticles loaded with the PSMGFR N-10 peptide. The NME7-AB is added free in solution at the concentrations indicated. Solution color change from pink to purple/blue from particle aggregation indicates binding between the MUC1* peptide on the particles and NME7 free in solution. This result shows that NME7 in solution has two binding sites for the MUC1* peptide. The Fab of the anti-MUC1* antibody fully inhibits the binding, showing that particle aggregation is due to the specific interaction of MUC1* peptide and NME7. (B) shows NME7-AB added free in solution over a wider range of concentrations. Particle aggregation, indicating NME7 can simultaneously bind to two peptides is observed. (C) shows all proteins added in solution. NME7-AB wined purple almost immediately. NM23-RS (H1 dimer) also began to change almost immediately to purple. The T74D breast cancer cell line Lysate, which contains native NME7 turns noticeably purple also.

Example 16

Figure 34:
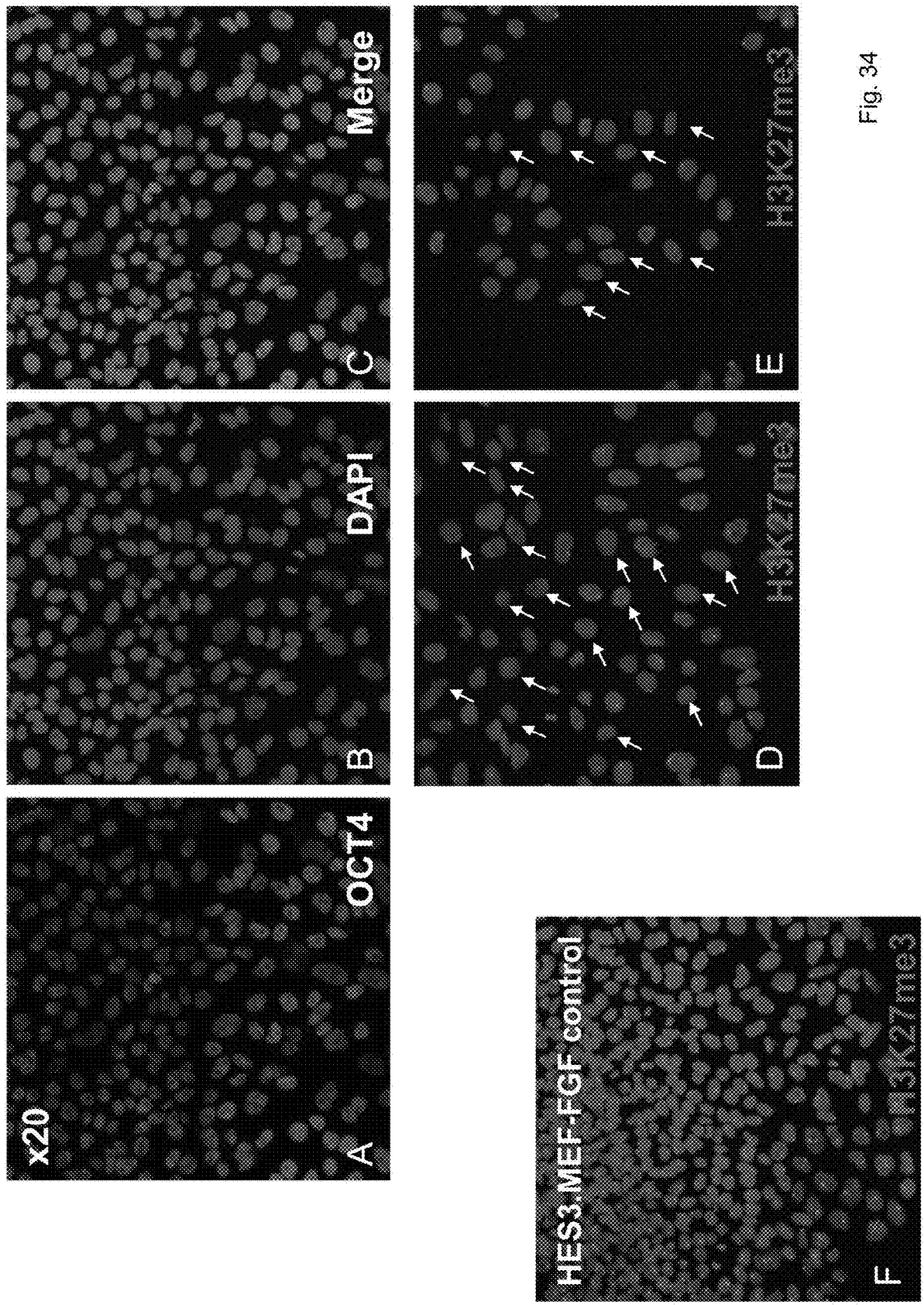
FIGS. 34A-34F show photographs of human embryonic stem (ES) cells grown in standard FGF media or in an NME7 media then stained for DAPI, OCT4 and H3K27me3 that stains Histone-3 which is condensed in the nucleus (red dot) if the cell has inactivated an X chromosome, indicating it is no longer completely naïve.
Figure 36:
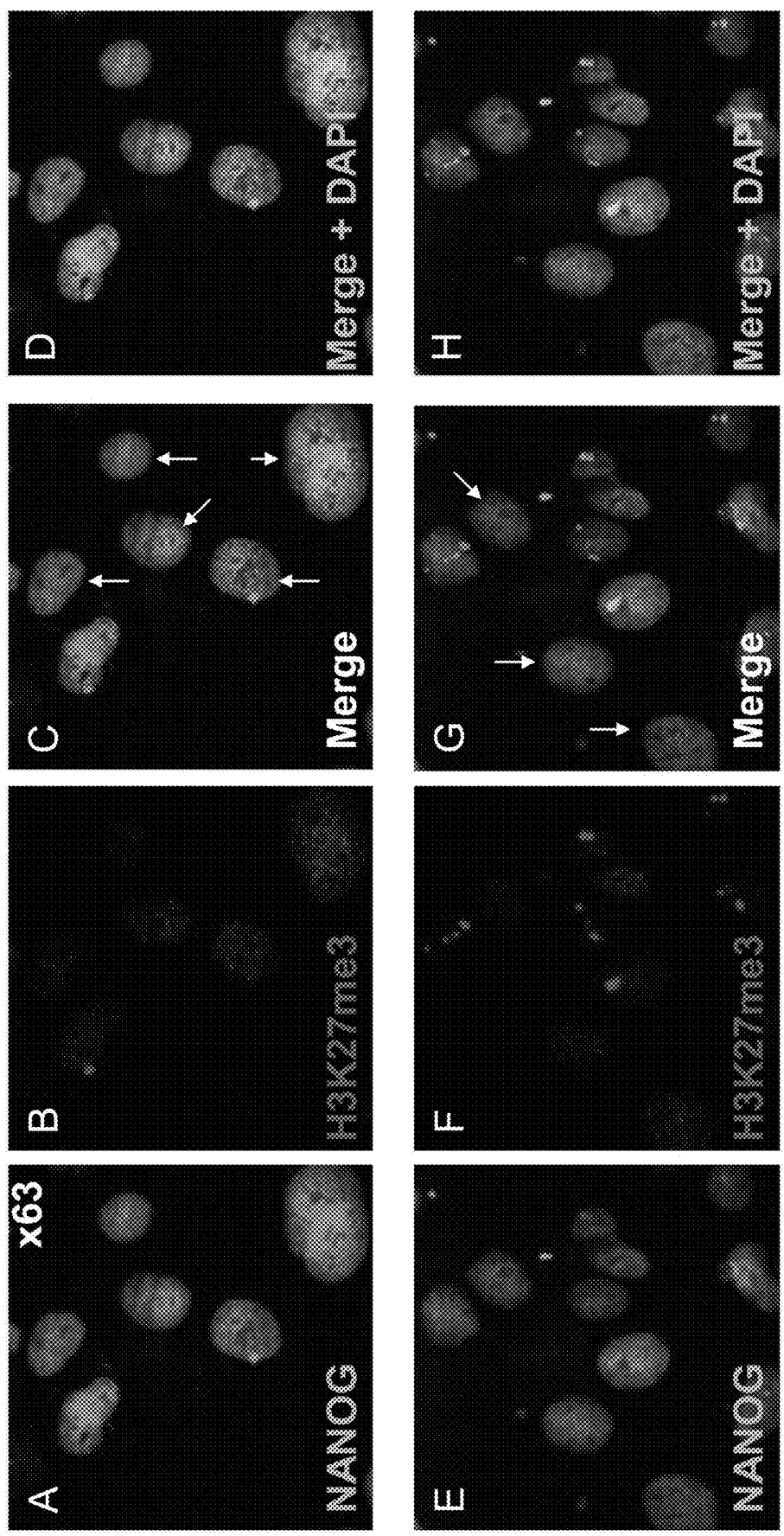
FIGS. 36A-36H show photographs of human embryonic stem (ES) cells grown in an NME1 (NM23-S120G dimers) media then stained for DAPI, OCT4 and H3K27me3 that stains Histone-3 which is condensed in the nucleus (red dot) if the cell has inactivated an X chromosome, indicating it is no longer completely naïve.
Figure 37:
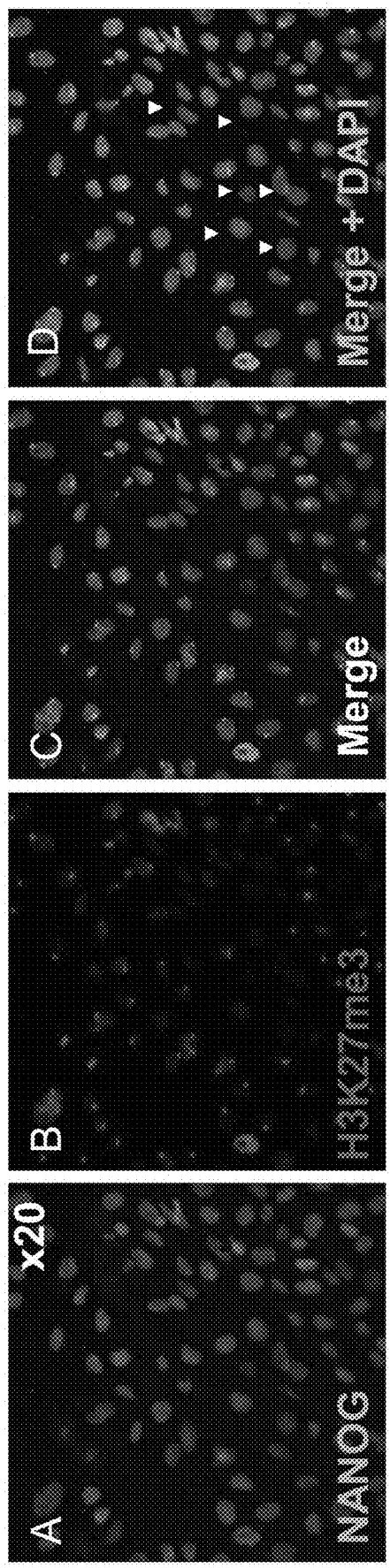
FIG. 37A-37D show photographs of human embryonic stem (ES) cells grown in NME1 (NM23-S120G dimers) media then stained for DAPI, OCT4 and H3K27me3 that stains Histone-3 which is condensed in the nucleus (red dot) if the cell has inactivated an X chromosome, indicating it is no longer completely naïve.
Figure 38:
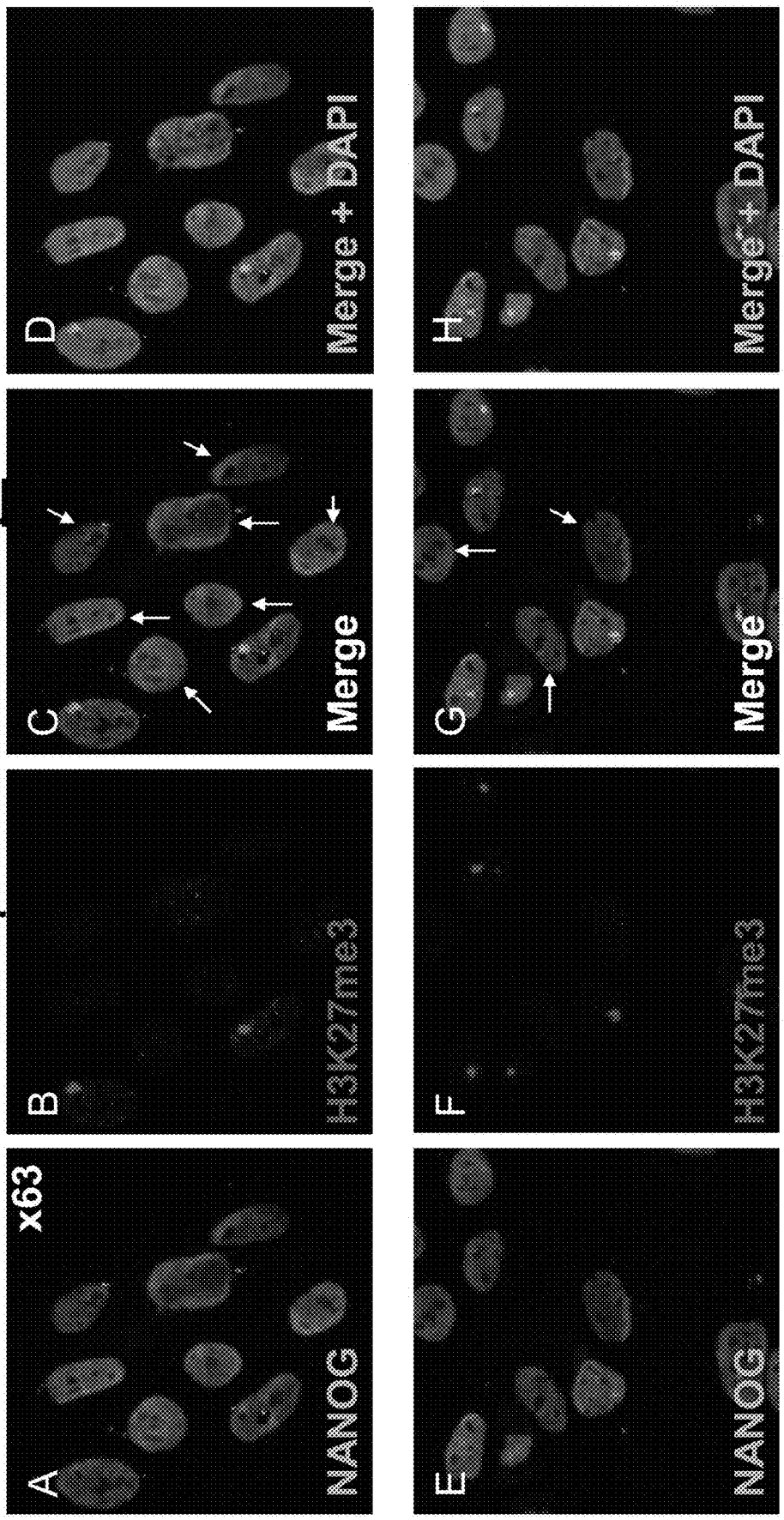
FIG. 38A-38H show photographs of human embryonic stem (ES) cells grown in NME1 (NM23-S120G dimers) media then stained for DAPI, OCT4 and H3K27me3 that stains Histone-3 which is condensed in the nucleus (red dot) if the cell has inactivated an X chromosome, indicating it is no longer completely naïve.
Figure 39:
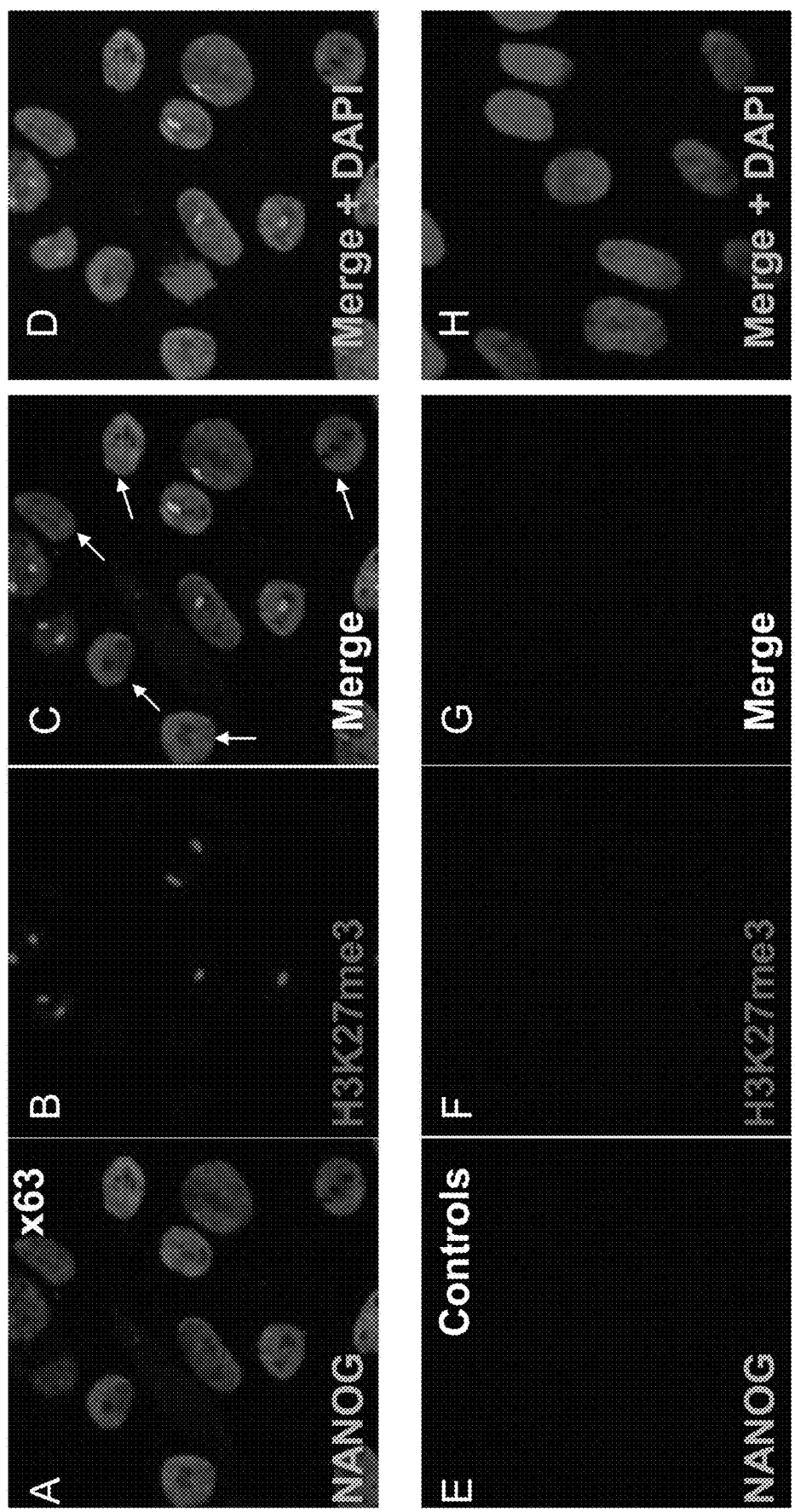
FIG. 39A-39H show photographs of human embryonic stem (ES) cells grown in NME1 (NM23-S120G dimers) media then stained for DAPI, OCT4 and H3K27me3 that stains Histone-3 which is condensed in the nucleus (red dot) if the cell has inactivated an X chromosome, indicating it is no longer completely naïve.
Figure 40:
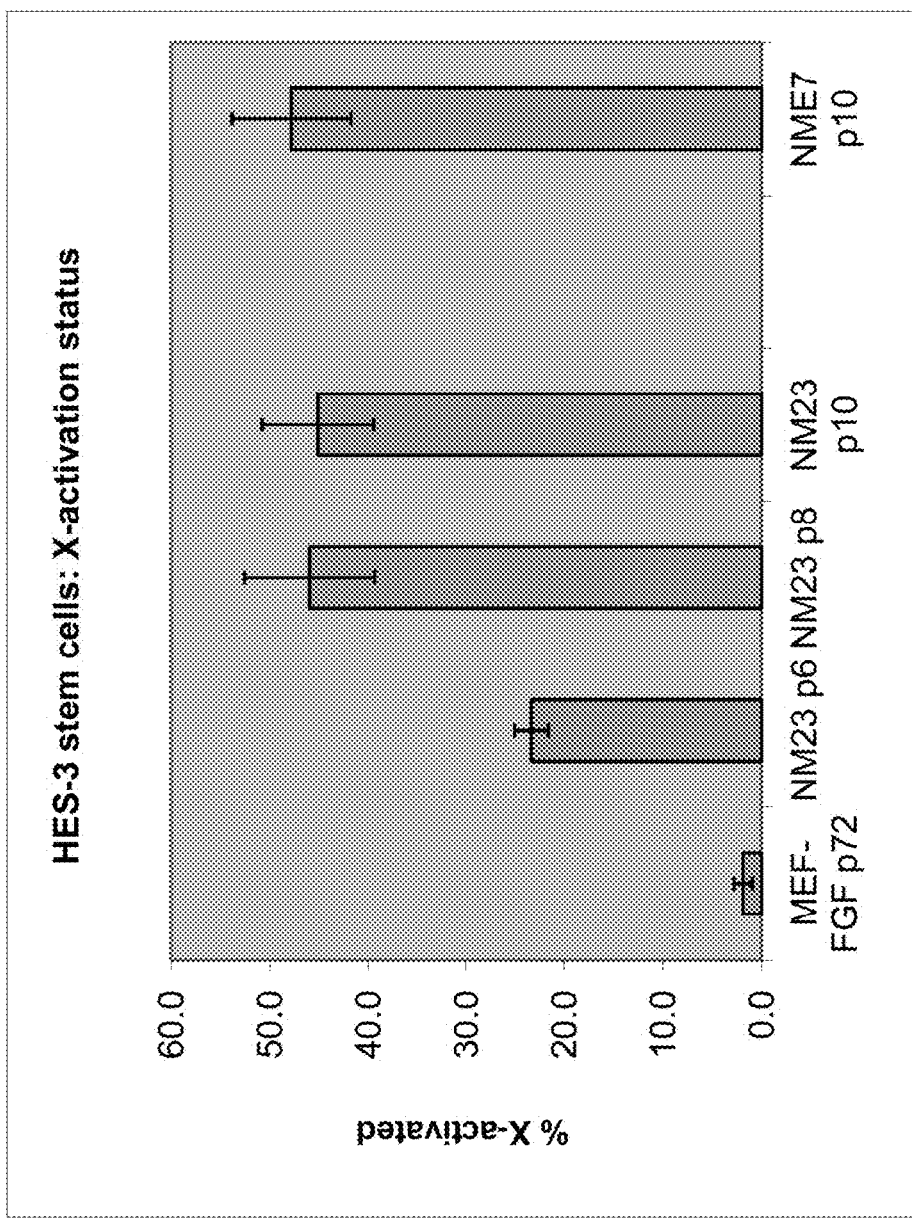
FIG. 40 shows a bar graph of automated counting of the percentage of cells that are pre-X-inactivation as a function of passage number and whether cells were cultured in NME1 or NME7.

Human ES and iPS Cells Cultured in NME1 Dimers or NME7 are in the Naïve State as Evidenced by Lack of Condensed Histone-3 in the Nucleus which would have Indicated X-Inactivation, a Hallmark of the Primed State Human ES (HES-3 stem cells, BioTime Inc) and iPS (SC101A-Ipsc, System Biosciences) cells were cultured in Minimal Media ("MM") plus either NME1 dimers (NM23-RS) or NME7 (NME7-AB construct) for 8-10 passages. The cells were plated onto a Vita™ plate (ThermoFisher) that had been coated with 12.5 ug/mL of an anti-MUC1* monoclonal antibody (MN-C3) that binds to the distal portion of the PSMGFR sequence of the MUC1* receptor. Periodically throughout the 10 passages, samples of the stem cells were assayed by immunocytochemistry (ICC) and analyzed on a confocal microscope (Zeiss LSM 510 confocal microscope) to determine the cellular localization of Histone-3. If Histone-3 is condensed in the nucleus (appears as single dot), then a copy of the X chromosome has been inactivated and the cells are no longer in the pure ground state or naïve state. If the stem cells have reverted from the primed state (all commercially available stem cells have been driven to the primed state by culturing in FGF) to the naïve state, then Histone-3 will be seen as a "cloud," speckled throughout or not detectable. FIG. 34 F shows the control cells, from the same source except that they have been grown in FGF on MEFs according to standard protocols, all show Histone-3 (H3K27me3) condensed in the nucleus, confirming that they are all 100% in the primed state and not in the naïve state. Conversely, the same source cells that were cultured in NME7 for 10 passages have several fields of stem cells that do not have condensed Histone-3, indicating that they are pre-X-inactivation and in the true naïve state (see FIG. 34 D,E, white arrows point to cells negative for condensed Histone-3). Approximately 50% or more of these cells are in the naïve state as evidenced by the lack of condensed Histone-3 in the nucleus. FIG. 36 A-H shows that the same cells cultured in NM23-S120G dimers at passage 6 were only about 25-30% naïve. The "clouds" of Histone-3 staining can be seen in FIG. 36 B,F, while C,G show white arrows pointing to the cells that lack condensed Histone-3. Confocal ICC images of HES-3 cells cultured in NM23-S120G dimers over anti-MUC1* antibody surface for 8 passages (FIG. 37-39) are about 50% in the naïve state and devoid of Histone-3 staining in the nucleus.

Example 17

The Confocal Images of Histone-3 Staining Obtained in Example 16 were Quantified A semi-quantitative analysis of the X-activation status of HES-3 stem cells (BioTime Inc) was performed using immunofluorescence images collected on a confocal microscope (Zeiss LSM 510) comparing cells grown on MEFs with 4 ng/ml FGF (p72) versus 8 nM NME1 (p6, p8, p10) versus 8 nM NME7 (p10). 5-6 images of random fields of view at ×20 magnification were collected for each growth factor. Pluripotent stem cells were identified using Oct 3/4 (#sc-5279, Santa Cruz) and/or Nanog (#D73G4, Cell Signaling) staining. Pluripotent stem cells positive for H3K27me3 antibody (marker for Xist; #C36B11, Cell Signaling) were identified by a bright focused spot in the nucleus. Cells negative for H3K27me3 staining either had faint diffuse non-focused staining or it was absent. Total number of cells per image (positive and negative for H3K27me3 staining) were counted using the Cell Counter macro in Image J and data are expressed as a percentage of cells negative for H3K27me3 antibody (i.e. X-activated cells).

Example 18

Measuring the Cloning Efficiency of Human ES and iPS Cells Cultured in Either NME1-Dimers (8 nM) or NME7 (8 nM) Compared to Traditional Culture in FGF Media Over MEF Feeder Cells

Figure 41A:
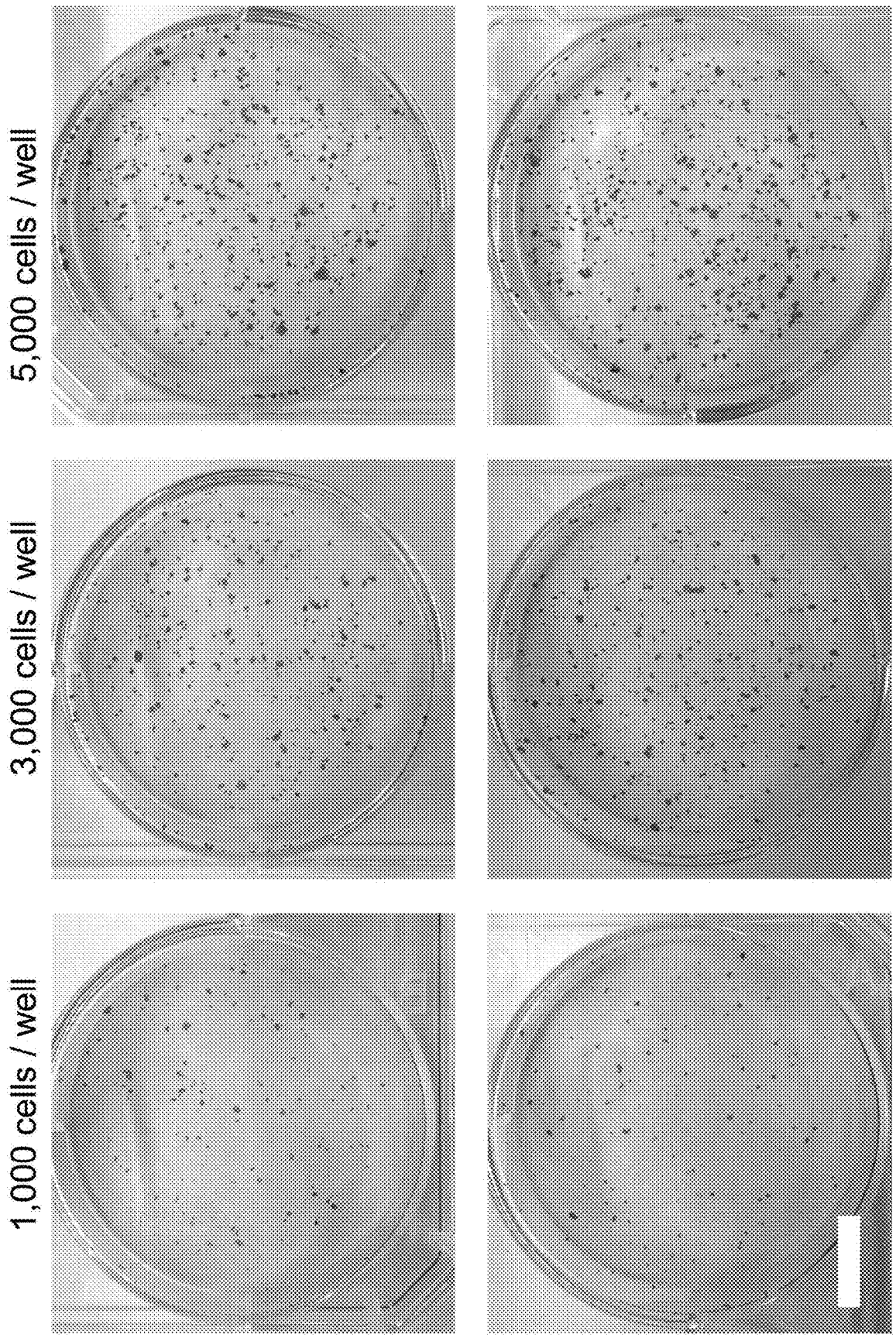
FIG. 41A shows photographs of human embryonic stem cells from a cloning efficiency assay wherein discrete colonies arising from 1,000, 3,000 or 5,000 single cells plated were stained with alkaline phosphatase that showed that stem cells cultured in NME-based media had a cloning efficiency of ~20%.
Figure 41B:
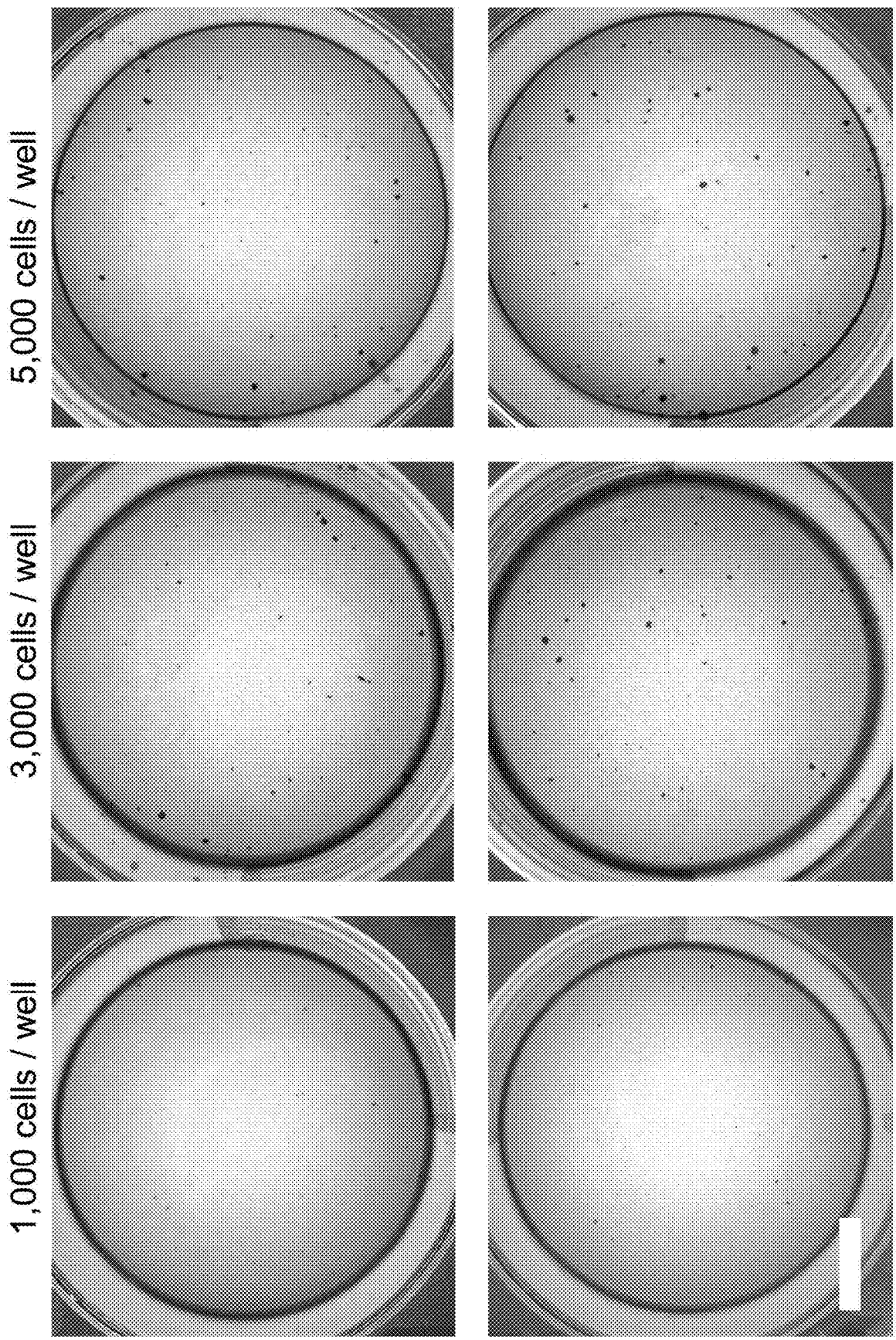
FIG. 41B shows photographs of human embryonic stem cells from a cloning efficiency assay wherein discrete colonies arising from 1,000, 3,000 or 5,000 single cells plated were stained with alkaline phosphatase that showed that stem cells cultured in FGF-based media had a cloning efficiency of ~1%.
Figure 42:
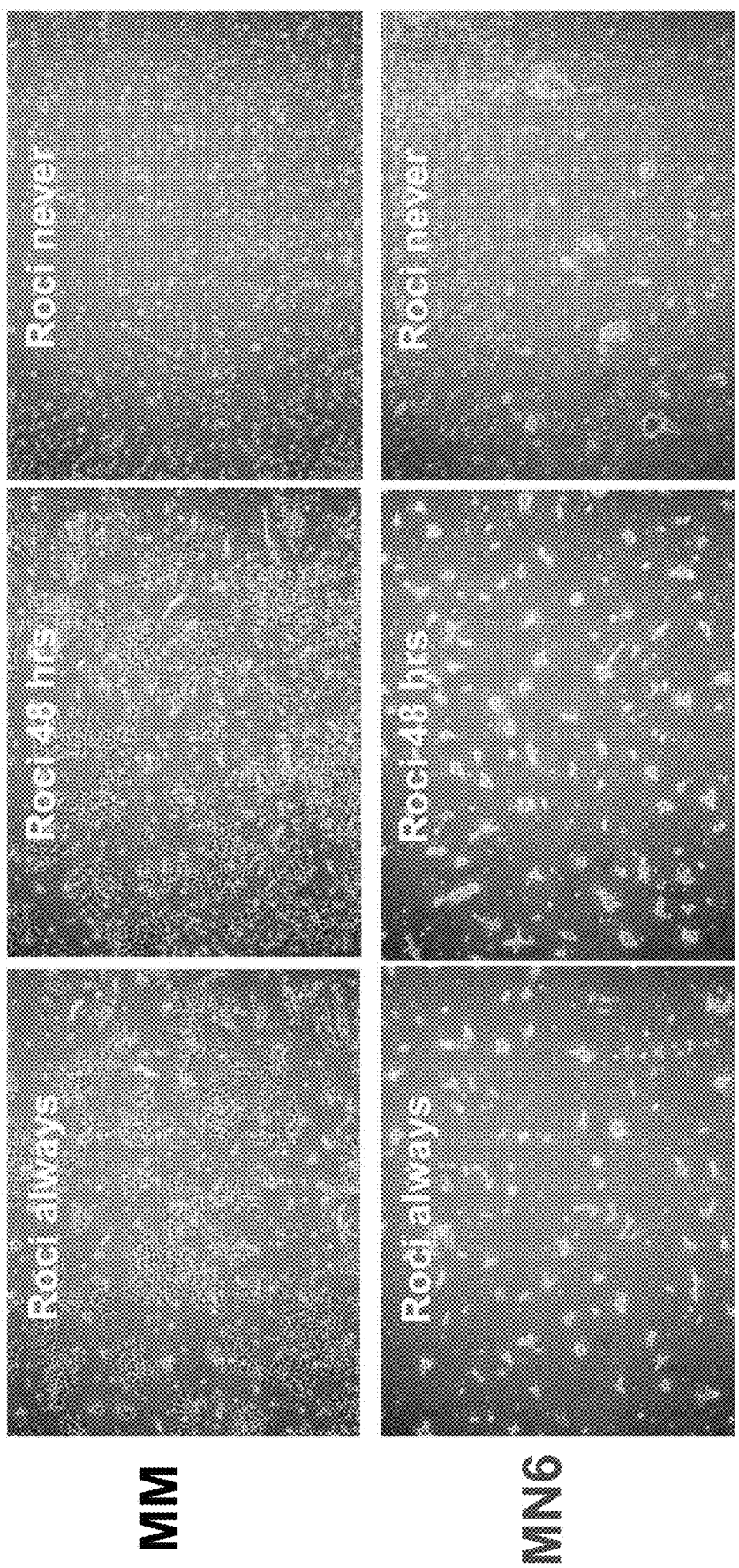
FIG. 42 shows Day 2 photographs (4×) of human iPS cells plated onto 6-well tissue culture plates that were coated with an anti-MUC1* antibody (MN-C3 or MN-C8) then cultured in NME1 dimers ("NM23-RS") in either Minimal stem cell Media (MM) or an even more minimal media called MN6, in the presence or absence of a rho kinase inhibitor (ROCi).
Figure 43:
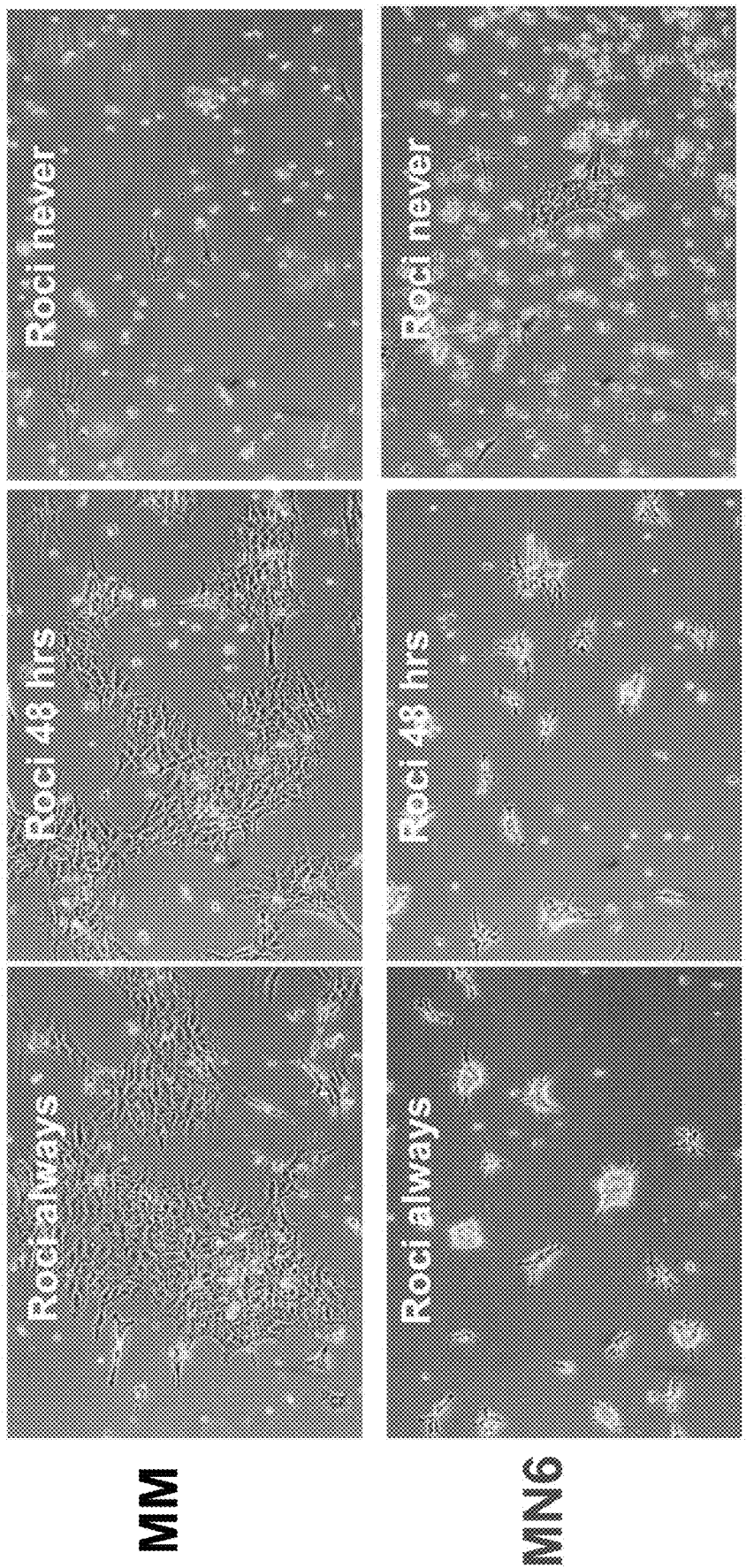
FIG. 43 shows Day 2 photographs (10×) of human iPS cells plated onto 6-well tissue culture plates that were coated with an anti-MUC1* antibody (MN-C3 or MN-C8) then cultured in NME1 dimers ("NM23-RS") in either Minimal stem cell Media (MM) or an even more minimal media called MN6, in the presence or absence of a rho kinase inhibitor (ROCi).
Figure 44:
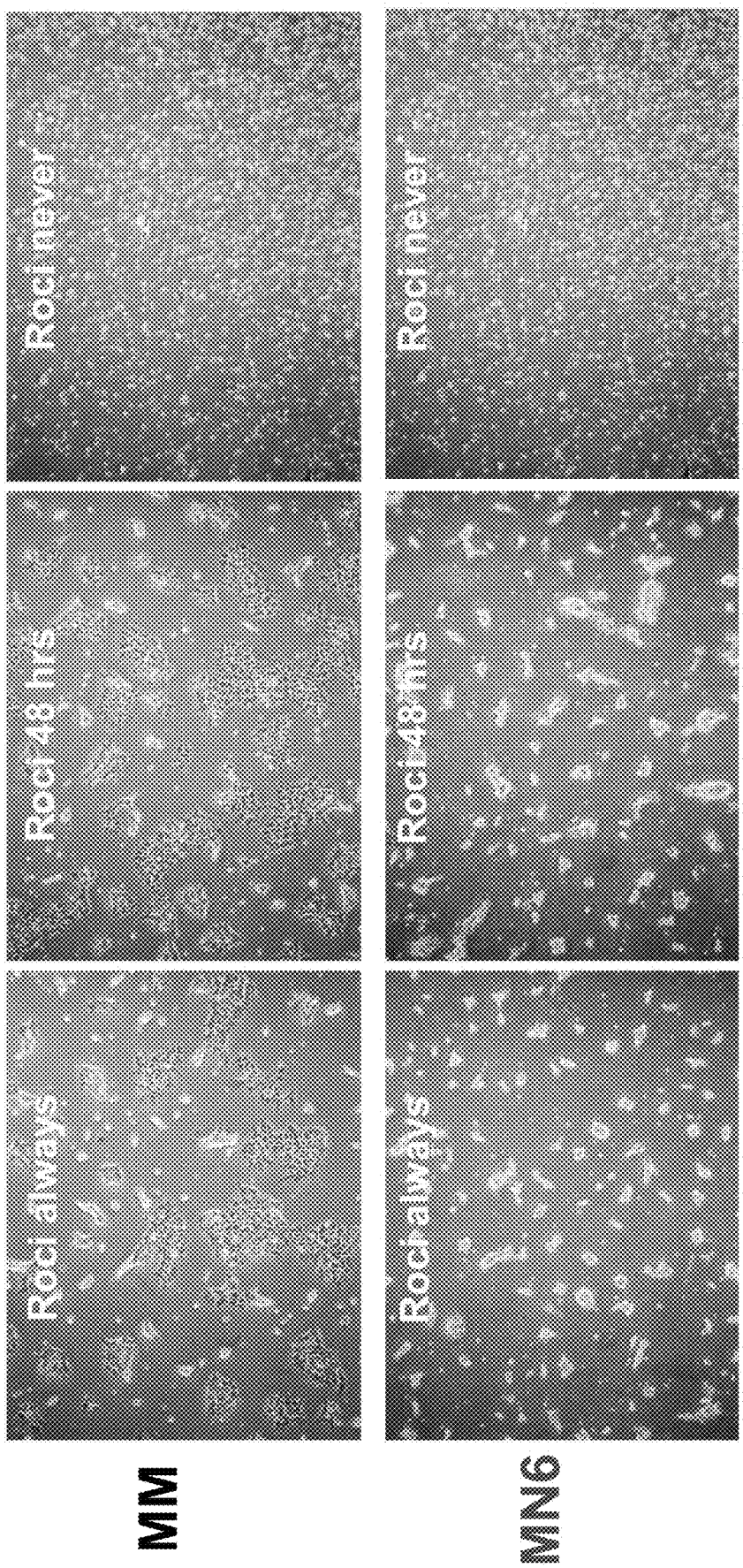
FIG. 44 shows Day 2 photographs (4×) of human iPS cells plated onto 6-well tissue culture plates that were coated with an anti-MUC1* antibody (MN-C3 or MN-C8) then cultured in NME7 in either Minimal stem cell Media (MM) or an even more minimal media called MN6, in the presence or absence of a rho kinase inhibitor (ROCi).
Figure 45:
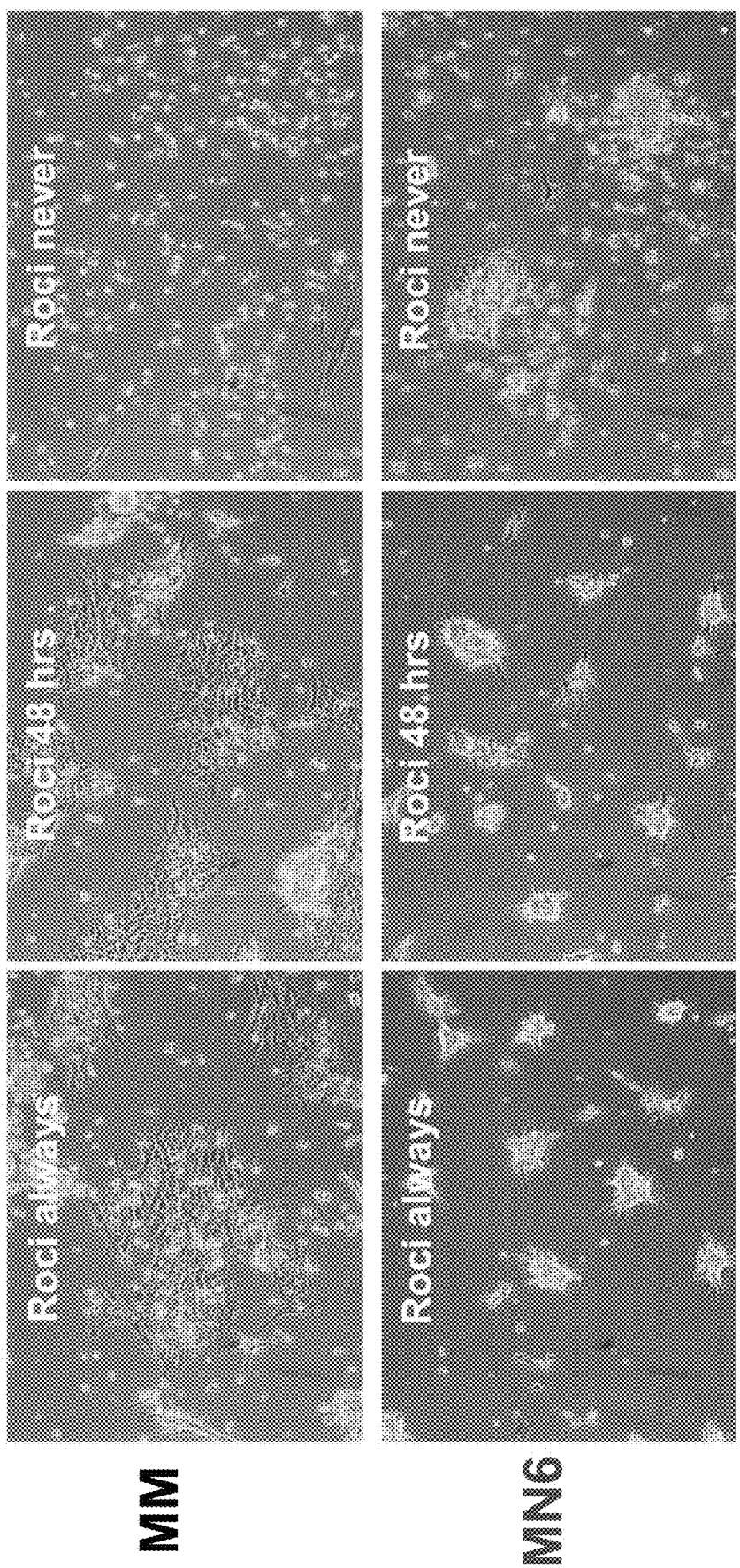
FIG. 45 shows Day 2 photographs (10×) of human iPS cells plated onto 6-well tissue culture plates that were coated with an anti-MUC1* antibody (MN-C3 or MN-C8) then cultured in NME7 in either Minimal stem cell Media (MM) or an even more minimal media called MN6, in the presence or absence of a rho kinase inhibitor (ROCi).

Human ES cells (HES-3, BioTime Inc.) and human iPS cells (SC101A-1, System Biosciences Inc.) were cultured in minimal media "MM" plus either NME1-dimers (8 nM) or NME7 (8 nM) for at least 10 passages. Cells were plated onto VITA™ 6-well plates (ThermoFisher) that had been coated with 12.5 µg/mL of a monoclonal anti-MUC1* antibody called "C3" or "MN-C3". Cells were plated at the following densities: 1,000 cells, 3,000 cells, and 5,000 cells per well. As a control, the same number of cells from the same parent cell line was plated over a layer of MEF feeder cells and cultured in 4 ng/mL bFGF. After 4 to 6 days, the cells were stained with alkaline phosphatase (Leukocyte Alkaline Phosphatase Kit, Sigma-Aldrich) according to package instructions and the number of discrete colonies that arose for each condition was counted. See FIG. 41A. The number of colonies per a number of cells plated and the calculated percentage efficiency is shown in FIG. 41B. Whether ES or iPS cells, the cloning efficiency of stem cells cultured in NME1 or NME7 was about 20%. However, Histone-3 ICC analysis of these cell populations showed that by passage 10, only ~50% of the cells were in the pre-X-inactivation state, which is the true naïve state. Therefore, the actual cloning efficiency of the naïve cells is at least double and is ~40%. The cloning efficiency of mouse naïve stem cells is ~30%. In this experiment, control cloning efficiency experiments were done in which the same cells were cultured in 4 ng/mL bFGF on MEF feeder cells and yielded cloning efficiencies of 1%.

Example 19

Human iPS and ES Cells Cultured in Either Minimal Media (MM) or E8 Media, Minus FGF and TGF-Beta, "MN6" Plus Either Recombinant Human NM23-RS (NME1 S120G Dimers) or NME7-AB

Figure 46:
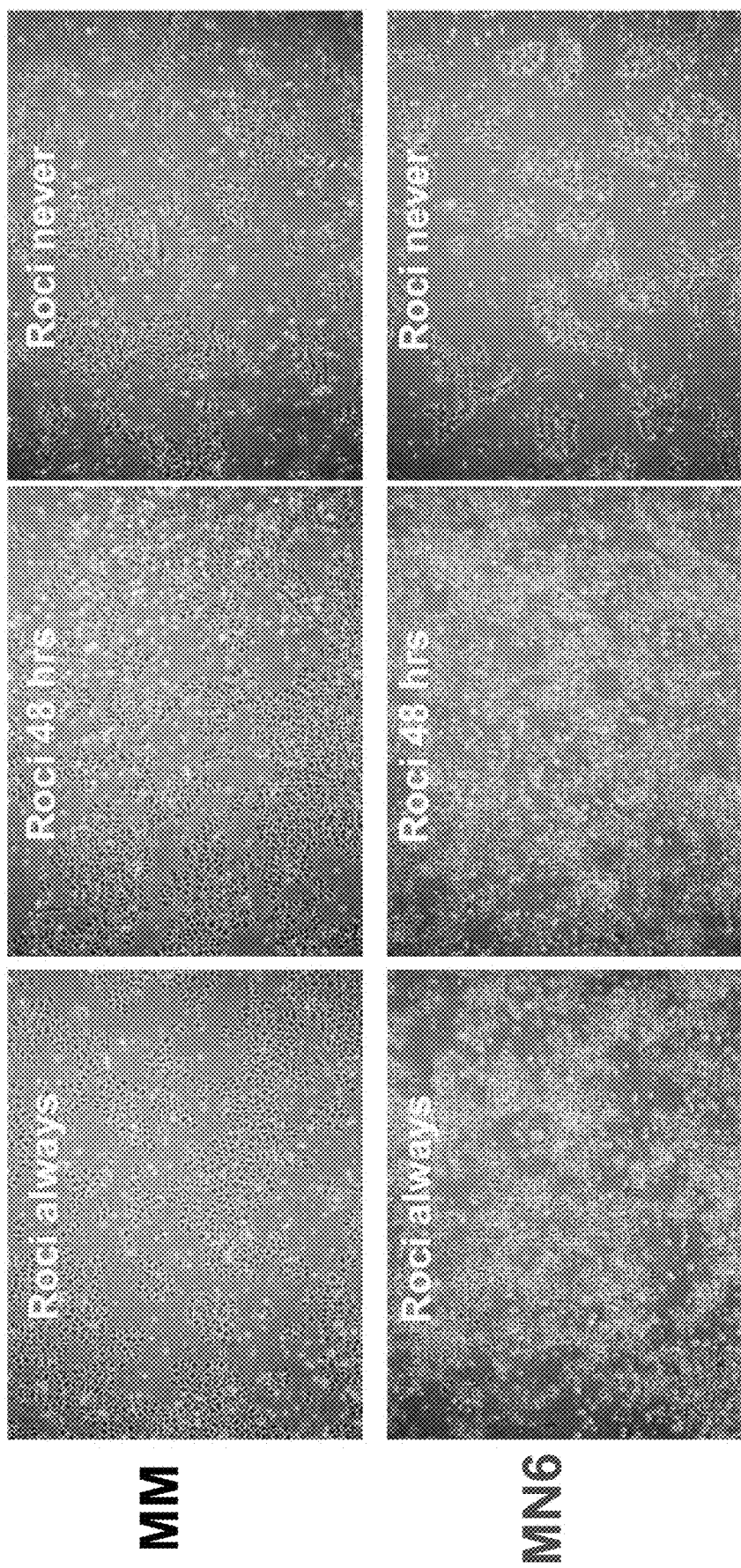
FIG. 46 shows Day 2 photographs (4×) of human iPS cells plated onto 6-well tissue culture plates that were coated with Matrigel then cultured in NME7 in either Minimal stem cell Media (MM) or an even more minimal media called MN6, in the presence or absence of a rho kinase inhibitor (ROCi).
Figure 47:
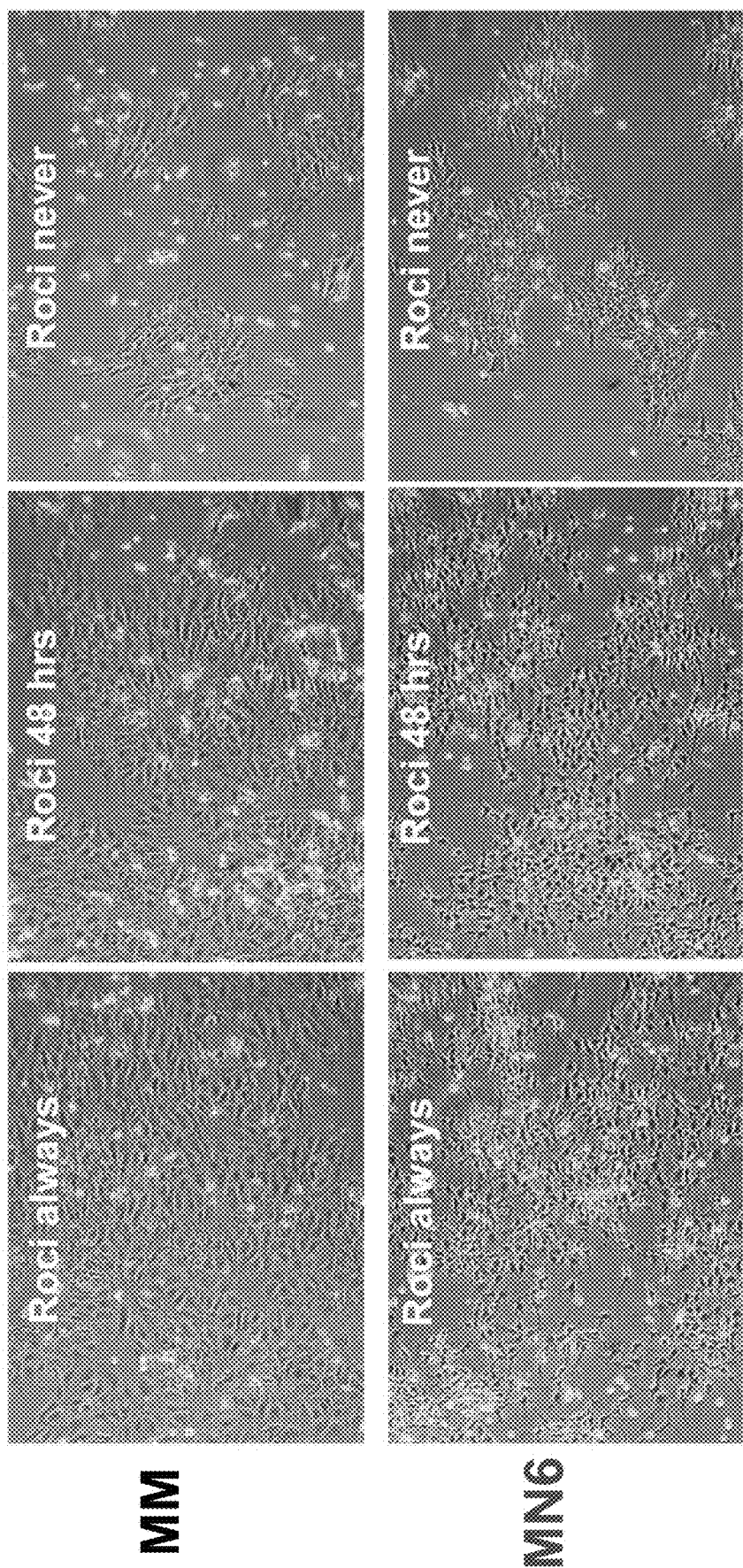
FIG. 47 shows Day 2 photographs (10×) of human iPS cells plated onto 6-well tissue culture plates that were coated with Matrigel then cultured in NME7 in either Minimal stem cell Media (MM) or an even more minimal media called MN6, in the presence or absence of a rho kinase inhibitor (ROCi).
Figure 48:
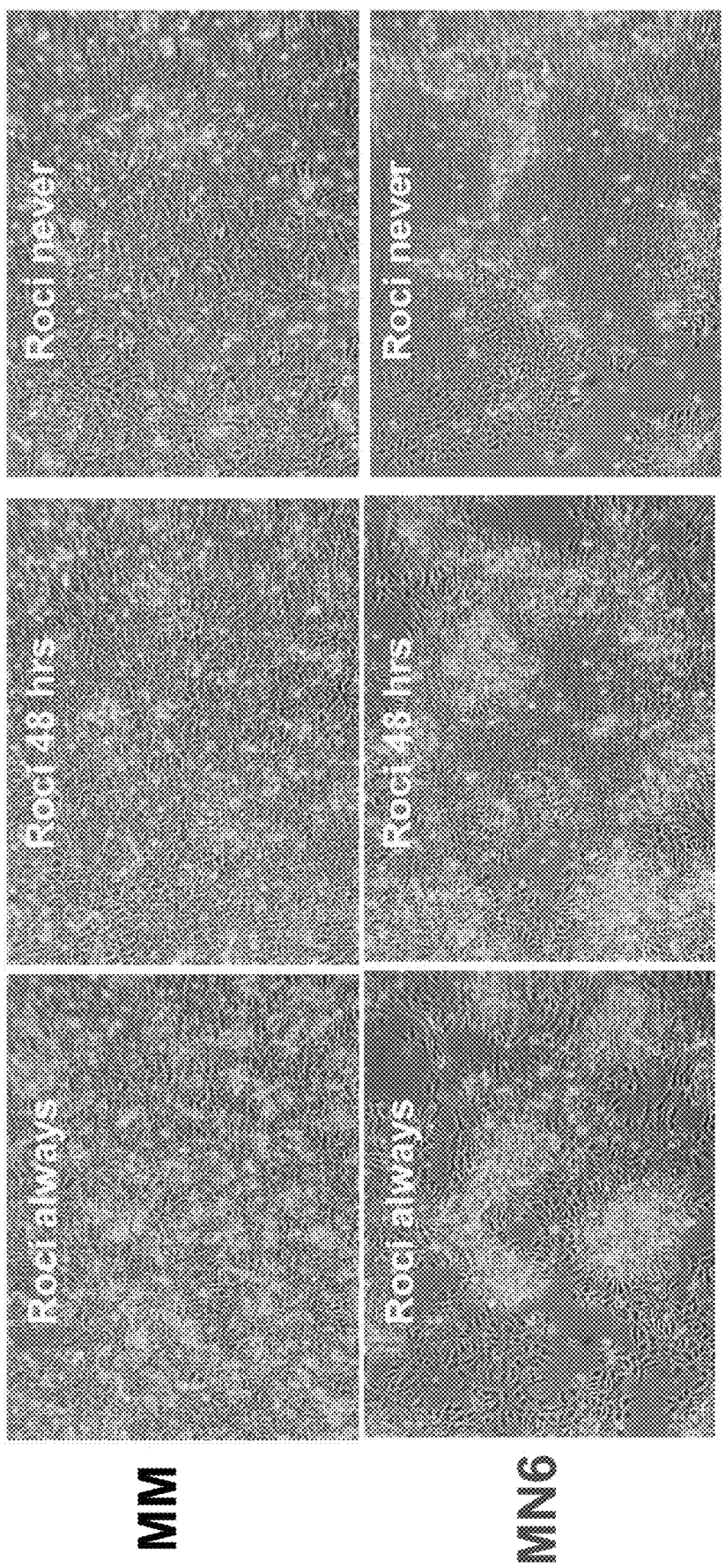
FIG. 48 shows Day 4 photographs (10×) of human iPS cells plated onto 6-well tissue culture plates that were coated with Matrigel then cultured in NME7 in either Minimal stem cell Media (MM) or an even more minimal media called MN6, in the presence or absence of a rho kinase inhibitor (ROCi).
Figure 49:
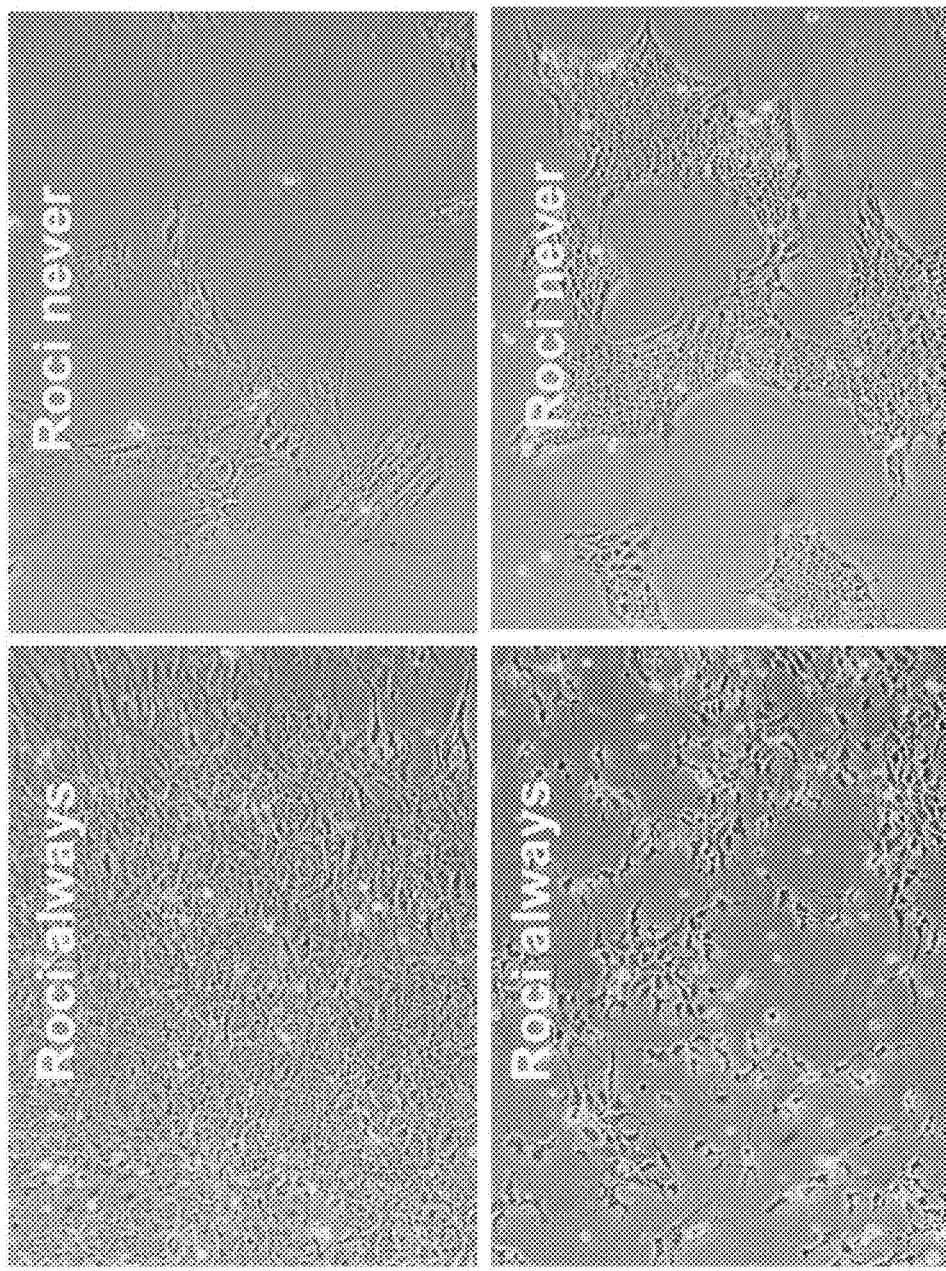
FIG. 49 shows Day 3 photographs (10×) of human embryonic stem (ES) cells plated onto 6-well tissue culture plates that were coated with Matrigel then cultured in NME7 in either Minimal stem cell Media (MM) or an even more minimal media called MN6, in the presence or absence of a rho kinase inhibitor (ROCi).
Figure 50:
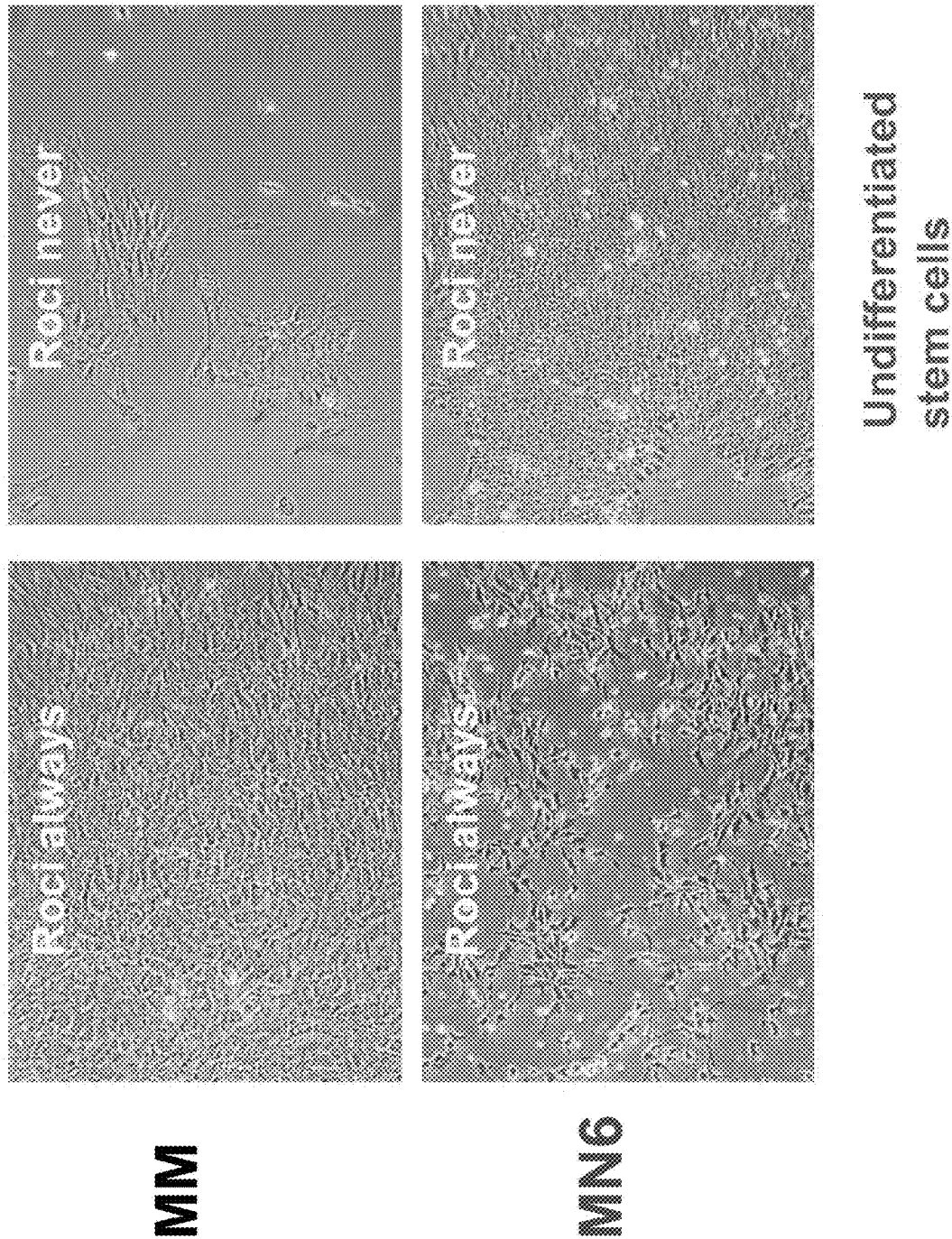
FIG. 50 shows Day 3 photographs (10×) of human embryonic stem (ES) plated onto 6-well tissue culture plates that were coated with Matrigel then cultured in NME1 dimers ("NM23-RS") in either Minimal stem cell Media (MM) or an even more minimal media called MN6, in the presence or absence of a rho kinase inhibitor (ROCi).

Human iPS cells (SC101A-1, System Biosciences Inc.) were plated onto COSTAR plates coated with 12.5 ug/mL of anti-MUC1* mab, C3, and cultured in minimal media ("MM") or E8 minus FGF and TGF-beta ("MN6") supplemented with 8 nM NM23-RS (NME1 S120G dimers) or NME7 (NME7-AB), wherein a rho kinase inhibitor (ROCi) was also added to the media (always), only for the first 48 hours, or never (see FIGS. 42-45). The figures indicate that in the presence of the ROCi, cells attach and have a spreading morphology leaving more cells attached after a media change. Cells cultured with either NM23-RS or NME7, in the absence of ROCi, have more cell attachment when the base media is MN6 rather than MM minimal media. When the same experiment is performed except that the cells are plated over matrigel, it doesn't matter whether ROCi is present or not (see FIGS. 46-48). The same experiment was performed using human ES cells (HES-3, BioTime Inc.) with essentially the same results (FIGS. 49-50).

Example 20

RT-PCR Quantified Expression of Naïve and Primed Genes for Human iPS and ES Cells on Matrigel, Cultured in Either Minimal Media (MM) or E8 Media, Minus FGF and TGF-Beta, "MN6," Plus Either Recombinant Human NM23-RS (NME1 S120G Dimers) or NME7-AB

Figure 51:
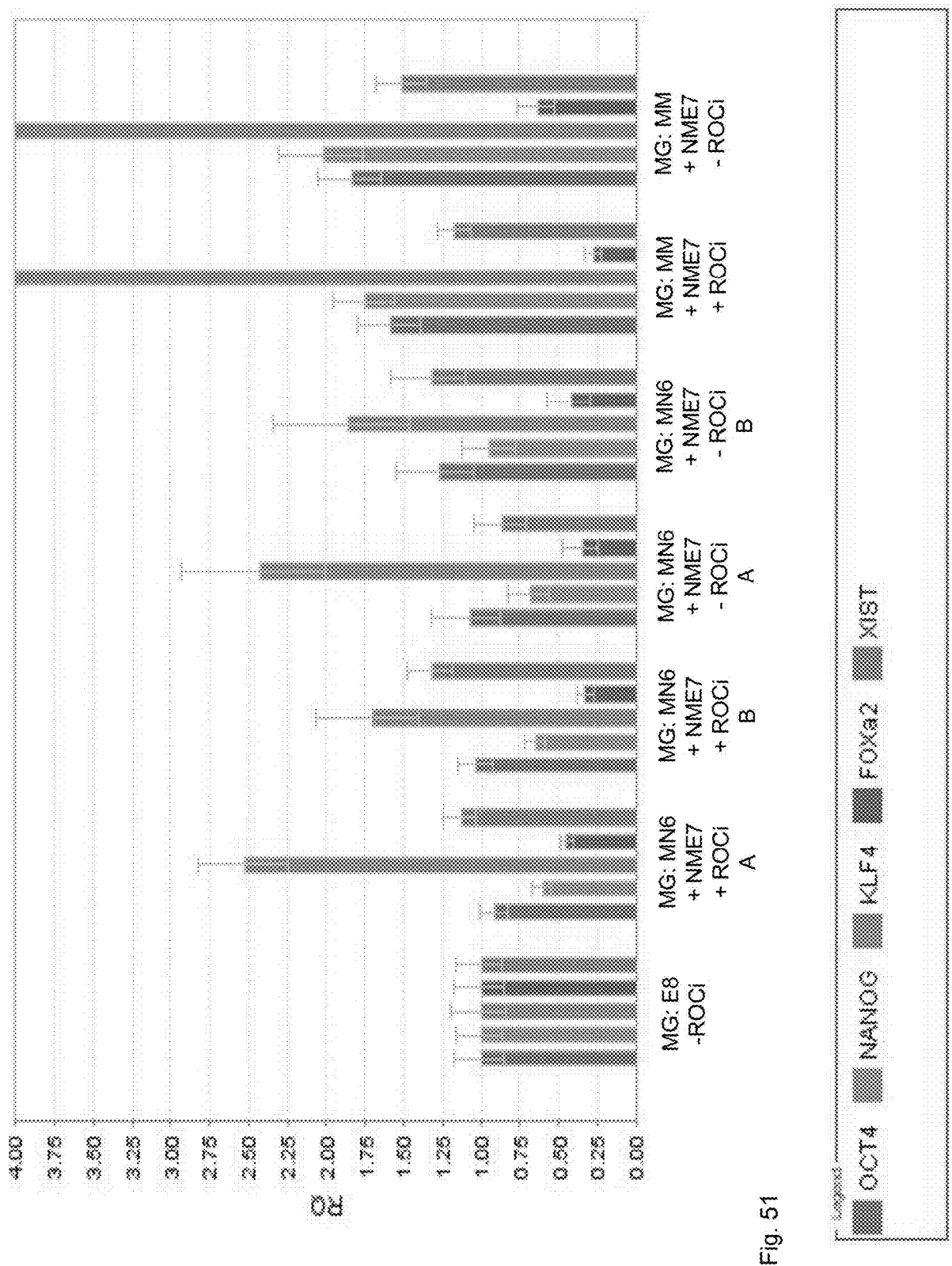
FIG. 51 shows graphs of RT-PCR measurements of pluripotency genes and as well as naïve and primed genes for stem cells plated onto Matrigel cultured in FGF-based media (standard bFGF in MM or E8), or NME7 added to MM media, or MN6 media, in the presence or absence of a rho kinase inhibitor (ROCi).

Human ES cells (HES-3, BioTime Inc.) plated onto Matrigel were cultured in either MN6 media or MM media supplemented with 8 nM NME7, plus/minus a rho kinase inhibitor (ROCi). For comparison, cells were also cultured in bFGF-containing E8 media. RT-PCR was performed as described above in Example 13 and normalized to the E8 control. Markers of the undesirable primed state are FOXA2, OTX, LHX, and XIST. Markers of the desirable naïve state are OCT4, NANOG, KLF4 and KLF2. FIG. 51 shows that cells cultured in MN6/NME7 had increased expression of some of the pluripotency genes compared to E8 and reduced expression of primed gene FOXA2.

Example 21

Figure 52:
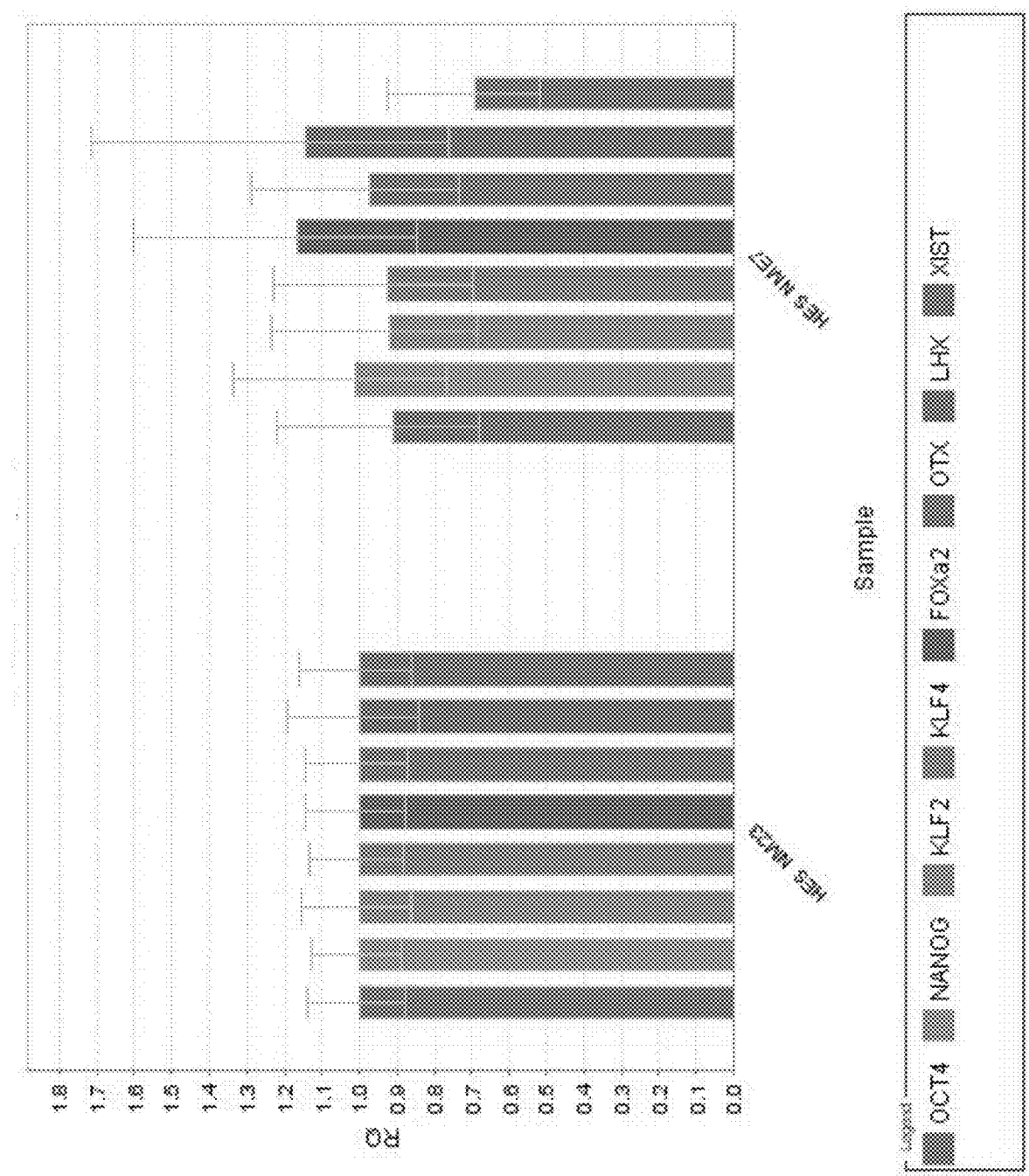
FIG. 52 shows a graph of RT-PCR measurement of naïve and primed genes for human embryonic stem cells plated onto plasticware coated with an antibody that recognizes the MUC1* extra cellular domain (MN-C3) and cultured in MM minimal media to which was added either NM23 dimers (NME1 S120G dimers) or NME7.

Human ES cells (HES-3, BioTime Inc.) were plated onto a VITA™ plate (ThermoFisher) coated with anti-MUC1* antibody (C3) and cultured in either recombinant human NM23 (NME1 S120G dimers) or NME7-AB in minimal media (MM). RT-PCR performed as described in Example 13. Markers of the undesirable primed state are FOXA2, OTX, LHX, and XIST. Markers of the desirable naïve state are OCT4, NANOG, KLF4 and KLF2. As FIG. 52 shows, there is essentially no difference between cells cultured in NM23 and NME7.

Example 22

RT-PCR Analysis of Human ES Cells Cultured in NME Proteins Versus FGF and Over a Variety of Surfaces in the Presence or Absence of a Rho Kinase Inhibitor

Figure 53:
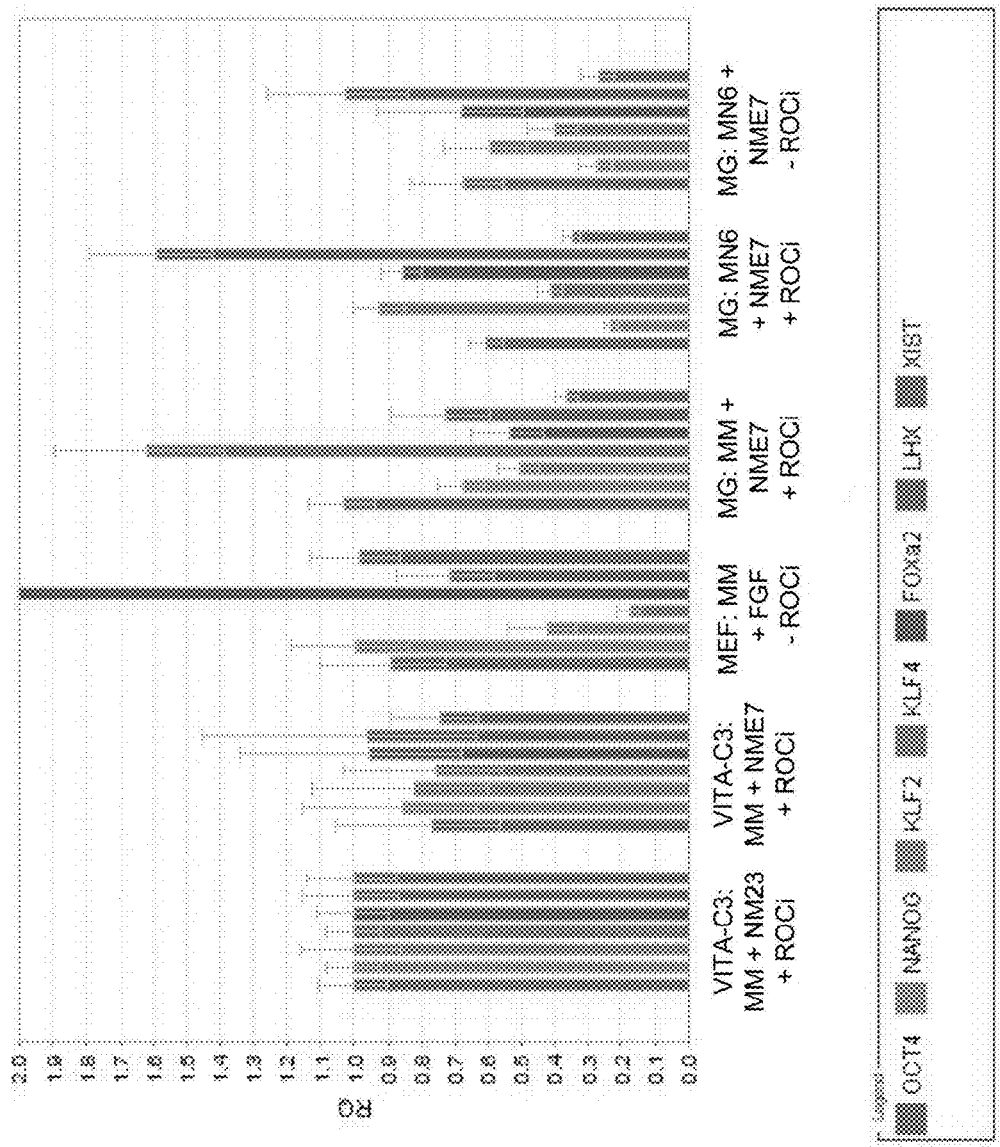
FIG. 53 shows a graph of RT-PCR measurements of pluripotency genes and as well as naïve and primed genes for human ES cells plated onto either plasticware coated with anti-MUC1* antibody (C3), MEF feeder cells, or Matrigel. Cells on the VITA/C3 antibody surface were cultured in either Minimal Media (MM) plus NM23 (NME1 dimers) or in NME7-AB. Cells plated over MEFs were cultured in MM plus FGF. Cells on Matrigel were cultured for a single passage in NME7 in MM media or MN6 media and in the presence or absence of a rho kinase inhibitor (ROCi).
Figure 54:
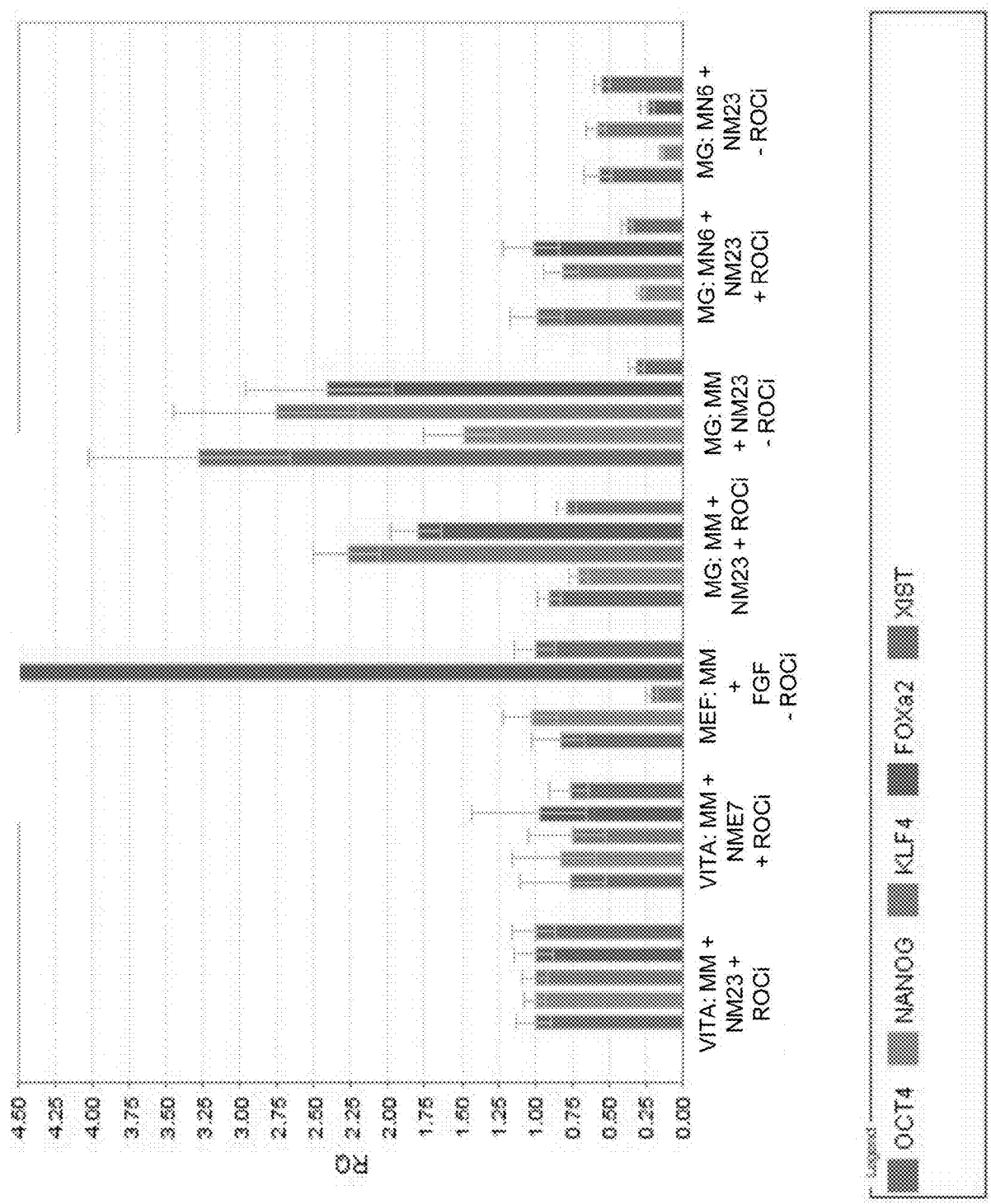
FIG. 54 shows a graph of RT-PCR measurements of pluripotency genes and as well as naïve and primed genes for human ES cells plated onto either plasticware coated with anti-MUC1* antibody (C3), MEF feeder cells, or Matrigel. Cells on the VITA/C3 antibody surface were cultured in either Minimal Media (MM) plus NM23 (NME1 dimers) or in NME7-AB. Cells plated over MEFs were cultured in MM plus FGF. Cells on Matrigel were cultured for a single passage in NM23 (NME1 dimers) in MM media or MN6 media and in the presence or absence of a rho kinase inhibitor (ROCi).

Human ES cells (HES-3, BioTime Inc.) were plated onto either a VITA™ plate (ThermoFisher) coated with anti-MUC1* antibody (C3), MEF feeder cells, or Matrigel. Cells on the VITA/C3 antibody surface were cultured for 3 passages in either Minimal Media (MM) plus NM23-H1 S120G dimers (NME1 dimers) or in NME7-AB. Cells plated over MEFs were cultured in MM plus FGF, according to standard practice, for 23 passages. Cells on Matrigel were cultured for a single passage in NME7 in MM media or MN6 media and in the presence or absence of a rho kinase inhibitor (ROCi). Markers of the undesirable primed state are FOXA2, OTX, LHX, and XIST. Markers of the desirable naïve state are OCT4, NANOG, KLF4 and KLF2. As FIG. 53 shows, gene expression profiles for NME7-AB and NM23-H1 dimers are essentially equal. Note that after only 3 passages in NME proteins, coming from FGF growth, cells are not yet completely naïve and XIST, an indicator of X-inactivation is still high. Referring to Example 17, at passage 6 only 25-30% of the cells had two active X chromosomes and at passage 10 more than 50% of cells were in the true naïve state, pre-X-inactivation. FIG. 53 shows that some of the naïve markers are lower (KLF2/4) and some of the primed markers higher (FOXA2) compared to NME grown cells. Growth in NME7 over Matrigel adversely affects the signature of gene expression with a decrease in naïve genes and an increase in primed genes compared to growth over a surface of MUC1* antibody. In the same experiment, cells plated onto Matrigel were also cultured in NM23-S120G dimers in MM media, or MN6 media, plus or minus a ROCi (rho kinase inhibitor) (FIG. 54). Again, the Matrigel surface negatively impacts the gene expression profile and appears to make the cells less naïve.

Example 23

Detection of NME7

Example 23.1

Detection of NME7 in Embryonic Stem Cells and iPS Cells

Human ES cells (BGO1v and HES-3) as well as iPS cells (SC101-A1) were cultured in NME-based media wherein cells were plated over a layer of anti-MUC1* antibody. To identify NME7 species, cells were harvested and lysed with RIPA buffer (Pierce), supplemented with protease inhibitor (Pierce). Cell lysates (20 uL) were separated by electrophoresis on a 12% SDS-PAGE reducing gel and transferred to a PVDF membrane (GE Healthcare). The blot was blocked with PBS-T containing 3% milk and then incubated with primary antibody (anti NM23-H7 clone B-9, Santa Cruz Biotechnology) at 4° C. overnight. After washing with PBS-T, the membrane was incubated with horseradish peroxidase (HRP)-conjugated secondary antibody (goat anti mouse, Pierce) for 1 hr at room temperature. Signals were detected with Immun-Star Chemiluminescence kit (Bio-Rad). The Western blots of FIG. 55 A,C show NME7 exist as ~40 kDa species as well as a lower molecular weight NME7 species of ~25-30 kDa, which may be an alternative splice isoform or a post translational modification such as cleavage.

Figure 56:
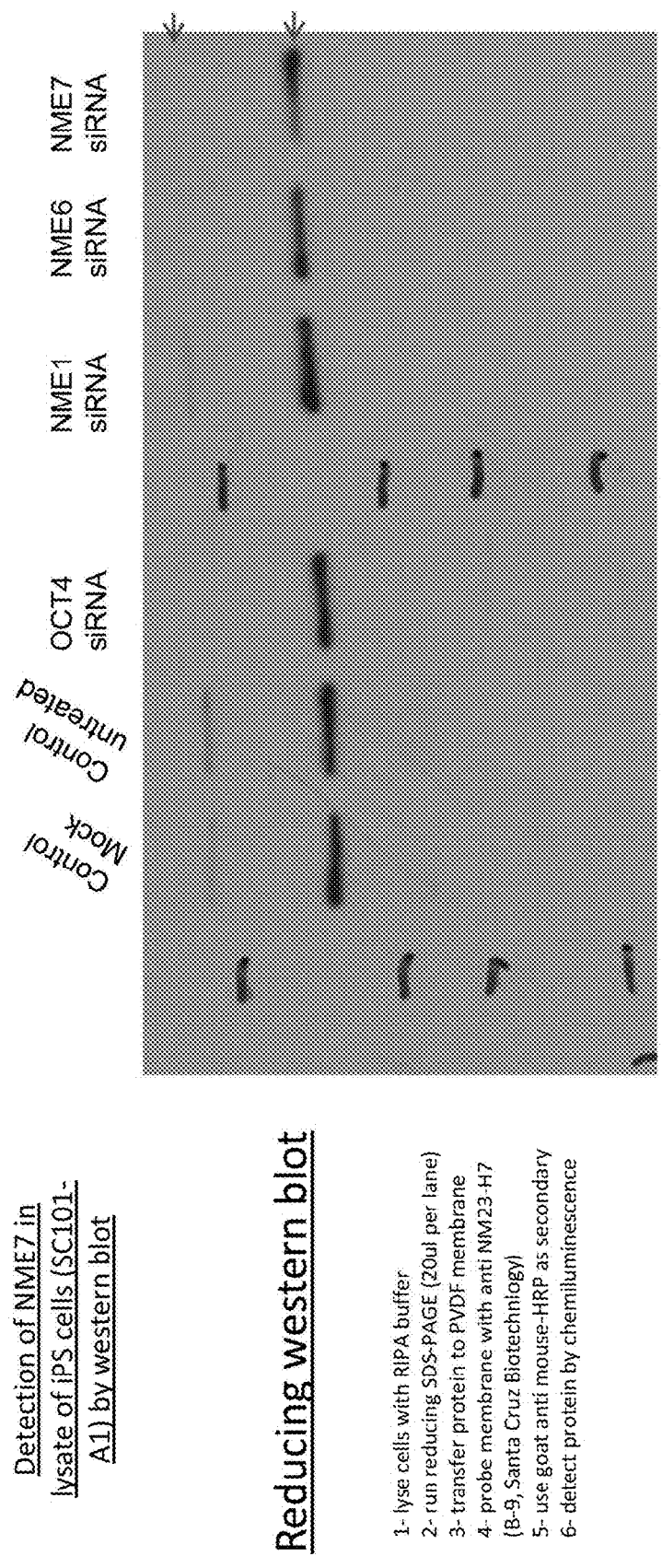
FIG. 56 is a photograph of a Western blot, probing for NME7 species in human stem cells, in some of which either OCT4, NME1, NME6 or NME7 was suppressed, but cells were cultured in NME7 containing media.
Figure 58:
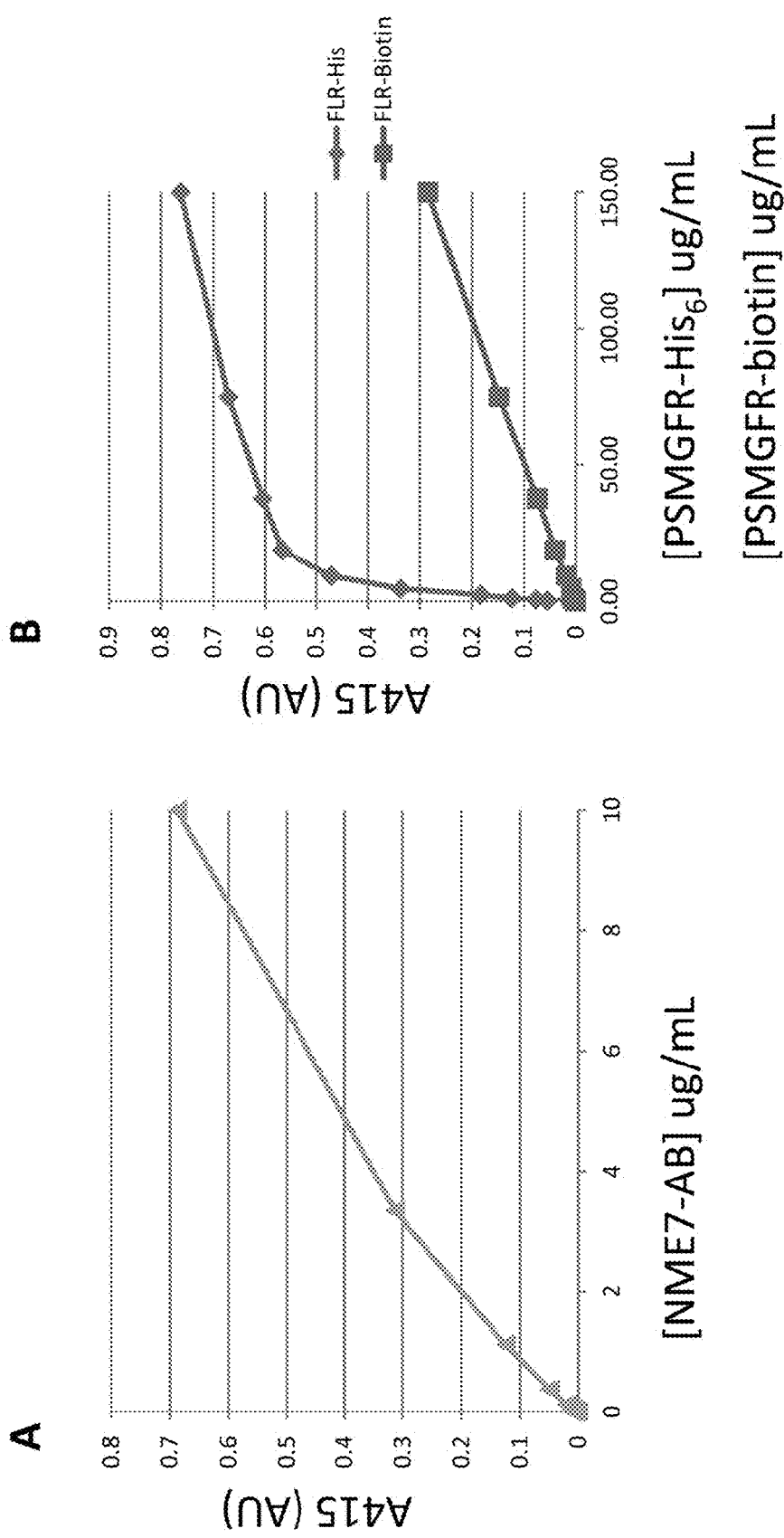
FIG. 58 shows graph of HRP signal from ELISA sandwich assay showing NME7-AB dimerizes MUC1* extra cellular domain peptide.

Additionally, human iPS cells (SC101-A1) were cultured as described above or in the presence of siRNA that suppressed OCT4, NME1, NME6 or NME7. The Western blot of FIG. 56 shows that when OCT4, NME6 or NME7 is suppressed, the high molecular weight band (~40 kDa) disappears. However, it did not disappear when NME1 was suppressed. This result is consistent with the idea that NME6, NME7 and OCT4 are critical pluripotency genes. The results are also consistent with the idea that the high molecular weight form is the expressed form (would disappear before a cleavage product) in response to suppression of related genes that regulate its expression.

Example 23.2

Detection of NME7 in iPS Conditioned Media iPS Conditioned media (20 uL) was separated by electrophoresis on either a 12% SDS-PAGE reducing gel and transferred to a PVDF membrane (GE Healthcare). The blot was blocked with PBS-T containing 3% milk and then incubated with primary antibody (anti NM23-H7 clone B-9, Santa Cruz Biotechnology) at 4° C. overnight. After washing with PBS-T, the membrane was incubated with horseradish peroxidase (HRP)-conjugated secondary antibody (goat anti mouse, Pierce) for 1 hr at room temperature. Signals were detected with Immun-Star Chemiluminescence kit (Bio-Rad). Western blot of FIG. 55 B show secreted NME7 species having an approximate molecular weight of 30 kDa. Note that the recombinant NME7-AB has a molecular weight of 33 kDa and as such can simultaneously bind to two MUC1* peptides and also fully supports pluripotent stem cell growth, induction of pluripotency and inhibits differentiation. The NME7 species of ~25-30 kDa may be an alternative splice isoform or a post translational modification such as cleavage, which may enable secretion from the cell.

Example 23.3

NME7 Immuno-Precipitation and Analysis by Mass Spectrophotometry

A pull down assay was performed using an NME7 specific antibody (NM23 H7 B9, Santa Cruz) on a panel of MUC1*-positive cells. Breast cancer cells (T47D) as well as human ES (BGO1v and HES-3) and iPS(SC101-A1) cells were cultured according to standard protocol (T47D) or cultured in NME-based media over a surface of anti-MUC1* antibody. Cells were lysed with RIPA buffer (Pierce), supplemented with protease inhibitor (Pierce). Cell lysates were supplemented with 10 ug of recombinant NME7-AB incubated at 4° C. for 2 h. Then NME7 was immuno-precipitated at 4° C. overnight with anti NM23-H7 (B-9, Santa Cruz Biotechnology) coupled to Dynabeads protein G (Life technologies). Beads were washed twice with PBS and immuno-precipitated proteins were separated by electrophoresis on a 12% SDS-PAGE reducing gel. Proteins were detected by silver staining (Pierce). The ~23 kDa bands of proteins that co-immunoprecipitated along with NME7, from the T47D sample and the BGO1v cells, were excised and analyzed by mass spec (Taplin Mass Spectrometry Facility, Harvard Medical School). Mass spec analysis showed that the protein bands that were excised all contained sequences from the NME7 NDPK A domain as shown below. The underlined sequences in the A domain of NME7 were identified by mass spec.

```
                                      (SEQ ID NO: 113)
MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALI

KPDAISKAGEIIEIINKAGFTITKLKMMMLSRKEALDFHVDHQSRPFFN

ELIQFITTGPIIAMEILRDDAICEWKRLLGPANSGVARTDASESIRALF

GTDGIRNAAHGPDSFASAAREMEEFFPSSGGCGPANTAKFTNCTCCIVK

PHAVSEGLLGKILMAIRDAGFEISAMQMFNMDRVNVEEFYEVYKGVVTE

YHDMVTEMYSGPCVAMEIQQNNATKTFREFCGPADPEIARHLRPGTLRA

IFGKTKIQNAVHCTDLPEDGLLEVQYFFKILDN
```

The higher molecular weight protein bands, ~30 kDa, that immunoprecipitated with NME7 were not analyzed by mass spec and may correspond to either an endogenous NME7 protein that may be a cleavage product or an alternative splice isoform or alternatively could be NME7-AB ~33 kDa that was added to the cell lysates.

Example 24

ELISA Assay Showing NME7-AB Simultaneously Binds to Two MUC1* Extra Cellular Domain Peptides The PSMGFR peptide bearing a C-terminal Cysteine (PSMGFR-Cys) was covalently coupled to BSA using Imject Maleimide activated BSA kit (Thermo Fisher). PSMGFR-Cys coupled BSA was diluted to 10 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and NME7, diluted in PBS-T+1% BSA, was added at different concentrations. After 1 h at RT the plate was washed 3× with PBS-T and anti-NM23-H7 (B-9, Santa Cruz Biotechnology), diluted in PBS-T+1% BSA, was added at 1/500 dilution. After 1 h at RT the plate was washed 3× with PBS-T and goat anti mouse-HRP, diluted in PBS-T+1% BSA, was added at 1/3333 dilution. After 1 h at RT the plate was washed 3× with PBS-T and binding of NME7 was measured at 415 nm using a ABTS solution (Pierce).

ELISA MUC1* dimerization: The protocol for NME7 binding was used and NME7 was used at 11.6 ug/mL.

After 1 h at RT the plate was washed 3× with PBS-T and HisTagged PSMGFR peptide (PSMGFR-His) or biotinylated PSMGFR peptide (PSMGFR-biotin), diluted in PBS-T+1% BSA, was added at different concentration. After 1 h at RT the plate was washed 3× with PBS-T and anti Histag-HRP (Abcam) or streptavidin-HRP (Pierce), diluted in PBS-T+1% BSA, was added at a concentration of 1/5000. After 1 h at RT the plate was washed 3× with PBS-T and binding of PSMGFR peptide to NME7 already bound to another PSMGFR peptide (which could not signal by anti-His antibody or by streptavidin) coupled BSA was measured at 415 nm using a ABTS solution (Pierce).

Example 25

NME6 Cloning, Expression and Purification

WT NME6 cDNA, codon optimized for expression in *E. coli* was synthesized by our request by Genscript, N.J. The WT NME6 cDNA was then amplified by polymerase chain reaction (PCR) using the following primer: 5'-atcgacatatgacgcaaaatctgggctcggaaatg-3' (SEQ ID NO:114) and 5'-actgcctcgagtgccggacccagaccacccgtgc-3' (SEQ ID NO:115). After digestion with NdeI and XhoI restriction enzymes (New England Biolabs), the purified fragment was cloned into the pET21b vector (Novagen) digested with the same restriction enzymes.

Example 26

NME6 Protein Expression/Purification

Figure 59:
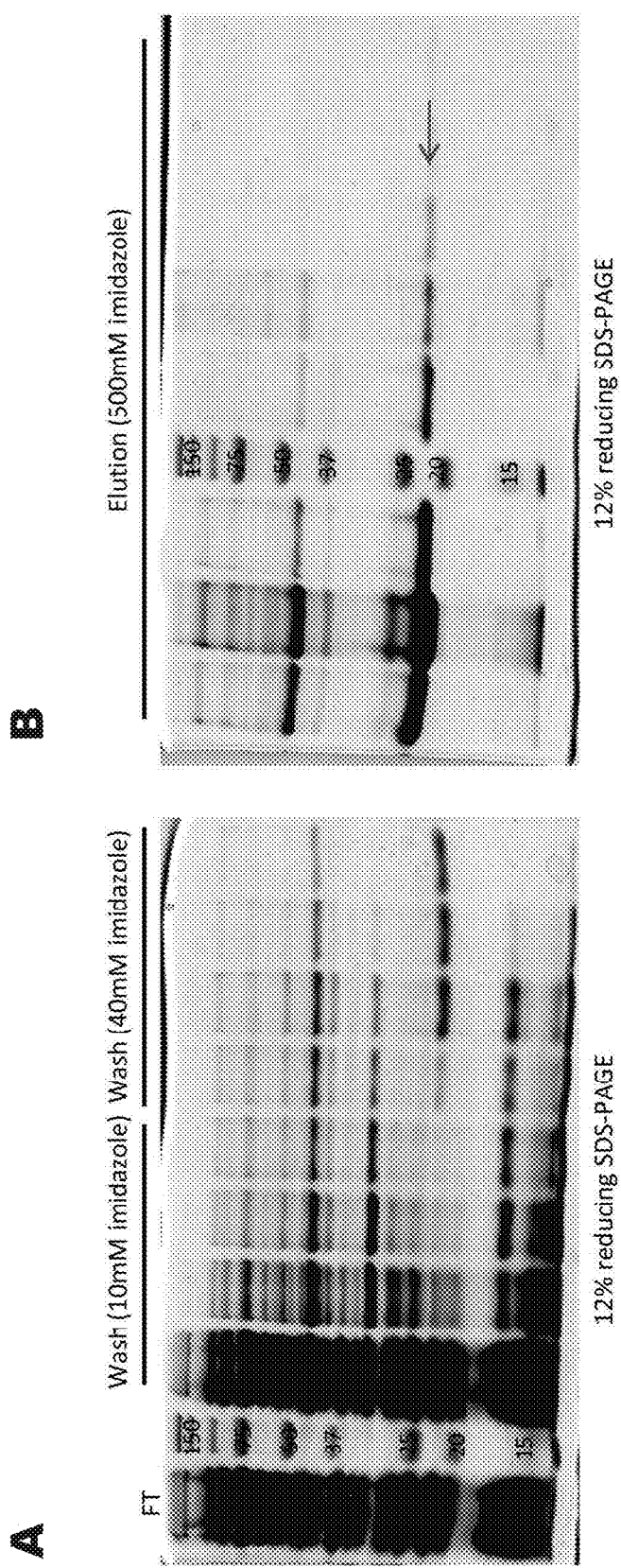
FIGS. 59A-59B show photographs of SDS-PAGE gels showing expression and purification of NME6 in E. coli.

LB broth (Luria-Bertani broth) was inoculated with 1/10 of an overnight culture and cultured at 37° C. until OD600 reached ~0.5. At this point, recombinant protein expression was induced with 0.4 mM Isopropyl-β-D-thio-galactoside (IPTG, Gold Biotechnology) and culture was stopped after 5 h. After harvesting the cells by centrifugation (6000 rpm for 10 min at 4° C.), cell pellet was resuspended with running buffer: PBS pH7.4, 360 mM NaCl, 10 mM imidazole and 8M urea. Cell suspension was incubated on a rotating platform (275 rpm) for 30 min at 37° C. and sonicated on ice for 5 min. Insoluble cell debris was removed by centrifugation (20000 rpm for 30 min at 4° C.). The cleared lysate was then applied to a Ni-NTA column (Qiagen) equilibrated with the running buffer. The column was washed with 4 CV of running buffer, then 4 CV of running buffer supplemented with 30 mM imidazole before eluting the protein off the column with the running buffer (8 CV) supplemented with 420 mM imidazole. The protein was then refolded by dialysis, (FIG. 59).

Example 27

Refolding Protocol

1. Dialyse overnight against 100 mM Tris pH 8.0, 4M urea, 0.2 mM imidazole, 0.4M L-arginine, 1 mM EDTA and 5% glycerol
2. Dialyse 24 h against 100 mM Tris pH 8.0, 2M urea, 0.2 mM imidazole, 0.4M L-arginine, 1 mM EDTA and 5% glycerol
3. Dialyse 24 h against 100 mM Tris pH 8.0, 1M urea, 0.2 mM imidazole, 0.4M L-arginine, 1 mM EDTA and 5% glycerol
4. Dialyse 8 h against 100 mM Tris pH 8.0, 0.2 mM imidazole, 0.4M L-arginine, 1 mM EDTA and 5% glycerol
5. Dialyse overnight against 25 mM Tris pH 8.0, 0.2 mM imidazole, 0.1M L-arginine, 1 mM EDTA and 5% glycerol
6. Dialyse 3×3 h against PBS pH 7.4, 0.2 mM imidazole, 1 mM EDTA and 5% glycerol
7. Dialyse overnight against PBS pH 7.4, 0.2 mM imidazole, 1 mM EDTA and 5% glycerol
8. Centrifuge refolded protein (18,500 rpm) 30 min at 4° C. and collect supernatant for further purification.

The protein was further purified by size exclusion chromatography (Superdex 200).

All of the references cited herein are incorporated by reference in their entirety.

PARTIAL CITED REFERENCES LIST

Boyer L. A. et al. Cell 122, 947-956 (2005)
Dexheimer at al. Mol Cancer Ther 8(5):1363-1377 (2009)
Hikita et al. PLoS ONE 3(10), e3312 (2008)
Jaenisch, R. and Young, R. Cell 132, 567-582 (2008)
Kim, et al. Biochem Biophys Res Commun 307:281-289 (2003)
Lowry, W. E. et al. Proc. Natl. Acad. Sci. USA 105(8):2883-2888 (2008)
Mahanta et al. PLoS ONE 3(4):e2054 (2008)
Maherali, N. et al. Cell Stem Cell 1:55-70 (2007)
Nakagawa, M. et al. Nature Biotechnol 26(1):101-106 (2008)
Okabe-Kado, et al *FEBS Letters* 1995 363: 311-315
Okita, K et al. Nature 448:313-317 (2007)
Park, I. H. et al. Nature 451:141-146 (2008)
Takahashi, K. & Yamanaka, S. Cell 126, 663-676 (2006)
Takahashi, K. et al. Cell 131:861-872 (2007)
Wernig, M. et al. Nature 448, 318-324 (2007)
Wernig, M. et al. Cell Stem Cell 2, 10-12 (2008)
Woltjen, K., et al. Nature 458, 766-770 (2009)
Yamanaka, S. Cell stem Cell 1, 39-49 (2007)
Yu, J. et al. Science 324, 797-801 (2009)
Yu, J. et al. Science 318, 1917-1920 (2007)
Zou et al. MCB, 20(2):628-633 (2000)
Zhou et al. Cell Stem Cell 4:381-384 (2009)

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method for stimulating growth of stem or progenitor cells or for inducing cells to revert to a less mature state, the method comprising contacting cells with cell culture media that comprises a recombinant NME7 protein that comprises a nucleotide diphosphate kinase (NDPK) A domain and an NDPK B domain and does not comprise a targeting sequence.

2. The method according to claim 1, wherein the stem or progenitor cells are grown or the cells are induced to revert to the less mature state on a surface coated with anti-MUC1* antibody.

3. The method according to claim 1, wherein the recombinant NME7 is the only growth factor in the cell culture media.

4. The method according to claim 1, wherein the cell culture media does not comprise basic fibroblast growth factor (bFGF) and transforming growth factor beta (TGF-beta).

5. The method according to claim 1, wherein the cells are mature, somatic or progenitor cells.

6. The method according to claim 1, wherein the cells are human cells.

7. The method according to claim 1, wherein the cell culture media is free of serum.

8. The method according to claim 1, wherein the cell culture media further comprises insulin, selenium, transferrin, L ascorbic acid, or one or more non-essential amino acids.

9. The method according to claim 1, wherein the recombinant NME7 is characterized by a molecular weight of about 25 to 33 kilodaltons (kDa).

10. The method according to claim 1, wherein the recombinant NME7 protein is characterized by a molecular weight of about 30 kilodaltons (kDa).

11. The method according to claim 1, wherein the recombinant NME7 has a molecular weight of about 31 kilodaltons (kDa).

12. The method according to claim 1, wherein the recombinant NME7 is characterized by a molecular weight of about 33 kilodaltons (kDa).

13. The method according to claim 1, wherein the recombinant NME7 comprises the amino acid sentience of SEQ ID NO: 39 41 59 or 61.

14. The method according to claim 1, wherein the recombinant NME7 comprises an alternative splice isoform having an amino acid sequence of SEQ ID NO: 39, 41, 59 or 61.

15. The method according to claim 1, wherein the cell culture media further comprises an inhibitor of a rho associated kinase.

16. The method according to claim 1, wherein the cell culture media further comprises an activator of one or more signaling proteins in the PBK or RAC pathway.

17. The method according to claim 1, wherein the cell culture media further comprises an activator of one or more signaling proteins in the PBK or RAC pathway in the absence of a rho kinase inhibitor.

18. The method according to claim 1, wherein the cell culture media further comprises a nucleic acid that suppresses expression of NME1 or NME2.

19. The method according to claim 1, wherein the recombinant NME7 has superior high yield expression of the soluble, properly folded protein in *E. coli* compared with native NME7.

* * * * *

UNITED STATES PATENT AND TRADEMARK OFFICE
CERTIFICATE OF CORRECTION

| | | |
|---|---|---|
| PATENT NO. | : 11,591,565 B2 | |
| APPLICATION NO. | : 14/254749 | |
| DATED | : February 28, 2023 | |
| INVENTOR(S) | : Cynthia Bamdad and Benoit Smagghe | |

It is certified that error appears in the above-identified patent and that said Letters Patent is hereby corrected as shown below:

In the Claims

Column 198, Line 60, reading:
'sentience'
Should read:
--sequence--.

Signed and Sealed this
First Day of August, 2023

Katherine Kelly Vidal
*Director of the United States Patent and Trademark Office*